United States Patent [19]

Oya et al.

[11] Patent Number: 4,986,845
[45] Date of Patent: Jan. 22, 1991

[54] PYRAZOLE DERIVATIVES AND HERBICIDES CONTAINING THEM

[75] Inventors: Eiichi Oya; Junichi Watanabe; Yasuo Kondo; Takuya Kakuta, all of Funabashi; Koichi Suzuki, Shiraoka; Tsutomu Nawamaki, Shiraoka; Shigeomi Watanabe, Shiraoka, all of Japan

[73] Assignee: Nissan Chemical Industries Ltd., Tokyo, Japan

[21] Appl. No.: 369,523

[22] Filed: Jun. 21, 1989

[30] Foreign Application Priority Data

Jul. 15, 1988 [JP] Japan .................. 63-176758
Feb. 3, 1989 [JP] Japan .................... 1-26030

[51] Int. Cl.$^5$ .................. A01N 43/56; C07D 401/12; C07D 413/12; C07D 231/20
[52] U.S. Cl. ................................ 71/92; 71/90; 71/86; 71/87; 546/211; 544/140; 548/363; 548/364; 548/367; 548/374; 548/375; 548/376; 548/377; 548/116; 548/112; 548/119
[58] Field of Search ............... 71/92, 90, 86, 87; 548/363, 364, 367, 374, 375, 376, 377, 116, 112, 119; 546/211; 544/140

[56] References Cited

U.S. PATENT DOCUMENTS 4,643,757 2/1987 Baba et al. ................. 71/86

FOREIGN PATENT DOCUMENTS 0282944 9/1988 European Pat. Off. .
2277826 2/1976 France .

*Primary Examiner*—John M. Ford
*Attorney, Agent, or Firm*—Oblon, Spivak, McClelland, Maier & Neustadt

[57] ABSTRACT

A pyrazole derivative of the formula I

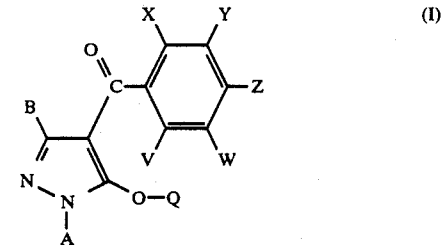

wherein A is $C_1$-$C_4$ alkyl, $C_2$-$C_4$ alkenyl or $C_2$-$C_4$ alkynyl; B is hydrogen, $C_1$-$C_3$ alkyl, halogen, $C_1$-$C_3$ haloalkyl, $C_1$-$C_3$ alkoxy, $C_1$-$C_3$ alkylthio, $C_2$-$C_4$ alkoxyalkyl, $C_2$-$C_4$ alkylthioalkyl or $C_2$-$C_4$ alkoxycarbonyl; X is $C_1$-$C_6$ alkyl, $C_1$-$C_6$ alkoxy, halogen, nitro, cyano, etc.; Y is —$OR^1$ (wherein $R^1$ is $C_3$-$C_8$ cycloalkyl, etc), —O—L—O—$R^1$ (wherein L is $C_1$-$C_6$ alkylene which may be substituted by $C_1$-$C_3$ alkyl), —O—L—OH, —O—L—O—L—O—$R^2$ (wherein $R^2$ is hydrogen, $C_1$-$C_6$ alkyl group, etc.), —O—L—$R^3$ (wherein $R^3$ is phenyl which may be substituted by $C_1$-$C_3$ alkyl, etc.), —O—M (wherein M is a 3- to 6-membered alicyclic group), —O—L—M, —O—L—$NR^4R^5$ (wherein each of $R^4$ and $R^5$ is hydrogen or $C_1$-$C_6$ alkyl, or $R^4$ and $R^5$ form a ring together with the adjacent nitrogen atom), —O—L—$COOR^4$, —O—CH=CH—$COOR^4$, —O—L—CN, —O—L—C(O)—$R^2$, —O—L—S(O)$_n$—$R^4$ (wherein n is an integer of from 0 to 2), —O—$COOR^4$, —O—$CONR^4R^5$, —OP(O)(OR$^4$)$_2$, —S(O)$_n$$R^1$, or —S-(O)$_n$—L—O—$R^1$; Z is halogen, nitro, $C_1$-$C_3$ alkoxy, etc.; V is hydrogen, halogen, $C_1$-$C_4$ alkyl or $C_1$-$C_4$ alkoxy; W is hydrogen, halogen, $C_1$-$C_4$ alkyl, etc.; Q is hydrogen, $C_1$-$C_6$ alkyl which may be substituted by halogen, . . . —C(O)—$R^7$ (wherein $R^7$ is phenyl which may be substituted), —S(O)$_2R^7$, —P(O)(OR$^7$)$_2$, —L—C(O)—$R^7$, —L—C(O)—N($R^8$)($R^9$) (wherein each of $R^8$ and $R^9$ is hydrogen or $C_1$-$C_6$ alkyl), —L—$R^{10}$ (wherein $R^{10}$ is phenyl group may be substituted, $C_1$-$C_6$ alkyl, $C_1$-$C_7$ alkoxy, or hydroxyl), —L—N($R^8$)($R^9$), —L—$OR^{11}$ (wherein $R^{11}$ is hydrogen, $C_1$-$C_6$ alkyl, or $C_1$-$C_6$ alkenyl), —L—OC(O)$R^{12}$ (wherein $R^{12}$ is $C_1$-$C_6$ alkyl or $C_1$-$C_6$ alkoxy), —L—S-(O)$_n$$R^{11}$, —L—SC(O)$R^8$,

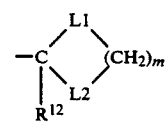

(wherein each of L1 and L2 is methylene, oxygen or sulfur, $R^{12}$ is hydrogen or $C_1$-$C_3$ alkyl, and m is 2 or 3); and a salt thereof.

5 Claims, No Drawings

PYRAZOLE DERIVATIVES AND HERBICIDES CONTAINING THEM

The present invention relates to novel 4-benzoyl-pyrazole derivatives and selective herbicides containing such derivatives as active ingredients, which are useful particularly as upland field herbicides.

Various herbicides have been developed for practical use from extensive research and development of herbicides for many years, and such herbicides have contributed to a reduction of the labor force required for controlling weeds or to improvement of the productivity of agricultural or horticultural plants.

Even now, it is still desired to develop a new herbicide having superior herbicidal properties. In particular, it is desired to develp an agricultural or horticultural herbicide which is capable of selectively controlling weeds without adversely affecting the crop plant and at a low dose. However, conventional herbicides do not necessarily provide such desired herbicidal properties.

On the other hand, certain compounds of 4-benzoylpyrazole derivatives are known to have herbicidal activities. For example, pyrazolate (common name) and pyrazoxyfen (common name) are practically used as herbicides for paddy fields. While exhibiting excellent herbicidal activities as paddy field herbicides, these compounds are not suitable as upland herbicides since their herbicidal activities are weak against weeds of upland fields. Among 4-benzoylpyrazole derivatives, it is desired to develop a superior compound useful as an upland field herbicide.

The present invention provides a pyrazole derivative having the formula:

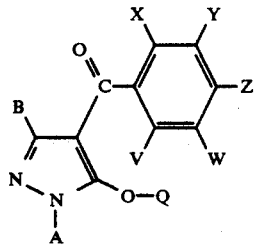

(I)

wherein

A is a $C_1$–$C_4$ alkyl group, a $C_2$–$C_4$ alkenyl group or a $C_2$–$C_4$ alkynyl group;

B is a hydrogen atom, a $C_1$–$C_3$ alkyl group, a halogen atom, a $C_1$–$C_3$ haloalkyl group, a $C_1$–$C_3$ alkoxy group, a $C_1$–$C_3$ alkylthio group, a $C_2$–$C_4$ alkoxyalkyl group, a $C_2$–$C_4$ alkylthioaalkyl group or a $C_2$–$C_4$ alkoxycarbonyl group;

X is a $C_1$–$C_6$ alkyl group, a $C_1$–$C_6$ alkoxy group, a halogen atom, a nitro group, a cyano group, a $C_1$–$C_6$ haloalkyl group, a $C_2$–$C_6$ alkoxyalkyl group, a $C_2$–$C_6$ alkylcarbonyl group, a $C_2$–$C_6$ alkoxycarbonyl group, an aminocarbonyl group substituted independently by hydrogen or by a $C_1$–$C_6$ alkyl group, a $C_1$–$C_6$ haloalkoxy group, a $C_1$–$C_6$ alkylthio group or a $C_2$–$C_6$ alkylthioalkyl group;

Y is —$OR^1$ (Wherein $R^1$ is a $C_3$–$C_8$ cycloalkyl group, a $C_4$–$C_8$ cycloalkylalkyl group, a $C_3$–$C_6$ alkenyl group, a $C_2$–$C_6$ alkynyl group, a $C_1$–$C_6$ haloalkyl group, a $C_3$–$C_8$ halocycloalkylalkyl group, a $C_3$–$C_6$ haloalkenyl group, a $C_2$–$C_6$ haloalkynyl group, a $C_2$–$C_6$ nitroalkyl group or a phenyl group which may be substituted by a $C_1$–$C_3$ alkyl group, a halogen atom, a nitro group or a $C_1$–$C_3$ alkoxy group), —O—L—O—$R^1$ (Wherein L is a $C_1$–$C_6$ alkylene group which may be substituted by a $C_1$–$C_3$ alkyl group, and $R_1$ is as defined above), —O—L—OH (wherein L is as defined above), —O—L—O—L—O—$R^2$ (wherein L is as defined above, and $R^2$ is a hydrogen atom, a $C_1$–$C_6$ alkyl group or a phenyl group which may be substituted by a $C_1$–$C_3$ alkyl group, a halogen atom, a nitro group or a $C_1$–$C_3$ alkoxy group), —O—L—$R^3$ (wherein L is as defined above, and $R^3$ is a phenyl group which may be substituted by a $C_1$–$C_3$ alkyl group, a halogen atom, a nitro group or a $C_1$–$C_3$ alkoxy group), —O—M (wherein M is a 3- to 6-membered alicyclic group containing not more than two sulfur or oxygen atoms and formed by a linkage of from 1 to 4 carbon atoms), —O—L—M (wherein L and M are as defined above), —O—L—$NR^4R^5$ (wherein L is as defined above and each of $R^4$ and $R^5$ which may be the same or different is a hydrogen atom or a $C_1$–$C_6$ alkyl group, or $R^4$ and $R^5$ form a ring together with the adjacent nitrogen atom), —O—L-$COOR^4$ (wherein L and $R^4$ are as defined above), —O—CH=CH—$COOR^4$ (wherein $R^4$ is as defined above), —O—L—CN (wherein L is as defined above), —O—L—C(O)—$R^2$ (wherein L and $R^2$ are as defined above), —O—L—S(O)$_n$—$R^4$ (wherein L and $R^4$ are as defined above, and n is an integer of from 0 to 2), —O—$COOR^4$ (wherein $R^4$ are as defined above), —O—$CONR^4R^5$ (wherein $R^4$ and $R^5$ are as defined above), —OP(O)(O$R^4$)$_2$ (wherein $R^4$ is as defined above), —S(O)$_nR^1$ (wherein $R^1$ and n are as defined above), or —S(O)$_n$—L—O—$R^1$ (wherein L, $R^1$ and n are as defined above);

Z is a halogen atom, a nitro group, a $C_1$–$C_3$ alkoxy group, a trifluoromethyl group, a trifluoromethoxy group, a cyano group or —S(O)$_nR^6$ (wherein n is as defined above, and $R^6$ is a $C_1$–$C_3$ alkyl group or a $C_1$–$C_3$ haloalkyl group);

V is a hydrogen atom, a halogen atom, a $C_1$–$C_4$ alkyl group or a $C_1$–$C_4$ alkoxy group;

W is a hydrogen atom, a halogen atom, a $C_1$–$C_4$ alkyl group, a $C_1$–$C_4$ haloalkyl group, a $C_1$–$C_4$ alkoxy group, a $C_2$–$C_6$ alkoxyalkyl group, a $C_2$–$C_5$ alkoxycarbonyl group, a $C_1$–$C_3$ haloalkoxy group, a nitro group, a cyano group or —S(O)$_n$—$R^6$ (wherein n and $R^6$ are as defined above); and Q is a hydrogen atom, a $C_1$–$C_6$ alkyl group which may be substituted by a halogen atom, a $C_1$–$C_6$ alkenyl group which may be substituted by a halogen atom, a $C_1$–$C_6$ alkynyl group which may be substituted by a halogen atom, a cyanomethyl group, —C(O)—$R^7$ (wherein $R^7$ is a phenyl group which may be substituted by the same or different substituents selected from the group consisting of a $C_1$–$C_6$ alkyl group, a $C_1$–$C_6$ alkenyl group, a $C_1$–$C_6$ alkynyl group, a $C_1$–$C_6$ haloalkyl group, a $C_1$–$C_6$ haloalkenyl group, a $C_1$–$C_6$ haloalkynyl group, a halogen atom, a nitro group and a trifluoromethyl group, a $C_1$–$C_6$ alkyl group, a $C_1$–$C_6$ alkoxy group, or a hydroxyl group), —S(O)$_2R^7$ (wherein $R^7$ is as defined above), —P(O)(O$R^7$)$_2$ (wherein $R^7$ is as defined above), —L—C(O)—$R^7$ (wherein L and $R^7$ are as defined above), —L—C(O)—N($R^8$)($R^9$) (wherein L is as defined above, and each of $R^8$ and $R^9$ which may be the same or different is a hydrogen atom or a $C_1$–$C_6$ alkyl group), —L—$R^{10}$ (wherein L is as defined above, and $R^{10}$ is a phenyl group which may be substituted by the sam or different substituents selected from the group consisting of a halogen atom, a nitro group and a trifluoromethyl group, a $C_1$-$C_6$ alkyl group, a $C_1$-$C_6$ alkoxy group, or a hydroxyl group), —L—N($R^8$)($R^9$) (wherein L, $R^8$ and $R^9$ are as defined above), —L—$OR^{11}$ (wherein L is as defined above, and $R^{11}$ is a hydrogen atom, a $C_1$-$C_6$ alkyl group, or a $C_1$-$C_6$ alkenyl group), —L—OC(O)$R^{12}$ (wherein L is as defined above, and $R^{12}$ is a $C_1$-$C_6$ alkyl group or a $C_1C_6$ alkoxy group), —L—S(O)$_n$$R^{11}$ (wherein L, n and $R^{11}$ are as defined above), —L—SC(O)$R^8$ (wherein L and $R^8$ are as defined above),

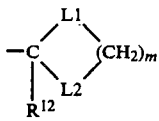

(wherein each of L1 and L2 which may be the same or different is a methylene group, an oxygen atom or a sulfur atom, $R^{12}$ is a hydrogen atom or a $C_1$-$C_3$ alkyl group, and m is 2 or 3); and a salt thereof.

The present invention also provides a selective herbicidal composition comprising a herbicidally effective amount of at least one pyrazole derivative of the formula I as defined above or its salt and an agricultural carrier or diluent.

Further, the present invention provides a method for selectively controlling weeds, which comprises applying the pyrazole derivative of the formula I as defined above or its salt to the locus to be protected.

Furthermore, the present invention provides a substituted benzene derivative of the formula:

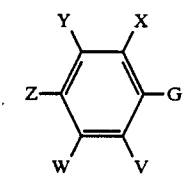

(II)

wherein G is a carboxyl group, a halocarbonyl group or a cyanocarbonyl group, and X, Y, Z, V and W are as defined above.

Now, the present invention will be described in detail with reference to the preferred embodiments.

In the compound of the formula I of the present inveniton, A, B, X, Y, Z and Q are preferably selected from the following substituents, respectively:

A: Me, Et, n-Pr, i-Pr, $CH_2CH=CH_2$, $CH_2C\equiv CH$, t-Bu

B: H, Me, Et, n-Pr, i-Pr, Cl, Br, $CH_2Cl$, $CF_3$, OMe, OEt, OPr-i, SMe, $CH_2OMe$, $CH_2SMe$, $CO_2Me$, $CO_2Et$

X: Me, Et, n-Pr, i-Pr, n-Bu, i-Bu, s-Bu, t-Bu, OMe, OEt, OPr-n, OPr-n, OPr-i, OBu-n, OBu-i, OBU-s, OBu-t, F, Cl, Br, I, $NO_2CN$, $CH_2F$, $CHF_2$, $CF_3$, $CH_2CF_3$, $CH_2Cl$, $CCl_3$, CHClMe, $CH_2CH_2Cl$, $CHClCH_2Cl$, $CH_2Br$, CHBrMe, $CH_2CH_2Br$, $CH_2OMe$, $CH_2OEt$, $CH_2OPr$-n, $CH_2OPr$-i, $CH_2OBu$-n, $CH_2OBu$-i, $CH_2OBu$-s, $CH_2OBu$-t, CHMeOMe, CHMiOEt, CHMeOPr-n, CHMeOPr-i, CHMeOBu-n, CHMeOBu-i, CHMeObu-s, CHMeOBu-t, $CH_2CH_2OMe$, $CH_2CH_2OEt$, $CH_2CH_2OPr$-i, Ac, COEt, COPr-n, COPr-i, COOMe, COOEt, COOPr-i, CONHMe, CONHEt, $CONMe_2$, $CONEt_2$, CONEtMe, $OCHF_2$, $OCF_3$, $OCH_2CF_3$, SMe, SEt, $CH_2SMe$, $CH_2SEt$, CHMeSMe, CHMeSEt

Y:

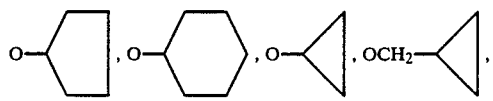

OCHMeCH=$CH_2$, $OCMe_2CH=CH_2$, $OCH_2$-CMe=$CH_2$, $OCH_2CH$=CHMe, $OCH_2CH$=$CMe_2$, $OCH_2C\equiv CH$, $OCHMeC\equiv CH$, $OCHMe_2C\equiv CH$, $OCH_2\equiv CMe$, $OCH_2CH_2F$, $OCH_2CHF_2$, $OCH_2CF_3$, $OCH_2CH_2Cl$, $OCHMeCH_2Cl$, $OCH_2CCl_3$, $OCH_2CH_2CH_2Cl$, $OCH_2CH_2Br$,

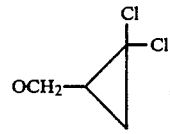

$OCH_2CCl$=$CH_2$, $OCH_2CH_2CH$=$CH_2$, $OCH_2CCl$=CHCl, $OCH_2CH_2NO_2$, OPh,OPh-Me-2 OPh-Cl-4, OPh-$NO_2$-4, $OPH_2CH_2OMe$, $OCH_2C$-$H_2OEt$, $OCH_2CH_2OPr$-n, $OCH_2CH_2OPr$-i, $OCH_2C$-$H_2OBu$-n, $OCH_2CH_2OBu$-i, $OCH_2CH_2Bu$-s, $OCH_2CH_2OBu$-t, OCHMe$CH_2OMe$, $OCH_2C$-$H_2OPh$, $OCH_2CH_2OCH_2CH_2OMe$, $OCH_2CH_2OH$, $OCH_2CH_2OCHMeCH_2OMe$, $OCH_2Ph$, OCHMePh, $OCH_2Ph$-4-Me, $OCH_2Ph$-4-Cl, $OCH_2CH_2Ph$,

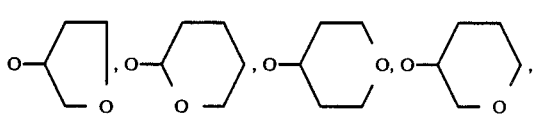

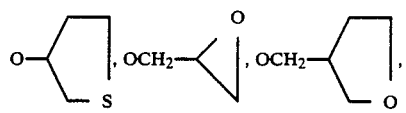

$OCH_2CH_2NH_2$, $OCH_2CH_2NHMe$, $OCH_2CH_2NMe_2$, $OCH_2CH_2NEt_2$,

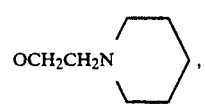

$OCH_2COOMe$, $OCH_2COOEt$, $OCH_2COOPr$-n, $OCH_2COOPr$-i, $OCH_2COOBu$-t, OCHMeCOOMe, OCHMeCOOEt OCHMeCOOPr-n, OCHMeCOOPr-i, OCHMeCOOBu-t $OCH_2CH_2CN$, $OCH_2CN$, OCHMeCN, $OCH_2SMe$, $OCH_2C(O)Ph$,

OCH$_2$C(O)Me, OCH$_2$CH$_2$SMe, OCH$_2$CH$_2$SOMe, OCH$_2$CH$_2$SO$_2$Me, OCH$_2$CH$_2$SEt, OCH$_2$CH$_2$SO$_2$Et, OCOOMe, OCOOEt, OCOOPr-i, OCONH$_2$, OCONHMe, OCONMe$_2$, OP(O)(OMe)$_2$, OP(O)(OEt)$_2$,

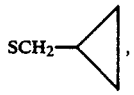

SCH$_2$CH=CH$_2$, SCH$_2$C≡CH, SCH$_2$CF$_3$, SCH$_2$CH$_2$Cl, SCH$_2$CCl$_3$,

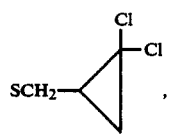

SPh, SCH$_2$CH$_2$OMe, SCH$_2$CH$_2$OEt, SCH$_2$CH$_2$OPr-i, SCH$_2$CH$_2$OPh,

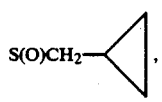

S(O)CH$_2$=CH$_2$, S(O)CH$_2$CH=CH, S(O)CH$_2$CF$_3$, S(O)CH$_2$CH$_2$Cl,

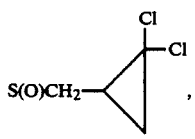

S(O)Ph, S(O)CH$_2$CH$_2$OMe, S(O)CH$_2$CH$_2$OEt, S(O)CH$_2$CH$_2$OPr-i, S(O)CH$_2$CH$_2$OPh,

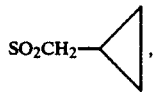

SO$_2$CH$_2$CH=CH$_2$, SO$_2$CH$_2$C≡CH, SO$_2$CH$_2$CF$_3$, SO$_2$CH$_2$CH$_2$Cl, SO$_2$CH$_2$

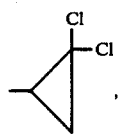

SO$_2$Ph, SO$_2$CH$_2$CH$_2$OMe, SO$_2$CH$_2$CH$_2$OEt, SO$_2$CH$_2$CH$_2$OPr-i,

Z : F, Cl, Br, I, NO$_2$, OMe, OEt, OPr-n, OPr-i, CF$_3$, CN, SMe, SOMe, SO$_2$Me, SCF$_3$, SOCF$_3$, SO$_2$CF$_3$.

Q : H, Me, Et, n-Pr, i-Pr, n-Bu, i-Bu, s-Bu, t-Bu, CH$_2$CH$_2$Cl, CH$_2$CF$_3$, CHClMe, CH$_2$CH$_2$Br, CHClCH$_2$Cl, CH$_2$CH=CH$_2$, CH$_2$CMe=CH$_2$, CH$_2$CH=CHMe, CH$_2$C≡CH, CH$_2$CCl=CH$_2$, CH$_2$CN, CH$_2$Ph, CH$_2$Ph-Cl-2, CH$_2$Ph-Cl-3, CH$_2$Ph-Me-2,

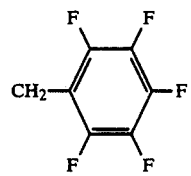

CH$_2$Ph-Me$_2$-2,4, CH$_2$Ph-Me-4, CHMePh, CHEtPh, CH$_2$Ph-NO$_2$-2, CH$_2$Ph-CF$_3$-3, CH$_2$OMe, CH$_2$OEt, CH$_2$OH, CHMeOH, CH$_2$NHMe, CH$_2$NMe$_2$, CHMeNM$_2$, CH$_2$COPh, CH$_2$COPh-NO$_2$-4, CH$_2$COPh-Me-4, CH$_2$COPh-Cl-4, CH$_2$COPh-Me$_2$-2,4, CH$_2$COPh-CF$_3$-4, CH$_2$Ac, CH$_2$COEt, CHMeAc, CH$_2$CO$_2$Me, CH$_2$CO$_2$Et, CH$_2$CO$_2$Pr-n, CH$_2$CO$_2$Pr-i, CH$_2$CO$_2$Bu-t, CH$_2$CO$_2$H, CHMeCO$_2$H, CH$_2$CONHMe, CH$_2$CONMe$_2$, CH$_2$CONHEt, CH$_2$CONEt$_2$, CH$_2$CONPr-n$_2$, CH$_2$OCH$_2$CH=CH$_2$, CH$_2$OAc, CH$_2$COEt, CH$_2$COPr-i, CH$_2$COBu-t, CH$_2$OCO$_2$Me, CH$_2$OCO$_2$Et, CH$_2$OCO$_2$Pr-i, CH$_2$OCO$_2$Bu-t, CH$_2$SMe, CH$_2$SEt, CH$_2$SCH$_2$CH=CH$_2$, CH$_2$SAc, CH$_2$SCOBu-t, CH$_2$SO$_2$Me, CH$_2$SO$_2$Et, CH$_2$SO$_2$CH$_2$CH=CH$_2$, CH$_2$NHCH$_2$CH=CH$_2$, CH$_2$NMeCH$_2$CH=CH$_2$, CH$_2$NHAc, CH$_2$NHCOEt, CH$_2$NHCO$_2$Me, CH$_2$NHCO$_2$Et, CH$_2$NMeCO$_2$Me, COPh, COPh-Me-4, COPh-NO$_2$-2, COPh-Cl$_2$-2,4, Ac, COEt, COPr-n, COPr-i, COBu-n, COBu-t, COCH$_2$Cl, COCHCl$_2$, COCCl$_3$, COCF$_3$, COCH$_2$OMe, COCH$_2$OPh, COCH$_2$CH=CHCH$_3$, CO$_2$Me, CO$_2$Et, CO$_2$Bu-t, CO$_2$Pr-i, CONHMe, CONMe$_2$, CONHEt, CONEt$_2$, CONPr-n$_2$, CON(CH$_2$CH=CH$_2$)$_2$, CONMePh,

CO$_2$CH$_2$Ph, CO$_2$Ph, SO$_2$Me, SO$_2$Et, SO$_2$CH$_2$CH=CH$_2$, SO$_2$Ph, SO$_2$Ph-Me-4, SO$_2$Ph-Cl-4, SO$_2$Ph-(NO$_2$)$_2$-2,4 SO$_2$CF$_3$, P(=O)(OMe)$_2$, P(=O)(OEt)$_2$, P(=O)(OPr-n)$_2$, P(=O)(OPr-i)$_2$, P(=S)(OMe)$_2$, P(=S)(OEt)$_2$, P(=O)OMeOPh, P(=O)(OCH$_2$CH=CH$_2$)$_2$, P(=O)O-PhOCH$_2$CH=CH$_2$

When Q is a hydrogen atom, the compound may readily from a salt with a metal or with an organic base.

As such a metal, sodium, potassium, calcium, lithium, barium, magnesium, iron, copper, nickel or manganese may be mentioned.

As such an organic base, methylamine, dimethylamine, trimethylamine, ethylamine, diethylamine, triethylamine, n-propylamine, di-n-propylamine, i-propylamine, di-i-propylamine, n-butylamine, i-butylamine, sec-butylamine, tert-butylamine, piperidine, pyrrolidine, morpholine, pyridine, N,N-dimethylaniline or choline may be mentioned.

In the course of researches on the herbicidal properties of various organic compounds with an aim to develop useful herbicides, the present inventors have found that the above-mentioned compound of the present invention exhibits excellent herbicidal activities against narrow leaf weeds (gramineous and cyperaceous weeds) and against broad leaf weeds and no substantial phytotoxicity against useful plants e.g. crop plants such as *Zea mays* (corn), *Sorghum bicolor* (sorgo), *Triticum spp* (wheat) and *Hordeum vulgare* (barley). The present invention has been accomplished on the basis of this discovery.

The compound of the present invention exhibits strong herbicidal activities in each of soil treatment, soil incorporation treatment and foliage treatment. On the other hand, it exhibits no phytotoxicity against crop plants such as *Zea mays, Sorghum bicolor, Triticum spp* and *Hordeum vulgare* in a practical application in any of soil treatment, soil incorporation treatment and foliage treatment. Thus, the compound of the present invention has high selectivity and it is extremely effective for controlling weeds during the cultivation of these crop plants. Namely, the compound of the present invention exhibits strong herbicidal activities against noxious weeds such as *Setaria viridis* (green foxtail), *Echinochloa crus-galli* (barnyardgrass), *Amarathus lividus* (livid amaranth), *Polygonum longisetum* (persicaria blumei gross), *Xanthium strumarium* (cocklebur), *Abutilon theophrasti* (velvet leaf) and *Cyperus esculentus* (yellow nutsedge), which develop during the cultivation of *Zea mays* or *Sorphum bicolor.* The herbicidal activities against gramineous weeds and *Cyperus esculentus* are remarkablly high and extremely unique. Heretofore, during the cultivation of *Zea mays* or *Sorghum bicolor,* it has been common to employ atranzine or cyanazine as a triazine-type herbicide, or alachlor or metolachlor as an acid anilide type herbicide. However, atranzine and cyanazine have poor herbicidal activities against gramineous weeds although they show high activities against broad leaf weeds, and their activities against *Cyperus esculentus* are very low. On the other hand, alachlor and metolachlor have poor activities against broad leaf weeds although their activities against gramineous weeds are high, and their activities against *Cyperus esculentus* are very poor. Thus, it has been difficult to eradicate all the weed species by a single application of such herbicides.

As a result of various studies, the present inventors have found the compound of the present invention which exhibits excellent herbicidal effects against a wide range of weeds, and the present invention has been accomplished on the basis of this discovery. The compound of the present invention also has a feature that it exhibits no phytotoxicity against crop plants such as *Zea mays, Sorqhum bicolor, Triticum spp* and *Hordeum vulgare* and thus can safely be applied to the fields for such crop plants.

Further, the compound of the present invention includes a compound which shows selectivity between *Oryza sativa* (rice) and *Echinochloa crus-qalli* (barnyardgrass), and it also includes a compound having selectivity for a useful plant such as *Goxxypium spp* (cotton), *Beta vulgaris* (sugar beat) or *Clycine max* (soybean).

Heretofore, it has been known that 4-benzoylpyrazole derivatives have excellent herbicidal activities. For example, pyrazolate (common name) is commercially available and widely used for practical application. However, such conventional herbicides are restricted in their application to paddy fields, and their activities are very poor in their application to upland fields. Whereas, as a result of extensive research for many years on 4-benzoylpyrazole derivatives, the present inventors have finally found that the compound of the present invention which simultaneously satisfies the various conditions for substituents in the structure as specified above, exhibits strong herbicidal activities in the application to upland fields in each of soil treatment, soil incorporation treatment and foliage treatment. It has been found that the compound of the present invention exhibits particularly high activities against gramineous weeds and *Cyperus esculentus.*

The compound of the present invention can readily be prepared by any one of the following reactions.

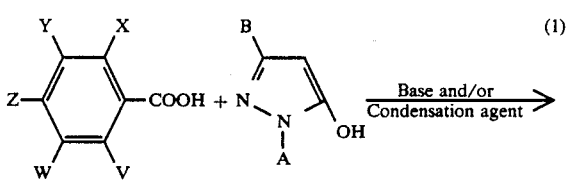

(1)

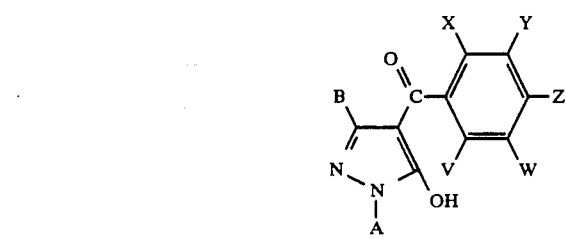

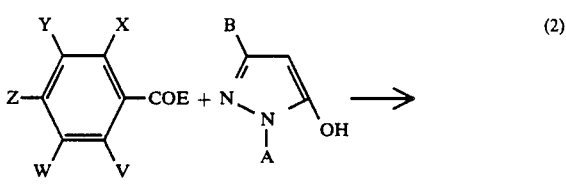

(2)

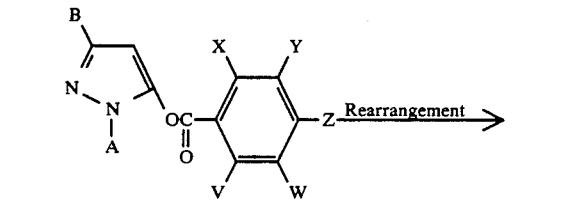

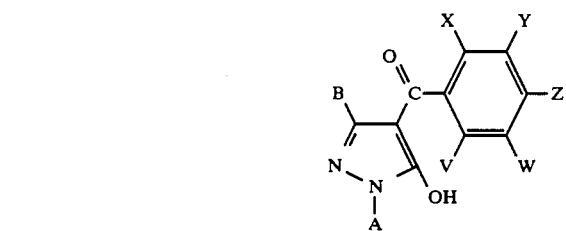

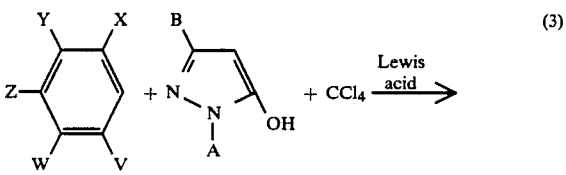

(3)

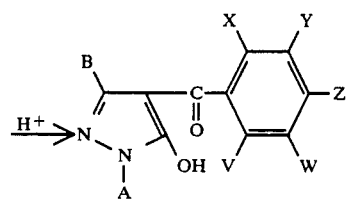

-continued

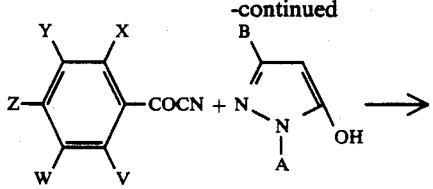 (4)

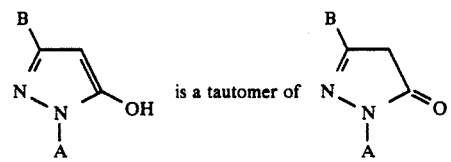

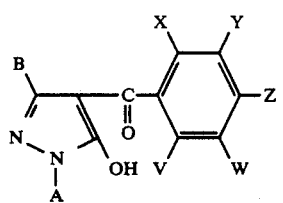

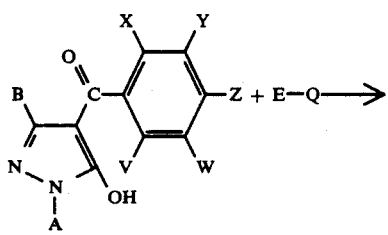 (5)

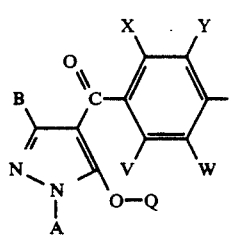

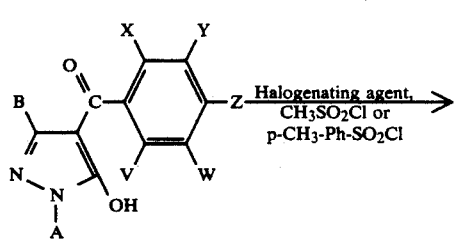 (6)

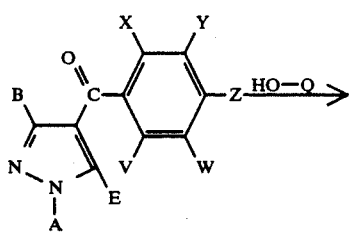

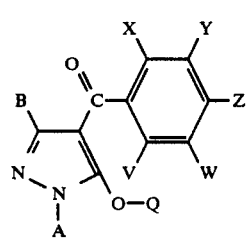

In the above formulas, A, B, V, W, X, Y, Z and Q are as defined above, E is a halogen atom, a methanesulfonyloxy group or a p-toluenesulfonyloxy group. Further, and may be represented by either formula.

Reaction scheme (1) represents a reaction wherein benzoic acid having suitable substituents and 5-hydroxypyrazole are reacted in an inert solvent in the presence of a condensation agent and a base to obtain 4-benzoyl-5-hydroxypyrazole. The condensation agent is used in an amount of from 1.0 to 1.5 mols per mol of the benzoic acid and pyrazole. As the condensation agent, N,N'-dicyclohexylcarbodiimide may be mentioned. The solvent may be any aolvent so long as it is inert to the reaction. Particularly preferred is tert-butyl alcohol, tert-amyl alcohol or isopropyl alcohol. The base may not necessarily be required. However, in general, the yield can be improved by using a base. There is no particular restriction as to the base, but potassium carbonate or sodium carbonate may preferably be employed. The reaction temperature may range from room temperature to boiling point of the solvent, but is peferably from 50° to 100° C.

The reaction time is usually from 0.5 to 20 hours.

Reaction scheme (2) shows a reaction wherein benzoyl chloride having suitable substituents and 5-hydroxypyrazole are reacted to form a benzoyl ester, which is then rearranged to a 4-benzoyl compound.

The benzoyl esterification can be accomplished in an inert solvent (such as an aromatic hydrocarbon, a fatty acid ester, a halogenated hydrocarbon, an ether, acetonitrile, dimethylsulfoxide or N,N'-dimethylformamide) or in a two phase system with such a solvent and water or in a mixture of such solvents in the presence of a suitable dehydrochlorinating agent (e.g. an inorganic base such as sodium hydroxide, potassium hydroxide or sodium hydrogencarbonate, or an organic base such as pyridine or triethylamine) at a temperature of from room temperature to 100° C. for from 10 minutes to 5 hours.

The rearrangement reaction can be accomplished by means of a Lewis acid such as anhydrous aluminum chloride or a base. As the base, potassium carbonate, calcium hydroxide or sodium carbonate may be used. The Lewis acid or base is used usually in an amount of from 1 to 10 mol times.

No solvent is required. However, in some cases, it is advantageous to use a solvent having a suitable boiling point to improve the operation efficiency or the yield. As such an advantageous example, use of dioxane, toluene or xylene diglyme, may be mentioned.

The reaction temperature is usually from 50° to 150° C., and the reaction time is usually from 15 minutes to 30 hours.

Reaction scheme (3) shows a reaction wherein a benzene derivative, a 5-hydroxypyrazole derivative and carbon tetrachloride are condensed in the presence of a Lewis acid in an inert solvent or in the absence of a solvent, followed by hydrolysis to obtain a 4-benzoyl-5-hydroxypyrazole derivative. As the Lewis acid, anhydrous aluminum chloride or anhydrous aluminum bromide in an amount of at least the theoretical amount for the reaction is preferred. The solvent may be of any type so long as it is inert to the reaction. However, a chlorine-type solvent such as methylene chloride, dichloroethane or tetrachloroethane is preferred. The temperature for condensation may range from 0° C. to the boiling point of the solvent, but it is preferably from 10° to 80° C. The hydrolysis is conducted in the presence of hydrochloric acid or sulfuric acid. The temperature for the hydrolysis is preferably from room temperature to 100° C. The time for the hydrolysis is usually from 0.1 to 10 hours.

Reaction scheme (4) shows a reaction wherein a benzoyl cyanide derivative and a 5-hydroxypyrazole derivative are reacted in the presence of a Lewis acid and a base in an inert solvent or in the absence of a solvent to obtain a 4-benzoyl-5-hydroxypyrazole. As the Lewis acid, zinc chloride, aluminum chloride or aluminum bromide may be used. As the base, pyridine or triethylamine may be mentioned. The Lewis acid and the base are used usually in an amount of from 1 to 10 mol times. As the solvent, methylene chloride, dichloroethane or tetrachloroethane may be mentioned. The reaction temperature is usually from 0° to 80° C., preferably from 10° to 50° C. The reaction time is from 0.5 to 20 hours.

Reaction scheme (5) shows a reaction wherein 4-benzoyl-5-hydroxyyrazole is condensed with a halide, a methanesulfonic acid ester or a p-toluenesulfonic acid ester.

For this reaction, it is preferred to employ from 1 to 3 mol times of a dehydrohalogenating agent. As such a dehydrohalogenating agent, an inorganic base such as sodium hydroxide, potassium hydroxide, sodium carbonate, sodium hydrogencarbonate or potassium carbonate, or an organic base such as pyridine or triethylaine, may be mentioned.

There is no particular restriction as to the solvent so long as it is inert to the reaction. A wide range of solvents including an aromatic hydrocarbon, a fatty acid ester, a halogenated hydrocarbon, an ether, a ketone, an aliphatic hydrocarbon, acetonitrile, dimethylsulfoxide and dimethylformamide may be used.

The reaction temperature may be optionally selected within a range of from room temperature to the boiling point of the solvent. The reaction time is usually from 30 minutes to 30 hours.

Reaction scheme (6) shows a reaction wherein 4-benzoyl-5-hydroxypyrazole is converted to a 5 halogeno compound by a halogenating agent, or to a methanesulfonate compound or a p-toluenesulfonate compound by methane sulfonyl chloride or p-toluenesulfonyl chloride, followed by condensation with a suitable alcohol or acid.

As the halogenating agent, phosphorus oxychloride, phosphorus pentachloride or thionyl chloride may be mentioned.

As the solvent, a wide range of solvents inert to the reaction, such as dimethylformamide, may be employed. However, the reaction can be conducted without any solvent.

The reaction temperature is preferably from 30° to 150° C, and the reaction time is usually from 30 minutes to 10 hours. In some cases, the reaction time may be shortened or the yield may be improved by an addition of a dehydrohalogenating agent.

The condensation reaction with an alcohol or acid is conducted by an addition of a dehydrohalogenating agent.

As such a dehydrohalogenating agent, a base such as sodium hydroxide, potassium hydroxide, sodium carbonate, potassium carbonate, sodium alkoxide or sodium hydride may be employed.

The solvent may be any solvent which is inert to the reaction (such as an aromatic hydrocarbon, an ether, a ketone or N,N'-dimethylformamide). The reaction temperature may be selected within a range of from room temperature to the boiling point of the solvent.

The substituted benzene derivatives used as the starting materials for the compounds of the present invention have novel structures, and they may readily be prepared by a proper combination of various known syntheses. For instance, compounds wherein the substituent Z in the benzene ring is —S(O)$_n$CH$_3$ can be prepared in accordance with the following reaction schemes.

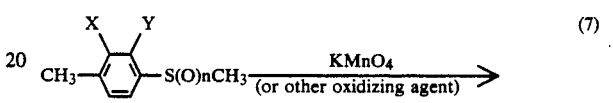

(7)

(8)

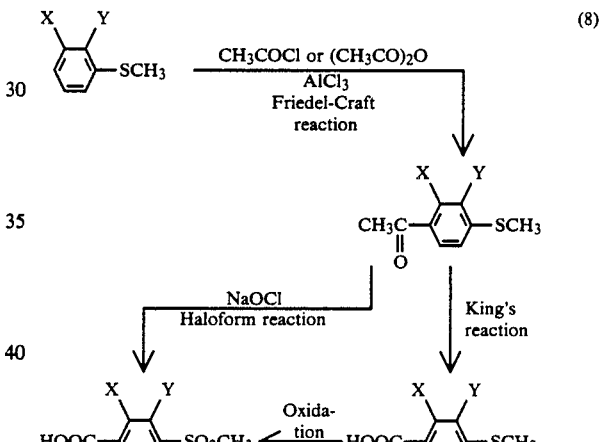

(9)

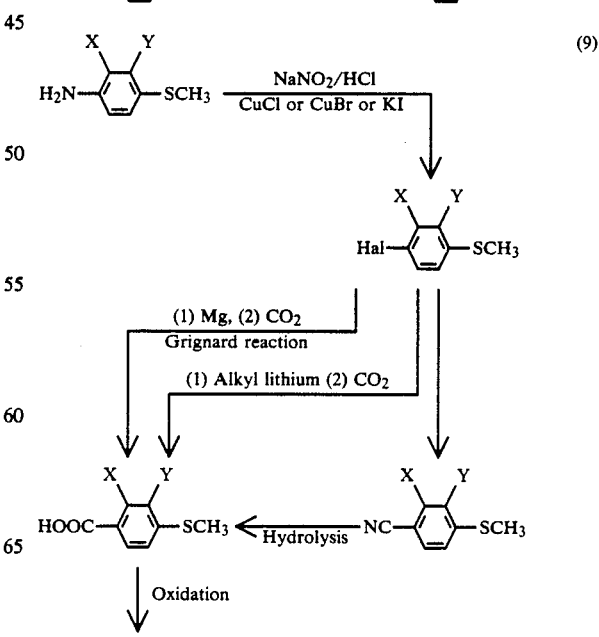

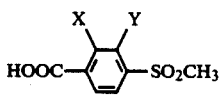

In the above formulas, X and Y are as defined above, and Hal is a halogen atom.

Now, the preparation of the substituted benzene derivatives and pyrazole derivatives will be described in detail with reference to Examples. However, it should be understood that the present invention is by no means restricted by such specific Examples.

EXAMPLE 1

Preparation of 4-(2-chloro-4-methanesulfonyl-3-(2-methoxy)ethoxybenzoyl)-1-ethyl-5-hydroxypyrazole (1) (2-methoxy)ethyl 2-chloro-4-methanesulfonyl-3-(2-methoxy)ethoxybenzoate 1.2 g of 2-chloro-3-hydroxy-4-methanesulfonylbenzoic acid, 1.4 g of potassium carbonate and 2.1 g of 2-bromoethyl methyl ether were put into 20 ml of N,N-dimethylformamide and reacted under heating at a temperature of from 60° to 70° C. for from 6 to 7 hours. Then, the solvent was distilled off, and after an addition of water, the reaction mixture was extracted with chloroform. The extract was dried over anhydrous sodium sulfate, and the solvent was distilled off to obtain 1.9 g of a crude product of the above identified compound.

(2) 2-chloro-4-methanesulfonyl-3-(2-methoxy)ethoxybenzoic acid 1.9 g of the crude product of (2-methoxy)ethyl 2-chloro-4-methanesulfonyl-3-(2-methoxy)ethoxybenzoate was dissolved in 50 ml of ethanol, and 20 ml of an aqueous solution containing 1 g of sodium hydroxide was added thereto. The mixture was stirred at room temperature for 30 minutes. Then, ethanol was distilled off, and water was added to the residue. The mixture was washed with chloroform, then acidified with concentrated hydrochloric acid and extracted with chloroform. The extract was dried over anhydrous sodium sulfate. Then, the solvent was distilled off to obtain 1.4 g of a crude product of the above identified compound. To the crude product, n-hexane was added, and the mixture was left to stand, whereby the desired product was gradually crystallized. Melting point: 89°–92° C.

(3) 4-(2-chloro-4-methanesulfonyl-3-(2-methoxy)ethoxybenzoyl)-1-ethyl-5-hydroxypyrazole 1.2 g of the crude product of 2-chloro-4-methanesulfonyl-3-(2-methoxy)ethoxybenzoic acid, 0.3 g of potassium carbonate, 0.45 g of 1-ethyl-5-hydroxypyrazole and 0.77 g of N,N'-dicyclohexyl carbodiimide were put into 40 ml of t-amyl alcohol, and the mixture was stirred under heating at a temperature of from 80° to 90° C. for from 4 to 5 hours. The solvent was distilled off, and a dilute potassium carbonate aqueous solution was added to the residue. The mixture was washed with chloroform. The aqueous layer was acidified with concentrated hydrochloric acid and extracted with chloroform. The extract was dried over anhydrous sodium sulfate. Then, the solvent was distilled off to obtain a crude product of the above identified compound. The crude product was recrystallized from ethanol to obtain 0.3 g of the desired product. Melting point: 159°–160° C.

EXAMPLE 2

Preparation of 4-(3-benzyloxy-2-chloro-4-methanesulfonylbenzoyl)-1-ethyl-5-hydroxypyrazole (1)Benzyl 3-benzyloxy-2-chloro-4-methanesulfonylbenzoate 1.5 g of 2-chloro-3-hydroxy-4-methanesulfonylbenzoic acid, 1.7 g of potassium carbonate and 5.1 g of benzyl bromide were put into 50 ml of dimethylformamide, and the mixture was stirred at room temperature overnight and then heated at a temperature of from 60° to 70° C. for 3 hours. The solvent was distilled off, and water was added to the residue. The mixture was extracted with chloroform. The extract was dried over anhydrous sodium sulfate. Then, the solvent was distilled off to obtain a crude product of the above identified compound. The crude product was recrystallized from ethanol to obtain 2.5 g of the desired product.

(2) 3-benzyloxy-2-chloro-4-methanesulfonylbenzoic acid 2.5 g of benzyl 3-benzyloxy-2-chloro-4-methanesulfonylbenzoate was put into 50 ml of ethanol, and 25 ml of an aqueous solution containing 1 g of sodium hydrochloride was added thereto. The mixture was stirred at room temperature for 30 minutes. Then, ethanol was distilled off, and water was added to the residue. The mixture was washed with chloroform. The aqueous layer was acidified with concentrated hydrochloric acid and then extracted with chloroform. The extract was dried over anhydrous sodium sulfate. Then, the solvent was distilled off to obtain a crude product of the above identified compound. The crude product was washed with ethanol-isopropyl ether to obtain 1.0 g of the desired product.

(3) 4-(3-benzyloxy-2-chloro-4-methanesulfonylbenzol)-ethyl-5-hydroxypyrazol 1.0 g of 3-benzyloxy-2-chloro-4-methanesulfonylbenzoic acid, 0.23 g of potassium carbonate, 0.24 g of 1-ethyl-5-hydroxy-pyrazole and 0.59 g of N,N'-dicyclohexylcarbodiimide were put into 20 ml of t-amyl alcohol, and the mixture was stirred under heating at a temperature of from 80° to 90° C. for 4 hours. The solvent was distilled off, and then an aqueous potassium carbonate solution was added to the residue. The mixture was washed with chloroform. The aqueous layer was acidified with concentrated hydrochloric acid and then extracted with chloroform. The extract was dried over anhydrous sodium sulfate. Then, the solvent was distilled off to obtain a crude product of the above identified compound. The crude product was recrystallized from ethanol to obtain 0.3 g of the desired product. Melting point: 162°–165° C.

The physical properties of the benzoic acids and the pyrazole derivatives prepared in accordance with the preceeding Examples will be given in Tables 1 and 2 including those of the preceeding Examples.

TABLE 1

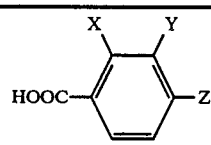

| X | Y | Z | Melting point (°C.) |
|---|---|---|---|
| Cl | OCH₂–△ (OCH₂-cyclopropyl) | SO₂Me | 102~107 |
| Cl | OCH₂CH₂OPh | SO₂Me | 147~151 |

TABLE 1-continued

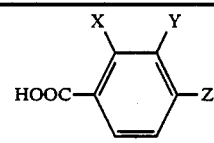

| X | Y | Z | Melting point (°C.) |
|---|---|---|---|
| Cl | O-cyclopentyl | SO₂Me | 153~157 |
| Cl | OCH₂CH₂CH=CH₂ | SO₂Me | 90~94 |
| Cl | OCH₂CH=CHMe | SO₂Me | 113~118 |
| Cl | OCH₂CH₂OMe | SO₂Me | 89~92 |

TABLE 2

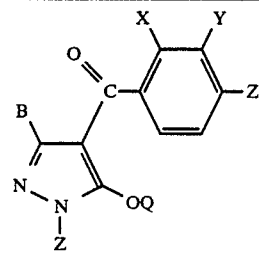

| Compound No. | A | B | X | Y | Z | Q | Melting point (°C.) |
|---|---|---|---|---|---|---|---|
| 1 | Et | H | Cl | OCH₂CH₂OMe | SO₂Me | H | 159~160 |
| 2 | Et | H | Cl | OCH₂Ph | SO₂Me | H | 162~165 |
| 3 | Et | H | Cl | O-cyclopentyl 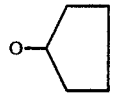 | SO₂Me | H | 156~159 |
| 4 | Et | H | Cl | OCH₂–△ 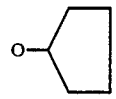 | SO₂Me | H | 153~157 |
| 5 | Et | H | Cl | OCH₂CH₂OPh | SO₂Me | H | 148~150 |
| 6 | Et | H | Cl | OCH₂C≡CH | SO₂Me | H | 150.7~152.4 |
| 7 | Et | H | Cl | OCH₂CH₂OEt | SO₂Me | H | 152.3~154.9 |
| 8 | Et | H | Cl | OCH₂CH₂CH=CH₂ | SO₂Me | H | 131~134 |
| 9 | Et | H | Cl | OCH₂CH₂SMe | SO₂Me | H | Oily substance |
| 10 | Et | H | Cl | OCH₂CH₂SO₂Me | SO₂Me | H | 206~208 |
| 11 | Et | H | Cl | OCH₂CH₂OPr-i | SO₂Me | H | 171~174 |
| 12 | Et | H | Cl | OCH₂-cyclopropyl(Cl,Cl) 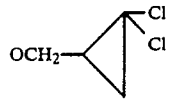 | SO₂Me | H | 191~193 |
| 13 | Me | Me | Cl | OCH₂CH₂-cyclopropyl(Cl,Cl) 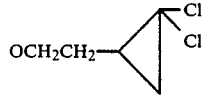 | SO₂Me | H | 181~183.5 |
| 14 | Et | H | Cl | OCH₂CH₂-cyclopropyl(Cl,Cl) 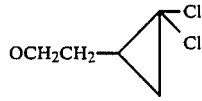 | SO₂Me | H | 100~101 |

TABLE 2-continued

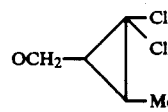

| Compound No. | A | B | X | Y | Z | Q | Melting point (°C.) |
|---|---|---|---|---|---|---|---|
| 15 | Et | H | Cl | 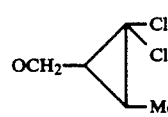 | SO₂Me | H | 171~173 |
| 16 | Me | Me | Cl | 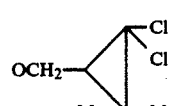 | SO₂Me | H | 138~142 |
| 17 | Me | Me | Cl | 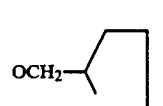 | SO₂Me | H | 100.5~101 |
| 18 | Et | H | Cl | 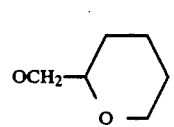 | SO₂Me | H | 154~158 |
| 19 | Et | H | Cl | 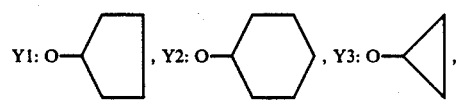 | SO₂Me | H | 175~179 |
| 20 | i-Pr | H | Cl | OCH₂CH₂OMe | SO₂Me | H | 180~183 |

Compounds which can be prepared in the same manner as the preceding Examples will be given in Tables 3 to 8 including those of the preceding Examples. However, the present invention is not restricted to such compounds.

Various symbols used in Tables 3 to 8 have the following meanings.

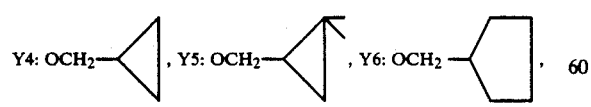

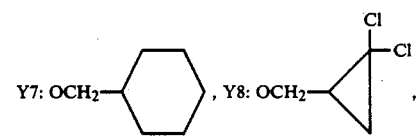

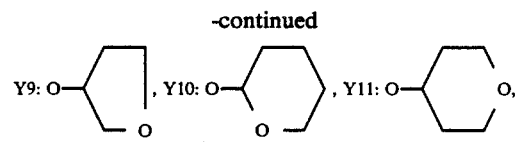

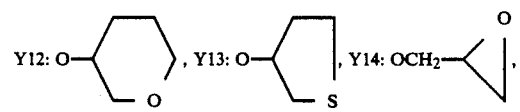

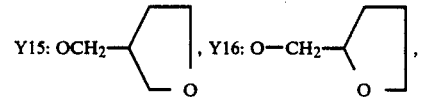

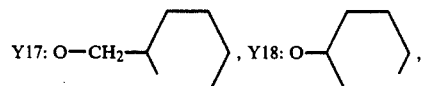

-continued

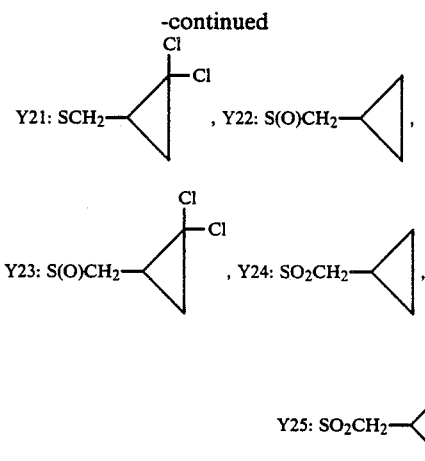

TABLE 3

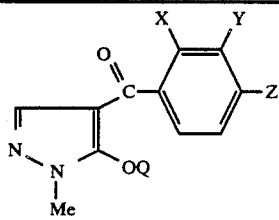

| X | Y | Z | Q |
|---|---|---|---|
| Me | Y1 | SO$_2$Me | H |
| Me | Y2 | SO$_2$Me | H |
| Me | Y3 | SO$_2$Me | H |
| Me | Y4 | SO$_2$Me | H |
| Me | Y5 | SO$_2$Me | H |
| Me | Y6 | SO$_2$Me | H |
| Me | Y7 | SO$_2$Me | H |
| Me | OCH$_2$CH=CH$_2$ | SO$_2$Me | H |
| Me | OCHMeCH=CH$_2$ | SO$_2$Me | H |
| Me | OCMe$_2$CH=CH$_2$ | SO$_2$Me | H |
| Me | OCH$_2$CMe=CH$_2$ | SO$_2$Me | H |
| Me | OCH$_2$CH=CHMe | SO$_2$Me | H |
| Me | OCH$_2$CH=CMe$_2$ | SO$_2$Me | H |
| Me | OCH$_2$CH$_2$CH=CH$_2$ | SO$_2$Me | H |
| Me | OCH$_2$C≡CH | SO$_2$Me | H |
| Me | OCHMeC≡CH | SO$_2$Me | H |
| Me | OCMe$_2$C≡CH | SO$_2$Me | H |
| Me | OCH$_2$C≡CMe | SO$_2$Me | H |
| Me | OCH$_2$CH$_2$F | SO$_2$Me | H |
| Me | OCH$_2$CHF$_2$ | SO$_2$Me | H |
| Me | OCH$_2$CF$_3$ | SO$_2$Me | H |
| Me | OCH$_2$CH$_2$Cl | SO$_2$Me | H |
| Me | OCH$_2$CCl$_3$ | SO$_2$Me | H |
| Me | OCHMeCH$_2$Cl | SO$_2$Me | H |
| Me | OCH$_2$CH$_2$Cl | SO$_2$Me | H |
| Me | OCH$_2$CH$_2$Br | SO$_2$Me | H |
| Me | Y8 | SO$_2$Me | H |
| Me | OCH$_2$CCl=CH$_2$ | SO$_2$Me | H |
| Me | OCH$_2$CCl=CHCl | SO$_2$Me | H |
| Me | OCH$_2$CH$_2$NO$_2$ | SO$_2$Me | H |
| Me | OPh | SO$_2$Me | H |
| Me | OPh—Me-2 | SO$_2$Me | H |
| Me | OPh—Cl-4 | SO$_2$Me | H |
| Me | OPh—NO$_2$-4 | SO$_2$Me | H |
| Me | OCH$_2$CH$_2$OMe | SO$_2$Me | H |
| Me | OCH$_2$CH$_2$OEt | SO$_2$Me | H |
| Me | OCH$_2$CH$_2$OPr-n | SO$_2$Me | H |
| Me | OCH$_2$CH$_2$OPr-i | SO$_2$Me | H |
| Me | OCH$_2$CH$_2$OBu-n | SO$_2$Me | H |
| Me | OCH$_2$CH$_2$OBu-i | SO$_2$Me | H |
| Me | OCH$_2$CH$_2$OBu-s | SO$_2$Me | H |
| Me | OCH$_2$CH$_2$OBu-t | SO$_2$Me | H |
| Me | OCH$_2$CH$_2$—Y4 | SO$_2$Me | H |
| Me | OCHMeCH$_2$OMe | SO$_2$Me | H |
| Me | OCH$_2$CHMeOMe | SO$_2$Me | H |
| Me | OCH$_2$CH$_2$OPh | SO$_2$Me | H |

TABLE 3-continued

| X | Y | Z | Q |
|---|---|---|---|
| Me | OCH$_2$CH$_2$OCH$_2$CH$_2$OMe | SO$_2$Me | H |
| Me | OCH$_2$CH$_2$OCH$_2$CH$_2$OPr-i | SO$_2$Me | H |
| Me | OCH$_2$CH$_2$OCHMeCH$_2$OMe | SO$_2$Me | H |
| Me | OCH$_2$CH$_2$OH | SO$_2$Me | H |
| Me | OCH$_2$Ph | SO$_2$Me | H |
| Me | OCHMePh | SO$_2$Me | H |
| Me | OCH$_2$CH$_2$Ph | SO$_2$Me | H |
| Me | OCH$_2$Ph-2-Cl | SO$_2$Me | H |
| Me | OCH$_2$Ph-3-Me | SO$_2$Me | H |
| Me | OCH$_2$Ph-4-OMe | SO$_2$Me | H |
| Me | OCH$_2$Ph-4-NO$_2$ | SO$_2$Me | H |
| Me | Y9 | SO$_2$Me | H |
| Me | Y10 | SO$_2$Me | H |
| Me | Y11 | SO$_2$Me | H |
| Me | Y12 | SO$_2$Me | H |
| Me | Y13 | SO$_2$Me | H |
| Me | Y14 | SO$_2$Me | H |
| Me | Y15 | SO$_2$Me | H |
| Me | Y16 | SO$_2$Me | H |
| Me | Y17 | SO$_2$Me | H |
| Me | Y18 | SO$_2$Me | H |
| Me | OCH$_2$CH$_2$NH$_2$ | SO$_2$Me | H |
| Me | OCH$_2$CH$_2$NHMe | SO$_2$Me | H |
| Me | OCH$_2$CH$_2$NHPr-i | SO$_2$Me | H |
| Me | OCH$_2$CH$_2$NME$_2$ | SO$_2$Me | H |
| Me | OCH$_2$CH$_2$NEt$_2$ | SO$_2$Me | H |
| Me | Y19 | SO$_2$Me | H |
| Me | OCH$_2$COOMe | SO$_2$Me | H |
| Me | OCH$_2$COOEt | SO$_2$Me | H |
| Me | OCH$_2$COOPr-i | SO$_2$Me | H |
| Me | OCH$_2$COOBu-i | SO$_2$Me | H |
| Me | OCH$_2$COOBu-t | SO$_2$Me | H |
| Me | OCH$_2$COO—Y4 | SO$_2$Me | H |
| Me | OCHMeCOOMe | SO$_2$Me | H |
| Me | OCHMeCOOEt | SO$_2$Me | H |
| Me | OCHMeCOOPr-i | SO$_2$Me | H |
| Me | OCH$_2$CH$_2$CN | SO$_2$Me | H |
| Me | OCH$_2$SMe | SO$_2$Me | H |
| Me | OCH$_2$CH$_2$SMe | SO$_2$Me | H |
| Me | OCH$_2$CH$_2$S(O)Me | SO$_2$Me | H |
| Me | OCH$_2$CH$_2$SO$_2$Me | SO$_2$Me | H |
| Me | OCH$_2$CH$_2$SPr-i | SO$_2$Me | H |
| Me | OCH$_2$CH$_2$S(O)Pr-i | SO$_2$Me | H |
| Me | OCH$_2$CH$_2$SO$_2$Pr-i | SO$_2$Me | H |
| Me | OCOOMe | SO$_2$Me | H |
| Me | OCOOPr-i | SO$_2$Me | H |
| Me | OCONH$_2$ | SO$_2$Me | H |
| Me | OCONHMe | SO$_2$Me | H |
| Me | OCONMe$_2$ | SO$_2$Me | H |
| Me | OP(O)(OMe)$_2$ | SO$_2$Me | H |
| Me | Y20 | SO$_2$Me | H |
| Me | SCH$_2$CH=CH$_2$ | SO$_2$Me | H |
| Me | SCH$_2$CH=CMe$_2$ | SO$_2$Me | H |
| Me | SCH$_2$C≡CH | SO$_2$Me | H |
| Me | SCH$_2$CF$_3$ | SO$_2$Me | H |
| Me | SCH$_2$CCl$_3$ | SO$_2$Me | H |
| Me | Y21 | SO$_2$Me | H |
| Me | SPh | SO$_2$Me | H |
| Me | SCH$_2$CH$_2$OMe | SO$_2$Me | H |
| Me | SCH$_2$CH$_2$OEt | SO$_2$Me | H |
| Me | SCH$_2$CH$_2$OPr-i | SO$_2$Me | H |
| Me | Y22 | SO$_2$Me | H |
| Me | S(O)CH$_2$CH=CH$_2$ | SO$_2$Me | H |
| Me | S(O)CH$_2$CH=CMe$_2$ | SO$_2$Me | H |
| Me | S(O)CH$_2$C≡CH | SO$_2$Me | H |
| Me | S(O)CH$_2$CH$_2$Cl | SO$_2$Me | H |
| Me | Y23 | SO$_2$Me | H |
| Me | SO$_2$CH$_2$CH=CH$_2$ | SO$_2$Me | H |
| Me | SO$_2$CH$_2$CH=CMe$_2$ | SO$_2$Me | H |
| Me | SO$_2$CH$_2$C≡CH | SO$_2$Me | H |

TABLE 3-continued

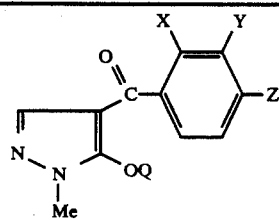

| X | Y | Z | Q |
|---|---|---|---|
| Me | SO$_2$CH$_2$CF$_3$ | SO$_2$Me | H |
| Me | SO$_2$CH$_2$CH$_2$Cl | SO$_2$Me | H |
| Me | Y24 | SO$_2$Me | H |
| Me | Y25 | SO$_2$Me | H |
| Me | SO$_2$Ph | SO$_2$Me | H |
| Me | SO$_2$CH$_2$CH$_2$OMe | SO$_2$Me | H |
| Me | SO$_2$CH$_2$CH$_2$OEt | SO$_2$Me | H |
| Me | SO$_2$CH$_2$CH$_2$OPr-i | SO$_2$Me | H |
| Me | OCH$_2$CH$_2$OMe | SO$_2$Me | CH$_2$Ph |
| Me | OCH$_2$CH$_2$OEt | SO$_2$Me | CH$_2$Ph |
| Me | OCH$_2$CH$_2$OPr-i | SO$_2$Me | CH$_2$Ph |
| Me | OCHMeCH$_2$OMe | SO$_2$Me | CH$_2$Ph |
| Me | OCH$_2$CH$_2$SMe | SO$_2$Me | CH$_2$Ph |
| Me | OCH$_2$CH$_2$S(O)Me | SO$_2$Me | CH$_2$Ph |
| Me | OCH$_2$CH$_2$SO$_2$Me | SO$_2$Me | CH$_2$Ph |
| Me | OCH$_2$CH$_2$SPr-i | SO$_2$Me | CH$_2$Ph |
| Me | OCH$_2$CH$_2$S(O)Pr-i | SO$_2$Me | CH$_2$Ph |
| Me | OCH$_2$CH$_2$SO$_2$Pr-i | SO$_2$Me | CH$_2$Ph |
| Me | SCH$_2$CH$_2$OMe | SO$_2$Me | CH$_2$Ph |
| Me | SCH$_2$CH$_2$OPr-i | SO$_2$Me | CH$_2$Ph |
| Me | SO$_2$CH$_2$CH$_2$OMe | SO$_2$Me | CH$_2$Ph |
| Me | SO$_2$CH$_2$OPr-i | SO$_2$Me | CH$_2$Ph |
| Me | OCH$_2$CH$_2$OMe | SO$_2$Me | CH$_2$COPh |
| Me | OCH$_2$CH$_2$OPr-i | SO$_2$Me | CH$_2$COPh |
| Me | OCH$_2$CH$_2$SMe | SO$_2$Me | CH$_2$COPh |
| Me | OCH$_2$CH$_2$SOMe | SO$_2$Me | CH$_2$COPh |
| Me | OCH$_2$CH$_2$SO$_2$Me | SO$_2$Me | CH$_2$COPh |
| Me | OCH$_2$CH$_2$SPr-i | SO$_2$Me | CH$_2$COPh |
| Me | OCH$_2$CH$_2$SO$_2$Pr-i | SO$_2$Me | CH$_2$COPh |
| Me | SCH$_2$CH$_2$OMe | SO$_2$Me | CH$_2$COPh |
| Me | SCH$_2$CH$_2$OPr-i | SO$_2$Me | CH$_2$COPh |
| Me | SO$_2$CH$_2$CH$_2$OMe | SO$_2$Me | CH$_2$COPh |
| Me | SO$_2$CH$_2$CH$_2$OPr-i | SO$_2$Me | CH$_2$COPh |
| Me | OCH$_2$CH$_2$OMe | Cl | H |
| Me | OCH$_2$CH$_2$OEt | Cl | H |
| Me | OCH$_2$CH$_2$OPr-i | Cl | H |
| Me | OCHMeCH$_2$OMe | Cl | H |
| Me | OCH$_2$COOMe | Cl | H |
| Me | OCH$_2$CH$_2$SMe | Cl | H |
| Me | OCH$_2$CH$_2$SO$_2$Me | Cl | H |
| Me | SCH$_2$CH$_2$OMe | Cl | H |
| Me | SO$_2$CH$_2$CH$_2$OMe | Cl | H |
| Me | OCH$_2$CH$_2$OMe | Cl | CH$_2$Ph |
| Me | OCH$_2$CH$_2$SMe | Cl | CH$_2$Ph |
| Me | OCH$_2$CH$_2$SOMe | Cl | CH$_2$Ph |
| Me | OCH$_2$CH$_2$SO$_2$Me | Cl | CH$_2$Ph |
| Me | SCH$_2$CH$_2$OMe | Cl | CH$_2$Ph |
| Me | SO$_2$CH$_2$CH$_2$OMe | Cl | CH$_2$Ph |
| Me | OCH$_2$CH$_2$OMe | Cl | CH$_2$COPh |
| Me | OCH$_2$CH$_2$SMe | Cl | CH$_2$COPh |
| Me | OCH$_2$CH$_2$SO$_2$Me | Cl | CH$_2$COPh |
| Me | SCH$_2$CH$_2$OMe | Cl | CH$_2$COPh |
| Me | SCH$_2$CH$_2$OEt | Cl | CH$_2$COPh |
| Me | SO$_2$CH$_2$CH$_2$OMe | Cl | CH$_2$COPh |
| Cl | Y1 | SO$_2$Me | H |
| Cl | Y2 | SO$_2$Me | H |
| Cl | Y3 | SO$_2$Me | H |
| Cl | Y4 | SO$_2$Me | H |
| Cl | Y5 | SO$_2$Me | H |
| Cl | Y6 | SO$_2$Me | H |
| Cl | Y7 | SO$_2$Me | H |
| Cl | OCH$_2$CH=CH$_2$ | SO$_2$Me | H |
| Cl | OCHMeCH=CH$_2$ | SO$_2$Me | H |
| Cl | OCMe$_2$CH=CH$_2$ | SO$_2$Me | H |
| Cl | OCH$_2$CMe=CH$_2$ | SO$_2$Me | H |
| Cl | OCH$_2$CH=CHMe | SO$_2$Me | H |
| Cl | OCH$_2$CH=CMe$_2$ | SO$_2$Me | H |
| Cl | OCH$_2$CH$_2$CH=CH$_2$ | SO$_2$Me | H |
| Cl | OCH$_2$C≡CH | SO$_2$Me | H |
| Cl | OCHMeC≡CH | SO$_2$Me | H |

TABLE 3-continued

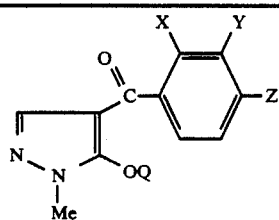

| X | Y | Z | Q |
|---|---|---|---|
| Cl | OCMe$_2$C≡CH | SO$_2$Me | H |
| Cl | OCH$_2$C≡CMe | SO$_2$Me | H |
| Cl | OCH$_2$CH$_2$F | SO$_2$Me | H |
| Cl | OCH$_2$CHF$_2$ | SO$_2$Me | H |
| Cl | OCH$_2$CF$_3$ | SO$_2$Me | H |
| Cl | OCH$_2$CH$_2$Cl | SO$_2$Me | H |
| Cl | OCH$_2$CCl$_3$ | SO$_2$Me | H |
| Cl | OCHMeCH$_2$Cl | SO$_2$Me | H |
| Cl | OCH$_2$CH$_2$CH$_2$Cl | SO$_2$Me | H |
| Cl | OCH$_2$CH$_2$Br | SO$_2$Me | H |
| Cl | Y8 | SO$_2$Me | H |
| Cl | OCH$_2$CCl=CH$_2$ | SO$_2$Me | H |
| Cl | OCH$_2$CCl=CHCl | SO$_2$Me | H |
| Cl | OCH$_2$CH$_2$NO$_2$ | SO$_2$Me | H |
| Cl | OPh | SO$_2$Me | H |
| Cl | OPh—Me-2 | SO$_2$Me | H |
| Cl | OPh—Cl-4 | SO$_2$Me | H |
| Cl | OPh—NO$_2$-4 | SO$_2$Me | H |
| Cl | OCH$_2$CH$_2$OMe | SO$_2$Me | H |
| Cl | OCH$_2$CH$_2$OEt | SO$_2$Me | H |
| Cl | OCH$_2$CH$_2$OPr-n | SO$_2$Me | H |
| Cl | OCH$_2$CH$_2$OPr-i | SO$_2$Me | H |
| Cl | OCH$_2$CH$_2$OBu-n | SO$_2$Me | H |
| Cl | OCH$_2$CH$_2$OBu-i | SO$_2$Me | H |
| Cl | OCH$_2$CH$_2$OBu-s | SO$_2$Me | H |
| Cl | OCH$_2$CH$_2$OBu-t | SO$_2$Me | H |
| Cl | OCH$_2$CH$_2$—Y4 | SO$_2$Me | H |
| Cl | OCHMeCH$_2$OMe | SO$_2$Me | H |
| Cl | OCH$_2$CHMeOMe | SO$_2$Me | H |
| Cl | OCH$_2$CH$_2$OPh | SO$_2$Me | H |
| Cl | OCH$_2$CH$_2$OCH$_2$CH$_2$OMe | SO$_2$Me | H |
| Cl | OCH$_2$CH$_2$OCH$_2$CH$_2$OPr-i | SO$_2$Me | H |
| Cl | OCH$_2$CH$_2$OCHMeCH$_2$OMe | SO$_2$Me | H |
| Cl | OCH$_2$CH$_2$OH | SO$_2$Me | H |
| Cl | OCH$_2$Ph | SO$_2$Me | H |
| Cl | OCHMePh | SO$_2$Me | H |
| Cl | OCH$_2$CH$_2$Ph | SO$_2$Me | H |
| Cl | OCH$_2$Ph-2-Cl | SO$_2$Me | H |
| Cl | OCH$_2$Ph-3-Me | SO$_2$Me | H |
| Cl | OCH$_2$Ph-4-OMe | SO$_2$Me | H |
| Cl | OCH$_2$Ph-4-NO$_2$ | SO$_2$Me | H |
| Cl | Y9 | SO$_2$Me | H |
| Cl | Y10 | SO$_2$Me | H |
| Cl | Y11 | SO$_2$Me | H |
| Cl | Y12 | SO$_2$Me | H |
| Cl | Y13 | SO$_2$Me | H |
| Cl | Y14 | SO$_2$Me | H |
| Cl | Y15 | SO$_2$Me | H |
| Cl | Y16 | SO$_2$Me | H |
| Cl | Y17 | SO$_2$Me | H |
| Cl | Y18 | SO$_2$Me | H |
| Cl | OCH$_2$CH$_2$NH$_2$ | SO$_2$Me | H |
| Cl | OCH$_2$CH$_2$NHMe | SO$_2$Me | H |
| Cl | OCH$_2$CH$_2$NHPr-i | SO$_2$Me | H |
| Cl | OCH$_2$CH$_2$NMe$_2$ | SO$_2$Me | H |
| Cl | OCH$_2$CH$_2$NEt$_2$ | SO$_2$Me | H |
| Cl | Y19 | SO$_2$Me | H |
| Cl | OCH$_2$COOMe | SO$_2$Me | H |
| Cl | OCH$_2$COOEt | SO$_2$Me | H |
| Cl | OCH$_2$COOPr-i | SO$_2$Me | H |
| Cl | OCH$_2$COOBu-i | SO$_2$Me | H |
| Cl | OCH$_2$COOBu-t | SO$_2$Me | H |
| Cl | OCH$_2$COO—Y4 | SO$_2$Me | H |
| Cl | OCHMeCOOMe | SO$_2$Me | H |
| Cl | OCHMeCOOEt | SO$_2$Me | H |
| Cl | OCHMeCOOPr-i | SO$_2$Me | H |
| Cl | OCH$_2$CH$_2$CN | SO$_2$Me | H |
| Cl | OCH$_2$SMe | SO$_2$Me | H |
| Cl | OCH$_2$CH$_2$SMe | SO$_2$Me | H |
| Cl | OCH$_2$CH$_2$S(O)Me | SO$_2$Me | H |

TABLE 3-continued

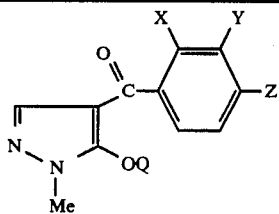

| X | Y | Z | Q |
|---|---|---|---|
| Cl | OCH₂CH₂SO₂Me | SO₂Me | H |
| Cl | OCH₂CH₂SPr-i | SO₂Me | H |
| Cl | OCH₂CH₂S(O)Pr-i | SO₂Me | H |
| Cl | OCH₂CH₂SO₂Pr-i | SO₂Me | H |
| Cl | OCOOMe | SO₂Me | H |
| Cl | OCOOPr-i | SO₂Me | H |
| Cl | OCONH₂ | SO₂Me | H |
| Cl | OCONHMe | SO₂Me | H |
| Cl | OCONMe₂ | SO₂Me | H |
| Cl | OP(O)(OMe)₂ | SO₂Me | H |
| Cl | Y20 | SO₂Me | H |
| Cl | SCH₂CH=CH₂ | SO₂Me | H |
| Cl | SCH₂CH=CMe₂ | SO₂Me | H |
| Cl | SCH₂C≡CH | SO₂Me | H |
| Cl | SCH₂CF₃ | SO₂Me | H |
| Cl | SCH₂CCl₃ | SO₂Me | H |
| Cl | Y21 | SO₂Me | H |
| Cl | SPh | SO₂Me | H |
| Cl | SCH₂CH₂OMe | SO₂Me | H |
| Cl | SCH₂CH₂OEt | SO₂Me | H |
| Cl | SCH₂CH₂OPr-i | SO₂Me | H |
| Cl | Y22 | SO₂Me | H |
| Cl | S(O)CH₂CH=CH₂ | SO₂Me | H |
| Cl | S(O)CH₂CH=CMe₂ | SO₂Me | H |
| Cl | S(O)CH₂C≡CH | SO₂Me | H |
| Cl | S(O)CH₂CH₂Cl | SO₂Me | H |
| Cl | Y23 | SO₂Me | H |
| Cl | SO₂CH₂CH=CH₂ | SO₂Me | H |
| Cl | SO₂CH₂CH=CMe₂ | SO₂Me | H |
| Cl | SO₂CH₂C≡CH | SO₂Me | H |
| Cl | SO₂CH₂CF₃ | SO₂Me | H |
| Cl | SO₂CH₂CH₂Cl | SO₂Me | H |
| Cl | Y24 | SO₂Me | H |
| Cl | Y25 | SO₂Me | H |
| Cl | SO₂Ph | SO₂Me | H |
| Cl | SO₂CH₂CH₂OMe | SO₂Me | H |
| Cl | SO₂CH₂CH₂OEt | SO₂Me | H |
| Cl | SO₂CH₂CH₂OPr-i | SO₂Me | H |
| Cl | OCH₂CH₂OMe | SO₂Me | CH₂Ph |
| Cl | OCH₂CH₂OEt | SO₂Me | CH₂Ph |
| Cl | OCH₂CH₂OPr-i | SO₂Me | CH₂Ph |
| Cl | OCHMeCH₂OMe | SO₂Me | CH₂Ph |
| Cl | OCH₂CH₂SMe | SO₂Me | CH₂Ph |
| Cl | OCH₂CH₂S(O)Me | SO₂Me | CH₂Ph |
| Cl | OCH₂CH₂SO₂Me | SO₂Me | CH₂Ph |
| Cl | OCH₂CH₂SPr-i | SO₂Me | CH₂Ph |
| Cl | OCH₂CH₂S(O)Pr-i | SO₂Me | CH₂Ph |
| Cl | OCH₂CH₂SO₂Pr-i | SO₂Me | CH₂Ph |
| Cl | SCH₂CH₂OMe | SO₂Me | CH₂Ph |
| Cl | SCH₂CH₂OPr-i | SO₂Me | CH₂Ph |
| Cl | SO₂CH₂CH₂OMe | SO₂Me | CH₂Ph |
| Cl | SO₂CH₂CH₂OPr-i | SO₂Me | CH₂Ph |
| Cl | OCH₂CH₂OMe | SO₂Me | CH₂COPh |
| Cl | OCH₂CH₂OPr-i | SO₂Me | CH₂COPh |
| Cl | OCH₂CH₂SMe | SO₂Me | CH₂COPh |
| Cl | OCH₂CH₂SOMe | SO₂Me | CH₂COPh |
| Cl | OCH₂CH₂SO₂Me | SO₂Me | CH₂COPh |
| Cl | OCH₂CH₂SPr-i | SO₂Me | CH₂COPh |
| Cl | OCH₂CH₂SO₂Pr-i | SO₂Me | CH₂COPh |
| Cl | SCH₂CH₂OMe | SO₂Me | CH₂COPh |
| Cl | SCH₂CH₂OPr-i | SO₂Me | CH₂COPh |
| Cl | SO₂CH₂CH₂OMe | SO₂Me | CH₂COPh |
| Cl | SO₂CH₂CH₂OPr-i | SO₂Me | CH₂COPh |
| Cl | OCH₂CH₂OMe | Cl | H |
| Cl | OCH₂CH₂OEt | Cl | H |
| Cl | OCH₂CH₂OPr-i | Cl | H |
| Cl | OCHMeCH₂OMe | Cl | H |
| Cl | OCH₂COOMe | Cl | H |
| Cl | OCH₂CH₂SMe | Cl | H |
| Cl | OCH₂CH₂SO₂Me | Cl | H |

TABLE 3-continued

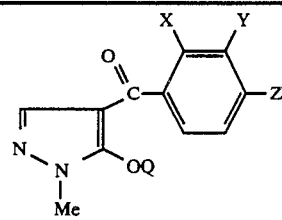

| X | Y | Z | Q |
|---|---|---|---|
| Cl | SCH₂CH₂OMe | Cl | H |
| Cl | SO₂CH₂CH₂OMe | Cl | H |
| Cl | OCH₂CH₂OMe | Cl | CH₂Ph |
| Cl | OCH₂CH₂SMe | Cl | CH₂Ph |
| Cl | OCH₂CH₂SOMe | Cl | CH₂Ph |
| Cl | OCH₂CH₂SO₂Me | Cl | CH₂Ph |
| Cl | SCH₂CH₂OMe | Cl | CH₂Ph |
| Cl | SO₂CH₂CH₂OMe | Cl | CH₂Ph |
| Cl | OCH₂CH₂OMe | Cl | CH₂COPh |
| Cl | OCH₂CH₂SMe | Cl | CH₂COPh |
| Cl | OCH₂CH₂SO₂Me | Cl | CH₂COPh |
| Cl | SCH₂CH₂OMe | Cl | CH₂COPh |
| Cl | SCH₂CH₂OEt | Cl | CH₂COPh |
| Cl | SO₂CH₂CH₂OMe | Cl | CH₂COPh |
| OMe | Y1 | SO₂Me | H |
| OMe | Y2 | SO₂Me | H |
| OMe | Y3 | SO₂Me | H |
| OMe | Y4 | SO₂Me | H |
| OMe | Y5 | SO₂Me | H |
| OMe | Y6 | SO₂Me | H |
| OMe | Y7 | SO₂Me | H |
| OMe | OCH₂CH=CH₂ | SO₂Me | H |
| OMe | OCHMeCH=CH₂ | SO₂Me | H |
| OMe | OCMe₂CH=CH₂ | SO₂Me | H |
| OMe | OCH₂CMe=CH₂ | SO₂Me | H |
| OMe | OCH₂CH=CHMe | SO₂Me | H |
| OMe | OCH₂CH=CMe₂ | SO₂Me | H |
| OMe | OCH₂CH₂CH=CH₂ | SO₂Me | H |
| OMe | OCH₂C≡CH | SO₂Me | H |
| OMe | OCHMeC≡CH | SO₂Me | H |
| OMe | OCMe₂C≡CH | SO₂Me | H |
| OMe | OCH₂C≡CMe | SO₂Me | H |
| OMe | OCH₂CH₂F | SO₂Me | H |
| OMe | OCH₂CHF₂ | SO₂Me | H |
| OMe | OCH₂CF₃ | SO₂Me | H |
| OMe | OCH₂CH₂Cl | SO₂Me | H |
| OMe | OCH₂CCl₃ | SO₂Me | H |
| OMe | OCHMeCH₂Cl | SO₂Me | H |
| OMe | OCH₂CH₂CH₂Cl | SO₂Me | H |
| OMe | OCH₂CH₂Br | SO₂Me | H |
| OMe | Y8 | SO₂Me | H |
| OMe | OCH₂CCl=CH₂ | SO₂Me | H |
| OMe | OCH₂CCl=CHCl | SO₂Me | H |
| OMe | OCH₂CH₂NO₂ | SO₂Me | H |
| OMe | OPh | SO₂Me | H |
| OMe | OPh—Me-2 | SO₂Me | H |
| OMe | OPh—Cl-4 | SO₂Me | H |
| OMe | OPh—NO₂-4 | SO₂Me | H |
| OMe | OCH₂CH₂OMe | SO₂Me | H |
| OMe | OCH₂CH₂OEt | SO₂Me | H |
| OMe | OCH₂CH₂OPr-n | SO₂Me | H |
| OMe | OCH₂CH₂OPr-i | SO₂Me | H |
| OMe | OCH₂CH₂OBu-n | SO₂Me | H |
| OMe | OCH₂CH₂OBu-i | SO₂Me | H |
| OMe | OCH₂CH₂OBu-s | SO₂Me | H |
| OMe | OCH₂CH₂OBu-t | SO₂Me | H |
| OMe | OCH₂CH₂-Y4 | SO₂Me | H |
| OMe | OCHMeCH₂OMe | SO₂Me | H |
| OMe | OCH₂CHMeOMe | SO₂Me | H |
| OMe | OCH₂CH₂OPh | SO₂Me | H |
| OMe | OCH₂CH₂OCH₂CH₂OMe | SO₂Me | H |
| OMe | OCH₂CH₂OCH₂CH₂OPr-i | SO₂Me | H |
| OMe | OCH₂CH₂OCHMeCH₂OMe | SO₂Me | H |
| OMe | OCH₂CH₂OH | SO₂Me | H |
| OMe | OCH₂Ph | SO₂Me | H |
| OMe | OCHMePh | SO₂Me | H |
| OMe | OCH₂CH₂Ph | SO₂Me | H |
| OMe | OCH₂Ph-2-Cl | SO₂Me | H |
| OMe | OCH₂Ph-3-Me | SO₂Me | H |
| OMe | OCH₂Ph-4-OMe | SO₂Me | H |

TABLE 3-continued

| X | Y | Z | Q |
|---|---|---|---|
| OMe | OCH$_2$Ph-4-NO$_2$ | SO$_2$Me | H |
| OMe | Y9 | SO$_2$Me | H |
| OMe | Y10 | SO$_2$Me | H |
| OMe | Y11 | SO$_2$Me | H |
| OMe | Y12 | SO$_2$Me | H |
| OMe | Y13 | SO$_2$Me | H |
| OMe | Y14 | SO$_2$Me | H |
| OMe | Y15 | SO$_2$Me | H |
| OMe | Y16 | SO$_2$Me | H |
| OMe | Y17 | SO$_2$Me | H |
| OMe | Y18 | SO$_2$Me | H |
| OMe | OCH$_2$CH$_2$NH$_2$ | SO$_2$Me | H |
| OMe | OCH$_2$CH$_2$NHMe | SO$_2$Me | H |
| OMe | OCH$_2$CH$_2$NHPr-i | SO$_2$Me | H |
| OMe | OCH$_2$CH$_2$NMe$_2$ | SO$_2$Me | H |
| OMe | OCH$_2$CH$_2$NEt$_2$ | SO$_2$Me | H |
| OMe | Y19 | SO$_2$Me | H |
| OMe | OCH$_2$COOMe | SO$_2$Me | H |
| OMe | OCH$_2$COOEt | SO$_2$Me | H |
| OMe | OCH$_2$COOPr-i | SO$_2$Me | H |
| OMe | OCH$_2$COOBu-i | SO$_2$Me | H |
| OMe | OCH$_2$COOBu-t | SO$_2$Me | H |
| OMe | OCH$_2$COO-Y4 | SO$_2$Me | H |
| OMe | OCHMeCOOMe | SO$_2$Me | H |
| OMe | OCHMeCOOEt | SO$_2$Me | H |
| OMe | OCHMeCOOPr-i | SO$_2$Me | H |
| OMe | OCH$_2$CH$_2$CN | SO$_2$Me | H |
| OMe | OCH$_2$SMe | SO$_2$Me | H |
| OMe | OCH$_2$CH$_2$SMe | SO$_2$Me | H |
| OMe | OCH$_2$CH$_2$S(O)Me | SO$_2$Me | H |
| OMe | OCH$_2$CH$_2$SO$_2$Me | SO$_2$Me | H |
| OMe | OCH$_2$CH$_2$SPr-i | SO$_2$Me | H |
| OMe | OCH$_2$CH$_2$S(O)Pr-i | SO$_2$Me | H |
| OMe | OCH$_2$CH$_2$SO$_2$Pr-i | SO$_2$Me | H |
| OMe | OCOOMe | SO$_2$Me | H |
| OMe | OCOOPr-i | SO$_2$Me | H |
| OMe | OCONH$_2$ | SO$_2$Me | H |
| OMe | OCONHMe | SO$_2$Me | H |
| OMe | OCONMe$_2$ | SO$_2$Me | H |
| OMe | OP(O)(OMe)$_2$ | SO$_2$Me | H |
| OMe | Y20 | SO$_2$Me | H |
| OMe | SCH$_2$CH=CH$_2$ | SO$_2$Me | H |
| OMe | SCH$_2$CH=CMe$_2$ | SO$_2$Me | H |
| OMe | SCH$_2$C≡CH | SO$_2$Me | H |
| OMe | SCH$_2$CF$_3$ | SO$_2$Me | H |
| OMe | SCH$_2$CCl$_3$ | SO$_2$Me | H |
| OMe | Y21 | SO$_2$Me | H |
| OMe | SPh | SO$_2$Me | H |
| OMe | SCH$_2$CH$_2$OMe | SO$_2$Me | H |
| OMe | SCH$_2$CH$_2$OEt | SO$_2$Me | H |
| OMe | SCH$_2$CH$_2$OPr-i | SO$_2$Me | H |
| OMe | Y22 | SO$_2$Me | H |
| OMe | S(O)CH$_2$CH=CH$_2$ | SO$_2$Me | H |
| OMe | S(O)CH$_2$CH=CMe$_2$ | SO$_2$Me | H |
| OMe | S(O)CH$_2$C≡CH | SO$_2$Me | H |
| OMe | S(O)CH$_2$CH$_2$Cl | SO$_2$Me | H |
| OMe | Y23 | SO$_2$Me | H |
| OMe | SO$_2$CH$_2$CH=CH$_2$ | SO$_2$Me | H |
| OMe | SO$_2$CH$_2$CH=CMe$_2$ | SO$_2$Me | H |
| OMe | SO$_2$CH$_2$C≡CH | SO$_2$Me | H |
| OMe | SO$_2$CH$_2$CF$_3$ | SO$_2$Me | H |
| OMe | SO$_2$CH$_2$CH$_2$Cl | SO$_2$Me | H |
| OMe | Y24 | SO$_2$Me | H |
| OMe | Y25 | SO$_2$Me | H |
| OMe | SO$_2$Ph | SO$_2$Me | H |
| OMe | SO$_2$CH$_2$CH$_2$OMe | SO$_2$Me | H |
| OMe | SO$_2$CH$_2$CH$_2$OEt | SO$_2$Me | H |
| OMe | SO$_2$CH$_2$CH$_2$OPr-i | SO$_2$Me | H |
| OMe | OCH$_2$CH$_2$OMe | SO$_2$Me | CH$_2$Ph |
| OMe | OCH$_2$CH$_2$OEt | SO$_2$Me | CH$_2$Ph |
| OMe | OCH$_2$CH$_2$OPr-i | SO$_2$Me | CH$_2$Ph |
| OMe | OCHMeCH$_2$OMe | SO$_2$Me | CH$_2$Ph |
| OMe | OCH$_2$CH$_2$SMe | SO$_2$Me | CH$_2$Ph |
| OMe | OCH$_2$CH$_2$S(O)Me | SO$_2$Me | CH$_2$Ph |
| OMe | OCH$_2$CH$_2$SO$_2$Me | SO$_2$Me | CH$_2$Ph |
| OMe | OCH$_2$CH$_2$SPr-i | SO$_2$Me | CH$_2$Ph |
| OMe | OCH$_2$CH$_2$S(O)Pr-i | SO$_2$Me | CH$_2$Ph |
| OMe | OCH$_2$CH$_2$SO$_2$Pr-i | SO$_2$Me | CH$_2$Ph |
| OMe | SCH$_2$CH$_2$OMe | SO$_2$Me | CH$_2$Ph |
| OMe | SCH$_2$CH$_2$OPr-i | SO$_2$Me | CH$_2$Ph |
| OMe | SO$_2$CH$_2$CH$_2$OMe | SO$_2$Me | CH$_2$Ph |
| OMe | SO$_2$CH$_2$CH$_2$OPr-i | SO$_2$Me | CH$_2$Ph |
| OMe | OCH$_2$CH$_2$OMe | SO$_2$Me | CH$_2$COPh |
| OMe | OCH$_2$CH$_2$OPr-i | SO$_2$Me | CH$_2$COPh |
| OMe | OCH$_2$CH$_2$SMe | SO$_2$Me | CH$_2$COPh |
| OMe | OCH$_2$CH$_2$SOMe | SO$_2$Me | CH$_2$COPh |
| OMe | OCH$_2$CH$_2$SO$_2$Me | SO$_2$Me | CH$_2$COPh |
| OMe | OCH$_2$CH$_2$SPr-i | SO$_2$Me | CH$_2$COPh |
| OMe | OCH$_2$CH$_2$SO$_2$Pr-i | SO$_2$Me | CH$_2$COPh |
| OMe | SCH$_2$CH$_2$OMe | SO$_2$Me | CH$_2$COPh |
| OMe | SCH$_2$CH$_2$OPr-i | SO$_2$Me | CH$_2$COPh |
| OMe | SO$_2$CH$_2$CH$_2$OMe | SO$_2$Me | CH$_2$COPh |
| OMe | SO$_2$CH$_2$CH$_2$OPr-i | SO$_2$Me | CH$_2$COPh |
| OMe | OCH$_2$CH$_2$OMe | Cl | H |
| OMe | OCH$_2$CH$_2$OEt | Cl | H |
| OMe | OCH$_2$CH$_2$OPr-i | Cl | H |
| OMe | OCHMeCH$_2$OMe | Cl | H |
| OMe | OCH$_2$COOMe | Cl | H |
| OMe | OCH$_2$CH$_2$SMe | Cl | H |
| OMe | OCH$_2$CH$_2$SO$_2$Me | Cl | H |
| OMe | SCH$_2$CH$_2$OMe | Cl | H |
| OMe | SO$_2$CH$_2$CH$_2$OMe | Cl | H |
| OMe | OCH$_2$CH$_2$OMe | Cl | CH$_2$Ph |
| OMe | OCH$_2$CH$_2$SMe | Cl | CH$_2$Ph |
| OMe | OCH$_2$CH$_2$SOMe | Cl | CH$_2$Ph |
| OMe | OCH$_2$CH$_2$SO$_2$Me | Cl | CH$_2$Ph |
| OMe | SCH$_2$CH$_2$OMe | Cl | CH$_2$Ph |
| OMe | SO$_2$CH$_2$CH$_2$OMe | Cl | CH$_2$Ph |
| OMe | OCH$_2$CH$_2$OMe | Cl | CH$_2$COPh |
| OMe | OCH$_2$CH$_2$SMe | Cl | CH$_2$COPh |
| OMe | OCH$_2$CH$_2$SO$_2$Me | Cl | CH$_2$COPh |
| OMe | SCH$_2$CH$_2$OMe | Cl | CH$_2$COPh |
| OMe | SCH$_2$CH$_2$OEt | Cl | CH$_2$COPh |
| OMe | SO$_2$CH$_2$CH$_2$OMe | Cl | CH$_2$COPh |
| CH$_2$OMe | Y1 | SO$_2$Me | H |
| CH$_2$OMe | Y2 | SO$_2$Me | H |
| CH$_2$OMe | Y3 | SO$_2$Me | H |
| CH$_2$OMe | Y4 | SO$_2$Me | H |
| CH$_2$OMe | Y5 | SO$_2$Me | H |
| CH$_2$OMe | Y6 | SO$_2$Me | H |
| CH$_2$OMe | Y7 | SO$_2$Me | H |
| CH$_2$OMe | OCH$_2$CH=CH$_2$ | SO$_2$Me | H |
| CH$_2$OMe | OCHMeCH=CH$_2$ | SO$_2$Me | H |
| CH$_2$OMe | OCMe$_2$CH=CH$_2$ | SO$_2$Me | H |
| CH$_2$OMe | OCH$_2$CMe=CH$_2$ | SO$_2$Me | H |
| CH$_2$OMe | OCH$_2$CH=CHMe | SO$_2$Me | H |
| CH$_2$OMe | OCH$_2$CH=CMe$_2$ | SO$_2$Me | H |
| CH$_2$OMe | OCH$_2$CH$_2$CH=CH$_2$ | SO$_2$Me | H |
| CH$_2$OMe | OCH$_2$C≡CH | SO$_2$Me | H |
| CH$_2$OMe | OCHMeC≡CH | SO$_2$Me | H |
| CH$_2$OMe | OCMe$_2$C≡CH | SO$_2$Me | H |
| CH$_2$OMe | OCH$_2$C≡CMe | SO$_2$Me | H |
| CH$_2$OMe | OCH$_2$CH$_2$F | SO$_2$Me | H |
| CH$_2$OMe | OCH$_2$CHF$_2$ | SO$_2$Me | H |
| CH$_2$OMe | OCH$_2$CF$_3$ | SO$_2$Me | H |
| CH$_2$OMe | OCH$_2$CH$_2$Cl | SO$_2$Me | H |
| CH$_2$OMe | OCH$_2$CCl$_3$ | SO$_2$Me | H |
| CH$_2$OMe | OCHMeCH$_2$Cl | SO$_2$Me | H |
| CH$_2$OMe | OCH$_2$CH$_2$CH$_2$Cl | SO$_2$Me | H |
| CH$_2$OMe | OCH$_2$CH$_2$Br | SO$_2$Me | H |

TABLE 3-continued

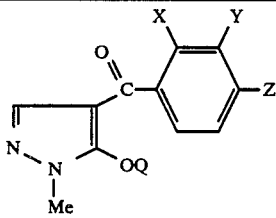

| X | Y | Z | Q |
|---|---|---|---|
| CH$_2$OMe | Y8 | SO$_2$Me | H |
| CH$_2$OMe | OCH$_2$CCl=CH$_2$ | SO$_2$Me | H |
| CH$_2$OMe | OCH$_2$CCl=CHCl | SO$_2$Me | H |
| CH$_2$OMe | OCH$_2$CH$_2$NO$_2$ | SO$_2$Me | H |
| CH$_2$OMe | OPh | SO$_2$Me | H |
| CH$_2$OMe | OPh—Me-2 | SO$_2$Me | H |
| CH$_2$OMe | OPh—Cl-4 | SO$_2$Me | H |
| CH$_2$OMe | OPh—NO$_2$-4 | SO$_2$Me | H |
| CH$_2$OMe | OCH$_2$CH$_2$OMe | SO$_2$Me | H |
| CH$_2$OMe | OCH$_2$CH$_2$OEt | SO$_2$Me | H |
| CH$_2$OMe | OCH$_2$CH$_2$OPr-n | SO$_2$Me | H |
| CH$_2$OMe | OCH$_2$CH$_2$OPr-i | SO$_2$Me | H |
| CH$_2$OMe | OCH$_2$CH$_2$OBu-n | SO$_2$Me | H |
| CH$_2$OMe | OCH$_2$CH$_2$OBu-i | SO$_2$Me | H |
| CH$_2$OMe | OCH$_2$CH$_2$OBu-s | SO$_2$Me | H |
| CH$_2$OMe | OCH$_2$CH$_2$OBu-t | SO$_2$Me | H |
| CH$_2$OMe | OCH$_2$CH$_2$-Y4 | SO$_2$Me | H |
| CH$_2$OMe | OCHMeCH$_2$OMe | SO$_2$Me | H |
| CH$_2$OMe | OCH$_2$CHMeOMe | SO$_2$Me | H |
| CH$_2$OMe | OCH$_2$CH$_2$OPh | SO$_2$Me | H |
| CH$_2$OMe | OCH$_2$CH$_2$OCH$_2$CH$_2$OMe | SO$_2$Me | H |
| CH$_2$OMe | OCH$_2$CH$_2$OCH$_2$CH$_2$OPr-i | SO$_2$Me | H |
| CH$_2$OMe | OCH$_2$CH$_2$OCHMeCH$_2$OMe | SO$_2$Me | H |
| CH$_2$OMe | OCH$_2$CH$_2$OH | SO$_2$Me | H |
| CH$_2$OMe | OCH$_2$Ph | SO$_2$Me | H |
| CH$_2$OMe | OCHMePh | SO$_2$Me | H |
| CH$_2$OMe | OCH$_2$CH$_2$Ph | SO$_2$Me | H |
| CH$_2$OMe | OCH$_2$Ph-2-Cl | SO$_2$Me | H |
| CH$_2$OMe | OCH$_2$Ph-3-Me | SO$_2$Me | H |
| CH$_2$OMe | OCH$_2$Ph-4-OMe | SO$_2$Me | H |
| CH$_2$OMe | OCH$_2$Ph-4-NO$_2$ | SO$_2$Me | H |
| CH$_2$OMe | Y9 | SO$_2$Me | H |
| CH$_2$OMe | Y10 | SO$_2$Me | H |
| CH$_2$OMe | Y11 | SO$_2$Me | H |
| CH$_2$OMe | Y12 | SO$_2$Me | H |
| CH$_2$OMe | Y13 | SO$_2$Me | H |
| CH$_2$OMe | Y14 | SO$_2$Me | H |
| CH$_2$OMe | Y15 | SO$_2$Me | H |
| CH$_2$OMe | Y16 | SO$_2$Me | H |
| CH$_2$OMe | Y17 | SO$_2$Me | H |
| CH$_2$OMe | Y18 | SO$_2$Me | H |
| CH$_2$OMe | OCH$_2$CH$_2$NH$_2$ | SO$_2$Me | H |
| CH$_2$OMe | OCH$_2$CH$_2$NHMe | SO$_2$Me | H |
| CH$_2$OMe | OCH$_2$CH$_2$NHPr-i | SO$_2$Me | H |
| CH$_2$OMe | OCH$_2$CH$_2$NMe$_2$ | SO$_2$Me | H |
| CH$_2$OMe | OCH$_2$CH$_2$NEt$_2$ | SO$_2$Me | H |
| CH$_2$OMe | Y19 | SO$_2$Me | H |
| CH$_2$OMe | OCH$_2$COOMe | SO$_2$Me | H |
| CH$_2$OMe | OCH$_2$COOEt | SO$_2$Me | H |
| CH$_2$OMe | OCH$_2$COOPr-i | SO$_2$Me | H |
| CH$_2$OMe | OCH$_2$COOBu-i | SO$_2$Me | H |
| CH$_2$OMe | OCH$_2$COOBu-t | SO$_2$Me | H |
| CH$_2$OMe | OCH$_2$COO-Y4 | SO$_2$Me | H |
| CH$_2$OMe | OCHMeCOOMe | SO$_2$Me | H |
| CH$_2$OMe | OCHMeCOOEt | SO$_2$Me | H |
| CH$_2$OMe | OCHMeCOOPr-i | SO$_2$Me | H |
| CH$_2$OMe | OCH$_2$CH$_2$CN | SO$_2$Me | H |
| CH$_2$OMe | OCH$_2$SMe | SO$_2$Me | H |
| CH$_2$OMe | OCH$_2$CH$_2$SMe | SO$_2$Me | H |
| CH$_2$OMe | OCH$_2$CH$_2$S(O)Me | SO$_2$Me | H |
| CH$_2$OMe | OCH$_2$CH$_2$SO$_2$Me | SO$_2$Me | H |
| CH$_2$OMe | OCH$_2$CH$_2$SPr-i | SO$_2$Me | H |
| CH$_2$OMe | OCH$_2$CH$_2$S(O)Pr-i | SO$_2$Me | H |
| CH$_2$OMe | OCH$_2$CH$_2$SO$_2$Pr-i | SO$_2$Me | H |
| CH$_2$OMe | OCOOMe | SO$_2$Me | H |
| CH$_2$OMe | OCOOPr-i | SO$_2$Me | H |
| CH$_2$OMe | OCONH$_2$ | SO$_2$Me | H |
| CH$_2$OMe | OCONHMe | SO$_2$Me | H |
| CH$_2$OMe | OCONMe$_2$ | SO$_2$Me | H |
| CH$_2$OMe | OP(O)(OMe)$_2$ | SO$_2$Me | H |

TABLE 3-continued

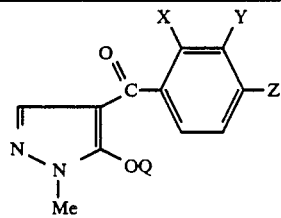

| X | Y | Z | Q |
|---|---|---|---|
| CH$_2$OMe | Y20 | SO$_2$Me | H |
| CH$_2$OMe | SCH$_2$CH=CH$_2$ | SO$_2$Me | H |
| CH$_2$OMe | SCH$_2$CH=CMe$_2$ | SO$_2$Me | H |
| CH$_2$OMe | SCH$_2$C≡CH | SO$_2$Me | H |
| CH$_2$OMe | SCH$_2$CF$_3$ | SO$_2$Me | H |
| CH$_2$OMe | SCH$_2$CCl$_3$ | SO$_2$Me | H |
| CH$_2$OMe | Y21 | SO$_2$Me | H |
| CH$_2$OMe | SPh | SO$_2$Me | H |
| CH$_2$OMe | SCH$_2$CH$_2$OMe | SO$_2$Me | H |
| CH$_2$OMe | SCH$_2$CH$_2$OEt | SO$_2$Me | H |
| CH$_2$OMe | SCH$_2$CH$_2$OPr-i | SO$_2$Me | H |
| CH$_2$OMe | Y22 | SO$_2$Me | H |
| CH$_2$OMe | S(O)CH$_2$CH=CH$_2$ | SO$_2$Me | H |
| CH$_2$OMe | S(O)CH$_2$CH=CMe$_2$ | SO$_2$Me | H |
| CH$_2$OMe | S(O)CH$_2$C≡CH | SO$_2$Me | H |
| CH$_2$OMe | S(O)CH$_2$CH$_2$Cl | SO$_2$Me | H |
| CH$_2$OMe | Y23 | SO$_2$Me | H |
| CH$_2$OMe | SO$_2$CH$_2$CH=CH$_2$ | SO$_2$Me | H |
| CH$_2$OMe | SO$_2$CH$_2$CH=CMe$_2$ | SO$_2$Me | H |
| CH$_2$OMe | SO$_2$CH$_2$C≡CH | SO$_2$Me | H |
| CH$_2$OMe | SO$_2$CH$_2$CF$_3$ | SO$_2$Me | H |
| CH$_2$OMe | SO$_2$CH$_2$CH$_2$Cl | SO$_2$Me | H |
| CH$_2$OMe | Y24 | SO$_2$Me | H |
| CH$_2$OMe | SO$_2$Ph | SO$_2$Me | H |
| CH$_2$OMe | SO$_2$CH$_2$CH$_2$OMe | SO$_2$Me | H |
| CH$_2$OMe | SO$_2$CH$_2$CH$_2$OEt | SO$_2$Me | H |
| CH$_2$OMe | SO$_2$CH$_2$CH$_2$OPr-i | SO$_2$Me | H |
| CH$_2$OMe | OCH$_2$CH$_2$OMe | SO$_2$Me | CH$_2$Ph |
| CH$_2$OMe | OCH$_2$CH$_2$OEt | SO$_2$Me | CH$_2$Ph |
| CH$_2$OMe | OCH$_2$CH$_2$OPr-i | SO$_2$Me | CH$_2$Ph |
| CH$_2$OMe | OCHMeCH$_2$OMe | SO$_2$Me | CH$_2$Ph |
| CH$_2$OMe | OCH$_2$CH$_2$SMe | SO$_2$Me | CH$_2$Ph |
| CH$_2$OMe | OCH$_2$CH$_2$S(O)Me | SO$_2$Me | CH$_2$Ph |
| CH$_2$OMe | OCH$_2$CH$_2$SO$_2$Me | SO$_2$Me | CH$_2$Ph |
| CH$_2$OMe | OCH$_2$CH$_2$SPr-i | SO$_2$Me | CH$_2$Ph |
| CH$_2$OMe | OCH$_2$CH$_2$S(O)Pr-i | SO$_2$Me | CH$_2$Ph |
| CH$_2$OMe | OCH$_2$CH$_2$SO$_2$Pr-i | SO$_2$Me | CH$_2$Ph |
| CH$_2$OMe | SCH$_2$CH$_2$OMe | SO$_2$Me | CH$_2$Ph |
| CH$_2$OMe | SCH$_2$CH$_2$OPr-i | SO$_2$Me | CH$_2$Ph |
| CH$_2$OMe | SO$_2$CH$_2$CH$_2$OMe | SO$_2$Me | CH$_2$Ph |
| CH$_2$OMe | SO$_2$CH$_2$CH$_2$OPr-i | SO$_2$Me | CH$_2$Ph |
| CH$_2$OMe | OCH$_2$CH$_2$OMe | SO$_2$Me | CH$_2$COPh |
| CH$_2$OMe | OCH$_2$CH$_2$OPr-i | SO$_2$Me | CH$_2$COPh |
| CH$_2$OMe | OCH$_2$CH$_2$SMe | SO$_2$Me | CH$_2$COPh |
| CH$_2$OMe | OCH$_2$CH$_2$SOMe | SO$_2$Me | CH$_2$COPh |
| CH$_2$OMe | OCH$_2$CH$_2$SO$_2$Me | SO$_2$Me | CH$_2$COPh |
| CH$_2$OMe | OCH$_2$CH$_2$SPr-i | SO$_2$Me | CH$_2$COPh |
| CH$_2$OMe | OCH$_2$CH$_2$SO$_2$Pr-i | SO$_2$Me | CH$_2$COPh |
| CH$_2$OMe | SCH$_2$CH$_2$OMe | SO$_2$Me | CH$_2$COPh |
| CH$_2$OMe | SCH$_2$CH$_2$OPr-i | SO$_2$Me | CH$_2$COPh |
| CH$_2$OMe | SO$_2$CH$_2$CH$_2$OMe | SO$_2$Me | CH$_2$COPh |
| CH$_2$OMe | SO$_2$CH$_2$CH$_2$OPr-i | SO$_2$Me | CH$_2$COPh |
| CH$_2$OMe | OCH$_2$CH$_2$OMe | Cl | H |
| CH$_2$OMe | OCH$_2$CH$_2$OEt | Cl | H |
| CH$_2$OMe | OCH$_2$CH$_2$OPr-i | Cl | H |
| CH$_2$OMe | OCHMeCH$_2$OMe | Cl | H |
| CH$_2$OMe | OCH$_2$COOMe | Cl | H |
| CH$_2$OMe | OCH$_2$CH$_2$SMe | Cl | H |
| CH$_2$OMe | OCH$_2$CH$_2$SO$_2$Me | Cl | H |
| CH$_2$OMe | SCH$_2$CH$_2$OMe | Cl | H |
| CH$_2$OMe | SO$_2$CH$_2$CH$_2$OMe | Cl | H |
| CH$_2$OMe | OCH$_2$CH$_2$OMe | Cl | CH$_2$Ph |
| CH$_2$OMe | OCH$_2$CH$_2$SMe | Cl | CH$_2$Ph |
| CH$_2$OMe | OCH$_2$CH$_2$SOMe | Cl | CH$_2$Ph |
| CH$_2$OMe | OCH$_2$CH$_2$SO$_2$Me | Cl | CH$_2$Ph |
| CH$_2$OMe | SCH$_2$CH$_2$OMe | Cl | CH$_2$Ph |
| CH$_2$OMe | SO$_2$CH$_2$CH$_2$OMe | Cl | CH$_2$Ph |
| CH$_2$OMe | OCH$_2$CH$_2$OMe | Cl | CH$_2$COPh |
| CH$_2$OMe | OCH$_2$CH$_2$SMe | Cl | CH$_2$COPh |
| CH$_2$OMe | OCH$_2$CH$_2$SO$_2$Me | Cl | CH$_2$COPh |

TABLE 3-continued

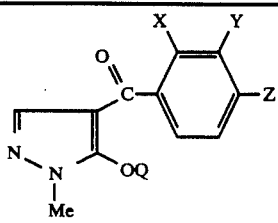

| X | Y | Z | Q |
|---|---|---|---|
| CH$_2$OMe | SCH$_2$CH$_2$OMe | Cl | CH$_2$COPh |
| CH$_2$OMe | SCH$_2$CH$_2$OEt | Cl | CH$_2$COPh |
| CH$_2$OMe | SO$_2$CH$_2$CH$_2$OMe | Cl | CH$_2$COPh |

TABLE 4

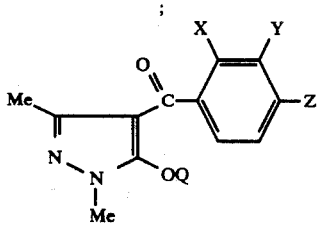

| X | Y | Z | Q |
|---|---|---|---|
| Me | Y1 | SO$_2$Me | H |
| Me | Y2 | SO$_2$Me | H |
| Me | Y3 | SO$_2$Me | H |
| Me | Y4 | SO$_2$Me | H |
| Me | Y5 | SO$_2$Me | H |
| Me | Y6 | SO$_2$Me | H |
| Me | Y7 | SO$_2$Me | H |
| Me | OCH$_2$CH=CH$_2$ | SO$_2$Me | H |
| Me | OCHMeCH=CH$_2$ | SO$_2$Me | H |
| Me | OCMe$_2$CH=CH$_2$ | SO$_2$Me | H |
| Me | OCH$_2$CMe=CH$_2$ | SO$_2$Me | H |
| Me | OCH$_2$CH=CHMe | SO$_2$Me | H |
| Me | OCH$_2$CH=CMe$_2$ | SO$_2$Me | H |
| Me | OCH$_2$CH$_2$CH=CH$_2$ | SO$_2$Me | H |
| Me | OCH$_2$C≡CH | SO$_2$Me | H |
| Me | OCHMeC≡CH | SO$_2$Me | H |
| Me | OCMe$_2$C≡CH | SO$_2$Me | H |
| Me | OCH$_2$C≡CMe | SO$_2$Me | H |
| Me | OCH$_2$CH$_2$F | SO$_2$Me | H |
| Me | OCH$_2$CHF$_2$ | SO$_2$Me | H |
| Me | OCH$_2$CF$_3$ | SO$_2$Me | H |
| Me | OCH$_2$CH$_2$Cl | SO$_2$Me | H |
| Me | OCH$_2$CCl$_3$ | SO$_2$Me | H |
| Me | OCHMeCH$_2$Cl | SO$_2$Me | H |
| Me | OCH$_2$CH$_2$CH$_2$Cl | SO$_2$Me | H |
| Me | OCH$_2$CH$_2$Br | SO$_2$Me | H |
| Me | Y8 | SO$_2$Me | H |
| Me | OCH$_2$CCl=CH$_2$ | SO$_2$Me | H |
| Me | OCH$_2$CCl=CHCl | SO$_2$Me | H |
| Me | OCH$_2$CH$_2$NO$_2$ | SO$_2$Me | H |
| Me | OPh | SO$_2$Me | H |
| Me | OPh—Me-2 | SO$_2$Me | H |
| Me | OPh—Cl-4 | SO$_2$Me | H |
| Me | OPh—NO$_2$-4 | SO$_2$Me | H |
| Me | OCH$_2$CH$_2$OMe | SO$_2$Me | H |
| Me | OCH$_2$CH$_2$OEt | SO$_2$Me | H |
| Me | OCH$_2$CH$_2$OPr-n | SO$_2$Me | H |
| Me | OCH$_2$CH$_2$OPr-i | SO$_2$Me | H |
| Me | OCH$_2$CH$_2$OBu-n | SO$_2$Me | H |
| Me | OCH$_2$CH$_2$OBu-i | SO$_2$Me | H |
| Me | OCH$_2$CH$_2$OBu-s | SO$_2$Me | H |
| Me | OCH$_2$CH$_2$OBu-t | SO$_2$Me | H |
| Me | OCH$_2$CH$_2$—Y4 | SO$_2$Me | H |
| Me | OCHMeCH$_2$OMe | SO$_2$Me | H |
| Me | OCH$_2$CHMeOMe | SO$_2$Me | H |
| Me | OCH$_2$CH$_2$OPh | SO$_2$Me | H |
| Me | OCH$_2$CH$_2$OCH$_2$CH$_2$OMe | SO$_2$Me | H |
| Me | OCH$_2$CH$_2$OCH$_2$CH$_2$OPr-i | SO$_2$Me | H |
| Me | OCH$_2$CH$_2$OCHMeCH$_2$OMe | SO$_2$Me | H |

TABLE 4-continued

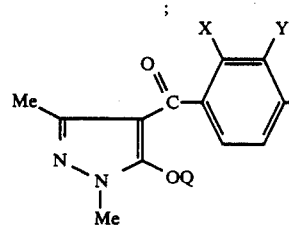

| X | Y | Z | Q |
|---|---|---|---|
| Me | OCH$_2$CH$_2$OH | SO$_2$Me | H |
| Me | OCH$_2$Ph | SO$_2$Me | H |
| Me | OCHMePh | SO$_2$Me | H |
| Me | OCH$_2$CH$_2$Ph | SO$_2$Me | H |
| Me | OCH$_2$Ph-2-Cl | SO$_2$Me | H |
| Me | OCH$_2$Ph-3-Me | SO$_2$Me | H |
| Me | OCH$_2$Ph-4-OMe | SO$_2$Me | H |
| Me | OCH$_2$Ph-4-NO$_2$ | SO$_2$Me | H |
| Me | Y9 | SO$_2$Me | H |
| Me | Y10 | SO$_2$Me | H |
| Me | Y11 | SO$_2$Me | H |
| Me | Y12 | SO$_2$Me | H |
| Me | Y13 | SO$_2$Me | H |
| Me | Y14 | SO$_2$Me | H |
| Me | Y15 | SO$_2$Me | H |
| Me | Y16 | SO$_2$Me | H |
| Me | Y17 | SO$_2$Me | H |
| Me | Y18 | SO$_2$Me | H |
| Me | OCH$_2$CH$_2$NH$_2$ | SO$_2$Me | H |
| Me | OCH$_2$CH$_2$NHMe | SO$_2$Me | H |
| Me | OCH$_2$CH$_2$NHPr-i | SO$_2$Me | H |
| Me | OCH$_2$CH$_2$NMe$_2$ | SO$_2$Me | H |
| Me | OCH$_2$CH$_2$NEt$_2$ | SO$_2$Me | H |
| Me | Y19 | SO$_2$Me | H |
| Me | OCH$_2$COOMe | SO$_2$Me | H |
| Me | OCH$_2$COOEt | SO$_2$Me | H |
| Me | OCH$_2$COOPr-i | SO$_2$Me | H |
| Me | OCH$_2$COOBu-i | SO$_2$Me | H |
| Me | OCH$_2$COOBu-t | SO$_2$Me | H |
| Me | OCH$_2$COO—Y4 | SO$_2$Me | H |
| Me | OCHMeCOOMe | SO$_2$Me | H |
| Me | OCHMeCOOEt | SO$_2$Me | H |
| Me | OCHMeCOOPr-i | SO$_2$Me | H |
| Me | OCH$_2$CH$_2$CN | SO$_2$Me | H |
| Me | OCH$_2$SMe | SO$_2$Me | H |
| Me | OCH$_2$CH$_2$SMe | SO$_2$Me | H |
| Me | OCH$_2$CH$_2$S(O)Me | SO$_2$Me | H |
| Me | OCH$_2$CH$_2$SO$_2$Me | SO$_2$Me | H |
| Me | OCH$_2$CH$_2$SPr-i | SO$_2$Me | H |
| Me | OCH$_2$CH$_2$S(O)Pr-i | SO$_2$Me | H |
| Me | OCH$_2$CH$_2$SO$_2$Pr-i | SO$_2$Me | H |
| Me | OCOOMe | SO$_2$Me | H |
| Me | OCOOPr-i | SO$_2$Me | H |
| Me | OCONH$_2$ | SO$_2$Me | H |
| Me | OCONHMe | SO$_2$Me | H |
| Me | OCONMe$_2$ | SO$_2$Me | H |
| Me | OP(O)(OMe)$_2$ | SO$_2$Me | H |
| Me | Y20 | SO$_2$Me | H |
| Me | SCH$_2$CH=CH$_2$ | SO$_2$Me | H |
| Me | SCH$_2$CH=CMe$_2$ | SO$_2$Me | H |
| Me | SCH$_2$C≡CH | SO$_2$Me | H |
| Me | SCH$_2$CF$_3$ | SO$_2$Me | H |
| Me | SCH$_2$CCl$_3$ | SO$_2$Me | H |
| Me | Y21 | SO$_2$Me | H |
| Me | SPh | SO$_2$Me | H |
| Me | SCH$_2$CH$_2$OMe | SO$_2$Me | H |
| Me | SCH$_2$CH$_2$OEt | SO$_2$Me | H |
| Me | SCH$_2$CH$_2$OPr-i | SO$_2$Me | H |
| Me | Y22 | SO$_2$Me | H |
| Me | S(O)CH$_2$CH=CH$_2$ | SO$_2$Me | H |
| Me | S(O)CH$_2$CH=CMe$_2$ | SO$_2$Me | H |
| Me | S(O)CH$_2$C≡CH | SO$_2$Me | H |
| Me | S(O)CH$_2$CH$_2$Cl | SO$_2$Me | H |
| Me | Y23 | SO$_2$Me | H |
| Me | SO$_2$CH$_2$CH=CH$_2$ | SO$_2$Me | H |
| Me | SO$_2$CH$_2$CH=CMe$_2$ | SO$_2$Me | H |
| Me | SO$_2$CH$_2$C≡CH | SO$_2$Me | H |
| Me | SO$_2$CH$_2$CF$_3$ | SO$_2$Me | H |
| Me | SO$_2$CH$_2$CH$_2$Cl | SO$_2$Me | H |

TABLE 4-continued

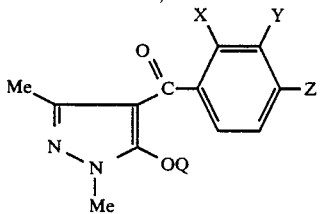

| X | Y | Z | Q |
|---|---|---|---|
| Me | Y24 | SO$_2$Me | H |
| Me | Y25 | SO$_2$Me | H |
| Me | SO$_2$Ph | SO$_2$Me | H |
| Me | SO$_2$CH$_2$CH$_2$OMe | SO$_2$Me | H |
| Me | SO$_2$CH$_2$CH$_2$OEt | SO$_2$Me | H |
| Me | SO$_2$CH$_2$CH$_2$OPr-i | SO$_2$Me | H |
| Me | OCH$_2$CH$_2$OMe | SO$_2$Me | CH$_2$Ph |
| Me | OCH$_2$CH$_2$OEt | SO$_2$Me | CH$_2$Ph |
| Me | OCH$_2$CH$_2$OPr-i | SO$_2$Me | CH$_2$Ph |
| Me | OCHMeCH$_2$OMe | SO$_2$Me | CH$_2$Ph |
| Me | OCH$_2$CH$_2$SMe | SO$_2$Me | CH$_2$Ph |
| Me | OCH$_2$CH$_2$S(O)Me | SO$_2$Me | CH$_2$Ph |
| Me | OCH$_2$CH$_2$SO$_2$Me | SO$_2$Me | CH$_2$Ph |
| Me | OCH$_2$CH$_2$SPr-i | SO$_2$Me | CH$_2$Ph |
| Me | OCH$_2$CH$_2$S(O)Pr-i | SO$_2$Me | CH$_2$Ph |
| Me | OCH$_2$CH$_2$SO$_2$Pr-i | SO$_2$Me | CH$_2$Ph |
| Me | SCH$_2$CH$_2$OMe | SO$_2$Me | CH$_2$Ph |
| Me | SCH$_2$CH$_2$OPr-i | SO$_2$Me | CH$_2$Ph |
| Me | SO$_2$CH$_2$CH$_2$OMe | SO$_2$Me | CH$_2$Ph |
| Me | SO$_2$CH$_2$CH$_2$OPr-i | SO$_2$Me | CH$_2$Ph |
| Me | OCH$_2$CH$_2$OMe | SO$_2$Me | CH$_2$COPh |
| Me | OCH$_2$CH$_2$OPr-i | SO$_2$Me | CH$_2$COPh |
| Me | OCH$_2$CH$_2$SMe | SO$_2$Me | CH$_2$COPh |
| Me | OCH$_2$CH$_2$SOMe | SO$_2$Me | CH$_2$COPh |
| Me | OCH$_2$CH$_2$SO$_2$Me | SO$_2$Me | CH$_2$COPh |
| Me | OCH$_2$CH$_2$SPr-i | SO$_2$Me | CH$_2$COPh |
| Me | OCH$_2$CH$_2$SO$_2$Pr-i | SO$_2$Me | CH$_2$COPh |
| Me | SCH$_2$CH$_2$OMe | SO$_2$Me | CH$_2$COPh |
| Me | SCH$_2$CH$_2$OPr-i | SO$_2$Me | CH$_2$COPh |
| Me | SO$_2$CH$_2$CH$_2$OMe | SO$_2$Me | CH$_2$COPh |
| Me | SO$_2$CH$_2$CH$_2$OPr-i | SO$_2$Me | CH$_2$COPh |
| Me | OCH$_2$CH$_2$OMe | Cl | H |
| Me | OCH$_2$CH$_2$OEt | Cl | H |
| Me | OCH$_2$CH$_2$OPr-i | Cl | H |
| Me | OCHMeCH$_2$OMe | Cl | H |
| Me | OCH$_2$COOMe | Cl | H |
| Me | OCH$_2$CH$_2$SMe | Cl | H |
| Me | OCH$_2$CH$_2$SO$_2$Me | Cl | H |
| Me | SCH$_2$CH$_2$OMe | Cl | H |
| Me | SO$_2$CH$_2$CH$_2$OMe | Cl | H |
| Me | OCH$_2$CH$_2$OMe | Cl | CH$_2$Ph |
| Me | OCH$_2$CH$_2$SMe | Cl | CH$_2$Ph |
| Me | OCH$_2$CH$_2$SOMe | Cl | CH$_2$Ph |
| Me | OCH$_2$CH$_2$SO$_2$Me | Cl | CH$_2$Ph |
| Me | SCH$_2$CH$_2$OMe | Cl | CH$_2$Ph |
| Me | SO$_2$CH$_2$CH$_2$OMe | Cl | CH$_2$Ph |
| Me | OCH$_2$CH$_2$OMe | Cl | CH$_2$COPh |
| Me | OCH$_2$CH$_2$SMe | Cl | CH$_2$COPh |
| Me | OCH$_2$CH$_2$SO$_2$Me | Cl | CH$_2$COPh |
| Me | SCH$_2$CH$_2$OMe | Cl | CH$_2$COPh |
| Me | SCH$_2$CH$_2$OEt | Cl | CH$_2$COPh |
| Me | SO$_2$CH$_2$CH$_2$OMe | Cl | CH$_2$COPh |
| Cl | Y1 | SO$_2$Me | H |
| Cl | Y2 | SO$_2$Me | H |
| Cl | Y3 | SO$_2$Me | H |
| Cl | Y4 | SO$_2$Me | H |
| Cl | Y5 | SO$_2$Me | H |
| Cl | Y6 | SO$_2$Me | H |
| Cl | Y7 | SO$_2$Me | H |
| Cl | OCH$_2$CH=CH$_2$ | SO$_2$Me | H |
| Cl | OCHMeCH=CH$_2$ | SO$_2$Me | H |
| Cl | OCMe$_2$CH=CH$_2$ | SO$_2$Me | H |
| Cl | OCH$_2$CMe=CH$_2$ | SO$_2$Me | H |
| Cl | OCH$_2$CH=CHMe | SO$_2$Me | H |
| Cl | OCH$_2$CH=CMe$_2$ | SO$_2$Me | H |
| Cl | OCH$_2$CH$_2$CH=CH$_2$ | SO$_2$Me | H |
| Cl | OCH$_2$C≡CH | SO$_2$Me | H |
| Cl | OCHMeC≡CH | SO$_2$Me | H |
| Cl | OCMe$_2$C≡CH | SO$_2$Me | H |

TABLE 4-continued

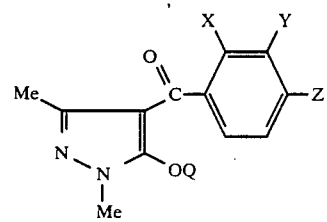

| X | Y | Z | Q |
|---|---|---|---|
| Cl | OCH$_2$C≡CMe | SO$_2$Me | H |
| Cl | OCH$_2$CH$_2$F | SO$_2$Me | H |
| Cl | OCH$_2$CHF$_2$ | SO$_2$Me | H |
| Cl | OCH$_2$CF$_3$ | SO$_2$Me | H |
| Cl | OCH$_2$CH$_2$Cl | SO$_2$Me | H |
| Cl | OCH$_2$CCl$_3$ | SO$_2$Me | H |
| Cl | OCHMeCH$_2$Cl | SO$_2$Me | H |
| Cl | OCH$_2$CH$_2$CH$_2$Cl | SO$_2$Me | H |
| Cl | OCH$_2$CH$_2$Br | SO$_2$Me | H |
| Cl | Y8 | SO$_2$Me | H |
| Cl | OCH$_2$CCl=CH$_2$ | SO$_2$Me | H |
| Cl | OCH$_2$CCl=CHCl | SO$_2$Me | H |
| Cl | OCH$_2$CH$_2$NO$_2$ | SO$_2$Me | H |
| Cl | OPh | SO$_2$Me | H |
| Cl | OPh—Me-2 | SO$_2$Me | H |
| Cl | OPh—Cl-4 | SO$_2$Me | H |
| Cl | OPh—NO$_2$-4 | SO$_2$Me | H |
| Cl | OCH$_2$CH$_2$OMe | SO$_2$Me | H |
| Cl | OCH$_2$CH$_2$OEt | SO$_2$Me | H |
| Cl | OCH$_2$CH$_2$OPr-n | SO$_2$Me | H |
| Cl | OCH$_2$CH$_2$OPr-i | SO$_2$Me | H |
| Cl | OCH$_2$CH$_2$OBu-n | SO$_2$Me | H |
| Cl | OCH$_2$CH$_2$OBu-i | SO$_2$Me | H |
| Cl | OCH$_2$CH$_2$OBu-s | SO$_2$Me | H |
| Cl | OCH$_2$CH$_2$OBu-t | SO$_2$Me | H |
| Cl | OCH$_2$CH$_2$—Y4 | SO$_2$Me | H |
| Cl | OCHMeCH$_2$OMe | SO$_2$Me | H |
| Cl | OCH$_2$CHMeOMe | SO$_2$Me | H |
| Cl | OCH$_2$CH$_2$OPh | SO$_2$Me | H |
| Cl | OCH$_2$CH$_2$OCH$_2$CH$_2$OMe | SO$_2$Me | H |
| Cl | OCH$_2$CH$_2$OCH$_2$CH$_2$OPr-i | SO$_2$Me | H |
| Cl | OCH$_2$CH$_2$OCHMeCH$_2$OMe | SO$_2$Me | H |
| Cl | OCH$_2$CH$_2$OH | SO$_2$Me | H |
| Cl | OCH$_2$Ph | SO$_2$Me | H |
| Cl | OCHMePh | SO$_2$Me | H |
| Cl | OCH$_2$CH$_2$Ph | SO$_2$Me | H |
| Cl | OCH$_2$Ph-2-Cl | SO$_2$Me | H |
| Cl | OCH$_2$Ph-3-Me | SO$_2$Me | H |
| Cl | OCH$_2$Ph-4-OMe | SO$_2$Me | H |
| Cl | OCH$_2$Ph-4-NO$_2$ | SO$_2$Me | H |
| Cl | Y9 | SO$_2$Me | H |
| Cl | Y10 | SO$_2$Me | H |
| Cl | Y11 | SO$_2$Me | H |
| Cl | Y12 | SO$_2$Me | H |
| Cl | Y13 | SO$_2$Me | H |
| Cl | Y14 | SO$_2$Me | H |
| Cl | Y15 | SO$_2$Me | H |
| Cl | Y16 | SO$_2$Me | H |
| Cl | Y17 | SO$_2$Me | H |
| Cl | Y18 | SO$_2$Me | H |
| Cl | OCH$_2$CH$_2$NH$_2$ | SO$_2$Me | H |
| Cl | OCH$_2$CH$_2$NHMe | SO$_2$Me | H |
| Cl | OCH$_2$CH$_2$NHPr-i | SO$_2$Me | H |
| Cl | OCH$_2$CH$_2$NMe$_2$ | SO$_2$Me | H |
| Cl | OCH$_2$CH$_2$NEt$_2$ | SO$_2$Me | H |
| Cl | Y19 | SO$_2$Me | H |
| Cl | OCH$_2$COOMe | SO$_2$Me | H |
| Cl | OCH$_2$COOEt | SO$_2$Me | H |
| Cl | OCH$_2$COOPr-i | SO$_2$Me | H |
| Cl | OCH$_2$COOBu-i | SO$_2$Me | H |
| Cl | OCH$_2$COOBu-t | SO$_2$Me | H |
| Cl | OCH$_2$COO—Y4 | SO$_2$Me | H |
| Cl | OCHMeCOOMe | SO$_2$Me | H |
| Cl | OCHMeCOOEt | SO$_2$Me | H |
| Cl | OCHMeCOOPr-i | SO$_2$Me | H |
| Cl | OCH$_2$CH$_2$CN | SO$_2$Me | H |
| Cl | OCH$_2$SMe | SO$_2$Me | H |
| Cl | OCH$_2$CH$_2$SMe | SO$_2$Me | H |
| Cl | OCH$_2$CH$_2$S(O)Me | SO$_2$Me | H |

TABLE 4-continued

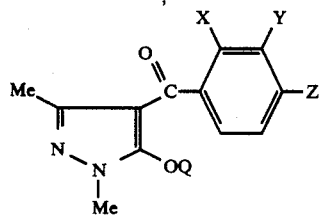

| X | Y | Z | Q |
|---|---|---|---|
| Cl | OCH$_2$CH$_2$SO$_2$Me | SO$_2$Me | H |
| Cl | OCH$_2$CH$_2$SPr-i | SO$_2$Me | H |
| Cl | OCH$_2$CH$_2$S(O)Pr-i | SO$_2$Me | H |
| Cl | OCH$_2$CH$_2$SO$_2$Pr-i | SO$_2$Me | H |
| Cl | OCOOMe | SO$_2$Me | H |
| Cl | OCOOPr-i | SO$_2$Me | H |
| Cl | OCONH$_2$ | SO$_2$Me | H |
| Cl | OCONHMe | SO$_2$Me | H |
| Cl | OCONMe$_2$ | SO$_2$Me | H |
| Cl | OP(O)(OMe)$_2$ | SO$_2$Me | H |
| Cl | Y20 | SO$_2$Me | H |
| Cl | SCH$_2$CH=CH$_2$ | SO$_2$Me | H |
| Cl | SCH$_2$CH=CMe$_2$ | SO$_2$Me | H |
| Cl | SCH$_2$C≡CH | SO$_2$Me | H |
| Cl | SCH$_2$CF$_3$ | SO$_2$Me | H |
| Cl | SCH$_2$CCl$_3$ | SO$_2$Me | H |
| Cl | Y21 | SO$_2$Me | H |
| Cl | SPh | SO$_2$Me | H |
| Cl | SCH$_2$CH$_2$OMe | SO$_2$Me | H |
| Cl | SCH$_2$CH$_2$OEt | SO$_2$Me | H |
| Cl | SCH$_2$CH$_2$OPr-i | SO$_2$Me | H |
| Cl | Y22 | SO$_2$Me | H |
| Cl | S(O)CH$_2$CH=CH$_2$ | SO$_2$Me | H |
| Cl | S(O)CH$_2$CH=CMe$_2$ | SO$_2$Me | H |
| Cl | S(O)CH$_2$C≡CH | SO$_2$Me | H |
| Cl | S(O)CH$_2$CH$_2$Cl | SO$_2$Me | H |
| Cl | Y23 | SO$_2$Me | H |
| Cl | SO$_2$CH$_2$CH=CH$_2$ | SO$_2$Me | H |
| Cl | SO$_2$CH$_2$CH=CMe$_2$ | SO$_2$Me | H |
| Cl | SO$_2$CH$_2$C≡CH | SO$_2$Me | H |
| Cl | SO$_2$CH$_2$CF$_3$ | SO$_2$Me | H |
| Cl | SO$_2$CH$_2$CH$_2$Cl | SO$_2$Me | H |
| Cl | Y24 | SO$_2$Me | H |
| Cl | Y25 | SO$_2$Me | H |
| Cl | SO$_2$Ph | SO$_2$Me | H |
| Cl | SO$_2$CH$_2$CH$_2$OMe | SO$_2$Me | H |
| Cl | SO$_2$CH$_2$CH$_2$OEt | SO$_2$Me | H |
| Cl | SO$_2$CH$_2$CH$_2$OPr-i | SO$_2$Me | H |
| Cl | OCH$_2$CH$_2$OMe | SO$_2$Me | CH$_2$Ph |
| Cl | OCH$_2$CH$_2$OEt | SO$_2$Me | CH$_2$Ph |
| Cl | OCH$_2$CH$_2$OPr-i | SO$_2$Me | CH$_2$Ph |
| Cl | OCHMeCH$_2$OMe | SO$_2$Me | CH$_2$Ph |
| Cl | OCH$_2$CH$_2$SMe | SO$_2$Me | CH$_2$Ph |
| Cl | OCH$_2$CH$_2$S(O)Me | SO$_2$Me | CH$_2$Ph |
| Cl | OCH$_2$CH$_2$SO$_2$Me | SO$_2$Me | CH$_2$Ph |
| Cl | OCH$_2$CH$_2$SPr-i | SO$_2$Me | CH$_2$Ph |
| Cl | OCH$_2$CH$_2$S(O)Pr-i | SO$_2$Me | CH$_2$Ph |
| Cl | OCH$_2$CH$_2$SO$_2$Pr-i | SO$_2$Me | CH$_2$Ph |
| Cl | SCH$_2$CH$_2$OMe | SO$_2$Me | CH$_2$Ph |
| Cl | SCH$_2$CH$_2$OPr-i | SO$_2$Me | CH$_2$Ph |
| Cl | SO$_2$CH$_2$CH$_2$OMe | SO$_2$Me | CH$_2$Ph |
| Cl | SO$_2$CH$_2$CH$_2$OPr-i | SO$_2$Me | CH$_2$Ph |
| Cl | OCH$_2$CH$_2$OMe | SO$_2$Me | CH$_2$COPh |
| Cl | OCH$_2$CH$_2$OPr-i | SO$_2$Me | CH$_2$COPh |
| Cl | OCH$_2$CH$_2$SMe | SO$_2$Me | CH$_2$COPh |
| Cl | OCH$_2$CH$_2$SOMe | SO$_2$Me | CH$_2$COPh |
| Cl | OCH$_2$CH$_2$SO$_2$Me | SO$_2$Me | CH$_2$COPh |
| Cl | OCH$_2$CH$_2$SPr-i | SO$_2$Me | CH$_2$COPh |
| Cl | OCH$_2$CH$_2$SO$_2$Pr-i | SO$_2$Me | CH$_2$COPh |
| Cl | SCH$_2$CH$_2$OMe | SO$_2$Me | CH$_2$COPh |
| Cl | SCH$_2$CH$_2$OPr-i | SO$_2$Me | CH$_2$COPh |
| Cl | SO$_2$CH$_2$CH$_2$OMe | SO$_2$Me | CH$_2$COPh |
| Cl | SO$_2$CH$_2$CH$_2$OPr-i | SO$_2$Me | CH$_2$COPh |
| Cl | OCH$_2$CH$_2$OMe | Cl | H |
| Cl | OCH$_2$CH$_2$OEt | Cl | H |
| Cl | OCH$_2$CH$_2$OPr-i | Cl | H |
| Cl | OCHMeCH$_2$OMe | Cl | H |
| Cl | OCH$_2$COOMe | Cl | H |
| Cl | OCH$_2$CH$_2$SMe | Cl | H |

TABLE 4-continued

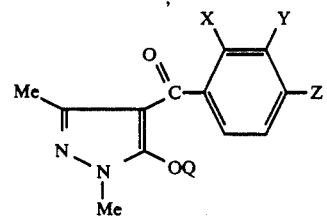

| X | Y | Z | Q |
|---|---|---|---|
| Cl | OCH$_2$CH$_2$SO$_2$Me | Cl | H |
| Cl | SCH$_2$CH$_2$OMe | Cl | H |
| Cl | SO$_2$CH$_2$CH$_2$OMe | Cl | H |
| Cl | OCH$_2$CH$_2$OMe | Cl | CH$_2$Ph |
| Cl | OCH$_2$CH$_2$SMe | Cl | CH$_2$Ph |
| Cl | OCH$_2$CH$_2$SOMe | Cl | CH$_2$Ph |
| Cl | OCH$_2$CH$_2$SO$_2$Me | Cl | CH$_2$Ph |
| Cl | SCH$_2$CH$_2$OMe | Cl | CH$_2$Ph |
| Cl | SO$_2$CH$_2$CH$_2$OMe | Cl | CH$_2$Ph |
| Cl | OCH$_2$CH$_2$OMe | Cl | CH$_2$COPh |
| Cl | OCH$_2$CH$_2$SMe | Cl | CH$_2$COPh |
| Cl | OCH$_2$CH$_2$SO$_2$Me | Cl | CH$_2$Ph |
| Cl | SCH$_2$CH$_2$OMe | Cl | CH$_2$COPh |
| Cl | SCH$_2$CH$_2$OEt | Cl | CH$_2$COPh |
| Cl | SO$_2$CH$_2$CH$_2$OMe | Cl | CH$_2$COPh |
| OMe | Y1 | SO$_2$Me | H |
| OMe | Y2 | SO$_2$Me | H |
| OMe | Y3 | SO$_2$Me | H |
| OMe | Y4 | SO$_2$Me | H |
| OMe | Y5 | SO$_2$Me | H |
| OMe | Y6 | SO$_2$Me | H |
| OMe | Y7 | SO$_2$Me | H |
| OMe | OCH$_2$CH=CH$_2$ | SO$_2$Me | H |
| OMe | OCHMeCH=CH$_2$ | SO$_2$Me | H |
| OMe | OCMe$_2$CH=CH$_2$ | SO$_2$Me | H |
| OMe | OCH$_2$CMe=CH$_2$ | SO$_2$Me | H |
| OMe | OCH$_2$CH=CHMe | SO$_2$Me | H |
| OMe | OCH$_2$CH=CMe$_2$ | SO$_2$Me | H |
| OMe | OCH$_2$CH$_2$CH=CH$_2$ | SO$_2$Me | H |
| OMe | OCH$_2$C≡CH | SO$_2$Me | H |
| OMe | OCHMeC≡CH | SO$_2$Me | H |
| OMe | OCMe$_2$C≡CH | SO$_2$Me | H |
| OMe | OCH$_2$C≡CMe | SO$_2$Me | H |
| OMe | OCH$_2$CH$_2$F | SO$_2$Me | H |
| OMe | OCH$_2$CHF$_2$ | SO$_2$Me | H |
| OMe | OCH$_2$CF$_3$ | SO$_2$Me | H |
| OMe | OCH$_2$CH$_2$Cl | SO$_2$Me | H |
| OMe | OCH$_2$CCl$_3$ | SO$_2$Me | H |
| OMe | OCHMeCH$_2$Cl | SO$_2$Me | H |
| OMe | OCH$_2$CH$_2$CH$_2$Cl | SO$_2$Me | H |
| OMe | OCH$_2$CH$_2$Br | SO$_2$Me | H |
| OMe | Y8 | SO$_2$Me | H |
| OMe | OCH$_2$CCl=CH$_2$ | SO$_2$Me | H |
| OMe | OCH$_2$CCl=CHCl | SO$_2$Me | H |
| OMe | OCH$_2$CH$_2$NO$_2$ | SO$_2$Me | H |
| OMe | OPh | SO$_2$Me | H |
| OMe | OPh—Me-2 | SO$_2$Me | H |
| OMe | OPh—Cl-4 | SO$_2$Me | H |
| OMe | OPh—NO$_2$-4 | SO$_2$Me | H |
| OMe | OCH$_2$CH$_2$OMe | SO$_2$Me | H |
| OMe | OCH$_2$CH$_2$OEt | SO$_2$Me | H |
| OMe | OCH$_2$CH$_2$OPr-n | SO$_2$Me | H |
| OMe | OCH$_2$CH$_2$OPr-i | SO$_2$Me | H |
| OMe | OCH$_2$CH$_2$OBu-n | SO$_2$Me | H |
| OMe | OCH$_2$CH$_2$OBu-i | SO$_2$Me | H |
| OMe | OCH$_2$CH$_2$OBu-s | SO$_2$Me | H |
| OMe | OCH$_2$CH$_2$OBu-t | SO$_2$Me | H |
| OMe | OCH$_2$CH$_2$—Y4 | SO$_2$Me | H |
| OMe | OCHMeCH$_2$OMe | SO$_2$Me | H |
| OMe | OCH$_2$CHMeOMe | SO$_2$Me | H |
| OMe | OCH$_2$CH$_2$OPh | SO$_2$Me | H |
| OMe | OCH$_2$CH$_2$OCH$_2$CH$_2$OMe | SO$_2$Me | H |
| OMe | OCH$_2$CH$_2$OCH$_2$CH$_2$OPr-i | SO$_2$Me | H |
| OMe | OCH$_2$CH$_2$OCHMeCH$_2$OMe | SO$_2$Me | H |
| OMe | OCH$_2$CH$_2$OH | SO$_2$Me | H |
| OMe | OCH$_2$Ph | SO$_2$Me | H |
| OMe | OCHMePh | SO$_2$Me | H |
| OMe | OCH$_2$CH$_2$Ph | SO$_2$Me | H |
| OMe | OCH$_2$Ph-2-Cl | SO$_2$Me | H |

TABLE 4-continued

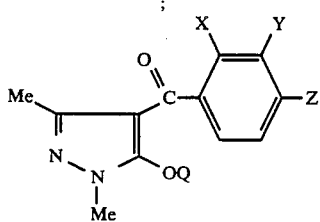

| X | Y | Z | Q |
|---|---|---|---|
| OMe | OCH$_2$Ph-3-Me | SO$_2$Me | H |
| OMe | OCH$_2$Ph-4-OMe | SO$_2$Me | H |
| OMe | OCH$_2$Ph-4-NO$_2$ | SO$_2$Me | H |
| OMe | Y9 | SO$_2$Me | H |
| OMe | Y10 | SO$_2$Me | H |
| OMe | Y11 | SO$_2$Me | H |
| OMe | Y12 | SO$_2$Me | H |
| OMe | Y13 | SO$_2$Me | H |
| OMe | Y14 | SO$_2$Me | H |
| OMe | Y15 | SO$_2$Me | H |
| OMe | Y16 | SO$_2$Me | H |
| OMe | Y17 | SO$_2$Me | H |
| OMe | Y18 | SO$_2$Me | H |
| OMe | OCH$_2$CH$_2$NH$_2$ | SO$_2$Me | H |
| OMe | OCH$_2$CH$_2$NHMe | SO$_2$Me | H |
| OMe | OCH$_2$CH$_2$NHPr-i | SO$_2$Me | H |
| OMe | OCH$_2$CH$_2$NMe$_2$ | SO$_2$Me | H |
| OMe | OCH$_2$CH$_2$NEt$_2$ | SO$_2$Me | H |
| OMe | Y19 | SO$_2$Me | H |
| OMe | OCH$_2$COOMe | SO$_2$Me | H |
| OMe | OCH$_2$COOEt | SO$_2$Me | H |
| OMe | OCH$_2$COOPr-i | SO$_2$Me | H |
| OMe | OCH$_2$COOBu-i | SO$_2$Me | H |
| OMe | OCH$_2$COOBu-t | SO$_2$Me | H |
| OMe | OCH$_2$COO—Y4 | SO$_2$Me | H |
| OMe | OCHMeCOOMe | SO$_2$Me | H |
| OMe | OCHMeCOOEt | SO$_2$Me | H |
| OMe | OCHMeCOOPr-i | SO$_2$Me | H |
| OMe | OCH$_2$CH$_2$CN | SO$_2$Me | H |
| OMe | OCH$_2$SMe | SO$_2$Me | H |
| OMe | OCH$_2$CH$_2$SMe | SO$_2$Me | H |
| OMe | OCH$_2$CH$_2$S(O)Me | SO$_2$Me | H |
| OMe | OCH$_2$CH$_2$SO$_2$Me | SO$_2$Me | H |
| OMe | OCH$_2$CH$_2$SPr-i | SO$_2$Me | H |
| OMe | OCH$_2$CH$_2$S(O)Pr-i | SO$_2$Me | H |
| OMe | OCH$_2$CH$_2$SO$_2$Pr-i | SO$_2$Me | H |
| OMe | OCOOMe | SO$_2$Me | H |
| OMe | OCOOPr-i | SO$_2$Me | H |
| OMe | OCONH$_2$ | SO$_2$Me | H |
| OMe | OCONHMe | SO$_2$Me | H |
| OMe | OCONMe$_2$ | SO$_2$Me | H |
| OMe | OP(O)(OMe)$_2$ | SO$_2$Me | H |
| OMe | Y20 | SO$_2$Me | H |
| OMe | SCH$_2$CH=CH$_2$ | SO$_2$Me | H |
| OMe | SCH$_2$CH=CMe$_2$ | SO$_2$Me | H |
| OMe | SCH$_2$C≡CH | SO$_2$Me | H |
| OMe | SCH$_2$CF$_3$ | SO$_2$Me | H |
| OMe | SCH$_2$CCl$_3$ | SO$_2$Me | H |
| OMe | Y21 | SO$_2$Me | H |
| OMe | SPh | SO$_2$Me | H |
| OMe | SCH$_2$CH$_2$OMe | SO$_2$Me | H |
| OMe | SCH$_2$CH$_2$OEt | SO$_2$Me | H |
| OMe | SCH$_2$CH$_2$OPr-i | SO$_2$Me | H |
| OMe | Y22 | SO$_2$Me | H |
| OMe | S(O)CH$_2$CH=CH$_2$ | SO$_2$Me | H |
| OMe | S(O)CH$_2$CH=CMe$_2$ | SO$_2$Me | H |
| OMe | S(O)CH$_2$C≡CH | SO$_2$Me | H |
| OMe | S(O)CH$_2$CH$_2$Cl | SO$_2$Me | H |
| OMe | Y23 | SO$_2$Me | H |
| OMe | SO$_2$CH$_2$CH=CH$_2$ | SO$_2$Me | H |
| OMe | SO$_2$CH$_2$CH=CMe$_2$ | SO$_2$Me | H |
| OMe | SO$_2$CH$_2$C≡CH | SO$_2$Me | H |
| OMe | SO$_2$CH$_2$CF$_3$ | SO$_2$Me | H |
| OMe | SO$_2$CH$_2$CH$_2$Cl | SO$_2$Me | H |
| OMe | Y24 | SO$_2$Me | H |
| OMe | Y25 | SO$_2$Me | H |
| OMe | SO$_2$Ph | SO$_2$Me | H |
| OMe | SO$_2$CH$_2$CH$_2$OMe | SO$_2$Me | H |
| OMe | SO$_2$CH$_2$CH$_2$OEt | SO$_2$Me | H |

TABLE 4-continued

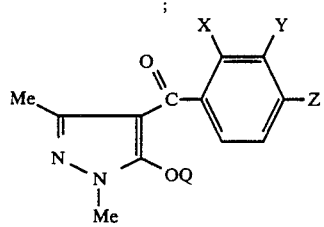

| X | Y | Z | Q |
|---|---|---|---|
| OMe | SO$_2$CH$_2$CH$_2$OPr-i | SO$_2$Me | H |
| OMe | OCH$_2$CH$_2$OMe | SO$_2$Me | CH$_2$Ph |
| OMe | OCH$_2$CH$_2$OEt | SO$_2$Me | CH$_2$Ph |
| OMe | OCH$_2$CH$_2$OPr-i | SO$_2$Me | CH$_2$Ph |
| OMe | OCHMeCH$_2$OMe | SO$_2$Me | CH$_2$Ph |
| OMe | OCH$_2$CH$_2$SMe | SO$_2$Me | CH$_2$Ph |
| OMe | OCH$_2$CH$_2$S(O)Me | SO$_2$Me | CH$_2$Ph |
| OMe | OCH$_2$CH$_2$SO$_2$Me | SO$_2$Me | CH$_2$Ph |
| OMe | OCH$_2$CH$_2$SPr-i | SO$_2$Me | CH$_2$Ph |
| OMe | OCH$_2$CH$_2$S(O)Pr-i | SO$_2$Me | CH$_2$Ph |
| OMe | OCH$_2$CH$_2$SO$_2$Pr-i | SO$_2$Me | CH$_2$Ph |
| OMe | SCH$_2$CH$_2$OMe | SO$_2$Me | CH$_2$Ph |
| OMe | SCH$_2$CH$_2$OPr-i | SO$_2$Me | CH$_2$Ph |
| OMe | SO$_2$CH$_2$CH$_2$OMe | SO$_2$Me | CH$_2$Ph |
| OMe | SO$_2$CH$_2$CH$_2$OPr-i | SO$_2$Me | CH$_2$Ph |
| OMe | OCH$_2$CH$_2$OMe | SO$_2$Me | CH$_2$COPh |
| OMe | OCH$_2$CH$_2$OPr-i | SO$_2$Me | CH$_2$COPh |
| OMe | OCH$_2$CH$_2$SMe | SO$_2$Me | CH$_2$COPh |
| OMe | OCH$_2$CH$_2$SOMe | SO$_2$Me | CH$_2$COPh |
| OMe | OCH$_2$CH$_2$SO$_2$Me | SO$_2$Me | CH$_2$COPh |
| OMe | OCH$_2$CH$_2$SPr-i | SO$_2$Me | CH$_2$COPh |
| OMe | OCH$_2$CH$_2$SO$_2$Pr-i | SO$_2$Me | CH$_2$COPh |
| OMe | SCH$_2$CH$_2$OMe | SO$_2$Me | CH$_2$COPh |
| OMe | SCH$_2$CH$_2$OPr-i | SO$_2$Me | CH$_2$COPh |
| OMe | SO$_2$CH$_2$CH$_2$OMe | SO$_2$Me | CH$_2$COPh |
| OMe | SO$_2$CH$_2$CH$_2$OPr-i | SO$_2$Me | CH$_2$COPh |
| OMe | OCH$_2$CH$_2$OMe | Cl | H |
| OMe | OCH$_2$CH$_2$OEt | Cl | H |
| OMe | OCH$_2$CH$_2$OPr-i | Cl | H |
| OMe | OCHMeCH$_2$OMe | Cl | H |
| OMe | OCH$_2$COOMe | Cl | H |
| OMe | OCH$_2$CH$_2$SMe | Cl | H |
| OMe | OCH$_2$CH$_2$SO$_2$Me | Cl | H |
| OMe | SCH$_2$CH$_2$OMe | Cl | H |
| OMe | SO$_2$CH$_2$CH$_2$OMe | Cl | H |
| OMe | OCH$_2$CH$_2$OMe | Cl | CH$_2$Ph |
| OMe | OCH$_2$CH$_2$SMe | Cl | CH$_2$Ph |
| OMe | OCH$_2$CH$_2$SOMe | Cl | CH$_2$Ph |
| OMe | OCH$_2$CH$_2$SO$_2$Me | Cl | CH$_2$Ph |
| OMe | SCH$_2$CH$_2$OMe | Cl | CH$_2$Ph |
| OMe | SO$_2$CH$_2$CH$_2$OMe | Cl | CH$_2$Ph |
| OMe | OCH$_2$CH$_2$OMe | Cl | CH$_2$COPh |
| OMe | OCH$_2$CH$_2$SMe | Cl | CH$_2$COPh |
| OMe | OCH$_2$CH$_2$SO$_2$Me | Cl | CH$_2$COPh |
| OMe | SCH$_2$CH$_2$OMe | Cl | CH$_2$COPh |
| OMe | SCH$_2$CH$_2$OEt | Cl | CH$_2$COPh |
| OMe | SO$_2$CH$_2$CH$_2$OMe | Cl | CH$_2$COPh |
| CH$_2$OMe | Y1 | SO$_2$Me | H |
| CH$_2$OMe | Y2 | SO$_2$Me | H |
| CH$_2$OMe | Y3 | SO$_2$Me | H |
| CH$_2$OMe | Y4 | SO$_2$Me | H |
| CH$_2$OMe | Y5 | SO$_2$Me | H |
| CH$_2$OMe | Y6 | SO$_2$Me | H |
| CH$_2$OMe | Y7 | SO$_2$Me | H |
| CH$_2$OMe | OCH$_2$CH=CH$_2$ | SO$_2$Me | H |
| CH$_2$OMe | OCHMeCH=CH$_2$ | SO$_2$Me | H |
| CH$_2$OMe | OCMe$_2$CH=CH$_2$ | SO$_2$Me | H |
| CH$_2$OMe | OCH$_2$CMe=CH$_2$ | SO$_2$Me | H |
| CH$_2$OMe | OCH$_2$CH=CHMe | SO$_2$Me | H |
| CH$_2$OMe | OCH$_2$CH=CMe$_2$ | SO$_2$Me | H |
| CH$_2$OMe | OCH$_2$CH$_2$CH=CH$_2$ | SO$_2$Me | H |
| CH$_2$OMe | OCH$_2$C≡CH | SO$_2$Me | H |
| CH$_2$OMe | OCHMeC≡CH | SO$_2$Me | H |
| CH$_2$OMe | OCMe$_2$C≡CH | SO$_2$Me | H |
| CH$_2$OMe | OCH$_2$C≡CMe | SO$_2$Me | H |
| CH$_2$OMe | OCH$_2$CH$_2$F | SO$_2$Me | H |
| CH$_2$OMe | OCH$_2$CHF$_2$ | SO$_2$Me | H |
| CH$_2$OMe | OCH$_2$CF$_3$ | SO$_2$Me | H |
| CH$_2$OMe | OCH$_2$CH$_2$Cl | SO$_2$Me | H |

TABLE 4-continued

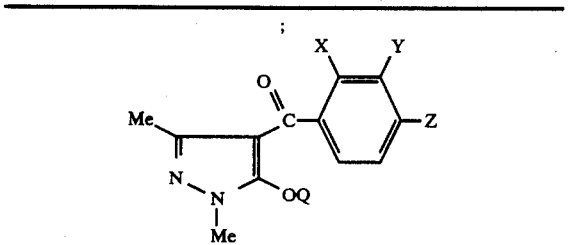

| X | Y | Z | Q |
|---|---|---|---|
| CH$_2$OMe | OCH$_2$CCl$_3$ | SO$_2$Me | H |
| CH$_2$OMe | OCHMeCH$_2$Cl | SO$_2$Me | H |
| CH$_2$OMe | OCH$_2$CH$_2$CH$_2$Cl | SO$_2$Me | H |
| CH$_2$OMe | OCH$_2$CH$_2$Br | SO$_2$Me | H |
| CH$_2$OMe | Y8 | SO$_2$Me | H |
| CH$_2$OMe | OCH$_2$CCl=CH$_2$ | SO$_2$Me | H |
| CH$_2$OMe | OCH$_2$CCl=CHCl | SO$_2$Me | H |
| CH$_2$OMe | OCH$_2$CH$_2$NO$_2$ | SO$_2$Me | H |
| CH$_2$OMe | OPh | SO$_2$Me | H |
| CH$_2$OMe | OPh—Me-2 | SO$_2$Me | H |
| CH$_2$OMe | OPh—Cl-4 | SO$_2$Me | H |
| CH$_2$OMe | OPh—NO$_2$-4 | SO$_2$Me | H |
| CH$_2$OMe | OCH$_2$CH$_2$OMe | SO$_2$Me | H |
| CH$_2$OMe | OCH$_2$CH$_2$OEt | SO$_2$Me | H |
| CH$_2$OMe | OCH$_2$CH$_2$OPr-n | SO$_2$Me | H |
| CH$_2$OMe | OCH$_2$CH$_2$OPr-i | SO$_2$Me | H |
| CH$_2$OMe | OCH$_2$CH$_2$OBu-n | SO$_2$Me | H |
| CH$_2$OMe | OCH$_2$CH$_2$OBu-i | SO$_2$Me | H |
| CH$_2$OMe | OCH$_2$CH$_2$OBu-s | SO$_2$Me | H |
| CH$_2$OMe | OCH$_2$CH$_2$OBu-t | SO$_2$Me | H |
| CH$_2$OMe | OCH$_2$CH$_2$—Y4 | SO$_2$Me | H |
| CH$_2$OMe | OCHMeCH$_2$OMe | SO$_2$Me | H |
| CH$_2$OMe | OCH$_2$CHMeOMe | SO$_2$Me | H |
| CH$_2$OMe | OCH$_2$CH$_2$OPh | SO$_2$Me | H |
| CH$_2$OMe | OCH$_2$CH$_2$OCH$_2$CH$_2$OMe | SO$_2$Me | H |
| CH$_2$OMe | OCH$_2$CH$_2$OCH$_2$CH$_2$OPr-i | SO$_2$Me | H |
| CH$_2$OMe | OCH$_2$CH$_2$OCHMeCH$_2$OMe | SO$_2$Me | H |
| CH$_2$OMe | OCH$_2$CH$_2$OH | SO$_2$Me | H |
| CH$_2$OMe | OCH$_2$Ph | SO$_2$Me | H |
| CH$_2$OMe | OCHMePh | SO$_2$Me | H |
| CH$_2$OMe | OCH$_2$CH$_2$Ph | SO$_2$Me | H |
| CH$_2$OMe | OCH$_2$Ph-2-Cl | SO$_2$Me | H |
| CH$_2$OMe | OCH$_2$Ph-3-Me | SO$_2$Me | H |
| CH$_2$OMe | OCH$_2$Ph-4-OMe | SO$_2$Me | H |
| CH$_2$OMe | OCH$_2$Ph-4-NO$_2$ | SO$_2$Me | H |
| CH$_2$OMe | Y9 | SO$_2$Me | H |
| CH$_2$OMe | Y10 | SO$_2$Me | H |
| CH$_2$OMe | Y11 | SO$_2$Me | H |
| CH$_2$OMe | Y12 | SO$_2$Me | H |
| CH$_2$OMe | Y13 | SO$_2$Me | H |
| CH$_2$OMe | Y14 | SO$_2$Me | H |
| CH$_2$OMe | Y15 | SO$_2$Me | H |
| CH$_2$OMe | Y16 | SO$_2$Me | H |
| CH$_2$OMe | Y17 | SO$_2$Me | H |
| CH$_2$OMe | Y18 | SO$_2$Me | H |
| CH$_2$OMe | OCH$_2$CH$_2$NH$_2$ | SO$_2$Me | H |
| CH$_2$OMe | OCH$_2$CH$_2$NHMe | SO$_2$Me | H |
| CH$_2$OMe | OCH$_2$CH$_2$NHPr-i | SO$_2$Me | H |
| CH$_2$OMe | OCH$_2$CH$_2$NMe$_2$ | SO$_2$Me | H |
| CH$_2$OMe | OCH$_2$CH$_2$NEt$_2$ | SO$_2$Me | H |
| CH$_2$OMe | Y19 | SO$_2$Me | H |
| CH$_2$OMe | OCH$_2$COOMe | SO$_2$Me | H |
| CH$_2$OMe | OCH$_2$COOEt | SO$_2$Me | H |
| CH$_2$OMe | OCH$_2$COOPr-i | SO$_2$Me | H |
| CH$_2$OMe | OCH$_2$COOBu-i | SO$_2$Me | H |
| CH$_2$OMe | OCH$_2$COOBu-t | SO$_2$Me | H |
| CH$_2$OMe | OCH$_2$COO—Y4 | SO$_2$Me | H |
| CH$_2$OMe | OCHMeCOOMe | SO$_2$Me | H |
| CH$_2$OMe | OCHMeCOOEt | SO$_2$Me | H |
| CH$_2$OMe | OCHMeCOOPr-i | SO$_2$Me | H |
| CH$_2$OMe | OCH$_2$CH$_2$CN | SO$_2$Me | H |
| CH$_2$OMe | OCH$_2$SMe | SO$_2$Me | H |
| CH$_2$OMe | OCH$_2$CH$_2$SMe | SO$_2$Me | H |
| CH$_2$OMe | OCH$_2$CH$_2$S(O)Me | SO$_2$Me | H |
| CH$_2$OMe | OCH$_2$CH$_2$SO$_2$Me | SO$_2$Me | H |
| CH$_2$OMe | OCH$_2$CH$_2$SPr-i | SO$_2$Me | H |
| CH$_2$OMe | OCH$_2$CH$_2$S(O)Pr-i | SO$_2$Me | H |
| CH$_2$OMe | OCH$_2$CH$_2$SO$_2$Pr-i | SO$_2$Me | H |
| CH$_2$OMe | OCOOMe | SO$_2$Me | H |

TABLE 4-continued

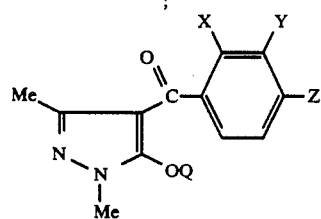

| X | Y | Z | Q |
|---|---|---|---|
| CH$_2$OMe | OCOOPr-i | SO$_2$Me | H |
| CH$_2$OMe | OCONH$_2$ | SO$_2$Me | H |
| CH$_2$OMe | OCONHMe | SO$_2$Me | H |
| CH$_2$OMe | OCONMe$_2$ | SO$_2$Me | H |
| CH$_2$OMe | OP(O)(OMe)$_2$ | SO$_2$Me | H |
| CH$_2$OMe | Y20 | SO$_2$Me | H |
| CH$_2$OMe | SCH$_2$CH=CH$_2$ | SO$_2$Me | H |
| CH$_2$OMe | SCH$_2$CH=CMe$_2$ | SO$_2$Me | H |
| CH$_2$OMe | SCH$_2$C≡CH | SO$_2$Me | H |
| CH$_2$OMe | SCH$_2$CF$_3$ | SO$_2$Me | H |
| CH$_2$OMe | SCH$_2$CCl$_3$ | SO$_2$Me | H |
| CH$_2$OMe | Y21 | SO$_2$Me | H |
| CH$_2$OMe | SPh | SO$_2$Me | H |
| CH$_2$OMe | SCH$_2$CH$_2$OMe | SO$_2$Me | H |
| CH$_2$OMe | SCH$_2$CH$_2$OEt | SO$_2$Me | H |
| CH$_2$OMe | SCH$_2$CH$_2$OPr-i | SO$_2$Me | H |
| CH$_2$OMe | Y22 | SO$_2$Me | H |
| CH$_2$OMe | S(O)CH$_2$CH=CH$_2$ | SO$_2$Me | H |
| CH$_2$OMe | S(O)CH$_2$CH=CMe$_2$ | SO$_2$Me | H |
| CH$_2$OMe | S(O)CH$_2$C≡CH | SO$_2$Me | H |
| CH$_2$OMe | S(O)CH$_2$CH$_2$Cl | SO$_2$Me | H |
| CH$_2$OMe | Y23 | SO$_2$Me | H |
| CH$_2$OMe | SO$_2$CH$_2$CH=CH$_2$ | SO$_2$Me | H |
| CH$_2$OMe | SO$_2$CH$_2$CH=CMe$_2$ | SO$_2$Me | H |
| CH$_2$OMe | SO$_2$CH$_2$C≡CH | SO$_2$Me | H |
| CH$_2$OMe | SO$_2$CH$_2$CF$_3$ | SO$_2$Me | H |
| CH$_2$OMe | SO$_2$CH$_2$CH$_2$Cl | SO$_2$Me | H |
| CH$_2$OMe | Y24 | SO$_2$Me | H |
| CH$_2$OMe | SO$_2$Ph | SO$_2$Me | H |
| CH$_2$OMe | SO$_2$CH$_2$CH$_2$OMe | SO$_2$Me | H |
| CH$_2$OMe | SO$_2$CH$_2$CH$_2$OEt | SO$_2$Me | H |
| CH$_2$OMe | SO$_2$CH$_2$CH$_2$OPr-i | SO$_2$Me | H |
| CH$_2$OMe | OCH$_2$CH$_2$OMe | SO$_2$Me | CH$_2$Ph |
| CH$_2$OMe | OCH$_2$CH$_2$OEt | SO$_2$Me | CH$_2$Ph |
| CH$_2$OMe | OCH$_2$CH$_2$OPr-i | SO$_2$Me | CH$_2$Ph |
| CH$_2$OMe | OCHMeCH$_2$OMe | SO$_2$Me | CH$_2$Ph |
| CH$_2$OMe | OCH$_2$CH$_2$SMe | SO$_2$Me | CH$_2$Ph |
| CH$_2$OMe | OCH$_2$CH$_2$S(O)Me | SO$_2$Me | CH$_2$Ph |
| CH$_2$OMe | OCH$_2$CH$_2$SO$_2$Me | SO$_2$Me | CH$_2$Ph |
| CH$_2$OMe | OCH$_2$CH$_2$SPr-i | SO$_2$Me | CH$_2$Ph |
| CH$_2$OMe | OCH$_2$CH$_2$S(O)Pr-i | SO$_2$Me | CH$_2$Ph |
| CH$_2$OMe | OCH$_2$CH$_2$SO$_2$Pr-i | SO$_2$Me | CH$_2$Ph |
| CH$_2$OMe | SCH$_2$CH$_2$OMe | SO$_2$Me | CH$_2$Ph |
| CH$_2$OMe | SCH$_2$CH$_2$OPr-i | SO$_2$Me | CH$_2$Ph |
| CH$_2$OMe | SO$_2$CH$_2$CH$_2$OMe | SO$_2$Me | CH$_2$Ph |
| CH$_2$OMe | SO$_2$CH$_2$CH$_2$OPr-i | SO$_2$Me | CH$_2$Ph |
| CH$_2$OMe | OCH$_2$CH$_2$OMe | SO$_2$Me | CH$_2$COPh |
| CH$_2$OMe | OCH$_2$CH$_2$OPr-i | SO$_2$Me | CH$_2$COPh |
| CH$_2$OMe | OCH$_2$CH$_2$SMe | SO$_2$Me | CH$_2$COPh |
| CH$_2$OMe | OCH$_2$CH$_2$SOMe | SO$_2$Me | CH$_2$COPh |
| CH$_2$OMe | OCH$_2$CH$_2$SO$_2$Me | SO$_2$Me | CH$_2$COPh |
| CH$_2$OMe | OCH$_2$CH$_2$SPr-i | SO$_2$Me | CH$_2$COPh |
| CH$_2$OMe | OCH$_2$CH$_2$SO$_2$Pr-i | SO$_2$Me | CH$_2$COPh |
| CH$_2$OMe | SCH$_2$CH$_2$OMe | SO$_2$Me | CH$_2$COPh |
| CH$_2$OMe | SCH$_2$CH$_2$OPr-i | SO$_2$Me | CH$_2$COPh |
| CH$_2$OMe | SO$_2$CH$_2$CH$_2$OMe | SO$_2$Me | CH$_2$COPh |
| CH$_2$OMe | SO$_2$CH$_2$CH$_2$OPr-i | SO$_2$Me | CH$_2$COPh |
| CH$_2$OMe | OCH$_2$CH$_2$OMe | Cl | H |
| CH$_2$OMe | OCH$_2$CH$_2$OEt | Cl | H |
| CH$_2$OMe | OCH$_2$CH$_2$OPr-i | Cl | H |
| CH$_2$OMe | OCHMeCH$_2$OMe | Cl | H |
| CH$_2$OMe | OCH$_2$COOMe | Cl | H |
| CH$_2$OMe | OCH$_2$CH$_2$SMe | Cl | H |
| CH$_2$OMe | OCH$_2$CH$_2$SO$_2$Me | Cl | H |
| CH$_2$OMe | SCH$_2$CH$_2$OMe | Cl | H |
| CH$_2$OMe | SO$_2$CH$_2$CH$_2$OMe | Cl | H |
| CH$_2$OMe | OCH$_2$CH$_2$OMe | Cl | CH$_2$Ph |
| CH$_2$OMe | OCH$_2$CH$_2$SMe | Cl | CH$_2$Ph |
| CH$_2$OMe | OCH$_2$CH$_2$SOMe | Cl | CH$_2$Ph |

TABLE 4-continued

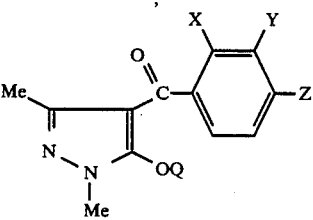

| X | Y | Z | Q |
|---|---|---|---|
| CH₂OMe | OCH₂CH₂SO₂Me | Cl | CH₂Ph |
| CH₂OMe | SCH₂CH₂OMe | Cl | CH₂Ph |
| CH₂OMe | SO₂CH₂CH₂OMe | Cl | CH₂Ph |
| CH₂OMe | OCH₂CH₂OMe | Cl | CH₂COPh |
| CH₂OMe | OCH₂CH₂SMe | Cl | CH₂COPh |
| CH₂OMe | OCH₂CH₂SO₂Me | Cl | CH₂COPh |
| CH₂OMe | SCH₂CH₂OMe | Cl | CH₂COPh |
| CH₂OMe | SCH₂CH₂OEt | Cl | CH₂COPh |
| CH₂OMe | SO₂CH₂CH₂OMe | Cl | CH₂COPh |

TABLE 5

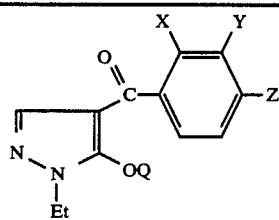

| X | Y | Z | Q |
|---|---|---|---|
| Me | Y1 | SO₂Me | H |
| Me | Y2 | SO₂Me | H |
| Me | Y3 | SO₂Me | H |
| Me | Y4 | SO₂Me | H |
| Me | Y5 | SO₂Me | H |
| Me | Y6 | SO₂Me | H |
| Me | Y7 | SO₂Me | H |
| Me | OCH₂CH=CH₂ | SO₂Me | H |
| Me | OCHMeCH=CH₂ | SO₂Me | H |
| Me | OCMe₂CH=CH₂ | SO₂Me | H |
| Me | OCH₂CMe=CH₂ | SO₂Me | H |
| Me | OCH₂CH=CHMe | SO₂Me | H |
| Me | OCH₂CH=CMe₂ | SO₂Me | H |
| Me | OCH₂CH₂CH=CH₂ | SO₂Me | H |
| Me | OCH₂C≡CH | SO₂Me | H |
| Me | OCHMeC≡CH | SO₂Me | H |
| Me | OCHMe₂C≡CH | SO₂Me | H |
| Me | OCH₂C≡CMe | SO₂Me | H |
| Me | OCH₂CH₂F | SO₂Me | H |
| Me | OCH₂CHF₂ | SO₂Me | H |
| Me | OCH₂CF₃ | SO₂Me | H |
| Me | OCH₂CH₂Cl | SO₂Me | H |
| Me | OCH₂CCl₃ | SO₂Me | H |
| Me | OCHMeCH₂Cl | SO₂Me | H |
| Me | OCH₂CH₂CH₂Cl | SO₂Me | H |
| Me | OCH₂CH₂Br | SO₂Me | H |
| Me | Y8 | SO₂Me | H |
| Me | OCH₂CCl=CH₂ | SO₂Me | H |
| Me | OCH₂CCl=CHCl | SO₂Me | H |
| Me | OCH₂CH₂NO₂ | SO₂Me | H |
| Me | OPh | SO₂Me | H |
| Me | OPh—Me-2 | SO₂Me | H |
| Me | OPh—Cl-4 | SO₂Me | H |
| Me | OPh—NO₂-4 | SO₂Me | H |
| Me | OCH₂CH₂OMe | SO₂Me | H |
| Me | OCH₂CH₂OEt | SO₂Me | H |
| Me | OCH₂CH₂OPr-n | SO₂Me | H |
| Me | OCH₂CH₂OPr-i | SO₂Me | H |
| Me | OCH₂CH₂OBu-n | SO₂Me | H |
| Me | OCH₂CH₂OBu-i | SO₂Me | H |
| Me | OCH₂CH₂OBu-s | SO₂Me | H |
| Me | OCH₂CH₂OBu-t | SO₂Me | H |
| Me | OCH₂CH₂—Y4 | SO₂Me | H |

TABLE 5-continued

| X | Y | Z | Q |
|---|---|---|---|
| Me | OCHMeCH₂OMe | SO₂Me | H |
| Me | OCH₂CHMeOMe | SO₂Me | H |
| Me | OCH₂CH₂OPh | SO₂Me | H |
| Me | OCH₂CH₂OCH₂CH₂OMe | SO₂Me | H |
| Me | OCH₂CH₂OCH₂CH₂OPr-i | SO₂Me | H |
| Me | OCH₂CH₂OCHMeCH₂OMe | SO₂Me | H |
| Me | OCH₂CH₂OH | SO₂Me | H |
| Me | OCH₂Ph | SO₂Me | H |
| Me | OCHMePh | SO₂Me | H |
| Me | OCH₂CH₂Ph | SO₂Me | H |
| Me | OCH₂Ph-2-Cl | SO₂Me | H |
| Me | OCH₂Ph-3-Me | SO₂Me | H |
| Me | OCH₂Ph-4-OMe | SO₂Me | H |
| Me | OCH₂Ph-4-NO₂ | SO₂Me | H |
| Me | Y9 | SO₂Me | H |
| Me | Y10 | SO₂Me | H |
| Me | Y11 | SO₂Me | H |
| Me | Y12 | SO₂Me | H |
| Me | Y13 | SO₂Me | H |
| Me | Y14 | SO₂Me | H |
| Me | Y15 | SO₂Me | H |
| Me | Y16 | SO₂Me | H |
| Me | Y17 | SO₂Me | H |
| Me | Y18 | SO₂Me | H |
| Me | OCH₂CH₂NH₂ | SO₂Me | H |
| Me | OCH₂CH₂NHMe | SO₂Me | H |
| Me | OCH₂CH₂NHPr-i | SO₂Me | H |
| Me | OCH₂CH₂NMe₂ | SO₂Me | H |
| Me | OCH₂CH₂NEt₂ | SO₂Me | H |
| Me | Y19 | SO₂Me | H |
| Me | OCH₂COOMe | SO₂Me | H |
| Me | OCH₂COOEt | SO₂Me | H |
| Me | OCH₂COOPr-i | SO₂Me | H |
| Me | OCH₂COOBu-i | SO₂Me | H |
| Me | OCH₂COOBu-t | SO₂Me | H |
| Me | OCH₂COO—Y4 | SO₂Me | H |
| Me | OCHMeCOOMe | SO₂Me | H |
| Me | OCHMeCOOEt | SO₂Me | H |
| Me | OCHMeCOOPr-i | SO₂Me | H |
| Me | OCH₂CH₂CN | SO₂Me | H |
| Me | OCH₂SMe | SO₂Me | H |
| Me | OCH₂CH₂SMe | SO₂Me | H |
| Me | OCH₂CH₂S(O)Me | SO₂Me | H |
| Me | OCH₂CH₂SO₂Me | SO₂Me | H |
| Me | OCH₂CH₂SPr-i | SO₂Me | H |
| Me | OCH₂CH₂S(O)Pr-i | SO₂Me | H |
| Me | OCH₂CH₂SO₂Pr-i | SO₂Me | H |
| Me | OCOOMe | SO₂Me | H |
| Me | OCOOPr-i | SO₂Me | H |
| Me | OCONH₂ | SO₂Me | H |
| Me | OCONHMe | SO₂Me | H |
| Me | OCONMe₂ | SO₂Me | H |
| Me | OP(O)(OMe)₂ | SO₂Me | H |
| Me | Y20 | SO₂Me | H |
| Me | SCH₂CH=CH₂ | SO₂Me | H |
| Me | SCH₂CH=CMe₂ | SO₂Me | H |
| Me | SCH₂C≡CH | SO₂Me | H |
| Me | SCH₂CF₃ | SO₂Me | H |
| Me | SCH₂CCl₃ | SO₂Me | H |
| Me | Y21 | SO₂Me | H |
| Me | SPh | SO₂Me | H |
| Me | SCH₂CH₂OMe | SO₂Me | H |
| Me | SCH₂CH₂OEt | SO₂Me | H |
| Me | SCH₂CH₂OPr-i | SO₂Me | H |
| Me | Y22 | SO₂Me | H |
| Me | S(O)CH₂CH=CH₂ | SO₂Me | H |
| Me | S(O)CH₂CH=CMe₂ | SO₂Me | H |
| Me | S(O)CH₂C≡CH | SO₂Me | H |
| Me | S(O)CH₂CH₂Cl | SO₂Me | H |
| Me | Y23 | SO₂Me | H |

TABLE 5-continued

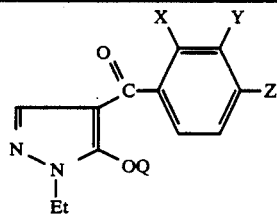

| X | Y | Z | Q |
|---|---|---|---|
| Me | SO$_2$CH$_2$CH=CH$_2$ | SO$_2$Me | H |
| Me | SO$_2$CH$_2$CH=CMe$_2$ | SO$_2$Me | H |
| Me | SO$_2$CH$_2$C≡CH | SO$_2$Me | H |
| Me | SO$_2$CH$_2$CF$_3$ | SO$_2$Me | H |
| Me | SO$_2$CH$_2$CH$_2$Cl | SO$_2$Me | H |
| Me | Y24 | SO$_2$Me | H |
| Me | Y25 | SO$_2$Me | H |
| Me | SO$_2$Ph | SO$_2$Me | H |
| Me | SO$_2$CH$_2$CH$_2$OMe | SO$_2$Me | H |
| Me | SO$_2$CH$_2$CH$_2$OEt | SO$_2$Me | H |
| Me | SO$_2$CH$_2$CH$_2$OPr-i | SO$_2$Me | H |
| Me | OCH$_2$CH$_2$OMe | SO$_2$Me | CH$_2$Ph |
| Me | OCH$_2$CH$_2$OEt | SO$_2$Me | CH$_2$Ph |
| Me | OCH$_2$CH$_2$OPr-i | SO$_2$Me | CH$_2$Ph |
| Me | OCHMeCH$_2$OMe | SO$_2$Me | CH$_2$Ph |
| Me | OCH$_2$CH$_2$SMe | SO$_2$Me | CH$_2$Ph |
| Me | OCH$_2$CH$_2$S(O)Me | SO$_2$Me | CH$_2$Ph |
| Me | OCH$_2$CH$_2$SO$_2$Me | SO$_2$Me | CH$_2$Ph |
| Me | OCH$_2$CH$_2$SPr-i | SO$_2$Me | CH$_2$Ph |
| Me | OCH$_2$CH$_2$S(O)Pr-i | SO$_2$Me | CH$_2$Ph |
| Me | OCH$_2$CH$_2$SO$_2$Pr-i | SO$_2$Me | CH$_2$Ph |
| Me | SCH$_2$CH$_2$OMe | SO$_2$Me | CH$_2$Ph |
| Me | SCH$_2$CH$_2$OPr-i | SO$_2$Me | CH$_2$Ph |
| Me | SO$_2$CH$_2$CH$_2$OMe | SO$_2$Me | CH$_2$Ph |
| Me | SO$_2$CH$_2$CH$_2$OPr-i | SO$_2$Me | CH$_2$Ph |
| Me | OCH$_2$CH$_2$OMe | SO$_2$Me | CH$_2$COPh |
| Me | OCH$_2$CH$_2$OPr-i | SO$_2$Me | CH$_2$COPh |
| Me | OCH$_2$CH$_2$SMe | SO$_2$Me | CH$_2$COPh |
| Me | OCH$_2$CH$_2$SOMe | SO$_2$Me | CH$_2$COPh |
| Me | OCH$_2$CH$_2$SO$_2$Me | SO$_2$Me | CH$_2$COPh |
| Me | OCH$_2$CH$_2$SPr-i | SO$_2$Me | CH$_2$COPh |
| Me | OCH$_2$CH$_2$SO$_2$Pr-i | SO$_2$Me | CH$_2$COPh |
| Me | SCH$_2$CH$_2$OMe | SO$_2$Me | CH$_2$COPh |
| Me | SCH$_2$CH$_2$OPr-i | SO$_2$Me | CH$_2$COPh |
| Me | SO$_2$CH$_2$CH$_2$OMe | SO$_2$Me | CH$_2$COPh |
| Me | SO$_2$CH$_2$CH$_2$OPr-i | SO$_2$Me | CH$_2$COPh |
| Me | OCH$_2$CH$_2$OMe | Cl | H |
| Me | OCH$_2$CH$_2$OEt | Cl | H |
| Me | OCH$_2$CH$_2$OPr-i | Cl | H |
| Me | OCHMeCH$_2$OMe | Cl | H |
| Me | OCH$_2$COOMe | Cl | H |
| Me | OCH$_2$CH$_2$SMe | Cl | H |
| Me | OCH$_2$CH$_2$SO$_2$Me | Cl | H |
| Me | SCH$_2$CH$_2$OMe | Cl | H |
| Me | SO$_2$CH$_2$CH$_2$OMe | Cl | H |
| Me | OCH$_2$CH$_2$OMe | Cl | CH$_2$Ph |
| Me | OCH$_2$CH$_2$SMe | Cl | CH$_2$Ph |
| Me | OCH$_2$CH$_2$SOMe | Cl | CH$_2$Ph |
| Me | OCH$_2$CH$_2$SO$_2$Me | Cl | CH$_2$Ph |
| Me | SCH$_2$SH$_2$OMe | Cl | CH$_2$Ph |
| Me | SO$_2$CH$_2$CH$_2$OMe | Cl | CH$_2$Ph |
| Me | OCH$_2$CH$_2$OMe | Cl | CH$_2$COPh |
| Me | OCH$_2$CH$_2$SMe | Cl | CH$_2$COPh |
| Me | OCH$_2$CH$_2$SO$_2$Me | Cl | CH$_2$COPh |
| Me | SCH$_2$CH$_2$OMe | Cl | CH$_2$COPh |
| Me | SCH$_2$CH$_2$OEt | Cl | CH$_2$COPh |
| Me | SO$_2$CH$_2$CH$_2$OMe | Cl | CH$_2$COPh |
| Cl | Y1 | SO$_2$Me | H |
| Cl | Y2 | SO$_2$Me | H |
| Cl | Y3 | SO$_2$Me | H |
| Cl | Y4 | SO$_2$Me | H |
| Cl | Y5 | SO$_2$Me | H |
| Cl | Y6 | SO$_2$Me | H |
| Cl | Y7 | SO$_2$Me | H |
| Cl | OCH$_2$CH=CH$_2$ | SO$_2$Me | H |
| Cl | OCHMeCH=CH$_2$ | SO$_2$Me | H |
| Cl | OCMe$_2$CH=CH$_2$ | SO$_2$Me | H |
| Cl | OCH$_2$CMe=CH$_2$ | SO$_2$Me | H |
| Cl | OCH$_2$CH=CHMe | SO$_2$Me | H |
| Cl | OCH$_2$CH=CMe$_2$ | SO$_2$Me | H |

TABLE 5-continued

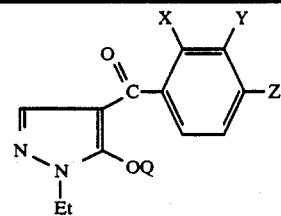

| X | Y | Z | Q |
|---|---|---|---|
| Cl | OCH$_2$CH$_2$CH=CH$_2$ | SO$_2$Me | H |
| Cl | OCH$_2$C≡CH | SO$_2$Me | H |
| Cl | OCHMeC≡CH | SO$_2$Me | H |
| Cl | OCHMe$_2$C≡CH | SO$_2$Me | H |
| Cl | OCH$_2$C≡CMe | SO$_2$Me | H |
| Cl | OCH$_2$CH$_2$F | SO$_2$Me | H |
| Cl | OCH$_2$CHF$_2$ | SO$_2$Me | H |
| Cl | OCH$_2$CF$_3$ | SO$_2$Me | H |
| Cl | OCH$_2$CH$_2$Cl | SO$_2$Me | H |
| Cl | OCH$_2$CCl$_3$ | SO$_2$Me | H |
| Cl | OCHMeCH$_2$Cl | SO$_2$Me | H |
| Cl | OCH$_2$CH$_2$CH$_2$Cl | SO$_2$Me | H |
| Cl | OCH$_2$CH$_2$Br | SO$_2$Me | H |
| Cl | Y8 | SO$_2$Me | H |
| Cl | OCH$_2$CCl=CH$_2$ | SO$_2$Me | H |
| Cl | OCH$_2$CCl=CHCl | SO$_2$Me | H |
| Cl | OCH$_2$CH$_2$NO$_2$ | SO$_2$Me | H |
| Cl | OPh | SO$_2$Me | H |
| Cl | OPh—Me-2 | SO$_2$Me | H |
| Cl | OPh—Cl-4 | SO$_2$Me | H |
| Cl | OPh—NO$_2$-4 | SO$_2$Me | H |
| Cl | OCH$_2$CH$_2$OMe | SO$_2$Me | H |
| Cl | OCH$_2$CH$_2$OEt | SO$_2$Me | H |
| Cl | OCH$_2$CH$_2$OPr-n | SO$_2$Me | H |
| Cl | OCH$_2$CH$_2$OPr-i | SO$_2$Me | H |
| Cl | OCH$_2$CH$_2$OBu-n | SO$_2$Me | H |
| Cl | OCH$_2$CH$_2$OBu-i | SO$_2$Me | H |
| Cl | OCH$_2$CH$_2$OBu-s | SO$_2$Me | H |
| Cl | OCH$_2$CH$_2$OBu-t | SO$_2$Me | H |
| Cl | OCH$_2$CH$_2$—Y4 | SO$_2$Me | H |
| Cl | OCHMeCH$_2$OMe | SO$_2$Me | H |
| Cl | OCH$_2$CHMeOMe | SO$_2$Me | H |
| Cl | OCH$_2$CH$_2$OPh | SO$_2$Me | H |
| Cl | OCH$_2$CH$_2$OCH$_2$CH$_2$OMe | SO$_2$Me | H |
| Cl | OCH$_2$CH$_2$OCH$_2$CH$_2$OPr-i | SO$_2$Me | H |
| Cl | OCH$_2$CH$_2$OCHMeCH$_2$OMe | SO$_2$Me | H |
| Cl | OCH$_2$CH$_2$OH | SO$_2$Me | H |
| Cl | OCH$_2$Ph | SO$_2$Me | H |
| Cl | OCHMePh | SO$_2$Me | H |
| Cl | OCH$_2$CH$_2$Ph | SO$_2$Me | H |
| Cl | OCH$_2$Ph-2-Cl | SO$_2$Me | H |
| Cl | OCH$_2$Ph-3-Me | SO$_2$Me | H |
| Cl | OCH$_2$Ph-4-OMe | SO$_2$Me | H |
| Cl | OCH$_2$Ph-4-NO$_2$ | SO$_2$Me | H |
| Cl | Y9 | SO$_2$Me | H |
| Cl | Y10 | SO$_2$Me | H |
| Cl | Y11 | SO$_2$Me | H |
| Cl | Y12 | SO$_2$Me | H |
| Cl | Y13 | SO$_2$Me | H |
| Cl | Y14 | SO$_2$Me | H |
| Cl | Y15 | SO$_2$Me | H |
| Cl | Y16 | SO$_2$Me | H |
| Cl | Y17 | SO$_2$Me | H |
| Cl | Y18 | SO$_2$Me | H |
| Cl | OCH$_2$CH$_2$NH$_2$ | SO$_2$Me | H |
| Cl | OCH$_2$CH$_2$NHMe | SO$_2$Me | H |
| Cl | OCH$_2$CH$_2$NHPr-i | SO$_2$Me | H |
| Cl | OCH$_2$CH$_2$NMe$_2$ | SO$_2$Me | H |
| Cl | OCH$_2$CH$_2$NEt$_2$ | SO$_2$Me | H |
| Cl | Y19 | SO$_2$Me | H |
| Cl | OCH$_2$COOMe | SO$_2$Me | H |
| Cl | OCH$_2$COOEt | SO$_2$Me | H |
| Cl | OCH$_2$COOPr-i | SO$_2$Me | H |
| Cl | OCH$_2$COOBu-i | SO$_2$Me | H |
| Cl | OCH$_2$COOBu-t | SO$_2$Me | H |
| Cl | OCH$_2$COO—Y4 | SO$_2$Me | H |
| Cl | OCHMeCOOMe | SO$_2$Me | H |
| Cl | OCHMeCOOEt | SO$_2$Me | H |
| Cl | OCHMeCOOPr-i | SO$_2$Me | H |
| Cl | OCH$_2$CH$_2$CN | SO$_2$Me | H |

TABLE 5-continued

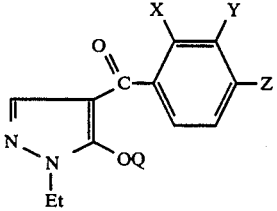

| X | Y | Z | Q |
|---|---|---|---|
| Cl | OCH$_2$SMe | SO$_2$Me | H |
| Cl | OCH$_2$CH$_2$SMe | SO$_2$Me | H |
| Cl | OCH$_2$CH$_2$S(O)Me | SO$_2$Me | H |
| Cl | OCH$_2$CH$_2$SO$_2$Me | SO$_2$Me | H |
| Cl | OCH$_2$CH$_2$SPr-i | SO$_2$Me | H |
| Cl | OCH$_2$CH$_2$S(O)Pr-i | SO$_2$Me | H |
| Cl | OCH$_2$CH$_2$CO$_2$Pr-i | SO$_2$Me | H |
| Cl | OCOOMe | SO$_2$Me | H |
| Cl | OCOOPr-i | SO$_2$Me | H |
| Cl | OCONH$_2$ | SO$_2$Me | H |
| Cl | OCONHMe | SO$_2$Me | H |
| Cl | OCONMe$_2$ | SO$_2$Me | H |
| Cl | OP(O)(OMe)$_2$ | SO$_2$Me | H |
| Cl | Y20 | SO$_2$Me | H |
| Cl | SCH$_2$CH=CH$_2$ | SO$_2$Me | H |
| Cl | SCH$_2$CH=CMe$_2$ | SO$_2$Me | H |
| Cl | SCH$_2$C≡CH | SO$_2$Me | H |
| Cl | SCH$_2$CF$_3$ | SO$_2$Me | H |
| Cl | SCH$_2$CCl$_3$ | SO$_2$Me | H |
| Cl | Y21 | SO$_2$Me | H |
| Cl | SPh | SO$_2$Me | H |
| Cl | SCH$_2$CH$_2$OMe | SO$_2$Me | H |
| Cl | SCH$_2$CH$_2$OEt | SO$_2$Me | H |
| Cl | SCH$_2$CH$_2$OPr-i | SO$_2$Me | H |
| Cl | Y22 | SO$_2$Me | H |
| Cl | S(O)CH$_2$CH=CH$_2$ | SO$_2$Me | H |
| Cl | S(O)CH$_2$CH=CMe$_2$ | SO$_2$Me | H |
| Cl | S(O)CH$_2$C≡CH | SO$_2$Me | H |
| Cl | S(O)CH$_2$CH$_2$Cl | SO$_2$Me | H |
| Cl | Y23 | SO$_2$Me | H |
| Cl | SO$_2$CH$_2$CH=CH$_2$ | SO$_2$Me | H |
| Cl | SO$_2$CH$_2$CH=CMe$_2$ | SO$_2$Me | H |
| Cl | SO$_2$CH$_2$C≡CH | SO$_2$Me | H |
| Cl | SO$_2$CH$_2$CF$_3$ | SO$_2$Me | H |
| Cl | SO$_2$CH$_2$CH$_2$Cl | SO$_2$Me | H |
| Cl | Y24 | SO$_2$Me | H |
| Cl | Y25 | SO$_2$Me | H |
| Cl | SO$_2$Ph | SO$_2$Me | H |
| Cl | SO$_2$CH$_2$CH$_2$OMe | SO$_2$Me | H |
| Cl | SO$_2$CH$_2$CH$_2$OEt | SO$_2$Me | H |
| Cl | SO$_2$CH$_2$CH$_2$OPr-i | SO$_2$Me | H |
| Cl | OCH$_2$CH$_2$OMe | SO$_2$Me | CH$_2$Ph |
| Cl | OCH$_2$CH$_2$OEt | SO$_2$Me | CH$_2$Ph |
| Cl | OCH$_2$CH$_2$OPr-i | SO$_2$Me | CH$_2$Ph |
| Cl | OCHMeCH$_2$OMe | SO$_2$Me | CH$_2$Ph |
| Cl | OCH$_2$CH$_2$SMe | SO$_2$Me | CH$_2$Ph |
| Cl | OCH$_2$CH$_2$S(O)Me | SO$_2$Me | CH$_2$Ph |
| Cl | OCH$_2$CH$_2$SO$_2$Me | SO$_2$Me | CH$_2$Ph |
| Cl | OCH$_2$CH$_2$SPr-i | SO$_2$Me | CH$_2$Ph |
| Cl | OCH$_2$CH$_2$S(O)Pr-i | SO$_2$Me | CH$_2$Ph |
| Cl | OCH$_2$CH$_2$SO$_2$Pr-i | SO$_2$Me | CH$_2$Ph |
| Cl | SCH$_2$CH$_2$OMe | SO$_2$Me | CH$_2$Ph |
| Cl | SCH$_2$CH$_2$OPr-i | SO$_2$Me | CH$_2$Ph |
| Cl | SO$_2$CH$_2$CH$_2$OMe | SO$_2$Me | CH$_2$Ph |
| Cl | SO$_2$CH$_2$CH$_2$OPr-i | SO$_2$Me | CH$_2$Ph |
| Cl | OCH$_2$CH$_2$OMe | SO$_2$Me | CH$_2$COPh |
| Cl | OCH$_2$CH$_2$OPr-i | SO$_2$Me | CH$_2$COPh |
| Cl | OCH$_2$CH$_2$SMe | SO$_2$Me | CH$_2$COPh |
| Cl | OCH$_2$CH$_2$SOMe | SO$_2$Me | CH$_2$COPh |
| Cl | OCH$_2$CH$_2$SO$_2$Me | SO$_2$Me | CH$_2$COPh |
| Cl | OCH$_2$CH$_2$SPr-i | SO$_2$Me | CH$_2$COPh |
| Cl | OCH$_2$CH$_2$SO$_2$Pr-i | SO$_2$Me | CH$_2$COPh |
| Cl | SCH$_2$CH$_2$OMe | SO$_2$Cl | CH$_2$COPh |
| Cl | SCH$_2$CH$_2$OPr-i | SO$_2$Me | CH$_2$COPh |
| Cl | SO$_2$CH$_2$CH$_2$OMe | SO$_2$Me | CH$_2$COPh |
| Cl | SO$_2$CH$_2$CH$_2$OPr-i | SO$_2$Me | CH$_2$COPh |
| Cl | OCH$_2$CH$_2$OMe | Cl | H |
| Cl | OCH$_2$CH$_2$OEt | Cl | H |
| Cl | OCH$_2$CH$_2$OPr-i | Cl | H |
| Cl | OCHMeCH$_2$OMe | Cl | H |
| Cl | OCH$_2$COOMe | Cl | H |
| Cl | OCH$_2$CH$_2$SMe | Cl | H |
| Cl | OCH$_2$CH$_2$SO$_2$Me | Cl | H |
| Cl | SCH$_2$CH$_2$OMe | Cl | H |
| Cl | SO$_2$CH$_2$CH$_2$OMe | Cl | H |
| Cl | OCH$_2$CH$_2$OMe | Cl | CH$_2$Ph |
| Cl | OCH$_2$CH$_2$SMe | Cl | CH$_2$Ph |
| Cl | OCH$_2$CH$_2$SOMe | Cl | CH$_2$Ph |
| Cl | OCH$_2$CH$_2$SO$_2$Me | Cl | CH$_2$Ph |
| Cl | SCH$_2$CH$_2$OMe | Cl | CH$_2$Ph |
| Cl | SO$_2$CH$_2$CH$_2$OMe | Cl | CH$_2$Ph |
| Cl | OCH$_2$CH$_2$OMe | Cl | CH$_2$COPh |
| Cl | OCH$_2$CH$_2$SMe | Cl | CH$_2$COPh |
| Cl | OCH$_2$CH$_2$SO$_2$Me | Cl | CH$_2$COPh |
| Cl | SCH$_2$CH$_2$OMe | Cl | CH$_2$COPh |
| Cl | SCH$_2$CH$_2$OEt | Cl | CH$_2$COPh |
| Cl | SO$_2$CH$_2$CH$_2$OMe | Cl | CH$_2$COPh |
| OMe | Y1 | SO$_2$Me | H |
| OMe | Y2 | SO$_2$Me | H |
| OMe | Y3 | SO$_2$Me | H |
| OMe | Y4 | SO$_2$Me | H |
| OMe | Y5 | SO$_2$Me | H |
| OMe | Y6 | SO$_2$Me | H |
| OMe | Y7 | SO$_2$Me | H |
| OMe | OCH$_2$CH=CH$_2$ | SO$_2$Me | H |
| OMe | OCHMeCH=CH$_2$ | SO$_2$Me | H |
| OMe | OCMe$_2$CH=CH$_2$ | SO$_2$Me | H |
| OMe | OCH$_2$CMe=CH$_2$ | SO$_2$Me | H |
| OMe | OCH$_2$CH=CHMe | SO$_2$Me | H |
| OMe | OCH$_2$CH=CMe$_2$ | SO$_2$Me | H |
| OMe | OCH$_2$CH$_2$CH=CH$_2$ | SO$_2$Me | H |
| OMe | OCH$_2$C≡CH | SO$_2$Me | H |
| OMe | OCHMeC≡CH | SO$_2$Me | H |
| OMe | OCHMe$_2$C≡CH | SO$_2$Me | H |
| OMe | OCH$_2$C≡CMe | SO$_2$Me | H |
| OMe | OCH$_2$CH$_2$F | SO$_2$Me | H |
| OMe | OCH$_2$CHF$_2$ | SO$_2$Me | H |
| OMe | OCH$_2$CF$_3$ | SO$_2$Me | H |
| OMe | OCH$_2$CH$_2$Cl | SO$_2$Me | H |
| OMe | OCH$_2$CCl$_3$ | SO$_2$Me | H |
| OMe | OCHMeCH$_2$Cl | SO$_2$Me | H |
| OMe | OCH$_2$CH$_2$CH$_2$Cl | SO$_2$Me | H |
| OMe | OCH$_2$CH$_2$Br | SO$_2$Me | H |
| OMe | Y8 | SO$_2$Me | H |
| OMe | OCH$_2$CCl=CH$_2$ | SO$_2$Me | H |
| OMe | OCH$_2$CCl=CHCl | SO$_2$Me | H |
| OMe | OCH$_2$CH$_2$NO$_2$ | SO$_2$Me | H |
| OMe | OPh | SO$_2$Me | H |
| OMe | OPh—Me-2 | SO$_2$Me | H |
| OMe | OPh—Cl-4 | SO$_2$Me | H |
| OMe | OPh—NO$_2$-4 | SO$_2$Me | H |
| OMe | OCH$_2$CH$_2$OMe | SO$_2$Me | H |
| OMe | OCH$_2$CH$_2$OEt | SO$_2$Me | H |
| OMe | OCH$_2$CH$_2$OPr-n | SO$_2$Me | H |
| OMe | OCH$_2$CH$_2$OPr-i | SO$_2$Me | H |
| OMe | OCH$_2$CH$_2$OBu-n | SO$_2$Me | H |
| OMe | OCH$_2$CH$_2$OBu-i | SO$_2$Me | H |
| OMe | OCH$_2$CH$_2$OBu-s | SO$_2$Me | H |
| OMe | OCH$_2$CH$_2$OBu-t | SO$_2$Me | H |
| OMe | OCH$_2$CH$_2$—Y4 | SO$_2$Me | H |
| OMe | OCHMeCH$_2$OMe | SO$_2$Me | H |
| OMe | OCH$_2$CHMeOMe | SO$_2$Me | H |
| OMe | OCH$_2$CH$_2$OPh | SO$_2$Me | H |
| OMe | OCH$_2$CH$_2$OCH$_2$CH$_2$OMe | SO$_2$Me | H |
| OMe | OCH$_2$CH$_2$OCH$_2$CH$_2$OPr-i | SO$_2$Me | H |
| OMe | OCH$_2$CH$_2$OCHMeCH$_2$OMe | SO$_2$Me | H |
| OMe | OCH$_2$CH$_2$OH | SO$_2$Me | H |
| OMe | OCH$_2$Ph | SO$_2$Me | H |
| OMe | OCHMePh | SO$_2$Me | H |
| OMe | OCH$_2$CH$_2$Ph | SO$_2$Me | H |

TABLE 5-continued

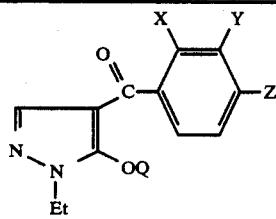

| X | Y | Z | Q |
|---|---|---|---|
| OMe | OCH₂Ph-2-Cl | SO₂Me | H |
| OMe | OCH₂Ph-3-Me | SO₂Me | H |
| OMe | OCH₂Ph-4-OMe | SO₂Me | H |
| OMe | OCH₂Ph-4-NO₂ | SO₂Me | H |
| OMe | Y9 | SO₂Me | H |
| OMe | Y10 | SO₂Me | H |
| OMe | Y11 | SO₂Me | H |
| OMe | Y12 | SO₂Me | H |
| OMe | Y13 | SO₂Me | H |
| OMe | Y14 | SO₂Me | H |
| OMe | Y15 | SO₂Me | H |
| OMe | Y16 | SO₂Me | H |
| OMe | Y17 | SO₂Me | H |
| OMe | Y18 | SO₂Me | H |
| OMe | OCH₂CH₂NH₂ | SO₂Me | H |
| OMe | OCH₂CH₂NHMe | SO₂Me | H |
| OMe | OCH₂CH₂NHPr-i | SO₂Me | H |
| OMe | OCH₂CH₂NMe₂ | SO₂Me | H |
| OMe | OCH₂CH₂NEt₂ | SO₂Me | H |
| OMe | Y19 | SO₂Me | H |
| OMe | OCH₂COOMe | SO₂Me | H |
| OMe | OCH₂COOEt | SO₂Me | H |
| OMe | OCH₂COOPr-i | SO₂Me | H |
| OMe | OCH₂COOBu-i | SO₂Me | H |
| OMe | OCH₂COOBu-t | SO₂Me | H |
| OMe | OCH₂COO—Y4 | SO₂Me | H |
| OMe | OCHMeCOOMe | SO₂Me | H |
| OMe | OCHMeCOOEt | SO₂Me | H |
| OMe | OCHMeCOOPr-i | SO₂Me | H |
| OMe | OCH₂CH₂CN | SO₂Me | H |
| OMe | OCH₂SMe | SO₂Me | H |
| OMe | OCH₂CH₂SMe | SO₂Me | H |
| OMe | OCH₂CH₂S(O)Me | SO₂Me | H |
| OMe | OCH₂CH₂SO₂Me | SO₂Me | H |
| OMe | OCH₂CH₂SPr-i | SO₂Me | H |
| OMe | OCH₂CH₂S(O)Pr-i | SO₂Me | H |
| OMe | OCH₂CH₂SO₂Pr-i | SO₂Me | H |
| OMe | OCOOMe | SO₂Me | H |
| OMe | OCOOPr-i | SO₂Me | H |
| OMe | OCONH₂ | SO₂Me | H |
| OMe | OCONHMe | SO₂Me | H |
| OMe | OCONMe₂ | SO₂Me | H |
| OMe | OP(O)(OMe)₂ | SO₂Me | H |
| OMe | Y20 | SO₂Me | H |
| OMe | SCH₂CH=CH₂ | SO₂Me | H |
| OMe | SCH₂CH=CMe₂ | SO₂Me | H |
| OMe | SCH₂C≡CH | SO₂Me | H |
| OMe | SCH₂CF₃ | SO₂Me | H |
| OMe | SCH₂CCl₃ | SO₂Me | H |
| OMe | Y21 | SO₂Me | H |
| OMe | SPh | SO₂Me | H |
| OMe | SCH₂CH₂OMe | SO₂Me | H |
| OMe | SCH₂CH₂OEt | SO₂Me | H |
| OMe | SCH₂CH₂OPr-i | SO₂Me | H |
| OMe | Y22 | SO₂Me | H |
| OMe | S(O)CH₂CH=CH₂ | SO₂Me | H |
| OMe | S(O)CH₂CH=CMe₂ | SO₂Me | H |
| OMe | S(O)CH₂C≡CH | SO₂Me | H |
| OMe | S(O)CH₂CH₂Cl | SO₂Me | H |
| OMe | Y23 | SO₂Me | H |
| OMe | SO₂CH₂CH=CH₂ | SO₂Me | H |
| OMe | SO₂CH₂CH=CMe₂ | SO₂Me | H |
| OMe | SO₂CH₂C≡CH | SO₂Me | H |
| OMe | SO₂CH₂CF₃ | SO₂Me | H |
| OMe | SO₂CH₂CH₂Cl | SO₂Me | H |
| OMe | Y24 | SO₂Me | H |
| OMe | Y25 | SO₂Me | H |
| OMe | SO₂Ph | SO₂Me | H |
| OMe | SO₂CH₂CH₂OMe | SO₂Me | H |
| OMe | SO₂CH₂CH₂OEt | SO₂Me | H |

TABLE 5-continued

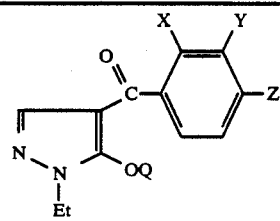

| X | Y | Z | Q |
|---|---|---|---|
| OMe | SO₂CH₂CH₂OPr-i | SO₂Me | H |
| OMe | OCH₂CH₂OMe | SO₂Me | CH₂Ph |
| OMe | OCH₂CH₂OEt | SO₂Me | CH₂Ph |
| OMe | OCH₂CH₂OPr-i | SO₂Me | CH₂Ph |
| OMe | OCHMeCH₂OMe | SO₂Me | CH₂Ph |
| OMe | OCH₂CH₂OMe | SO₂Me | CH₂Ph |
| OMe | OCH₂CH₂S(O)Me | SO₂Me | CH₂Ph |
| OMe | OCH₂CH₂SO₂Me | SO₂Me | CH₂Ph |
| OMe | OCH₂CH₂SPr-i | SO₂Me | CH₂Ph |
| OMe | OCH₂CH₂S(O)Pr-i | SO₂Me | CH₂Ph |
| OMe | OCH₂CH₂SO₂Pr-i | SO₂Me | CH₂Ph |
| OMe | SCH₂CH₂OMe | SO₂Me | CH₂Ph |
| OMe | SCH₂CH₂OPr-i | SO₂Me | CH₂Ph |
| OMe | SO₂CH₂CH₂OMe | SO₂Me | CH₂Ph |
| OMe | SO₂CH₂CH₂OPr-i | SO₂Me | CH₂Ph |
| OMe | OCH₂CH₂OMe | SO₂Me | CH₂COPh |
| OMe | OCH₂CH₂OPr-i | SO₂Me | CH₂COPh |
| OMe | OCH₂CH₂SMe | SO₂Me | CH₂COPh |
| OMe | OCH₂CH₂SOMe | SO₂Me | CH₂COPh |
| OMe | OCH₂CH₂SO₂Me | SO₂Me | CH₂COPh |
| OMe | OCH₂CH₂SPr-i | SO₂Me | CH₂COPh |
| OMe | OCH₂CH₂SO₂Pr-i | SO₂Me | CH₂COPh |
| OMe | SCH₂CH₂OMe | SO₂Cl | CH₂COPh |
| OMe | SCH₂CH₂OPr-i | SO₂Me | CH₂COPh |
| OMe | SO₂CH₂CH₂OMe | SO₂Me | CH₂COPh |
| OMe | SO₂CH₂CH₂OPr-i | SO₂Me | CH₂COPh |
| OMe | OCH₂CH₂OMe | Cl | H |
| OMe | OCH₂CH₂OEt | Cl | H |
| OMe | OCH₂CH₂OPr-i | Cl | H |
| OMe | OCHMeCH₂OMe | Cl | H |
| OMe | OCH₂COOMe | Cl | H |
| OMe | OCH₂CH₂SMe | Cl | H |
| OMe | OCH₂CH₂SO₂Me | Cl | H |
| OMe | SCH₂CH₂OMe | Cl | H |
| OMe | SO₂CH₂CH₂OMe | Cl | H |
| OMe | OCH₂CH₂OMe | Cl | CH₂Ph |
| OMe | OCH₂CH₂SMe | Cl | CH₂Ph |
| OMe | OCH₂CH₂SOMe | Cl | CH₂Ph |
| OMe | OCH₂CH₂SO₂Me | Cl | CH₂Ph |
| OMe | SCH₂SH₂OMe | Cl | CH₂Ph |
| OMe | SO₂CH₂CH₂OMe | Cl | CH₂Ph |
| OMe | OCH₂CH₂OMe | Cl | CH₂COPh |
| OMe | OCH₂CH₂SMe | Cl | CH₂COPh |
| OMe | OCH₂CH₂SO₂Me | Cl | CH₂COPh |
| OMe | SCH₂CH₂OMe | Cl | CH₂COPh |
| OMe | SCH₂CH₂OEt | Cl | CH₂COPh |
| OMe | SO₂CH₂CH₂OMe | Cl | CH₂COPh |
| CH₂OMe | Y1 | SO₂Me | H |
| CH₂OMe | Y2 | SO₂Me | H |
| CH₂OMe | Y3 | SO₂Me | H |
| CH₂OMe | Y4 | SO₂Me | H |
| CH₂OMe | Y5 | SO₂Me | H |
| CH₂OMe | Y6 | SO₂Me | H |
| CH₂OMe | Y7 | SO₂Me | H |
| CH₂OMe | OCH₂CH=CH₂ | SO₂Me | H |
| CH₂OMe | OCHMeCH=CH₂ | SO₂Me | H |
| CH₂OMe | OCMe₂CH=CH₂ | SO₂Me | H |
| CH₂OMe | OCH₂CMe=CH₂ | SO₂Me | H |
| CH₂OMe | OCH₂CH=CHMe | SO₂Me | H |
| CH₂OMe | OCH₂CH=CMe₂ | SO₂Me | H |
| CH₂OMe | OCH₂CH₂CH=CH₂ | SO₂Me | H |
| CH₂OMe | OCH₂C≡CH | SO₂Me | H |
| CH₂OMe | OCHMeC≡CH | SO₂Me | H |
| CH₂OMe | OCHMe₂C≡CH | SO₂Me | H |
| CH₂OMe | OCH₂C≡CMe | SO₂Me | H |
| CH₂OMe | OCH₂CH₂F | SO₂Me | H |
| CH₂OMe | OCH₂CHF₂ | SO₂Me | H |
| CH₂OMe | OCH₂CF₃ | SO₂Me | H |
| CH₂OMe | OCH₂CH₂Cl | SO₂Me | H |
| CH₂OMe | OCH₂CCl₃ | SO₂Me | H |

TABLE 5-continued

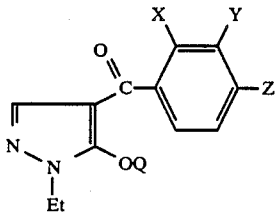

| X | Y | Z | Q |
|---|---|---|---|
| CH$_2$OMe | OCHMeCH$_2$Cl | SO$_2$Me | H |
| CH$_2$OMe | OCH$_2$CH$_2$CH$_2$Cl | SO$_2$Me | H |
| CH$_2$OMe | OCH$_2$CH$_2$Br | SO$_2$Me | H |
| CH$_2$OMe | Y8 | SO$_2$Me | H |
| CH$_2$OMe | OCH$_2$CCl=CH$_2$ | SO$_2$Me | H |
| CH$_2$OMe | OCH$_2$CCl=CHCl | SO$_2$Me | H |
| CH$_2$OMe | OCH$_2$CH$_2$NO$_2$ | SO$_2$Me | H |
| CH$_2$OMe | OPh | SO$_2$Me | H |
| CH$_2$OMe | OPh—Me-2 | SO$_2$Me | H |
| CH$_2$OMe | OPh—Cl-4 | SO$_2$Me | H |
| CH$_2$OMe | OPh—NO$_2$-4 | SO$_2$Me | H |
| CH$_2$OMe | OCH$_2$CH$_2$OMe | SO$_2$Me | H |
| CH$_2$OMe | OCH$_2$CH$_2$OEt | SO$_2$Me | H |
| CH$_2$OMe | OCH$_2$CH$_2$OPr-n | SO$_2$Me | H |
| CH$_2$OMe | OCH$_2$CH$_2$OPr-i | SO$_2$Me | H |
| CH$_2$OMe | OCH$_2$CH$_2$OBu-n | SO$_2$Me | H |
| CH$_2$OMe | OCH$_2$CH$_2$OBu-i | SO$_2$Me | H |
| CH$_2$OMe | OCH$_2$CH$_2$OBu-s | SO$_2$Me | H |
| CH$_2$OMe | OCH$_2$CH$_2$OBu-t | SO$_2$Me | H |
| CH$_2$OMe | OCH$_2$CH$_2$—Y4 | SO$_2$Me | H |
| CH$_2$OMe | OCHMeCH$_2$OMe | SO$_2$Me | H |
| CH$_2$OMe | OCH$_2$CHMeOMe | SO$_2$Me | H |
| CH$_2$OMe | OCH$_2$CH$_2$OPh | SO$_2$Me | H |
| CH$_2$OMe | OCH$_2$CH$_2$OCH$_2$CH$_2$OMe | SO$_2$Me | H |
| CH$_2$OMe | OCH$_2$CH$_2$OCH$_2$CH$_2$OPr-i | SO$_2$Me | H |
| CH$_2$OMe | OCH$_2$CH$_2$OCHMeCH$_2$OMe | SO$_2$Me | H |
| CH$_2$OMe | OCH$_2$CH$_2$OH | SO$_2$Me | H |
| CH$_2$OMe | OCH$_2$Ph | SO$_2$Me | H |
| CH$_2$OMe | OCHMePh | SO$_2$Me | H |
| CH$_2$OMe | OCH$_2$CH$_2$Ph | SO$_2$Me | H |
| CH$_2$OMe | OCH$_2$Ph-2-Cl | SO$_2$Me | H |
| CH$_2$OMe | OCH$_2$Ph-3-Me | SO$_2$Me | H |
| CH$_2$OMe | OCH$_2$Ph-4-OMe | SO$_2$Me | H |
| CH$_2$OMe | OCH$_2$Ph-4-NO$_2$ | SO$_2$Me | H |
| CH$_2$OMe | Y9 | SO$_2$Me | H |
| CH$_2$OMe | Y10 | SO$_2$Me | H |
| CH$_2$OMe | Y11 | SO$_2$Me | H |
| CH$_2$OMe | Y12 | SO$_2$Me | H |
| CH$_2$OMe | Y13 | SO$_2$Me | H |
| CH$_2$OMe | Y14 | SO$_2$Me | H |
| CH$_2$OMe | Y15 | SO$_2$Me | H |
| CH$_2$OMe | Y16 | SO$_2$Me | H |
| CH$_2$OMe | Y17 | SO$_2$Me | H |
| CH$_2$OMe | Y18 | SO$_2$Me | H |
| CH$_2$OMe | OCH$_2$CH$_2$NH$_2$ | SO$_2$Me | H |
| CH$_2$OMe | OCH$_2$CH$_2$NHMe | SO$_2$Me | H |
| CH$_2$OMe | OCH$_2$CH$_2$NHPr-i | SO$_2$Me | H |
| CH$_2$OMe | OCH$_2$CH$_2$NMe$_2$ | SO$_2$Me | H |
| CH$_2$OMe | OCH$_2$CH$_2$NEt$_2$ | SO$_2$Me | H |
| CH$_2$OMe | Y19 | SO$_2$Me | H |
| CH$_2$OMe | OCH$_2$COOMe | SO$_2$Me | H |
| CH$_2$OMe | OCH$_2$COOEt | SO$_2$Me | H |
| CH$_2$OMe | OCH$_2$COOPr-i | SO$_2$Me | H |
| CH$_2$OMe | OCH$_2$COOBu-i | SO$_2$Me | H |
| CH$_2$OMe | OCH$_2$COOBu-t | SO$_2$Me | H |
| CH$_2$OMe | OCH$_2$COO—Y4 | SO$_2$Me | H |
| CH$_2$OMe | OCHMeCOOMe | SO$_2$Me | H |
| CH$_2$OMe | OCHMeCOOEt | SO$_2$Me | H |
| CH$_2$OMe | OCHMeCOOPr-i | SO$_2$Me | H |
| CH$_2$OMe | OCH$_2$CH$_2$CN | SO$_2$Me | H |
| CH$_2$OMe | OCH$_2$SMe | SO$_2$Me | H |
| CH$_2$OMe | OCH$_2$CH$_2$SMe | SO$_2$Me | H |
| CH$_2$OMe | OCH$_2$CH$_2$S(O)Me | SO$_2$Me | H |
| CH$_2$OMe | OCH$_2$CH$_2$SO$_2$Me | SO$_2$Me | H |
| CH$_2$OMe | OCH$_2$CH$_2$SPr-i | SO$_2$Me | H |
| CH$_2$OMe | OCH$_2$CH$_2$S(O)Pr-i | SO$_2$Me | H |
| CH$_2$OMe | OCH$_2$CH$_2$CO$_2$Pr-i | SO$_2$Me | H |
| CH$_2$OMe | OCOOMe | SO$_2$Me | H |
| CH$_2$OMe | OCOOPr-i | SO$_2$Me | H |
| CH$_2$OMe | OCONH$_2$ | SO$_2$Me | H |

TABLE 5-continued

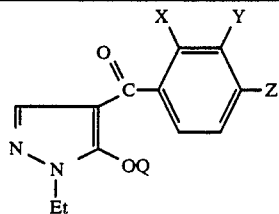

| X | Y | Z | Q |
|---|---|---|---|
| CH$_2$OMe | OCONHMe | SO$_2$Me | H |
| CH$_2$OMe | OCONMe$_2$ | SO$_2$Me | H |
| CH$_2$OMe | OP(O)(OMe)$_2$ | SO$_2$Me | H |
| CH$_2$OMe | Y20 | SO$_2$Me | H |
| CH$_2$OMe | SCH$_2$CH=CH$_2$ | SO$_2$Me | H |
| CH$_2$OMe | SCH$_2$CH=CMe$_2$ | SO$_2$Me | H |
| CH$_2$OMe | SCH$_2$C≡CH | SO$_2$Me | H |
| CH$_2$OMe | SCH$_2$CF$_3$ | SO$_2$Me | H |
| CH$_2$OMe | SCH$_2$CCl$_3$ | SO$_2$Me | H |
| CH$_2$OMe | Y21 | SO$_2$Me | H |
| CH$_2$OMe | SPh | SO$_2$Me | H |
| CH$_2$OMe | SCH$_2$CH$_2$OMe | SO$_2$Me | H |
| CH$_2$OMe | SCH$_2$CH$_2$OEt | SO$_2$Me | H |
| CH$_2$OMe | SCH$_2$CH$_2$OPr-i | SO$_2$Me | H |
| CH$_2$OMe | Y22 | SO$_2$Me | H |
| CH$_2$OMe | S(O)CH$_2$CH=CH$_2$ | SO$_2$Me | H |
| CH$_2$OMe | S(O)CH$_2$CH=CMe$_2$ | SO$_2$Me | H |
| CH$_2$OMe | S(O)CH$_2$C≡CH | SO$_2$Me | H |
| CH$_2$OMe | S(O)CH$_2$CH$_2$Cl | SO$_2$Me | H |
| CH$_2$OMe | Y23 | SO$_2$Me | H |
| CH$_2$OMe | SO$_2$CH$_2$CH=CH$_2$ | SO$_2$Me | H |
| CH$_2$OMe | SO$_2$CH$_2$CH=CMe$_2$ | SO$_2$Me | H |
| CH$_2$OMe | SO$_2$CH$_2$C≡CH | SO$_2$Me | H |
| CH$_2$OMe | SO$_2$CH$_2$CF$_3$ | SO$_2$Me | H |
| CH$_2$OMe | SO$_2$CH$_2$CH$_2$Cl | SO$_2$Me | H |
| CH$_2$OMe | Y24 | SO$_2$Me | H |
| CH$_2$OMe | SO$_2$Ph | SO$_2$Me | H |
| CH$_2$OMe | SO$_2$CH$_2$CH$_2$OMe | SO$_2$Me | H |
| CH$_2$OMe | SO$_2$CH$_2$CH$_2$OEt | SO$_2$Me | H |
| CH$_2$OMe | SO$_2$CH$_2$CH$_2$OPr-i | SO$_2$Me | H |
| CH$_2$OMe | OCH$_2$CH$_2$OMe | SO$_2$Me | CH$_2$Ph |
| CH$_2$OMe | OCH$_2$CH$_2$OEt | SO$_2$Me | CH$_2$Ph |
| CH$_2$OMe | OCH$_2$CH$_2$OPr-i | SO$_2$Me | CH$_2$Ph |
| CH$_2$OMe | OCHMeCH$_2$OMe | SO$_2$Me | CH$_2$Ph |
| CH$_2$OMe | OCH$_2$CH$_2$SMe | SO$_2$Me | CH$_2$Ph |
| CH$_2$OMe | OCH$_2$CH$_2$S(O)Me | SO$_2$Me | CH$_2$Ph |
| CH$_2$OMe | OCH$_2$CH$_2$SO$_2$Me | SO$_2$Me | CH$_2$Ph |
| CH$_2$OMe | OCH$_2$CH$_2$SPr-i | SO$_2$Me | CH$_2$Ph |
| CH$_2$OMe | OCH$_2$CH$_2$S(O)Pr-i | SO$_2$Me | CH$_2$Ph |
| CH$_2$OMe | OCH$_2$CH$_2$SO$_2$Pr-i | SO$_2$Me | CH$_2$Ph |
| CH$_2$OMe | SCH$_2$CH$_2$OMe | SO$_2$Me | CH$_2$Ph |
| CH$_2$OMe | SCH$_2$CH$_2$OPr-i | SO$_2$Me | CH$_2$Ph |
| CH$_2$OMe | SO$_2$CH$_2$CH$_2$OMe | SO$_2$Me | CH$_2$Ph |
| CH$_2$OMe | SO$_2$CH$_2$CH$_2$OPr-i | SO$_2$Me | CH$_2$Ph |
| CH$_2$OMe | OCH$_2$CH$_2$OMe | SO$_2$Me | CH$_2$COPh |
| CH$_2$OMe | OCH$_2$CH$_2$OPr-i | SO$_2$Me | CH$_2$COPh |
| CH$_2$OMe | OCH$_2$CH$_2$SMe | SO$_2$Me | CH$_2$COPh |
| CH$_2$OMe | OCH$_2$CH$_2$SOMe | SO$_2$Me | CH$_2$COPh |
| CH$_2$OMe | OCH$_2$CH$_2$SO$_2$Me | SO$_2$Me | CH$_2$COPh |
| CH$_2$OMe | OCH$_2$CH$_2$SPr-i | SO$_2$Me | CH$_2$COPh |
| CH$_2$OMe | OCH$_2$CH$_2$SO$_2$Pr-i | SO$_2$Me | CH$_2$COPh |
| CH$_2$OMe | SCH$_2$CH$_2$OMe | SO$_2$Cl | CH$_2$COPh |
| CH$_2$OMe | SCH$_2$CH$_2$OPr-i | SO$_2$Me | CH$_2$COPh |
| CH$_2$OMe | SO$_2$CH$_2$CH$_2$OMe | SO$_2$Me | CH$_2$COPh |
| CH$_2$OMe | SO$_2$CH$_2$CH$_2$OPr-i | SO$_2$Me | CH$_2$COPh |
| CH$_2$OMe | OCH$_2$CH$_2$OMe | Cl | H |
| CH$_2$OMe | OCH$_2$CH$_2$OEt | Cl | H |
| CH$_2$OMe | OCH$_2$CH$_2$OPr-i | Cl | H |
| CH$_2$OMe | OCHMeCH$_2$OMe | Cl | H |
| CH$_2$OMe | OCH$_2$COOMe | Cl | H |
| CH$_2$OMe | OCH$_2$CH$_2$SMe | Cl | H |
| CH$_2$OMe | OCH$_2$CH$_2$SO$_2$Me | Cl | H |
| CH$_2$OMe | SCH$_2$CH$_2$OMe | Cl | H |
| CH$_2$OMe | SO$_2$CH$_2$CH$_2$OMe | Cl | H |
| CH$_2$OMe | OCH$_2$CH$_2$OMe | Cl | CH$_2$Ph |
| CH$_2$OMe | OCH$_2$CH$_2$SMe | Cl | CH$_2$Ph |
| CH$_2$OMe | OCH$_2$CH$_2$SOMe | Cl | CH$_2$Ph |
| CH$_2$OMe | OCH$_2$CH$_2$SO$_2$Me | Cl | CH$_2$Ph |
| CH$_2$OMe | SCH$_2$CH$_2$OMe | Cl | CH$_2$Ph |
| CH$_2$OMe | SO$_2$CH$_2$CH$_2$OMe | Cl | CH$_2$Ph |

TABLE 5-continued

Structure: pyrazole with Et on N, OQ group, connected via C=O to phenyl bearing X, Y, Z substituents.

| X | Y | Z | Q |
|---|---|---|---|
| CH₂OMe | OCH₂CH₂OMe | Cl | CH₂COPh |
| CH₂OMe | OCH₂CH₂SMe | Cl | CH₂COPh |
| CH₂OMe | OCH₂CH₂SO₂Me | Cl | CH₂COPh |
| CH₂OMe | SCH₂CH₂OMe | Cl | CH₂COPh |
| CH₂OMe | SCH₂CH₂OEt | Cl | CH₂COPh |
| CH₂OMe | SO₂CH₂CH₂OMe | Cl | CH₂COPh |

TABLE 6

Structure: pyrazole with Me at 3-position, Et on N, OQ group, connected via C=O to phenyl bearing X, Y, Z substituents.

| X | Y | Z | Q |
|---|---|---|---|
| Me | Y1 | SO₂Me | H |
| Me | Y2 | SO₂Me | H |
| Me | Y3 | SO₂Me | H |
| Me | Y4 | SO₂Me | H |
| Me | Y5 | SO₂Me | H |
| Me | Y6 | SO₂Me | H |
| Me | Y7 | SO₂Me | H |
| Me | OCH₂CH=CH₂ | SO₂Me | H |
| Me | OCHMeCH=CH₂ | SO₂Me | H |
| Me | OCMe₂CH=CH₂ | SO₂Me | H |
| Me | OCH₂CMe=CH₂ | SO₂Me | H |
| Me | OCH₂CH=CHMe | SO₂Me | H |
| Me | OCH₂CH=CMe₂ | SO₂Me | H |
| Me | OCH₂CH₂CH=CH₂ | SO₂Me | H |
| Me | OCH₂C≡CH | SO₂Me | H |
| Me | OCHMeC≡CH | SO₂Me | H |
| Me | OCMe₂C≡CH | SO₂Me | H |
| Me | OCH₂C≡CMe | SO₂Me | H |
| Me | OCH₂F | SO₂Me | H |
| Me | OCH₂CHF₂ | SO₂Me | H |
| Me | OCH₂CF₃ | SO₂Me | H |
| Me | OCH₂CH₂Cl | SO₂Me | H |
| Me | OCH₂CCl₃ | SO₂Me | H |
| Me | OCHMeCH₂Cl | SO₂Me | H |
| Me | OCH₂CH₂CH₂Cl | SO₂Me | H |
| Me | OCH₂CH₂Br | SO₂Me | H |
| Me | Y8 | SO₂Me | H |
| Me | OCH₂CCl=CH₂ | SO₂Me | H |
| Me | OCH₂CCl=CHCl | SO₂Me | H |
| Me | OCH₂CH₂NO₂ | SO₂Me | H |
| Me | OPh | SO₂Me | H |
| Me | OPh—Me-2 | SO₂Me | H |
| Me | OPh—Cl-4 | SO₂Me | H |
| Me | OPh—NO₂-4 | SO₂Me | H |
| Me | OCH₂CH₂OMe | SO₂Me | H |
| Me | OCH₂CH₂OEt | SO₂Me | H |
| Me | OCH₂CH₂OPr-n | SO₂Me | H |
| Me | OCH₂CH₂OPr-i | SO₂Me | H |
| Me | OCH₂CH₂OBu-n | SO₂Me | H |
| Me | OCH₂CH₂OBu-i | SO₂Me | H |
| Me | OCH₂CH₂OBu-s | SO₂Me | H |
| Me | OCH₂CH₂OBu-t | SO₂Me | H |
| Me | OCH₂CH₂—Y4 | SO₂Me | H |
| Me | OCHMeCH₂OMe | SO₂Me | H |
| Me | OCH₂CHMeOMe | SO₂Me | H |
| Me | OCH₂CH₂OPh | SO₂Me | H |
| Me | OCH₂CH₂OCH₂CH₂OMe | SO₂Me | H |

TABLE 6-continued

| X | Y | Z | Q |
|---|---|---|---|
| Me | OCH₂CH₂OCH₂CH₂OPr-i | SO₂Me | H |
| Me | OCH₂CH₂OCHMeCH₂OMe | SO₂Me | H |
| Me | OCH₂CH₂OH | SO₂Me | H |
| Me | OCH₂Ph | SO₂Me | H |
| Me | OCHMePh | SO₂Me | H |
| Me | OCH₂CH₂Ph | SO₂Me | H |
| Me | OCH₂Ph-2-Cl | SO₂Me | H |
| Me | OCH₂Ph-3-Me | SO₂Me | H |
| Me | OCH₂Ph-4-OMe | SO₂Me | H |
| Me | OCH₂Ph-4-NO₂ | SO₂Me | H |
| Me | Y9 | SO₂Me | H |
| Me | Y10 | SO₂Me | H |
| Me | Y11 | SO₂Me | H |
| Me | Y12 | SO₂Me | H |
| Me | Y13 | SO₂Me | H |
| Me | Y14 | SO₂Me | H |
| Me | Y15 | SO₂Me | H |
| Me | Y16 | SO₂Me | H |
| Me | Y17 | SO₂Me | H |
| Me | Y18 | SO₂Me | H |
| Me | OCH₂CH₂NH₂ | SO₂Me | H |
| Me | OCH₂CH₂NHMe | SO₂Me | H |
| Me | OCH₂CH₂NHPr-i | SO₂Me | H |
| Me | OCH₂CH₂NMe₂ | SO₂Me | H |
| Me | OCH₂CH₂NEt₂ | SO₂Me | H |
| Me | Y19 | SO₂Me | H |
| Me | OCH₂COOMe | SO₂Me | H |
| Me | OCH₂COOEt | SO₂Me | H |
| Me | OCH₂COOPr-i | SO₂Me | H |
| Me | OCH₂COOBu-i | SO₂Me | H |
| Me | OCH₂COOBu-t | SO₂Me | H |
| Me | OCH₂COO—Y4 | SO₂Me | H |
| Me | OCHMeCOOMe | SO₂Me | H |
| Me | OCHMeCOOEt | SO₂Me | H |
| Me | OCHMeCOOPr-i | SO₂Me | H |
| Me | OCH₂CH₂CN | SO₂Me | H |
| Me | OCH₂SMe | SO₂Me | H |
| Me | OCH₂CH₂SMe | SO₂Me | H |
| Me | OCH₂CH₂S(O)Me | SO₂Me | H |
| Me | OCH₂CH₂SO₂Me | SO₂Me | H |
| Me | OCH₂CH₂SPr-i | SO₂Me | H |
| Me | OCH₂CH₂S(O)Pr-i | SO₂Me | H |
| Me | OCH₂CH₂SO₂Pr-i | SO₂Me | H |
| Me | OCOOMe | SO₂Me | H |
| Me | OCOOPr-i | SO₂Me | H |
| Me | OCONH₂ | SO₂Me | H |
| Me | OCONHMe | SO₂Me | H |
| Me | OCONMe₂ | SO₂Me | H |
| Me | OP(O)(OMe)₂ | SO₂Me | H |
| Me | Y20 | SO₂Me | H |
| Me | SCH₂CH=CH₂ | SO₂Me | H |
| Me | SCH₂CH=CMe₂ | SO₂Me | H |
| Me | SCH₂C≡CH | SO₂Me | H |
| Me | SCH₂CF₃ | SO₂Me | H |
| Me | SCH₂CCl₃ | SO₂Me | H |
| Me | Y21 | SO₂Me | H |
| Me | SPh | SO₂Me | H |
| Me | SCH₂CH₂OMe | SO₂Me | H |
| Me | SCH₂CH₂OEt | SO₂Me | H |
| Me | SCH₂CH₂OPr-i | SO₂Me | H |
| Me | Y22 | SO₂Me | H |
| Me | S(O)CH₂CH=CH₂ | SO₂Me | H |
| Me | S(O)CH₂CH=CMe₂ | SO₂Me | H |
| Me | S(O)CH₂C≡CH | SO₂Me | H |
| Me | S(O)CH₂CH₂Cl | SO₂Me | H |
| Me | Y23 | SO₂Me | H |
| Me | SO₂CH₂CH=CH₂ | SO₂Me | H |
| Me | SO₂CH₂CH=CMe₂ | SO₂Me | H |
| Me | SO₂CH₂C≡CH | SO₂Me | H |
| Me | SO₂CH₂CF₃ | SO₂Me | H |

TABLE 6-continued

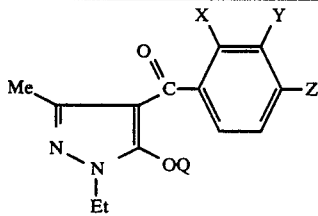

| X | Y | Z | Q |
|---|---|---|---|
| Me | SO₂CH₂CH₂Cl | SO₂Me | H |
| Me | Y24 | SO₂Me | H |
| Me | Y25 | SO₂Me | H |
| Me | SO₂Ph | SO₂Me | H |
| Me | SO₂CH₂CH₂OMe | SO₂Me | H |
| Me | SO₂CH₂CH₂OEt | SO₂Me | H |
| Me | SO₂CH₂CH₂OPr-i | SO₂Me | H |
| Me | OCH₂CH₂OMe | SO₂Me | CH₂Ph |
| Me | OCH₂CH₂OEt | SO₂Me | CH₂Ph |
| Me | OCH₂CH₂OPr-i | SO₂Me | CH₂Ph |
| Me | OCHMeCH₂OMe | SO₂Me | CH₂Ph |
| Me | OCH₂CH₂SMe | SO₂Me | CH₂Ph |
| Me | OCH₂CH₂S(O)Me | SO₂Me | CH₂Ph |
| Me | OCH₂CH₂SO₂Me | SO₂Me | CH₂Ph |
| Me | OCH₂CH₂SPr-i | SO₂Me | CH₂Ph |
| Me | OCH₂CH₂S(O)Pr-i | SO₂Me | CH₂Ph |
| Me | OCH₂CH₂SO₂Pr-i | SO₂Me | CH₂Ph |
| Me | SCH₂CH₂OMe | SO₂Me | CH₂Ph |
| Me | SCH₂CH₂OPr-i | SO₂Me | CH₂Ph |
| Me | SO₂CH₂CH₂OMe | SO₂Me | CH₂Ph |
| Me | SO₂CH₂CH₂OPr-i | SO₂Me | CH₂Ph |
| Me | OCH₂CH₂OMe | SO₂Me | CH₂COPh |
| Me | OCH₂CH₂OPr-i | SO₂Me | CH₂COPh |
| Me | OCH₂CH₂SMe | SO₂Me | CH₂COPh |
| Me | OCH₂CH₂SOMe | SO₂Me | CH₂COPh |
| Me | OCH₂CH₂SO₂Me | SO₂Me | CH₂COPh |
| Me | OCH₂CH₂SPr-i | SO₂Me | CH₂COPh |
| Me | OCH₂CH₂SO₂Pr-i | SO₂Me | CH₂COPh |
| Me | SCH₂CH₂OMe | SO₂Me | CH₂COPh |
| Me | SCH₂CH₂OPr-i | SO₂Me | CH₂COPh |
| Me | SO₂CH₂CH₂OMe | SO₂Me | CH₂COPh |
| Me | SO₂CH₂CH₂OPr-i | SO₂Me | CH₂COPh |
| Me | OCH₂CH₂OMe | Cl | H |
| Me | OCH₂CH₂OEt | Cl | H |
| Me | OCH₂CH₂OPr-i | Cl | H |
| Me | OCHMeCH₂OMe | Cl | H |
| Me | OCH₂COOMe | Cl | H |
| Me | OCH₂CH₂SMe | Cl | H |
| Me | OCH₂CH₂SO₂Me | Cl | H |
| Me | SCH₂CH₂OMe | Cl | H |
| Me | SO₂CH₂CH₂OMe | Cl | H |
| Me | OCH₂CH₂OMe | Cl | CH₂Ph |
| Me | OCH₂CH₂SMe | Cl | CH₂Ph |
| Me | OCH₂CH₂SOMe | Cl | CH₂Ph |
| Me | OCH₂CH₂SO₂Me | Cl | CH₂Ph |
| Me | SCH₂CH₂OMe | Cl | CH₂Ph |
| Me | SO₂CH₂CH₂OMe | Cl | CH₂Ph |
| Me | OCH₂CH₂OMe | Cl | CH₂COPh |
| Me | OCH₂CH₂SMe | Cl | CH₂COPh |
| Me | OCH₂CH₂SO₂Me | Cl | CH₂COPh |
| Me | SCH₂CH₂OMe | Cl | CH₂COPh |
| Me | SCH₂CH₂OEt | Cl | CH₂COPh |
| Me | SO₂CH₂CH₂OMe | Cl | CH₂COPh |
| Cl | Y1 | SO₂Me | H |
| Cl | Y2 | SO₂Me | H |
| Cl | Y3 | SO₂Me | H |
| Cl | Y4 | SO₂Me | H |
| Cl | Y5 | SO₂Me | H |
| Cl | Y6 | SO₂Me | H |
| Cl | Y7 | SO₂Me | H |
| Cl | OCH₂CH=CH₂ | SO₂Me | H |
| Cl | OCHMeCH=CH₂ | SO₂Me | H |
| Cl | OCMe₂CH=CH₂ | SO₂Me | H |
| Cl | OCH₂CMe=CH₂ | SO₂Me | H |
| Cl | OCH₂CH=CHMe | SO₂Me | H |
| Cl | OCH₂CH=CMe₂ | SO₂Me | H |
| Cl | OCH₂CH₂CH=CH₂ | SO₂Me | H |
| Cl | OCH₂C≡CH | SO₂Me | H |
| Cl | OCMeC≡CH | SO₂Me | H |
| Cl | OCMe₂C≡CH | SO₂Me | H |

TABLE 6-continued

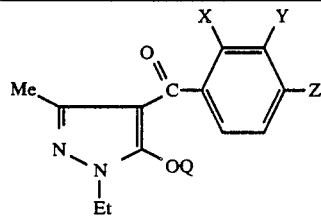

| X | Y | Z | Q |
|---|---|---|---|
| Cl | OCH₂C≡CMe | SO₂Me | H |
| Cl | OCH₂CH₂F | SO₂Me | H |
| Cl | OCH₂CHF₂ | SO₂Me | H |
| Cl | OCH₂CF₃ | SO₂Me | H |
| Cl | OCH₂CH₂Cl | SO₂Me | H |
| Cl | OCH₂CCl₃ | SO₂Me | H |
| Cl | OCHMeCH₂Cl | SO₂Me | H |
| Cl | OCH₂CH₂CH₂Cl | SO₂Me | H |
| Cl | OCH₂CH₂Br | SO₂Me | H |
| Cl | Y8 | SO₂Me | H |
| Cl | OCH₂CCl=CH₂ | SO₂Me | H |
| Cl | OCH₂CCl=CHCl | SO₂Me | H |
| Cl | OCH₂CH₂NO₂ | SO₂Me | H |
| Cl | OPh | SO₂Me | H |
| Cl | OPh—Me-2 | SO₂Me | H |
| Cl | OPh—Cl-4 | SO₂Me | H |
| Cl | OPh—NO₂-4 | SO₂Me | H |
| Cl | OCH₂CH₂OMe | SO₂Me | H |
| Cl | OCH₂CH₂OEt | SO₂Me | H |
| Cl | OCH₂CH₂OPr-n | SO₂Me | H |
| Cl | OCH₂CH₂OPr-i | SO₂Me | H |
| Cl | OCH₂CH₂OBu-n | SO₂Me | H |
| Cl | OCH₂CH₂OBu-i | SO₂Me | H |
| Cl | OCH₂CH₂OBu-s | SO₂Me | H |
| Cl | OCH₂CH₂OBu-t | SO₂Me | H |
| Cl | OCH₂CH₂—Y4 | SO₂Me | H |
| Cl | OCHMeCH₂OMe | SO₂Me | H |
| Cl | OCH₂CHMeOMe | SO₂Me | H |
| Cl | OCH₂CH₂OPh | SO₂Me | H |
| Cl | OCH₂CH₂OCH₂CH₂OMe | SO₂Me | H |
| Cl | OCH₂CH₂OCH₂CH₂OPr-i | SO₂Me | H |
| Cl | OCH₂CH₂OCHMeCH₂OMe | SO₂Me | H |
| Cl | OCH₂CH₂OH | SO₂Me | H |
| Cl | OCH₂Ph | SO₂Me | H |
| Cl | OCHMePh | SO₂Me | H |
| Cl | OCH₂CH₂Ph | SO₂Me | H |
| Cl | OCH₂Ph-2-Cl | SO₂Me | H |
| Cl | OCH₂Ph-3-Me | SO₂Me | H |
| Cl | OCH₂Ph-4-OMe | SO₂Me | H |
| Cl | OCH₂Ph-4-NO₂ | SO₂Me | H |
| Cl | Y9 | SO₂Me | H |
| Cl | Y10 | SO₂Me | H |
| Cl | Y11 | SO₂Me | H |
| Cl | Y12 | SO₂Me | H |
| Cl | Y13 | SO₂Me | H |
| Cl | Y14 | SO₂Me | H |
| Cl | Y15 | SO₂Me | H |
| Cl | Y16 | SO₂Me | H |
| Cl | Y17 | SO₂Me | H |
| Cl | Y18 | SO₂Me | H |
| Cl | OCH₂CH₂NH₂ | SO₂Me | H |
| Cl | OCH₂CH₂NHMe | SO₂Me | H |
| Cl | OCH₂CH₂NHPr-i | SO₂Me | H |
| Cl | OCH₂CH₂NMe₂ | SO₂Me | H |
| Cl | OCH₂CH₂NEt₂ | SO₂Me | H |
| Cl | Y19 | SO₂Me | H |
| Cl | OCH₂COOMe | SO₂Me | H |
| Cl | OCH₂COOEt | SO₂Me | H |
| Cl | OCH₂COOPr-i | SO₂Me | H |
| Cl | OCH₂COOBu-i | SO₂Me | H |
| Cl | OCH₂COOBu-t | SO₂Me | H |
| Cl | OCH₂COO—Y4 | SO₂Me | H |
| Cl | OCHMeCOOMe | SO₂Me | H |
| Cl | OCHMeCOOEt | SO₂Me | H |
| Cl | OCHMeCOOPr-i | SO₂Me | H |
| Cl | OCH₂CH₂CN | SO₂Me | H |
| Cl | OCH₂SMe | SO₂Me | H |
| Cl | OCH₂CH₂SMe | SO₂Me | H |
| Cl | OCH₂CH₂S(O)Me | SO₂Me | H |
| Cl | OCH₂CH₂SO₂Me | SO₂Me | H |

TABLE 6-continued

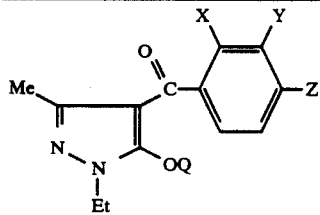

| X | Y | Z | Q |
|---|---|---|---|
| Cl | OCH$_2$CH$_2$SPr-i | SO$_2$Me | H |
| Cl | OCH$_2$CH$_2$S(O)Pr-i | SO$_2$Me | H |
| Cl | OCH$_2$CH$_2$SO$_2$Pr-i | SO$_2$Me | H |
| Cl | OCOOMe | SO$_2$Me | H |
| Cl | OCOOPr-i | SO$_2$Me | H |
| Cl | OCONH$_2$ | SO$_2$Me | H |
| Cl | OCONHMe | SO$_2$Me | H |
| Cl | OCONMe$_2$ | SO$_2$Me | H |
| Cl | OP(O)(OMe)$_2$ | SO$_2$Me | H |
| Cl | Y20 | SO$_2$Me | H |
| Cl | SCH$_2$CH=CH$_2$ | SO$_2$Me | H |
| Cl | SCH$_2$CH=CMe$_2$ | SO$_2$Me | H |
| Cl | SCH$_2$C≡CH | SO$_2$Me | H |
| Cl | SCH$_2$CF$_3$ | SO$_2$Me | H |
| Cl | SCH$_2$CCl$_3$ | SO$_2$Me | H |
| Cl | Y21 | SO$_2$Me | H |
| Cl | SPh | SO$_2$Me | H |
| Cl | SCH$_2$CH$_2$OMe | SO$_2$Me | H |
| Cl | SCH$_2$CH$_2$OEt | SO$_2$Me | H |
| Cl | SCH$_2$CH$_2$OPr-i | SO$_2$Me | H |
| Cl | Y22 | SO$_2$Me | H |
| Cl | S(O)CH$_2$CH=CH$_2$ | SO$_2$Me | H |
| Cl | S(O)CH$_2$CH=CMe$_2$ | SO$_2$Me | H |
| Cl | S(O)CH$_2$C≡CH | SO$_2$Me | H |
| Cl | S(O)CH$_2$CH$_2$Cl | SO$_2$Me | H |
| Cl | Y23 | SO$_2$Me | H |
| Cl | SO$_2$CH$_2$CH=CH$_2$ | SO$_2$Me | H |
| Cl | SO$_2$CH$_2$CH=CMe$_2$ | SO$_2$Me | H |
| Cl | SO$_2$CH$_2$C≡CH | SO$_2$Me | H |
| Cl | SO$_2$CH$_2$CF$_3$ | SO$_2$Me | H |
| Cl | SO$_2$CH$_2$CH$_2$Cl | SO$_2$Me | H |
| Cl | Y24 | SO$_2$Me | H |
| Cl | Y25 | SO$_2$Me | H |
| Cl | SO$_2$Ph | SO$_2$Me | H |
| Cl | SO$_2$CH$_2$CH$_2$OMe | SO$_2$Me | H |
| Cl | SO$_2$CH$_2$CH$_2$OEt | SO$_2$Me | H |
| Cl | SO$_2$CH$_2$CH$_2$OPr-i | SO$_2$Me | H |
| Cl | OCH$_2$CH$_2$OMe | SO$_2$Me | CH$_2$Ph |
| Cl | OCH$_2$CH$_2$OEt | SO$_2$Me | CH$_2$Ph |
| Cl | OCH$_2$CH$_2$OPr-i | SO$_2$Me | CH$_2$Ph |
| Cl | OCHMeCH$_2$OMe | SO$_2$Me | CH$_2$Ph |
| Cl | OCH$_2$CH$_2$SMe | SO$_2$Me | CH$_2$Ph |
| Cl | OCH$_2$CH$_2$S(O)Me | SO$_2$Me | CH$_2$Ph |
| Cl | OCH$_2$CH$_2$SO$_2$Me | SO$_2$Me | CH$_2$Ph |
| Cl | OCH$_2$CH$_2$SPr-i | SO$_2$Me | CH$_2$Ph |
| Cl | OCH$_2$CH$_2$S(O)Pr-i | SO$_2$Me | CH$_2$Ph |
| Cl | OCH$_2$CH$_2$SO$_2$Pr-i | SO$_2$Me | CH$_2$Ph |
| Cl | SCH$_2$CH$_2$OMe | SO$_2$Me | CH$_2$Ph |
| Cl | SCH$_2$CH$_2$OPr-i | SO$_2$Me | CH$_2$Ph |
| Cl | SO$_2$CH$_2$CH$_2$OMe | SO$_2$Me | CH$_2$Ph |
| Cl | SO$_2$CH$_2$CH$_2$OPr-i | SO$_2$Me | CH$_2$Ph |
| Cl | OCH$_2$CH$_2$OMe | SO$_2$Me | CH$_2$COPh |
| Cl | OCH$_2$CH$_2$OPr-i | SO$_2$Me | CH$_2$COPh |
| Cl | OCH$_2$CH$_2$SMe | SO$_2$Me | CH$_2$COPh |
| Cl | OCH$_2$CH$_2$SOMe | SO$_2$Me | CH$_2$COPh |
| Cl | OCH$_2$CH$_2$SO$_2$Me | SO$_2$Me | CH$_2$COPh |
| Cl | OCH$_2$CH$_2$SPr-i | SO$_2$Me | CH$_2$COPh |
| Cl | OCH$_2$CH$_2$SO$_2$Pr-i | SO$_2$Me | CH$_2$COPh |
| Cl | SCH$_2$CH$_2$OMe | SO$_2$Me | CH$_2$COPh |
| Cl | SCH$_2$CH$_2$OPr-i | SO$_2$Me | CH$_2$COPh |
| Cl | SO$_2$CH$_2$CH$_2$OMe | SO$_2$Me | CH$_2$COPh |
| Cl | SO$_2$CH$_2$CH$_2$OPr-i | SO$_2$Me | CH$_2$COPh |
| Cl | OCH$_2$CH$_2$OMe | Cl | H |
| Cl | OCH$_2$CH$_2$OEt | Cl | H |
| Cl | OCH$_2$CH$_2$OPr-i | Cl | H |
| Cl | OCHMeCH$_2$OMe | Cl | H |
| Cl | OCH$_2$COOMe | Cl | H |
| Cl | OCH$_2$CH$_2$SMe | Cl | H |
| Cl | OCH$_2$CH$_2$SO$_2$Me | Cl | H |
| Cl | SCH$_2$CH$_2$OMe | Cl | H |

TABLE 6-continued

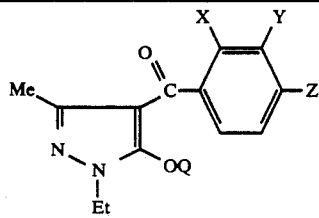

| X | Y | Z | Q |
|---|---|---|---|
| Cl | SO$_2$CH$_2$CH$_2$OMe | Cl | H |
| Cl | OCH$_2$CH$_2$OMe | Cl | CH$_2$Ph |
| Cl | OCH$_2$CH$_2$SMe | Cl | CH$_2$Ph |
| Cl | OCH$_2$CH$_2$SOMe | Cl | CH$_2$Ph |
| Cl | OCH$_2$CH$_2$SO$_2$Me | Cl | CH$_2$Ph |
| Cl | SCH$_2$CH$_2$OMe | Cl | CH$_2$Ph |
| Cl | SO$_2$CH$_2$CH$_2$OMe | Cl | CH$_2$Ph |
| Cl | OCH$_2$CH$_2$OMe | Cl | CH$_2$COPh |
| Cl | OCH$_2$CH$_2$SMe | Cl | CH$_2$COPh |
| Cl | OCH$_2$CH$_2$SO$_2$Me | Cl | CH$_2$COPh |
| Cl | SCH$_2$CH$_2$OMe | Cl | CH$_2$COPh |
| Cl | SCH$_2$CH$_2$OEt | Cl | CH$_2$COPh |
| Cl | SO$_2$CH$_2$CH$_2$OMe | Cl | CH$_2$COPh |
| OMe | Y1 | SO$_2$Me | H |
| OMe | Y2 | SO$_2$Me | H |
| OMe | Y3 | SO$_2$Me | H |
| OMe | Y4 | SO$_2$Me | H |
| OMe | Y5 | SO$_2$Me | H |
| OMe | Y6 | SO$_2$Me | H |
| OMe | Y7 | SO$_2$Me | H |
| OMe | OCH$_2$CH=CH$_2$ | SO$_2$Me | H |
| OMe | OCHMeCH=CH$_2$ | SO$_2$Me | H |
| OMe | OCMe$_2$CH=CH$_2$ | SO$_2$Me | H |
| OMe | OCH$_2$CMe=CH$_2$ | SO$_2$Me | H |
| OMe | OCH$_2$CH=CHMe | SO$_2$Me | H |
| OMe | OCH$_2$CH=CMe$_2$ | SO$_2$Me | H |
| OMe | OCH$_2$CH$_2$CH=CH$_2$ | SO$_2$Me | H |
| OMe | OCH$_2$C≡CH | SO$_2$Me | H |
| OMe | OCHMeC≡CH | SO$_2$Me | H |
| OMe | OCMe$_2$C≡CH | SO$_2$Me | H |
| OMe | OCH$_2$C≡CMe | SO$_2$Me | H |
| OMe | OCH$_2$CH$_2$F | SO$_2$Me | H |
| OMe | OCH$_2$CHF$_2$ | SO$_2$Me | H |
| OMe | OCH$_2$CF$_3$ | SO$_2$Me | H |
| OMe | OCH$_2$CH$_2$Cl | SO$_2$Me | H |
| OMe | OCH$_2$CCl$_3$ | SO$_2$Me | H |
| OMe | OCHMeCH$_2$Cl | SO$_2$Me | H |
| OMe | OCH$_2$CH$_2$CH$_2$Cl | SO$_2$Me | H |
| OMe | OCH$_2$CH$_2$Br | SO$_2$Me | H |
| OMe | Y8 | SO$_2$Me | H |
| OMe | OCH$_2$CCl=CH$_2$ | SO$_2$Me | H |
| OMe | OCH$_2$CCl=CHCl | SO$_2$Me | H |
| OMe | OCH$_2$CH$_2$NO$_2$ | SO$_2$Me | H |
| OMe | OPh | SO$_2$Me | H |
| OMe | OPh—Me-2 | SO$_2$Me | H |
| OMe | OPh—Cl-4 | SO$_2$Me | H |
| OMe | OPh—NO$_2$-4 | SO$_2$Me | H |
| OMe | OCH$_2$CH$_2$OMe | SO$_2$Me | H |
| OMe | OCH$_2$CH$_2$OEt | SO$_2$Me | H |
| OMe | OCH$_2$CH$_2$OPr-n | SO$_2$Me | H |
| OMe | OCH$_2$CH$_2$OPr-i | SO$_2$Me | H |
| OMe | OCH$_2$CH$_2$OBu-n | SO$_2$Me | H |
| OMe | OCH$_2$CH$_2$OBu-i | SO$_2$Me | H |
| OMe | OCH$_2$CH$_2$OBu-s | SO$_2$Me | H |
| OMe | OCH$_2$CH$_2$OBu-t | SO$_2$Me | H |
| OMe | OCH$_2$CH$_2$—Y4 | SO$_2$Me | H |
| OMe | OCHMeCH$_2$OMe | SO$_2$Me | H |
| OMe | OCH$_2$CHMeOMe | SO$_2$Me | H |
| OMe | OCH$_2$CH$_2$OPh | SO$_2$Me | H |
| OMe | OCH$_2$CH$_2$OCH$_2$CH$_2$OMe | SO$_2$Me | H |
| OMe | OCH$_2$CH$_2$OCH$_2$CH$_2$OPr-i | SO$_2$Me | H |
| OMe | OCH$_2$CH$_2$OCHMeCH$_2$OMe | SO$_2$Me | H |
| OMe | OCH$_2$CH$_2$OH | SO$_2$Me | H |
| OMe | OCH$_2$Ph | SO$_2$Me | H |
| OMe | OCHMePh | SO$_2$Me | H |
| OMe | OCH$_2$CH$_2$Ph | SO$_2$Me | H |
| OMe | OCH$_2$Ph-2-Cl | SO$_2$Me | H |
| OMe | OCH$_2$Ph-3-Me | SO$_2$Me | H |
| OMe | OCH$_2$Ph-4-OMe | SO$_2$Me | H |
| OMe | OCH$_2$Ph-4-NO$_2$ | SO$_2$Me | H |

TABLE 6-continued

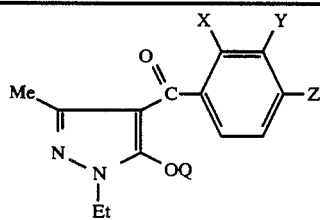

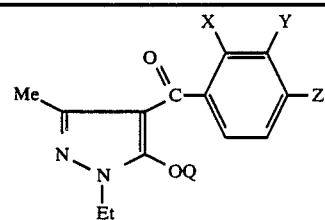

| X | Y | Z | Q |
|---|---|---|---|
| OMe | Y9 | SO$_2$Me | H |
| OMe | Y10 | SO$_2$Me | H |
| OMe | Y11 | SO$_2$Me | H |
| OMe | Y12 | SO$_2$Me | H |
| OMe | Y13 | SO$_2$Me | H |
| OMe | Y14 | SO$_2$Me | H |
| OMe | Y15 | SO$_2$Me | H |
| OMe | Y16 | SO$_2$Me | H |
| OMe | Y17 | SO$_2$Me | H |
| OMe | Y18 | SO$_2$Me | H |
| OMe | OCH$_2$CH$_2$NH$_2$ | SO$_2$Me | H |
| OMe | OCH$_2$CH$_2$NHMe | SO$_2$Me | H |
| OMe | OCH$_2$CH$_2$NHPr-i | SO$_2$Me | H |
| OMe | OCH$_2$CH$_2$NMe$_2$ | SO$_2$Me | H |
| OMe | OCH$_2$CH$_2$NEt$_2$ | SO$_2$Me | H |
| OMe | Y19 | SO$_2$Me | H |
| OMe | OCH$_2$COOMe | SO$_2$Me | H |
| OMe | OCH$_2$COOEt | SO$_2$Me | H |
| OMe | OCH$_2$COOPr-i | SO$_2$Me | H |
| OMe | OCH$_2$COOBu-i | SO$_2$Me | H |
| OMe | OCH$_2$COOBu-t | SO$_2$Me | H |
| OMe | OCH$_2$COO—Y4 | SO$_2$Me | H |
| OMe | OCHMeCOOMe | SO$_2$Me | H |
| OMe | OCHMeCOOEt | SO$_2$Me | H |
| OMe | OCHMeCOOPr-i | SO$_2$Me | H |
| OMe | OCH$_2$CH$_2$CN | SO$_2$Me | H |
| OMe | OCH$_2$SMe | SO$_2$Me | H |
| OMe | OCH$_2$CH$_2$SMe | SO$_2$Me | H |
| OMe | OCH$_2$CH$_2$S(O)Me | SO$_2$Me | H |
| OMe | OCH$_2$CH$_2$SO$_2$Me | SO$_2$Me | H |
| OMe | OCH$_2$CH$_2$SPr-i | SO$_2$Me | H |
| OMe | OCH$_2$CH$_2$S(O)Pr-i | SO$_2$Me | H |
| OMe | OCH$_2$CH$_2$SO$_2$Pr-i | SO$_2$Me | H |
| OMe | OCOOMe | SO$_2$Me | H |
| OMe | OCOOPr-i | SO$_2$Me | H |
| OMe | OCONH$_2$ | SO$_2$Me | H |
| OMe | OCONHMe | SO$_2$Me | H |
| OMe | OCONMe$_2$ | SO$_2$Me | H |
| OMe | OP(O)(OMe)$_2$ | SO$_2$Me | H |
| OMe | Y20 | SO$_2$Me | H |
| OMe | SCH$_2$CH=CH$_2$ | SO$_2$Me | H |
| OMe | SCH$_2$CH=CMe$_2$ | SO$_2$Me | H |
| OMe | SCH$_2$C≡CH | SO$_2$Me | H |
| OMe | SCH$_2$CF$_3$ | SO$_2$Me | H |
| OMe | SCH$_2$CCl$_3$ | SO$_2$Me | H |
| OMe | Y21 | SO$_2$Me | H |
| OMe | SPh | SO$_2$Me | H |
| OMe | SCH$_2$CH$_2$OMe | SO$_2$Me | H |
| OMe | SCH$_2$CH$_2$OEt | SO$_2$Me | H |
| OMe | SCH$_2$CH$_2$OPr-i | SO$_2$Me | H |
| OMe | Y22 | SO$_2$Me | H |
| OMe | S(O)CH$_2$CH=CH$_2$ | SO$_2$Me | H |
| OMe | S(O)CH$_2$CH=CMe$_2$ | SO$_2$Me | H |
| OMe | S(O)CH$_2$C≡CH | SO$_2$Me | H |
| OMe | S(O)CH$_2$CH$_2$Cl | SO$_2$Me | H |
| OMe | Y23 | SO$_2$Me | H |
| OMe | SO$_2$CH$_2$CH=CH$_2$ | SO$_2$Me | H |
| OMe | SO$_2$CH$_2$CH=CMe$_2$ | SO$_2$Me | H |
| OMe | SO$_2$CH$_2$C≡CH | SO$_2$Me | H |
| OMe | SO$_2$CH$_2$CF$_3$ | SO$_2$Me | H |
| OMe | SO$_2$CH$_2$CH$_2$Cl | SO$_2$Me | H |
| OMe | Y24 | SO$_2$Me | H |
| OMe | Y25 | SO$_2$Me | H |
| OMe | SO$_2$Ph | SO$_2$Me | H |
| OMe | SO$_2$CH$_2$CH$_2$OMe | SO$_2$Me | H |
| OMe | SO$_2$CH$_2$CH$_2$OEt | SO$_2$Me | H |
| OMe | SO$_2$CH$_2$CH$_2$OPr-i | SO$_2$Me | H |
| OMe | OCH$_2$CH$_2$OMe | SO$_2$Me | CH$_2$Ph |
| OMe | OCH$_2$CH$_2$OEt | SO$_2$Me | CH$_2$Ph |
| OMe | OCH$_2$CH$_2$OPr-i | SO$_2$Me | CH$_2$Ph |
| OMe | OCHMeCH$_2$OMe | SO$_2$Me | CH$_2$Ph |
| OMe | OCH$_2$CH$_2$SMe | SO$_2$Me | CH$_2$Ph |
| OMe | OCH$_2$CH$_2$S(O)Me | SO$_2$Me | CH$_2$Ph |
| OMe | OCH$_2$CH$_2$SO$_2$Me | SO$_2$Me | CH$_2$Ph |
| OMe | OCH$_2$CH$_2$SPr-i | SO$_2$Me | CH$_2$Ph |
| OMe | OCH$_2$CH$_2$S(O)Pr-i | SO$_2$Me | CH$_2$Ph |
| OMe | OCH$_2$CH$_2$SO$_2$Pr-i | SO$_2$Me | CH$_2$Ph |
| OMe | SCH$_2$CH$_2$OMe | SO$_2$Me | CH$_2$Ph |
| OMe | SCH$_2$CH$_2$OPr-i | SO$_2$Me | CH$_2$Ph |
| OMe | SO$_2$CH$_2$CH$_2$OMe | SO$_2$Me | CH$_2$Ph |
| OMe | SO$_2$CH$_2$CH$_2$OPr-i | SO$_2$Me | CH$_2$Ph |
| OMe | OCH$_2$CH$_2$OMe | SO$_2$Me | CH$_2$COPh |
| OMe | OCH$_2$CH$_2$OPr-i | SO$_2$Me | CH$_2$COPh |
| OMe | OCH$_2$CH$_2$SMe | SO$_2$Me | CH$_2$COPh |
| OMe | OCH$_2$CH$_2$SOMe | SO$_2$Me | CH$_2$COPh |
| OMe | OCH$_2$CH$_2$SO$_2$Me | SO$_2$Me | CH$_2$COPh |
| OMe | OCH$_2$CH$_2$SPr-i | SO$_2$Me | CH$_2$COPh |
| OMe | OCH$_2$CH$_2$SO$_2$Pr-i | SO$_2$Me | CH$_2$COPh |
| OMe | SCH$_2$CH$_2$OMe | SO$_2$Me | CH$_2$COPh |
| OMe | SCH$_2$CH$_2$OPr-i | SO$_2$Me | CH$_2$COPh |
| OMe | SO$_2$CH$_2$CH$_2$OMe | SO$_2$Me | CH$_2$COPh |
| OMe | SO$_2$CH$_2$CH$_2$OPr-i | SO$_2$Me | CH$_2$COPh |
| OMe | OCH$_2$CH$_2$OMe | Cl | H |
| OMe | OCH$_2$CH$_2$OEt | Cl | H |
| OMe | OCH$_2$CH$_2$OPr-i | Cl | H |
| OMe | OCHMeCH$_2$OMe | Cl | H |
| OMe | OCH$_2$COOMe | Cl | H |
| OMe | OCH$_2$CH$_2$SMe | Cl | H |
| OMe | OCH$_2$CH$_2$SO$_2$Me | Cl | H |
| OMe | SCH$_2$CH$_2$OMe | Cl | H |
| OMe | SO$_2$CH$_2$CH$_2$OMe | Cl | H |
| OMe | OCH$_2$CH$_2$OMe | Cl | CH$_2$Ph |
| OMe | OCH$_2$CH$_2$SMe | Cl | CH$_2$Ph |
| OMe | OCH$_2$CH$_2$SOMe | Cl | CH$_2$Ph |
| OMe | OCH$_2$CH$_2$SO$_2$Me | Cl | CH$_2$Ph |
| OMe | SCH$_2$CH$_2$OMe | Cl | CH$_2$Ph |
| OMe | SO$_2$CH$_2$CH$_2$OMe | Cl | CH$_2$Ph |
| OMe | OCH$_2$CH$_2$OMe | Cl | CH$_2$COPh |
| OMe | OCH$_2$CH$_2$SMe | Cl | CH$_2$COPh |
| OMe | OCH$_2$CH$_2$SO$_2$Me | Cl | CH$_2$COPh |
| OMe | SCH$_2$CH$_2$OMe | Cl | CH$_2$COPh |
| OMe | SCH$_2$CH$_2$OEt | Cl | CH$_2$COPh |
| OMe | SO$_2$CH$_2$CH$_2$OMe | Cl | CH$_2$COPh |
| CH$_2$OMe | Y1 | SO$_2$Me | H |
| CH$_2$OMe | Y2 | SO$_2$Me | H |
| CH$_2$OMe | Y3 | SO$_2$Me | H |
| CH$_2$OMe | Y4 | SO$_2$Me | H |
| CH$_2$OMe | Y5 | SO$_2$Me | H |
| CH$_2$OMe | Y6 | SO$_2$Me | H |
| CH$_2$OMe | Y7 | SO$_2$Me | H |
| CH$_2$OMe | OCH$_2$CH=CH$_2$ | SO$_2$Me | H |
| CH$_2$OMe | OCHMeCH=CH$_2$ | SO$_2$Me | H |
| CH$_2$OMe | OCMe$_2$CH=CH$_2$ | SO$_2$Me | H |
| CH$_2$OMe | OCH$_2$CMe=CH$_2$ | SO$_2$Me | H |
| CH$_2$OMe | OCH$_2$CH=CHMe | SO$_2$Me | H |
| CH$_2$OMe | OCH$_2$CH=CMe$_2$ | SO$_2$Me | H |
| CH$_2$OMe | OCH$_2$CH$_2$CH=CH$_2$ | SO$_2$Me | H |
| CH$_2$OMe | OCH$_2$C≡CH | SO$_2$Me | H |
| CH$_2$OMe | OCHMeC≡CH | SO$_2$Me | H |
| CH$_2$OMe | OCMe$_2$C≡CH | SO$_2$Me | H |
| CH$_2$OMe | OCH$_2$C≡CMe | SO$_2$Me | H |
| CH$_2$OMe | OCH$_2$CH$_2$F | SO$_2$Me | H |
| CH$_2$OMe | OCH$_2$CHF$_2$ | SO$_2$Me | H |
| CH$_2$OMe | OCH$_2$CF$_3$ | SO$_2$Me | H |
| CH$_2$OMe | OCH$_2$CH$_2$Cl | SO$_2$Me | H |
| CH$_2$OMe | OCH$_2$CCl$_3$ | SO$_2$Me | H |
| CH$_2$OMe | OCHMeCH$_2$Cl | SO$_2$Me | H |
| CH$_2$OMe | OCH$_2$CH$_2$CH$_2$Cl | SO$_2$Me | H |
| CH$_2$OMe | OCH$_2$CH$_2$Br | SO$_2$Me | H |
| CH$_2$OMe | Y8 | SO$_2$Me | H |

TABLE 6-continued

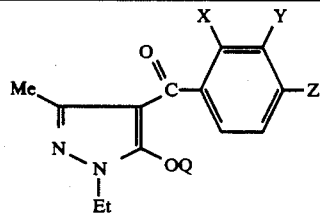

| X | Y | Z | Q |
|---|---|---|---|
| CH$_2$OMe | OCH$_2$CCl=CH$_2$ | SO$_2$Me | H |
| CH$_2$OMe | OCH$_2$CCl=CHCl | SO$_2$Me | H |
| CH$_2$OMe | OCH$_2$CH$_2$NO$_2$ | SO$_2$Me | H |
| CH$_2$OMe | OPh | SO$_2$Me | H |
| CH$_2$OMe | OPh—Me-2 | SO$_2$Me | H |
| CH$_2$OMe | OPh—Cl-4 | SO$_2$Me | H |
| CH$_2$OMe | OPh—NO$_2$-4 | SO$_2$Me | H |
| CH$_2$OMe | OCH$_2$CH$_2$OMe | SO$_2$Me | H |
| CH$_2$OMe | OCH$_2$CH$_2$OEt | SO$_2$Me | H |
| CH$_2$OMe | OCH$_2$CH$_2$OPr-n | SO$_2$Me | H |
| CH$_2$OMe | OCH$_2$CH$_2$OPr-i | SO$_2$Me | H |
| CH$_2$OMe | OCH$_2$CH$_2$OBu-n | SO$_2$Me | H |
| CH$_2$OMe | OCH$_2$CH$_2$OBu-i | SO$_2$Me | H |
| CH$_2$OMe | OCH$_2$CH$_2$OBu-s | SO$_2$Me | H |
| CH$_2$OMe | OCH$_2$CH$_2$OBu-t | SO$_2$Me | H |
| CH$_2$OMe | OCH$_2$CH$_2$—Y4 | SO$_2$Me | H |
| CH$_2$OMe | OCHMeCH$_2$OMe | SO$_2$Me | H |
| CH$_2$OMe | OCH$_2$CHMeOMe | SO$_2$Me | H |
| CH$_2$OMe | OCH$_2$CH$_2$OPh | SO$_2$Me | H |
| CH$_2$OMe | OCH$_2$CH$_2$OCH$_2$CH$_2$OMe | SO$_2$Me | H |
| CH$_2$OMe | OCH$_2$CH$_2$OCH$_2$CH$_2$OPr-i | SO$_2$Me | H |
| CH$_2$OMe | OCH$_2$CH$_2$OCHMeCH$_2$OMe | SO$_2$Me | H |
| CH$_2$OMe | OCH$_2$CH$_2$OH | SO$_2$Me | H |
| CH$_2$OMe | OCH$_2$Ph | SO$_2$Me | H |
| CH$_2$OMe | OCHMePh | SO$_2$Me | H |
| CH$_2$OMe | OCH$_2$CH$_2$Ph | SO$_2$Me | H |
| CH$_2$OMe | OCH$_2$Ph-2-Cl | SO$_2$Me | H |
| CH$_2$OMe | OCH$_2$Ph-3-Me | SO$_2$Me | H |
| CH$_2$OMe | OCH$_2$Ph-4-OMe | SO$_2$Me | H |
| CH$_2$OMe | OCH$_2$Ph-4-NO$_2$ | SO$_2$Me | H |
| CH$_2$OMe | Y9 | SO$_2$Me | H |
| CH$_2$OMe | Y10 | SO$_2$Me | H |
| CH$_2$OMe | Y11 | SO$_2$Me | H |
| CH$_2$OMe | Y12 | SO$_2$Me | H |
| CH$_2$OMe | Y13 | SO$_2$Me | H |
| CH$_2$OMe | Y14 | SO$_2$Me | H |
| CH$_2$OMe | Y15 | SO$_2$Me | H |
| CH$_2$OMe | Y16 | SO$_2$Me | H |
| CH$_2$OMe | Y17 | SO$_2$Me | H |
| CH$_2$OMe | Y18 | SO$_2$Me | H |
| CH$_2$OMe | OCH$_2$CH$_2$NH$_2$ | SO$_2$Me | H |
| CH$_2$OMe | OCH$_2$CH$_2$NHMe | SO$_2$Me | H |
| CH$_2$OMe | OCH$_2$CH$_2$NHPr-i | SO$_2$Me | H |
| CH$_2$OMe | OCH$_2$CH$_2$NMe$_2$ | SO$_2$Me | H |
| CH$_2$OMe | OCH$_2$CH$_2$NEt$_2$ | SO$_2$Me | H |
| CH$_2$OMe | Y19 | SO$_2$Me | H |
| CH$_2$OMe | OCH$_2$COOMe | SO$_2$Me | H |
| CH$_2$OMe | OCH$_2$COOEt | SO$_2$Me | H |
| CH$_2$OMe | OCH$_2$COOPr-i | SO$_2$Me | H |
| CH$_2$OMe | OCH$_2$COOBu-i | SO$_2$Me | H |
| CH$_2$OMe | OCH$_2$COOBu-t | SO$_2$Me | H |
| CH$_2$OMe | OCH$_2$COO—Y4 | SO$_2$Me | H |
| CH$_2$OMe | OCHMeCOOMe | SO$_2$Me | H |
| CH$_2$OMe | OCHMeCOOEt | SO$_2$Me | H |
| CH$_2$OMe | OCHMeCOOPr-i | SO$_2$Me | H |
| CH$_2$OMe | OCH$_2$CH$_2$CN | SO$_2$Me | H |
| CH$_2$OMe | OCH$_2$SMe | SO$_2$Me | H |
| CH$_2$OMe | OCH$_2$CH$_2$SMe | SO$_2$Me | H |
| CH$_2$OMe | OCH$_2$CH$_2$S(O)Me | SO$_2$Me | H |
| CH$_2$OMe | OCH$_2$CH$_2$SO$_2$Me | SO$_2$Me | H |
| CH$_2$OMe | OCH$_2$CH$_2$SPr-i | SO$_2$Me | H |
| CH$_2$OMe | OCH$_2$CH$_2$S(O)Pr-i | SO$_2$Me | H |
| CH$_2$OMe | OCH$_2$CH$_2$SO$_2$Pr-i | SO$_2$Me | H |
| CH$_2$OMe | OCOOMe | SO$_2$Me | H |
| CH$_2$OMe | OCOOPr-i | SO$_2$Me | H |
| CH$_2$OMe | OCONH$_2$ | SO$_2$Me | H |
| CH$_2$OMe | OCONHMe | SO$_2$Me | H |
| CH$_2$OMe | OCONMe$_2$ | SO$_2$Me | H |
| CH$_2$OMe | OP(O)(OMe)$_2$ | SO$_2$Me | H |
| CH$_2$OMe | Y20 | SO$_2$Me | H |

TABLE 6-continued

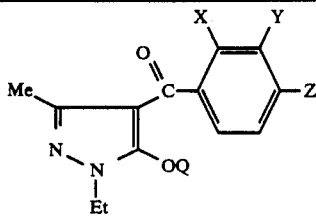

| X | Y | Z | Q |
|---|---|---|---|
| CH$_2$OMe | SCH$_2$CH=CH$_2$ | SO$_2$Me | H |
| CH$_2$OMe | SCH$_2$CH=CMe$_2$ | SO$_2$Me | H |
| CH$_2$OMe | SCH$_2$C≡CH | SO$_2$Me | H |
| CH$_2$OMe | SCH$_2$CF$_3$ | SO$_2$Me | H |
| CH$_2$OMe | SCH$_2$CCl$_3$ | SO$_2$Me | H |
| CH$_2$OMe | Y21 | SO$_2$Me | H |
| CH$_2$OMe | SPh | SO$_2$Me | H |
| CH$_2$OMe | SCH$_2$CH$_2$OMe | SO$_2$Me | H |
| CH$_2$OMe | SCH$_2$CH$_2$OEt | SO$_2$Me | H |
| CH$_2$OMe | SCH$_2$CH$_2$OPr-i | SO$_2$Me | H |
| CH$_2$OMe | Y22 | SO$_2$Me | H |
| CH$_2$OMe | S(O)CH$_2$CH=CH$_2$ | SO$_2$Me | H |
| CH$_2$OMe | S(O)CH$_2$CH=CMe$_2$ | SO$_2$Me | H |
| CH$_2$OMe | S(O)CH$_2$C≡CH | SO$_2$Me | H |
| CH$_2$OMe | S(O)CH$_2$CH$_2$Cl | SO$_2$Me | H |
| CH$_2$OMe | Y23 | SO$_2$Me | H |
| CH$_2$OMe | SO$_2$CH$_2$CH=CH$_2$ | SO$_2$Me | H |
| CH$_2$OMe | SO$_2$CH$_2$CH=CMe$_2$ | SO$_2$Me | H |
| CH$_2$OMe | SO$_2$CH$_2$C≡CH | SO$_2$Me | H |
| CH$_2$OMe | SO$_2$CH$_2$CF$_3$ | SO$_2$Me | H |
| CH$_2$OMe | SO$_2$CH$_2$Cl | SO$_2$Me | H |
| CH$_2$OMe | Y24 | SO$_2$Me | H |
| CH$_2$OMe | SO$_2$Ph | SO$_2$Me | H |
| CH$_2$OMe | SO$_2$CH$_2$CH$_2$OMe | SO$_2$Me | H |
| CH$_2$OMe | SO$_2$CH$_2$CH$_2$OEt | SO$_2$Me | H |
| CH$_2$OMe | SO$_2$CH$_2$CH$_2$OPr-i | SO$_2$Me | H |
| CH$_2$OMe | OCH$_2$CH$_2$OMe | SO$_2$Me | CH$_2$Ph |
| CH$_2$OMe | OCH$_2$CH$_2$OEt | SO$_2$Me | CH$_2$Ph |
| CH$_2$OMe | OCH$_2$CH$_2$OPr-i | SO$_2$Me | CH$_2$Ph |
| CH$_2$OMe | OCHMeCH$_2$OMe | SO$_2$Me | CH$_2$Ph |
| CH$_2$OMe | OCH$_2$CH$_2$SMe | SO$_2$Me | CH$_2$Ph |
| CH$_2$OMe | OCH$_2$CH$_2$S(O)Me | SO$_2$Me | CH$_2$Ph |
| CH$_2$OMe | OCH$_2$CH$_2$SO$_2$Me | SO$_2$Me | CH$_2$Ph |
| CH$_2$OMe | OCH$_2$CH$_2$SPr-i | SO$_2$Me | CH$_2$Ph |
| CH$_2$OMe | OCH$_2$CH$_2$S(O)Pr-i | SO$_2$Me | CH$_2$Ph |
| CH$_2$OMe | OCH$_2$CH$_2$SO$_2$Pr-i | SO$_2$Me | CH$_2$Ph |
| CH$_2$OMe | SCH$_2$CH$_2$OMe | SO$_2$Me | CH$_2$Ph |
| CH$_2$OMe | SCH$_2$CH$_2$OPr-i | SO$_2$Me | CH$_2$Ph |
| CH$_2$OMe | SO$_2$CH$_2$CH$_2$OMe | SO$_2$Me | CH$_2$Ph |
| CH$_2$OMe | SO$_2$CH$_2$CH$_2$OPr-i | SO$_2$Me | CH$_2$Ph |
| CH$_2$OMe | OCH$_2$CH$_2$OMe | SO$_2$Me | CH$_2$COPh |
| CH$_2$OMe | OCH$_2$CH$_2$OPr-i | SO$_2$Me | CH$_2$COPh |
| CH$_2$OMe | OCH$_2$CH$_2$SMe | SO$_2$Me | CH$_2$COPh |
| CH$_2$OMe | OCH$_2$CH$_2$SOMe | SO$_2$Me | CH$_2$COPh |
| CH$_2$OMe | OCH$_2$CH$_2$SO$_2$Me | SO$_2$Me | CH$_2$COPh |
| CH$_2$OMe | OCH$_2$CH$_2$SPr-i | SO$_2$Me | CH$_2$COPh |
| CH$_2$OMe | OCH$_2$CH$_2$SO$_2$Pr-i | SO$_2$Me | CH$_2$COPh |
| CH$_2$OMe | SCH$_2$CH$_2$OMe | SO$_2$Me | CH$_2$COPh |
| CH$_2$OMe | SCH$_2$CH$_2$OPr-i | SO$_2$Me | CH$_2$COPh |
| CH$_2$OMe | SO$_2$CH$_2$CH$_2$OMe | SO$_2$Me | CH$_2$COPh |
| CH$_2$OMe | SO$_2$CH$_2$CH$_2$OPr-i | SO$_2$Me | CH$_2$COPh |
| CH$_2$OMe | OCH$_2$CH$_2$OMe | Cl | H |
| CH$_2$OMe | OCH$_2$CH$_2$OEt | Cl | H |
| CH$_2$OMe | OCH$_2$CH$_2$OPr-i | Cl | H |
| CH$_2$OMe | OCHMeCH$_2$OMe | Cl | H |
| CH$_2$OMe | OCH$_2$COOMe | Cl | H |
| CH$_2$OMe | OCH$_2$CH$_2$SMe | Cl | H |
| CH$_2$OMe | OCH$_2$CH$_2$SO$_2$Me | Cl | H |
| CH$_2$OMe | SCH$_2$CH$_2$OMe | Cl | H |
| CH$_2$OMe | SO$_2$CH$_2$CH$_2$OMe | Cl | H |
| CH$_2$OMe | OCH$_2$CH$_2$OMe | Cl | CH$_2$Ph |
| CH$_2$OMe | OCH$_2$CH$_2$SMe | Cl | CH$_2$Ph |
| CH$_2$OMe | OCH$_2$CH$_2$SOMe | Cl | CH$_2$Ph |
| CH$_2$OMe | OCH$_2$CH$_2$SO$_2$Me | Cl | CH$_2$Ph |
| CH$_2$OMe | SCH$_2$CH$_2$OMe | Cl | CH$_2$Ph |
| CH$_2$OMe | SO$_2$CH$_2$CH$_2$OMe | Cl | CH$_2$Ph |
| CH$_2$OMe | OCH$_2$CH$_2$OMe | Cl | CH$_2$COPh |
| CH$_2$OMe | OCH$_2$CH$_2$SMe | Cl | CH$_2$COPh |
| CH$_2$OMe | OCH$_2$CH$_2$SO$_2$Me | Cl | CH$_2$COPh |
| CH$_2$OMe | SCH$_2$CH$_2$OMe | Cl | CH$_2$COPh |

TABLE 6-continued

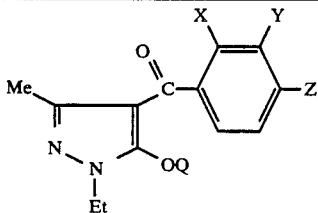

| X | Y | Z | Q |
|---|---|---|---|
| CH₂OMe | SCH₂CH₂OEt | Cl | CH₂COPh |
| CH₂OMe | SO₂CH₂CH₂OMe | Cl | CH₂COPh |

TABLE 7

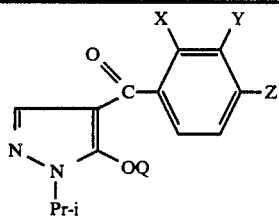

| X | Y | Z | Q |
|---|---|---|---|
| Me | Y1 | SO₂Me | H |
| Me | Y2 | SO₂Me | H |
| Me | Y3 | SO₂Me | H |
| Me | Y4 | SO₂Me | H |
| Me | Y5 | SO₂Me | H |
| Me | Y6 | SO₂Me | H |
| Me | Y7 | SO₂Me | H |
| Me | OCH₂CH=CH₂ | SO₂Me | H |
| Me | OCHMeCH=CH₂ | SO₂Me | H |
| Me | OCMe₂CH=CH₂ | SO₂Me | H |
| Me | OCH₂CMe=CH₂ | SO₂Me | H |
| Me | OCH₂CH=CHMe | SO₂Me | H |
| Me | OCH₂CH=CMe₂ | SO₂Me | H |
| Me | OCH₂CH₂CH=CH₂ | SO₂Me | H |
| Me | OCH₂C≡CH | SO₂Me | H |
| Me | OCHMeC≡CH | SO₂Me | H |
| Me | OCMe₂C≡CH | SO₂Me | H |
| Me | OCH₂C≡CMe | SO₂Me | H |
| Me | OCH₂CH₂F | SO₂Me | H |
| Me | OCH₂CHF₂ | SO₂Me | H |
| Me | OCH₂CF₃ | SO₂Me | H |
| Me | OCH₂CH₂Cl | SO₂Me | H |
| Me | OCH₂CCl₃ | SO₂Me | H |
| Me | OCHMeCH₂Cl | SO₂Me | H |
| Me | OCH₂CH₂CH₂Cl | SO₂Me | H |
| Me | OCH₂CH₂Br | SO₂Me | H |
| Me | Y8 | SO₂Me | H |
| Me | OCH₂CCl=CH₂ | SO₂Me | H |
| Me | OCH₂CCl=CHCl | SO₂Me | H |
| Me | OCH₂CH₂NO₂ | SO₂Me | H |
| Me | OPh | SO₂Me | H |
| Me | OPh—Me-2 | SO₂Me | H |
| Me | OPh—Cl-4 | SO₂Me | H |
| Me | OPh—NO₂-4 | SO₂Me | H |
| Me | OCH₂CH₂OMe | SO₂Me | H |
| Me | OCH₂CH₂OEt | SO₂Me | H |
| Me | OCH₂CH₂OPr-n | SO₂Me | H |
| Me | OCH₂CH₂OPr-i | SO₂Me | H |
| Me | OCH₂CH₂OBu-n | SO₂Me | H |
| Me | OCH₂CH₂OBu-i | SO₂Me | H |
| Me | OCH₂CH₂OBu-s | SO₂Me | H |
| Me | OCH₂CH₂OBu-t | SO₂Me | H |
| Me | OCH₂CH₂-Y4 | SO₂Me | H |
| Me | OCHMeCH₂OMe | SO₂Me | H |
| Me | OCH₂CHMeOMe | SO₂Me | H |
| Me | OCH₂CH₂OPh | SO₂Me | H |
| Me | OCH₂CH₂OCH₂CH₂OMe | SO₂Me | H |
| Me | OCH₂CH₂OCH₂CH₂OPr-i | SO₂Me | H |
| Me | OCH₂CH₂OCHMeCH₂OMe | SO₂Me | H |
| Me | OCH₂CH₂OH | SO₂Me | H |
| Me | OCH₂Ph | SO₂Me | H |

TABLE 7-continued

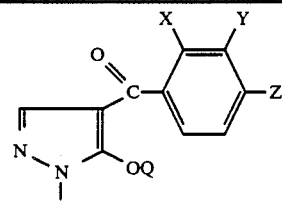

| X | Y | Z | Q |
|---|---|---|---|
| Me | OCHMePh | SO₂Me | H |
| Me | OCH₂CH₂Ph | SO₂Me | H |
| Me | OCH₂Ph-2-Cl | SO₂Me | H |
| Me | OCH₂Ph-3-Me | SO₂Me | H |
| Me | OCH₂Ph-4-OMe | SO₂Me | H |
| Me | OCH₂Ph-4-NO₂ | SO₂Me | H |
| Me | Y9 | SO₂Me | H |
| Me | Y10 | SO₂Me | H |
| Me | Y11 | SO₂Me | H |
| Me | Y12 | SO₂Me | H |
| Me | Y13 | SO₂Me | H |
| Me | Y14 | SO₂Me | H |
| Me | Y15 | SO₂Me | H |
| Me | Y16 | SO₂Me | H |
| Me | Y17 | SO₂Me | H |
| Me | Y18 | SO₂Me | H |
| Me | OCH₂CH₂NH₂ | SO₂Me | H |
| Me | OCH₂CH₂NHMe | SO₂Me | H |
| Me | OCH₂CH₂NHPr-i | SO₂Me | H |
| Me | OCH₂CH₂NMe₂ | SO₂Me | H |
| Me | OCH₂CH₂NEt₂ | SO₂Me | H |
| Me | Y19 | SO₂Me | H |
| Me | OCH₂COOMe | SO₂Me | H |
| Me | OCH₂COOEt | SO₂Me | H |
| Me | OCH₂COOPr-i | SO₂Me | H |
| Me | OCH₂COOBu-i | SO₂Me | H |
| Me | OCH₂COOBu-t | SO₂Me | H |
| Me | OCH₂COO-Y4 | SO₂Me | H |
| Me | OCHMeCOOMe | SO₂Me | H |
| Me | OCHMeCOOEt | SO₂Me | H |
| Me | OCHMeCOOPr-i | SO₂Me | H |
| Me | OCH₂CH₂CN | SO₂Me | H |
| Me | OCH₂SMe | SO₂Me | H |
| Me | OCH₂CH₂SMe | SO₂Me | H |
| Me | OCH₂CH₂S(O)Me | SO₂Me | H |
| Me | OCH₂CH₂SO₂Me | SO₂Me | H |
| Me | OCH₂CH₂SPr-i | SO₂Me | H |
| Me | OCH₂CH₂S(O)Pr-i | SO₂Me | H |
| Me | OCH₂CH₂SO₂Pr-i | SO₂Me | H |
| Me | OCOOMe | SO₂Me | H |
| Me | OCOOPr-i | SO₂Me | H |
| Me | OCONHG₂ | SO₂Me | H |
| Me | OCONHMe | SO₂Me | H |
| Me | OCONMe₂ | SO₂Me | H |
| Me | OP(O)(OMe)₂ | SO₂Me | H |
| Me | Y20 | SO₂Me | H |
| Me | SCH₂CH=CH₂ | SO₂Me | H |
| Me | SCH₂CH=CMe₂ | SO₂Me | H |
| Me | SCH₂C≡CH | SO₂Me | H |
| Me | SCH₂CF₃ | SO₂Me | H |
| Me | SCH₂CCl₃ | SO₂Me | H |
| Me | Y21 | SO₂Me | H |
| Me | SPh | SO₂Me | H |
| Me | SCH₂CH₂OMe | SO₂Me | H |
| Me | SCH₂CH₂OEt | SO₂Me | H |
| Me | SCH₂CH₂OPr-i | SO₂Me | H |
| Me | Y22 | SO₂Me | H |
| Me | S(O)CH₂CH=CH₂ | SO₂Me | H |
| Me | S(O)CH₂CH=CMe₂ | SO₂Me | H |
| Me | S(O)CH₂C≡CH | SO₂Me | H |
| Me | S(O)CH₂CH₂Cl | SO₂Me | H |
| Me | Y23 | SO₂Me | H |
| Me | SO₂CH₂CH=CH₂ | SO₂Me | H |
| Me | SO₂CH₂CH=CMe₂ | SO₂Me | H |
| Me | SO₂CH₂C≡CH | SO₂Me | H |
| Me | SO₂CH₂CF₃ | SO₂Me | H |
| Me | SO₂CH₂CH₂Cl | SO₂Me | H |
| Me | Y24 | SO₂Me | H |
| Me | Y25 | SO₂Me | H |
| Me | SO₂Ph | SO₂Me | H |

TABLE 7-continued

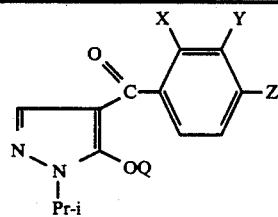

| X | Y | Z | Q |
|---|---|---|---|
| Me | SO₂CH₂CH₂OMe | SO₂Me | H |
| Me | SO₂CH₂CH₂OEt | SO₂Me | H |
| Me | SO₂CH₂CH₂OPr-i | SO₂Me | H |
| Me | OCH₂CH₂OMe | SO₂Me | CH₂Ph |
| Me | OCH₂CH₂OEt | SO₂Me | CH₂Ph |
| Me | OCH₂CH₂OPr-i | SO₂Me | CH₂Ph |
| Me | OCHMeCH₂OMe | SO₂Me | CH₂Ph |
| Me | OCH₂CH₂SMe | SO₂Me | CH₂Ph |
| Me | OCH₂CH₂S(O)Me | SO₂Me | CH₂Ph |
| Me | OCH₂CH₂SO₂Me | SO₂Me | CH₂Ph |
| Me | OCH₂CH₂SPr-i | SO₂Me | CH₂Ph |
| Me | OCH₂CH₂S(O)Pr-i | SO₂Me | CH₂Ph |
| Me | OCH₂CH₂SO₂Pr-i | SO₂Me | CH₂Ph |
| Me | SCH₂CH₂OMe | SO₂Me | CH₂Ph |
| Me | SCH₂CH₂OPr-i | SO₂Me | CH₂Ph |
| Me | SO₂CH₂CH₂OMe | SO₂Me | CH₂Ph |
| Me | SO₂CH₂CH₂OPr-i | SO₂Me | CH₂Ph |
| Me | OCH₂CH₂OMe | SO₂Me | CH₂COPh |
| Me | OCH₂CH₂OPr-i | SO₂Me | CH₂COPh |
| Me | OCH₂CH₂SMe | SO₂Me | CH₂COPh |
| Me | OCH₂CH₂SOMe | SO₂Me | CH₂COPh |
| Me | OCH₂CH₂SO₂Me | SO₂Me | CH₂COPh |
| Me | OCH₂CH₂SPr-i | SO₂Me | CH₂COPh |
| Me | OCH₂CH₂SO₂Pr-i | SO₂Me | CH₂COPh |
| Me | SCH₂CH₂OMe | SO₂Me | CH₂COPh |
| Me | SCH₂CH₂OPr-i | SO₂Me | CH₂COPh |
| Me | SO₂CH₂CH₂OMe | SO₂Me | CH₂COPh |
| Me | SO₂CH₂CH₂OPr-i | SO₂Me | CH₂COPh |
| Me | OCH₂CH₂OMe | Cl | H |
| Me | OCH₂CH₂OEt | Cl | H |
| Me | OCH₂CH₂OPr-i | Cl | H |
| Me | OCHMeCH₂OMe | Cl | H |
| Me | OCH₂COOMe | Cl | H |
| Me | OCH₂CH₂SMe | Cl | H |
| Me | OCH₂CH₂SO₂Me | Cl | H |
| Me | SCH₂CH₂OMe | Cl | H |
| Me | SO₂CH₂CH₂OMe | Cl | H |
| Me | OCH₂CH₂OMe | Cl | CH₂Ph |
| Me | OCH₂CH₂SMe | Cl | CH₂Ph |
| Me | OCH₂CH₂SOMe | Cl | CH₂Ph |
| Me | OCH₂CH₂SO₂Me | Cl | CH₂Ph |
| Me | SCH₂CH₂OMe | Cl | CH₂Ph |
| Me | SO₂CH₂CH₂OMe | Cl | CH₂Ph |
| Me | OCH₂CH₂OMe | Cl | CH₂COPh |
| Me | OCH₂CH₂SMe | Cl | CH₂COPh |
| Me | OCH₂CH₂SO₂Me | Cl | CH₂COPh |
| Me | SCH₂CH₂OMe | Cl | CH₂COPh |
| Me | SCH₂CH₂OEt | Cl | CH₂COPh |
| Me | SO₂CH₂CH₂OMe | Cl | CH₂COPh |
| Cl | Y1 | SO₂Me | H |
| Cl | Y2 | SO₂Me | H |
| Cl | Y3 | SO₂Me | H |
| Cl | Y4 | SO₂Me | H |
| Cl | Y5 | SO₂Me | H |
| Cl | Y6 | SO₂Me | H |
| Cl | Y7 | SO₂Me | H |
| Cl | OCH₂CH=CH₂ | SO₂Me | H |
| Cl | OCHMeCH=CH₂ | SO₂Me | H |
| Cl | OCMe₂CH=CH₂ | SO₂Me | H |
| Cl | OCH₂CMe=CH₂ | SO₂Me | H |
| Cl | OCH₂CH=CHMe | SO₂Me | H |
| Cl | OCH₂CH=CMe₂ | SO₂Me | H |
| Cl | OCH₂CH₂CH=CH₂ | SO₂Me | H |
| Cl | OCH₂C≡CH | SO₂Me | H |
| Cl | OCHMeC≡CH | SO₂Me | H |
| Cl | OCMe₂C≡CH | SO₂Me | H |
| Cl | OCH₂C≡CMe | SO₂Me | H |
| Cl | OCH₂CH₂F | SO₂Me | H |
| Cl | OCH₂CHF₂ | SO₂Me | H |

TABLE 7-continued

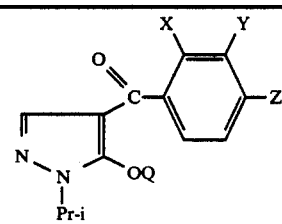

| X | Y | Z | Q |
|---|---|---|---|
| Cl | OCH₂CF₃ | SO₂Me | H |
| Cl | OCH₂CH₂Cl | SO₂Me | H |
| Cl | OCH₂CCl₃ | SO₂Me | H |
| Cl | OCHMeCH₂Cl | SO₂Me | H |
| Cl | OCH₂CH₂CH₂Cl | SO₂Me | H |
| Cl | OCH₂CH₂Br | SO₂Me | H |
| Cl | Y8 | SO₂Me | H |
| Cl | OCH₂CCl=CH₂ | SO₂Me | H |
| Cl | OCH₂CCl=CHCl | SO₂Me | H |
| Cl | OCH₂CH₂NO₂ | SO₂Me | H |
| Cl | OPh | SO₂Me | H |
| Cl | OPh-Me-2 | SO₂Me | H |
| Cl | OPh-Cl-4 | SO₂Me | H |
| Cl | OPh-NO₂-4 | SO₂Me | H |
| Cl | OCH₂CH₂OMe | SO₂Me | H |
| Cl | OCH₂CH₂OEt | SO₂Me | H |
| Cl | OCH₂CH₂OPr-n | SO₂Me | H |
| Cl | OCH₂CH₂OPr-i | SO₂Me | H |
| Cl | OCH₂CH₂OBu-n | SO₂Me | H |
| Cl | OCH₂CH₂OBu-i | SO₂Me | H |
| Cl | OCH₂CH₂OBu-s | SO₂Me | H |
| Cl | OCH₂CH₂OBu-t | SO₂Me | H |
| Cl | OCH₂CH₂-Y4 | SO₂Me | H |
| Cl | OCHMeCH₂OMe | SO₂Me | H |
| Cl | OCH₂CHMeOMe | SO₂Me | H |
| Cl | OCH₂CH₂OPh | SO₂Me | H |
| Cl | OCH₂CH₂OCH₂CH₂OMe | SO₂Me | H |
| Cl | OCH₂CH₂OCH₂CH₂OPr-i | SO₂Me | H |
| Cl | OCH₂CH₂OCHMeCH₂OMe | SO₂Me | H |
| Cl | OCH₂CH₂OH | SO₂Me | H |
| Cl | OCH₂Ph | SO₂Me | H |
| Cl | OCHMePh | SO₂Me | H |
| Cl | OCH₂CH₂Ph | SO₂Me | H |
| Cl | OCH₂Ph-2-Cl | SO₂Me | H |
| Cl | OCH₂Ph-3-Me | SO₂Me | H |
| Cl | OCH₂Ph-4-OMe | SO₂Me | H |
| Cl | OCH₂Ph-4-NO₂ | SO₂Me | H |
| Cl | Y9 | SO₂Me | H |
| Cl | Y10 | SO₂Me | H |
| Cl | Y11 | SO₂Me | H |
| Cl | Y12 | SO₂Me | H |
| Cl | Y13 | SO₂Me | H |
| Cl | Y14 | SO₂Me | H |
| Cl | Y15 | SO₂Me | H |
| Cl | Y16 | SO₂Me | H |
| Cl | Y17 | SO₂Me | H |
| Cl | Y18 | SO₂Me | H |
| Cl | OCH₂CH₂NH₂ | SO₂Me | H |
| Cl | OCH₂CH₂NHMe | SO₂Me | H |
| Cl | OCH₂CH₂NHPr-i | SO₂Me | H |
| Cl | OCH₂CH₂NMe₂ | SO₂Me | H |
| Cl | OCH₂CH₂NEt₂ | SO₂Me | H |
| Cl | Y19 | SO₂Me | H |
| Cl | OCH₂COOMe | SO₂Me | H |
| Cl | OCH₂COOEt | SO₂Me | H |
| Cl | OCH₂COOPr-i | SO₂Me | H |
| Cl | OCH₂COOBu-i | SO₂Me | H |
| Cl | OCH₂COOBu-t | SO₂Me | H |
| Cl | OCH₂COO-Y4 | SO₂Me | H |
| Cl | OCHMeCOOMe | SO₂Me | H |
| Cl | OCHMeCOOEt | SO₂Me | H |
| Cl | OCHMeCOOPr-i | SO₂Me | H |
| Cl | OCH₂CH₂CN | SO₂Me | H |
| Cl | OCH₂SMe | SO₂Me | H |
| Cl | OCH₂CH₂SMe | SO₂Me | H |
| Cl | OCH₂CH₂S(O)Me | SO₂Me | H |
| Cl | OCH₂CH₂SO₂Me | SO₂Me | H |
| Cl | OCH₂CH₂SPr-i | SO₂Me | H |
| Cl | OCH₂CH₂S(O)Pr-i | SO₂Me | H |
| Cl | OCH₂CH₂SO₂Pr-i | SO₂Me | H |

TABLE 7-continued

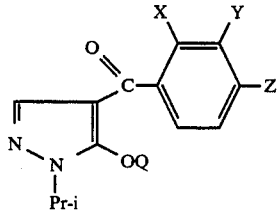

| X | Y | Z | Q |
|---|---|---|---|
| Cl | OCOOMe | SO₂Me | H |
| Cl | OCOOPr-i | SO₂Me | H |
| Cl | OCONH₂ | SO₂Me | H |
| Cl | OCONHMe | SO₂Me | H |
| Cl | OCONMe₂ | SO₂Me | H |
| Cl | OP(O)(OMe)₂ | SO₂Me | H |
| Cl | Y20 | SO₂Me | H |
| Cl | SCH₂CH=CH₂ | SO₂Me | H |
| Cl | SCH₂CH=CMe₂ | SO₂Me | H |
| Cl | SCH₂C≡CH | SO₂Me | H |
| Cl | SCH₂CF₃ | SO₂Me | H |
| Cl | SCH₂CCl₃ | SO₂Me | H |
| Cl | Y21 | SO₂Me | H |
| Cl | SPh | SO₂Me | H |
| Cl | SCH₂CH₂OMe | SO₂Me | H |
| Cl | SCH₂CH₂OEt | SO₂Me | H |
| Cl | SCH₂CH₂OPr-i | SO₂Me | H |
| Cl | Y22 | SO₂Me | H |
| Cl | S(O)CH₂CH=CH₂ | SO₂Me | H |
| Cl | S(O)CH₂CH=CMe₂ | SO₂Me | H |
| Cl | S(O)CH₂C≡CH | SO₂Me | H |
| Cl | S(O)CH₂CH₂Cl | SO₂Me | H |
| Cl | Y23 | SO₂Me | H |
| Cl | SO₂CH₂CH=CH₂ | SO₂Me | H |
| Cl | SO₂CH₂CH=CMe₂ | SO₂Me | H |
| Cl | SO₂CH₂C≡CH | SO₂Me | H |
| Cl | SO₂CH₂CF₃ | SO₂Me | H |
| Cl | SO₂CH₂CH₂Cl | SO₂Me | H |
| Cl | Y24 | SO₂Me | H |
| Cl | Y25 | SO₂Me | H |
| Cl | SO₂Ph | SO₂Me | H |
| Cl | SO₂CH₂CH₂OMe | SO₂Me | H |
| Cl | SO₂CH₂cH₂OEt | SO₂Me | H |
| Cl | SO₂CH₂CH₂OPr-i | SO₂Me | H |
| Cl | OCH₂CH₂OMe | SO₂Me | CH₂Ph |
| Cl | OCH₂CH₂OEt | SO₂Me | CH₂Ph |
| Cl | OCH₂CH₂OPr-i | SO₂Me | CH₂Ph |
| Cl | OCHMeCH₂OMe | SO₂Me | CH₂Ph |
| Cl | OCH₂CH₂SMe | SO₂Me | CH₂Ph |
| Cl | OCH₂CH₂S(O)Me | SO₂Me | CH₂Ph |
| Cl | OCH₃CH₂SO₂Me | SO₂Me | CH₂Ph |
| Cl | OCH₂CH₂SPr-i | SO₂Me | CH₂Ph |
| Cl | OCH₂CH₂S(O)Pr-i | SO₂Me | CH₂Ph |
| Cl | OCH₂CH₂SO₂Pr-i | SO₂Me | CH₂Ph |
| Cl | SCH₂CH₂OMe | SO₂Me | CH₂Ph |
| Cl | SCH₂CH₂OPr-i | SO₂Me | CH₂Ph |
| Cl | SO₂CH₂CH₂OMe | SO₂Me | CH₂Ph |
| Cl | SO₂CH₂CH₂OPr-i | SO₂Me | CH₂Ph |
| Cl | OCH₂CH₂OMe | SO₂Me | CH₂COPh |
| Cl | OCH₂CH₂OPr-i | SO₂Me | CH₂COPh |
| Cl | OCH₂CH₂SMe | SO₂Me | CH₂COPh |
| Cl | OCH₂CH₂SOMe | SO₂Me | CH₂COPh |
| Cl | OCH₂CH₂SO₂Me | SO₂Me | CH₂COPh |
| Cl | OCH₂CH₂SPr-i | SO₂Me | CH₂COPh |
| Cl | OCH₂CH₂SO₂Pr-i | SO₂Me | CH₂COPh |
| Cl | SCH₂CH₂OMe | SO₂Me | CH₂COPh |
| Cl | SCH₂CH₂OPr-i | SO₂Me | CH₂COPh |
| Cl | SO₂CH₂CH₂OMe | SO₂Me | CH₂COPh |
| Cl | SO₂CH₂CH₂OPr-i | SO₂Me | CH₂COPh |
| Cl | OCH₂CH₂OMe | Cl | H |
| Cl | OCH₂CH₂OEt | Cl | H |
| Cl | OCH₂CH₂OPr-i | Cl | H |
| Cl | OCHMeCH₂OMe | Cl | H |
| Cl | OCH₂COOMe | Cl | H |
| Cl | OCH₂CH₂SMe | Cl | H |
| Cl | OCH₂CH₂SO₂Me | Cl | H |
| Cl | SCH₂CH₂OMe | Cl | H |
| Cl | SO₂CH₂CH₂OMe | Cl | H |
| Cl | OCH₂CH₂OMe | Cl | CH₂Ph |
| Cl | OCH₂CH₂SMe | Cl | CH₂Ph |

TABLE 7-continued

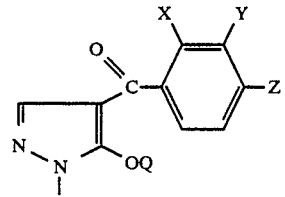

| X | Y | Z | Q |
|---|---|---|---|
| Cl | OCH₂CH₂SOMe | Cl | CH₂Ph |
| Cl | OCH₂CH₂SO₂Me | Cl | CH₂Ph |
| Cl | SCH₂CH₂OMe | Cl | CH₂Ph |
| Cl | SO₂CH₂CH₂OMe | Cl | CH₂Ph |
| Cl | OCH₂CH₂OMe | Cl | CH₂COPh |
| Cl | OCH₂CH₂SMe | Cl | CH₂COPh |
| Cl | OCH₂CH₂SO₂Me | Cl | CH₂COPh |
| Cl | SCH₂CH₂OMe | Cl | CH₂COPh |
| Cl | SCH₂CH₂OEt | Cl | CH₂COPh |
| Cl | SO₂CH₂CH₂OMe | Cl | CH₂COPh |
| OMe | Y1 | SO₂Me | H |
| OMe | Y2 | SO₂Me | H |
| OMe | Y3 | SO₂Me | H |
| OMe | Y4 | SO₂Me | H |
| OMe | Y5 | SO₂Me | H |
| OMe | Y6 | SO₂Me | H |
| OMe | Y7 | SO₂Me | H |
| OMe | OCH₂CH=CH₂ | SO₂Me | H |
| OMe | OCHMdCH=CH₂ | SO₂Me | H |
| OMe | OCMe₂CH=CH₂ | SO₂Me | H |
| OMe | OCH₂CMe=CH₂ | SO₂Me | H |
| OMe | OCH₂CH=CHMe | SO₂Me | H |
| OMe | OCH₂CH=CMe₂ | SO₂Me | H |
| OMe | OCH₂CH₂CH=CH₂ | SO₂Me | H |
| OMe | OCH₂C≡CH | SO₂Me | H |
| OMe | OCHMeC≡CH | SO₂Me | H |
| OMe | OCMe₂C≡CH | SO₂Me | H |
| OMe | OCH₂C≡CMe | SO₂Me | H |
| OMe | OCH₂CH₂F | SO₂Me | H |
| OMe | OCH₂CHF₂ | SO₂Me | H |
| OMe | OCH₂CF₃ | SO₂Me | H |
| OMe | OCH₂CH₂Cl | SO₂Me | H |
| OMe | OCH₂CCl₃ | SO₂Me | H |
| OMe | OCHMeCH₂Cl | SO₂Me | H |
| OMe | OCH₂CH₂CH₂Cl | SO₂Me | H |
| OMe | OCH₂CH₂Br | SO₂Me | H |
| OMe | Y8 | SO₂Me | H |
| OMe | OCH₂CCl=CH₂ | SO₂Me | H |
| OMe | OCH₂CCl=CHCl | SO₂Me | H |
| OMe | OCH₂CH₂NO₂ | SO₂Me | H |
| OMe | OPh | SO₂Me | H |
| OMe | OPh—Me-2 | SO₂Me | H |
| OMe | OPh—Cl-4 | SO₂Me | H |
| OMe | OPh—NO₂-4 | SO₂Me | H |
| OMe | OCH₂CH₂OMe | SO₂Me | H |
| OMe | OCH₂CH₂OEt | SO₂Me | H |
| OMe | OCH₂CH₂OPr-n | SO₂Me | H |
| OMe | OCH₂CH₂OPr-i | SO₂Me | H |
| OMe | OCH₂CH₂OBu-n | SO₂Me | H |
| OMe | OCH₂CH₂OBu-i | SO₂Me | H |
| OMe | OCH₂CH₂OBu-s | SO₂Me | H |
| OMe | OCH₂CH₂OBu-t | SO₂Me | H |
| OMe | OCH₂CH₂-Y4 | SO₂Me | H |
| OMe | OCHMeCH₂OMe | SO₂Me | H |
| OMe | OCH₂CHMeOMe | SO₂Me | H |
| OMe | OCH₂CH₂OPh | SO₂Me | H |
| OMe | OCH₂CH₂OCH₂CH₂OMe | SO₂Me | H |
| OMe | OCH₂CH₂OCH₂CH₂OPr-i | SO₂Me | H |
| OMe | OCH₂CH₂OCHMeCH₂OMe | SO₂Me | H |
| OMe | OCH₂CH₂OH | SO₂Me | H |
| OMe | OCH₂Ph | SO₂Me | H |
| OMe | OCHMePh | SO₂Me | H |
| OMe | OCH₂CH₂Ph | SO₂Me | H |
| OMe | OCH₂Ph-2-Cl | SO₂Me | H |
| OMe | OCH₂Ph-3-Me | SO₂Me | H |
| OMe | OCH₂Ph-4-OMe | SO₂Me | H |
| OMe | OCH₂Ph-4-NO₂ | SO₂Me | H |
| OMe | Y9 | SO₂Me | H |
| OMe | Y10 | SO₂Me | H |
| OMe | Y11 | SO₂Me | H |

TABLE 7-continued

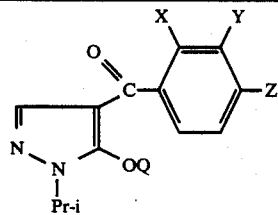

| X | Y | Z | Q |
|---|---|---|---|
| OMe | Y12 | SO$_2$Me | H |
| OMe | Y13 | SO$_2$Me | H |
| OMe | Y14 | SO$_2$Me | H |
| OMe | Y15 | SO$_2$Me | H |
| OMe | Y16 | SO$_2$Me | H |
| OMe | Y17 | SO$_2$Me | H |
| OMe | Y18 | SO$_2$Me | H |
| OMe | OCH$_2$CH$_2$NH$_2$ | SO$_2$Me | H |
| OMe | OCH$_2$CH$_2$NHMe | SO$_2$Me | H |
| OMe | OCH$_2$CH$_2$NHPr-i | SO$_2$Me | H |
| OMe | OCH$_2$CH$_2$NMe$_2$ | SO$_2$Me | H |
| OMe | OCH$_2$CH$_2$NEt$_2$ | SO$_2$Me | H |
| OMe | Y19 | SO$_2$Me | H |
| OMe | OCH$_2$COOMe | SO$_2$Me | H |
| OMe | OCH$_2$COOEt | SO$_2$Me | H |
| OMe | OCH$_2$COOPr-i | SO$_2$Me | H |
| OMe | OCH$_2$COOBu-i | SO$_2$Me | H |
| OMe | OCH$_2$COOBu-t | SO$_2$Me | H |
| OMe | OCH$_2$COO-Y4 | SO$_2$Me | H |
| OMe | OCHMeCOOMe | SO$_2$Me | H |
| OMe | OCHMeCOOEt | SO$_2$Me | H |
| OMe | OCHMeCOOPr-i | SO$_2$Me | H |
| OMe | OCH$_2$CH$_2$CN | SO$_2$Me | H |
| OMe | OCH$_2$SMe | SO$_2$Me | H |
| OMe | OCH$_2$CH$_2$SMe | SO$_2$Me | H |
| OMe | OCH$_2$CH$_2$S(O)Me | SO$_2$Me | H |
| OMe | OCH$_2$CH$_2$SO$_2$Me | SO$_2$Me | H |
| OMe | OCH$_2$CH$_2$SPr-i | SO$_2$Me | H |
| OMe | OCH$_2$CH$_2$S(O)Pr-i | SO$_2$Me | H |
| OMe | OCH$_2$CH$_2$SO$_2$Pr-i | SO$_2$Me | H |
| OMe | OCOOMe | SO$_2$Me | H |
| OMe | OCOOPr-i | SO$_2$Me | H |
| OMe | OCONH$_2$ | SO$_2$Me | H |
| OMe | OCONHMe | SO$_2$Me | H |
| OMe | OCONMe$_2$ | SO$_2$Me | H |
| OMe | OP(O)(OMe)$_2$ | SO$_2$Me | H |
| OMe | Y20 | SO$_2$Me | H |
| OMe | SCH$_2$CH=CH$_2$ | SO$_2$Me | H |
| OMe | SCH$_2$CH=CMe$_2$ | SO$_2$Me | H |
| OMe | SCH$_2$C≡CH | SO$_2$Me | H |
| OMe | SCH$_2$CF$_3$ | SO$_2$Me | H |
| OMe | SCH$_2$CCl$_3$ | SO$_2$Me | H |
| OMe | Y21 | SO$_2$Me | H |
| OMe | SPh | SO$_2$Me | H |
| OMe | SCH$_2$CH$_2$OMe | SO$_2$Me | H |
| OMe | SCH$_2$CH$_2$OEt | SO$_2$Me | H |
| OMe | SCH$_2$CH$_2$OPr-i | SO$_2$Me | H |
| OMe | Y22 | SO$_2$Me | H |
| OMe | S(O)CH$_2$CH=CH$_2$ | SO$_2$Me | H |
| OMe | S(O)CH$_2$CH=CMe$_2$ | SO$_2$Me | H |
| OMe | S(O)CH$_2$C≡CH | SO$_2$Me | H |
| OMe | S(O)CH$_2$CH$_2$Cl | SO$_2$Me | H |
| OMe | Y23 | SO$_2$Me | H |
| OMe | SO$_2$CH$_2$CH=CH$_2$ | SO$_2$Me | H |
| OMe | SO$_2$CH$_2$CH=CMe$_2$ | SO$_2$Me | H |
| OMe | SO$_2$CH$_2$C≡CH | SO$_2$Me | H |
| OMe | SO$_2$CH$_2$CF$_3$ | SO$_2$Me | H |
| OMe | SO$_2$CH$_2$CH$_2$Cl | SO$_2$Me | H |
| OMe | Y24 | SO$_2$Me | H |
| OMe | Y25 | SO$_2$Me | H |
| OMe | SO$_2$Ph | SO$_2$Me | H |
| OMe | SO$_2$CH$_2$CH$_2$OMe | SO$_2$Me | H |
| OMe | SO$_2$CH$_2$CH$_2$OEt | SO$_2$Me | H |
| OMe | SO$_2$CH$_2$CH$_2$OPr-i | SO$_2$Me | H |
| OMe | OCH$_2$CH$_2$OMe | SO$_2$Me | CH$_2$Ph |
| OMe | OCH$_2$CH$_2$OEt | SO$_2$Me | CH$_2$Ph |
| OMe | OCH$_2$CH$_2$OPr-i | SO$_2$Me | CH$_2$Ph |
| OMe | OCHMeCH$_2$OMe | SO$_2$Me | CH$_2$Ph |
| OMe | OCH$_2$CH$_2$SMe | SO$_2$Me | CH$_2$Ph |
| OMe | OCH$_2$CH$_2$S(O)Me | SO$_2$Me | CH$_2$Ph |

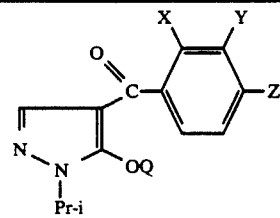

| X | Y | Z | Q |
|---|---|---|---|
| OMe | OCH$_2$CH$_2$SO$_2$Me | SO$_2$Me | CH$_2$Ph |
| OMe | OCH$_2$CH$_2$SPr-i | SO$_2$Me | CH$_2$Ph |
| OMe | OCH$_2$CH$_2$S(O)Pr-i | SO$_2$Me | CH$_2$Ph |
| OMe | OCH$_2$CH$_2$SO$_2$Pr-i | SO$_2$Me | CH$_2$Ph |
| OMe | SCH$_2$CH$_2$OMe | SO$_2$Me | CH$_2$Ph |
| OMe | SCH$_2$CH$_2$OPr-i | SO$_2$Me | CH$_2$Ph |
| OMe | SO$_2$CH$_2$CH$_2$OMe | SO$_2$Me | CH$_2$Ph |
| OMe | SO$_2$CH$_2$CH$_2$OPr-i | SO$_2$Me | CH$_2$Ph |
| OMe | OCH$_2$CH$_2$OMe | SO$_2$Me | CH$_2$COPh |
| OMe | OCH$_2$CH$_2$OPr-i | SO$_2$Me | CH$_2$COPh |
| OMe | OCH$_2$CH$_2$SMe | SO$_2$Me | CH$_2$COPh |
| OMe | OCH$_2$CH$_2$SOMe | SO$_2$Me | CH$_2$COPh |
| OMe | OCH$_2$CH$_2$SO$_2$Me | SO$_1$Me | CH$_2$COPh |
| OMe | OCH$_2$CH$_2$SPr-i | SO$_2$Me | CH$_2$COPh |
| OMe | OCH$_2$CH$_2$SO$_2$Pr-i | SO$_2$Me | CH$_2$COPh |
| OMe | SCH$_2$CH$_2$OMe | SO$_2$Me | CH$_2$COPh |
| OMe | SCH$_2$CH$_2$OPr-i | SO$_2$Me | CH$_2$COPh |
| OMe | SO$_2$CH$_2$CH$_2$OMe | SO$_2$Me | CH$_2$COPh |
| OMe | SO$_2$CH$_2$CH$_2$OPr-i | SO$_2$Me | CH$_2$COPh |
| OMe | OCH$_2$CH$_2$OMe | Cl | H |
| OMe | OCH$_2$CH$_2$OEt | Cl | H |
| OMe | OCH$_2$CH$_2$OPr-i | Cl | H |
| OMe | OCHMeCH$_2$OMe | Cl | H |
| OMe | OCH$_2$COOMe | Cl | H |
| OMe | OCH$_2$CH$_2$SMe | Cl | H |
| OMe | OCH$_2$CH$_2$SO$_2$Me | Cl | H |
| OMe | SCH$_2$CH$_2$OMe | Cl | H |
| OMe | SO$_2$CH$_2$CH$_2$OMe | Cl | H |
| OMe | OCH$_2$CH$_2$OMe | Cl | CH$_2$Ph |
| OMe | OCH$_2$CH$_2$SMe | Cl | CH$_2$Ph |
| OMe | OCH$_2$CH$_2$SOMe | Cl | CH$_2$Ph |
| OMe | OCH$_2$CH$_2$SO$_2$Me | Cl | CH$_2$Ph |
| OMe | SCH$_2$CH$_2$OMe | Cl | CH$_2$Ph |
| OMe | SO$_2$CH$_2$CH$_2$OMe | Cl | CH$_2$Ph |
| OMe | OCH$_2$CH$_2$OMe | Cl | CH$_2$COPh |
| OMe | OCH$_2$CH$_2$SMe | Cl | CH$_2$COPh |
| OMe | OCH$_2$CH$_2$SO$_2$Me | Cl | CH$_2$COPh |
| OMe | SCH$_2$CH$_2$OMe | Cl | CH$_2$COPh |
| OMe | SCH$_2$CH$_2$OEt | Cl | CH$_2$COPh |
| OMe | SO$_2$CH$_2$CH$_2$OMe | Cl | CH$_2$COPh |
| CH$_2$OMe | Y1 | SO$_2$Me | H |
| CH$_2$OMe | Y2 | SO$_2$Me | H |
| CH$_2$OMe | Y3 | SO$_2$Me | H |
| CH$_2$OMe | Y4 | SO$_2$Me | H |
| CH$_2$OMe | Y5 | SO$_2$Me | H |
| CH$_2$OMe | Y6 | SO$_2$Me | H |
| CH$_2$OMe | Y7 | SO$_2$Me | H |
| CH$_2$OMe | OCH$_2$CH=CH$_2$ | SO$_2$Me | H |
| CH$_2$OMe | OCHMeCH=CH$_2$ | SO$_2$Me | H |
| CH$_2$OMe | OCMe$_2$CH=CH$_2$ | SO$_2$Me | H |
| CH$_2$OMe | OCH$_2$CMe=CH$_2$ | SO$_2$Me | H |
| CH$_2$OMe | OCH$_2$CH=CHMe | SO$_2$Me | H |
| CH$_2$OMe | OCH$_2$CH=CMe$_2$ | SO$_2$Me | H |
| CH$_2$OMe | OCH$_2$CH$_2$CH=CH$_2$ | SO$_2$Me | H |
| CH$_2$OMe | OCH$_2$C≡CH | SO$_2$Me | H |
| CH$_2$OMe | OCHMeC≡CH | SO$_2$Me | H |
| CH$_2$OMe | OCMe$_2$C≡CH | SO$_2$Me | H |
| CH$_2$OMe | OCH$_2$C≡CMe | SO$_2$Me | H |
| CH$_2$OMe | OCH$_2$CH$_2$F | SO$_2$Me | H |
| CH$_2$OMe | OCH$_2$CHF$_2$ | SO$_2$Me | H |
| CH$_2$OMe | OCH$_2$CF$_3$ | SO$_2$Me | H |
| CH$_2$OMe | OCH$_2$CH$_2$Cl | SO$_2$Me | H |
| CH$_2$OMe | OCH$_2$CCl$_3$ | SO$_2$Me | H |
| CH$_2$OMe | OCHMeCH$_2$Cl | SO$_2$Me | H |
| CH$_2$OMe | OCH$_2$CH$_2$CH$_2$Cl | SO$_2$Me | H |
| CH$_2$OMe | OCH$_2$CH$_2$Br | SO$_2$Me | H |
| CH$_2$OMe | Y8 | SO$_2$Me | H |
| CH$_2$OMe | OCH$_2$CCl=CH$_2$ | SO$_2$Me | H |
| CH$_2$OMe | OCH$_2$CCl=CHCl | SO$_2$Me | H |
| CH$_2$OMe | OCH$_2$CH$_2$NO$_2$ | SO$_2$Me | H |

TABLE 7-continued

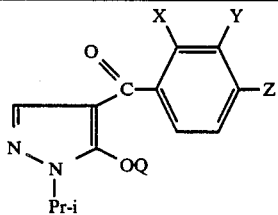

| X | Y | Z | Q |
|---|---|---|---|
| CH2OMe | OPh | SO2Me | H |
| CH2OMe | OPh—Me-2 | SO2Me | H |
| CH2OMe | OPh—Cl-4 | SO2Me | H |
| CH2OMe | OPh—N2-4 | SO2Me | H |
| CH2OMe | OCH2CH2OMe | SO2Me | H |
| CH2OMe | OCH2CH2OEt | SO2Me | H |
| CH2OMe | OCH2CH2OPr-n | SO2Me | H |
| CH2OMe | OCH2CH2OPr-i | SO2Me | H |
| CH2OMe | OCH2CH2OBu-n | SO2Me | H |
| CH2OMe | OCH2CH2OBu-i | SO2Me | H |
| CH2OMe | OCH2CH2OBu-s | SO2Me | H |
| CH2OMe | OCH2CH2OBu-t | SO2Me | H |
| CH2OMe | OCH2CH2-Y4 | SO2Me | H |
| CH2OMe | OCHMeCH2OMe | SO2Me | H |
| CH2OMe | OCH2CHMeOMe | SO2Me | H |
| CH2OMe | OCH2CH2OPh | SO2Me | H |
| CH2OMe | OCH2CH2OCH2CH2OMe | SO2Me | H |
| CH2OMe | OCH2CH2OCH2CH2OPr-i | SO2Me | H |
| CH2OMe | OCH2CH2OCHMeCH2OMe | SO2Me | H |
| CH2OMe | OCH2CH2OH | SO2Me | H |
| CH2OMe | OCH2Ph | SO2Me | H |
| CH2OMe | OCHMePh | SO2Me | H |
| CH2OMe | OCH2CH2Ph | SO2Me | H |
| CH2OMe | OCH2Ph-2-Cl | SO2Me | H |
| CH2OMe | OCH2Ph-3-Me | SO2Me | H |
| CH2OMe | OCH2Ph-4-OMe | SO2Me | H |
| CH2OMe | OCH2Ph-4-NO2 | SO2Me | H |
| CH2OMe | Y9 | SO2Me | H |
| CH2OMe | Y10 | SO2Me | H |
| CH2OMe | Y11 | SO2Me | H |
| CH2OMe | Y12 | SO2Me | H |
| CH2OMe | Y13 | SO2Me | H |
| CH2OMe | Y14 | SO2Me | H |
| CH2OMe | Y15 | SO2Me | H |
| CH2OMe | Y16 | SO2Me | H |
| CH2OMe | Y17 | SO2Me | H |
| CH2OMe | Y18 | SO2Me | H |
| CH2OMe | OCH2CH2NH2 | SO2Me | H |
| CH2OMe | OCH2CH2NHMe | SO2Me | H |
| CH2OMe | OCH2CH2NHPr-i | SO2Me | H |
| CH2OMe | OCH2CH2NMe2 | SO2Me | H |
| CH2OMe | OCH2CH2NEt2 | SO2Me | H |
| CH2OMe | Y19 | SO2Me | H |
| CH2OMe | OCH2COOMe | SO2Me | H |
| CH2OMe | OCH2COOEt | SO2Me | H |
| CH2OMe | OCH2COOPr-i | SO2Me | H |
| CH2OMe | OCH2COOBu-i | SO2Me | H |
| CH2OMe | OCH2COOBu-t | SO2Me | H |
| CH2OMe | OCH2COO-Y4 | SO2Me | H |
| CH2OMe | OCHMeCOOMe | SO2Me | H |
| CH2OMe | OCHMeCOOEt | SO2Me | H |
| CH2OMe | OCHMeCOOPr-i | SO2Me | H |
| CH2OMe | OCH2CH2CN | SO2Me | H |
| CH2OMe | OCH2SMe | SO2Me | H |
| CH2OMe | OCH2CH2SMe | SO2Me | H |
| CH2OMe | OCH2CH2S(O)Me | SO2Me | H |
| CH2OMe | OCH2CH2SO2Me | SO2Me | H |
| CH2OMe | OCH2CH2SPr-i | SO2Me | H |
| CH2OMe | OCH2CH2S(O)Pr-i | SO2Me | H |
| CH2OMe | OCH2CH2SO2Pr-i | SO2Me | H |
| CH2OMe | OCOOMe | SO2Me | H |
| CH2OMe | OCOOPr-i | SO2Me | H |
| CH2OMe | OCONH2 | SO2Me | H |
| CH2OMe | OCONHMe | SO2Me | H |
| CH2OMe | OCONMe2 | SO2Me | H |
| CH2OMe | OP(O)(OMe)2 | SO2Me | H |
| CH2OMe | Y20 | SO2Me | H |
| CH2OMe | SCH2CH=CH2 | SO2Me | H |
| CH2OMe | SCH2CH=CMe2 | SO2Me | H |
| CH2OMe | SCH2C≡CH | SO2Me | H |

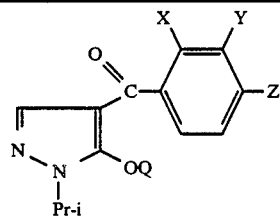

| X | Y | Z | Q |
|---|---|---|---|
| CH2OMe | SCH2CF3 | SO2Me | H |
| CH2OMe | SCH2CCl3 | SO2Me | H |
| CH2OMe | Y21 | SO2Me | H |
| CH2OMe | SPh | SO2Me | H |
| CH2OMe | SCH2CH2OMe | SO2Me | H |
| CH2OMe | SCH2CH2OEt | SO2Me | H |
| CH2OMe | SCH2CH2OPr-i | SO2Me | H |
| CH2OMe | Y22 | SO2Me | H |
| CH2OMe | S(O)CH2CH=CH2 | SO2Me | H |
| CH2OMe | S(O)CH2CH=CMe2 | SO2Me | H |
| CH2OMe | S(O)CH2C≡CH | SO2Me | H |
| CH2OMe | S(O)CH2CH2Cl | SO2Me | H |
| CH2OMe | Y23 | SO2Me | H |
| CH2OMe | SO2CH2CH=CH2 | SO2Me | H |
| CH2OMe | SO2CH2CH=CMe2 | SO2Me | H |
| CH2OMe | SO2CH2C≡CH | SO2Me | H |
| CH2OMe | SO2CH2CF3 | SO2Me | H |
| CH2OMe | SO2CH2CH2Cl | SO2Me | H |
| CH2OMe | Y24 | SO2Me | H |
| CH2OMe | SO2Ph | SO2Me | H |
| CH2OMe | SO2CH2CH2OMe | SO2Me | H |
| CH2OMe | SO2CH2CH2OEt | SO2Me | H |
| CH2OMe | SO2CH2CH2OPr-i | SO2Me | H |
| CH2OMe | OCH2CH2OMe | SO2Me | CH2Ph |
| CH2OMe | OCH2CH2OEt | SO2Me | CH2Ph |
| CH2OMe | OCH2CH2OPr-i | SO2Me | CH2Ph |
| CH2OMe | OCHMeCH2OMe | SO2Me | CH2Ph |
| CH2OMe | OCH2CH2SMe | SO2Me | CH2Ph |
| CH2OMe | OCH2CH2S(O)Me | SO2Me | CH2Ph |
| CH2OMe | OCH2CH2SO2Me | SO2Me | CH2Ph |
| CH2OMe | OCH2CH2SPr-i | SO2Me | CH2Ph |
| CH2OMe | OCH2CH2S(O)Pr-i | SO2Me | CH2Ph |
| CH2OMe | OCH2CH2SO2Pr-i | SO2Me | CH2Ph |
| CH2OMe | SCH2CH2OMe | SO2Me | CH2Ph |
| CH2OMe | SCH2CH2OPr-i | SO2Me | CH2Ph |
| CH2OMe | SO2CH2CH2OMe | SO2Me | CH2Ph |
| CH2OMe | SO2CH2CH2OPr-i | SO2Me | CH2Ph |
| CH2OMe | OCH2CH2OMe | SO2Me | CH2COPh |
| CH2OMe | OCH2CH2Pr-i | SO2Me | CH2COPh |
| CH2OMe | OCH2CH2SMe | SO2Me | CH2COPh |
| CH2OMe | OCH2CH2SOMe | SO2Me | CH2COPh |
| CH2OMe | OCH2CH2SO2Me | SO2Me | CH2COPh |
| CH2OMe | OCH2CH2SPr-i | SO2Me | CH2COPh |
| CH2OMe | OCH2CH2SO2Pr-i | SO2Me | CH2COPh |
| CH2OMe | SCH2CH2OMe | SO2Me | CH2COPh |
| CH2OMe | SCH2CH2OPr-i | SO2Me | CH2COPh |
| CH2OMe | SO2CH2CH2OMe | SO2Me | CH2COPh |
| CH2OMe | SO2CH2CH2OPr-i | SO2Me | CH2COPh |
| CH2OMe | OCH2CH2OMe | Cl | H |
| CH2OMe | OCH2CH2OEt | Cl | H |
| CH2OMe | OCH2CH2OPr-i | Cl | H |
| CH2OMe | OCHMeCH2OMe | Cl | H |
| CH2OMe | OCH2COOMe | Cl | H |
| CH2OMe | OCH2CH2SMe | Cl | H |
| CH2OMe | OCH2CH2SO2Me | Cl | H |
| CH2OMe | SCH2CH2OMe | Cl | H |
| CH2OMe | SO2CH2CH2OMe | Cl | H |
| CH2OMe | OCH2CH2OMe | Cl | CH2Ph |
| CH2OMe | OCH2CH2SMe | Cl | CH2Ph |
| CH2OMe | OCH2CH2SOMe | Cl | CH2Ph |
| CH2OMe | OCH2CH2SO2Me | Cl | CH2Ph |
| CH2OMe | SCH2CH2OMe | Cl | CH2Ph |
| CH2OMe | SO2CH2CH2OMe | Cl | CH2Ph |
| CH2OMe | OCH2CH2OMe | Cl | CH2COPh |
| CH2OMe | OCH2CH2SMe | Cl | CH2COPh |
| CH2OMe | OCH2CH2SO2Me | Cl | CH2COPh |
| CH2OMe | SCH2CH2OMe | Cl | CH2COPh |
| CH2OMe | SCH2CH2OEt | Cl | CH2COPh |

TABLE 7-continued

[Structure: pyrazole with X, Y substituents, C=O linked to phenyl ring with X, Y, Z substituents, OQ group, N-Pr-i]

| X | Y | Z | Q |
|---|---|---|---|
| CH₂OMe | SO₂CH₂CH₂OMe | Cl | CH₂COPh |

TABLE 8

[Structure: pyrazole with Me group, C=O linked to phenyl ring with X, Y, Z substituents, OQ group, N-Pr-i]

| X | Y | Z | Q |
|---|---|---|---|
| Me | Y1 | SO₂Me | H |
| Me | Y2 | SO₂Me | H |
| Me | Y3 | SO₂Me | H |
| Me | Y4 | SO₂Me | H |
| Me | Y5 | SO₂Me | H |
| Me | Y6 | SO₂Me | H |
| Me | Y7 | SO₂Me | H |
| Me | OCH₂CH=CH₂ | SO₂Me | H |
| Me | OCHMeCH=CH₂ | SO₂Me | H |
| Me | OCMe₂CH=CH₂ | SO₂Me | H |
| Me | OCH₂CMe=CH₂ | SO₂Me | H |
| Me | OCH₂CH=CHMe | SO₂Me | H |
| Me | OCH₂CH=CMe₂ | SO₂Me | H |
| Me | OCH₂CH₂CH=CH₂ | SO₂Me | H |
| Me | OCH₂C≡CH | SO₂Me | H |
| Me | OCHMeC≡CH | SO₂Me | H |
| Me | OCMe₂C≡CH | SO₂Me | H |
| Me | OCH₂C≡CMe | SO₂Me | H |
| Me | OCH₂CH₂F | SO₂Me | H |
| Me | OCH₂CHF₂ | SO₂Me | H |
| Me | OCH₂CF₃ | SO₂Me | H |
| Me | OCH₂CH₂Cl | SO₂Me | H |
| Me | OCH₂CCl₃ | SO₂Me | H |
| Me | OCHMeCH₂Cl | SO₂Me | H |
| Me | OCH₂CH₂CH₂Cl | SO₂Me | H |
| Me | OCH₂CH₂Br | SO₂Me | H |
| Me | Y8 | SO₂Me | H |
| Me | OCH₂CCl=CH₂ | SO₂Me | H |
| Me | OCH₂CCl=CHCl | SO₂Me | H |
| Me | OCH₂CH₂NO₂ | SO₂Me | H |
| Me | OPh | SO₂Me | H |
| Me | OPh—Me-2 | SO₂Me | H |
| Me | OPh—Cl-4 | SO₂Me | H |
| Me | OPh—NO₂-4 | SO₂Me | H |
| Me | OCH₂CH₂OMe | SO₂Me | H |
| Me | OCH₂CH₂OEt | SO₂Me | H |
| Me | OCH₂CH₂OPr-n | SO₂Me | H |
| Me | OCH₂CH₂OPr-i | SO₂Me | H |
| Me | OCH₂CH₂OBu-n | SO₂Me | H |
| Me | OCH₂CH₂OBu-i | SO₂Me | H |
| Me | OCH₂CH₂OBu-s | SO₂Me | H |
| Me | OCH₂CH₂OBu-t | SO₂Me | H |
| Me | OCH₂CH₂—Y4 | SO₂Me | H |
| Me | OCHMeCH₂OMe | SO₂Me | H |
| Me | OCH₂CHMeOMe | SO₂Me | H |
| Me | OCH₂CH₂OPh | SO₂Me | H |
| Me | OCH₂CH₂OCH₂CH₂OMe | SO₂Me | H |
| Me | OCH₂CH₂OCH₂CH₂OPr-i | SO₂Me | H |
| Me | OCH₂CH₂OCHMeCH₂OMe | SO₂Me | H |
| Me | OCH₂CH₂OH | SO₂Me | H |
| Me | OCH₂Ph | SO₂Me | H |
| Me | OCHMePh | SO₂Me | H |

TABLE 8-continued

[Structure: pyrazole with Me group, C=O linked to phenyl ring with X, Y, Z substituents, OQ group, N-Pr-i]

| X | Y | Z | Q |
|---|---|---|---|
| Me | OCH₂CH₂Ph | SO₂Me | H |
| Me | OCH₂Ph-2-Cl | SO₂Me | H |
| Me | OCH₂Ph-3-Me | SO₂Me | H |
| Me | OCH₂Ph-4-OMe | SO₂Me | H |
| Me | OCH₂Ph-4-NO₂ | SO₂Me | H |
| Me | Y9 | SO₂Me | H |
| Me | Y10 | SO₂Me | H |
| Me | Y11 | SO₂Me | H |
| Me | Y12 | SO₂Me | H |
| Me | Y13 | SO₂Me | H |
| Me | Y14 | SO₂Me | H |
| Me | Y15 | SO₂Me | H |
| Me | Y16 | SO₂Me | H |
| Me | Y17 | SO₂Me | H |
| Me | Y18 | SO₂Me | H |
| Me | OCH₂CH₂NH₂ | SO₂Me | H |
| Me | OCH₂CH₂NHMe | SO₂Me | H |
| Me | OCH₂CH₂NHPr-i | SO₂Me | H |
| Me | OCH₂CH₂NMe₂ | SO₂Me | H |
| Me | OCH₂CH₂NEt₂ | SO₂Me | H |
| Me | Y19 | SO₂Me | H |
| Me | OCH₂COOMe | SO₂Me | H |
| Me | OCH₂COOEt | SO₂Me | H |
| Me | OCH₂COOPr-i | SO₂Me | H |
| Me | OCH₂COOBu-i | SO₂Me | H |
| Me | OCH₂COOBu-t | SO₂Me | H |
| Me | OCH₂COO—Y4 | SO₂Me | H |
| Me | OCHMeCOOMe | SO₂Me | H |
| Me | OCHMeCOOEt | SO₂Me | H |
| Me | OCHMeCOOPr-i | SO₂Me | H |
| Me | OCH₂CH₂CN | SO₂Me | H |
| Me | OCH₂SMe | SO₂Me | H |
| Me | OCH₂CH₂SMe | SO₂Me | H |
| Me | OCH₂CH₂S(O)Me | SO₂Me | H |
| Me | OCH₂CH₂SO₂Me | SO₂Me | H |
| Me | OCH₂CH₂SPr-i | SO₂Me | H |
| Me | OCH₂CH₂S(O)Pr-i | SO₂Me | H |
| Me | OCH₂CH₂SO₂Pr-i | SO₂Me | H |
| Me | OCOOMe | SO₂Me | H |
| Me | OCOOPr-i | SO₂Me | H |
| Me | OCONH₂ | SO₂Me | H |
| Me | OCONHMe | SO₂Me | H |
| Me | OCONMe₂ | SO₂Me | H |
| Me | OP(O)(OMe)₂ | SO₂Me | H |
| Me | Y20 | SO₂Me | H |
| Me | SCH₂CH=CH₂ | SO₂Me | H |
| Me | SCH₂CH=CMe₂ | SO₂Me | H |
| Me | SCH₂C≡CH | SO₂Me | H |
| Me | SCH₂CF₃ | SO₂Me | H |
| Me | SCH₂CCl₃ | SO₂Me | H |
| Me | Y21 | SO₂Me | H |
| Me | SPh | SO₂Me | H |
| Me | SCH₂CH₂OMe | SO₂Me | H |
| Me | SCH₂CH₂OEt | SO₂Me | H |
| Me | SCH₂CH₂OPr-i | SO₂Me | H |
| Me | Y22 | SO₂Me | H |
| Me | S(O)CH₂CH=CH₂ | SO₂Me | H |
| Me | S(O)CH₂CH=CMe₂ | SO₂Me | H |
| Me | S(O)CH₂C≡CH | SO₂Me | H |
| Me | S(O)CH₂CH₂Cl | SO₂Me | H |
| Me | Y23 | SO₂Me | H |
| Me | SO₂CH₂CH=CH₂ | SO₂Me | H |
| Me | SO₂CH₂CH=CMe₂ | SO₂Me | H |
| Me | SO₂CH₂C≡CH | SO₂Me | H |
| Me | SO₂CH₂CF₃ | SO₂Me | H |
| Me | SO₂CH₂CH₂Cl | SO₂Me | H |
| Me | Y24 | SO₂Me | H |
| Me | Y25 | SO₂Me | H |
| Me | SO₂Ph | SO₂Me | H |
| Me | SO₂CH₂CH₂OMe | SO₂Me | H |

TABLE 8-continued

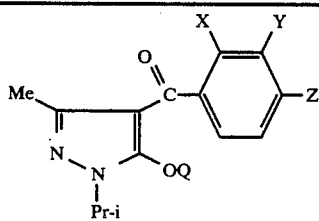

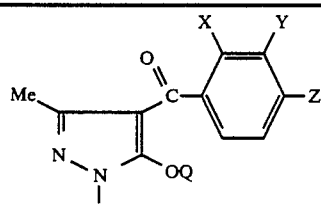

| X | Y | Z | Q |
|---|---|---|---|
| Me | SO$_2$CH$_2$CH$_2$OEt | SO$_2$Me | H |
| Me | SO$_2$CH$_2$CH$_2$OPr-i | SO$_2$Me | H |
| Me | OCH$_2$CH$_2$OMe | SO$_2$Me | CH$_2$Ph |
| Me | OCH$_2$CH$_2$OEt | SO$_2$Me | CH$_2$Ph |
| Me | OCH$_2$CH$_2$OPr-i | SO$_2$Me | CH$_2$Ph |
| Me | OCHMeCH$_2$OMe | SO$_2$Me | CH$_2$Ph |
| Me | OCH$_2$CH$_2$SMe | SO$_2$Me | CH$_2$Ph |
| Me | OCH$_2$CH$_2$S(O)Me | SO$_2$Me | CH$_2$Ph |
| Me | OCH$_2$CH$_2$SO$_2$Me | SO$_2$Me | CH$_2$Ph |
| Me | OCH$_2$CH$_2$SPr-i | SO$_2$Me | CH$_2$Ph |
| Me | OCH$_2$CH$_2$S(O)Pr-i | SO$_2$Me | CH$_2$Ph |
| Me | OCH$_2$CH$_2$SO$_2$Pr-i | SO$_2$Me | CH$_2$Ph |
| Me | SCH$_2$CH$_2$OMe | SO$_2$Me | CH$_2$Ph |
| Me | SCH$_2$CH$_2$OPr-i | SO$_2$Me | CH$_2$Ph |
| Me | SO$_2$CH$_2$CH$_2$OMe | SO$_2$Me | CH$_2$Ph |
| Me | SO$_2$CH$_2$CH$_2$OPr-i | SO$_2$Me | CH$_2$Ph |
| Me | OCH$_2$CH$_2$OMe | SO$_2$Me | CH$_2$COPh |
| Me | OCH$_2$CH$_2$OPr-i | SO$_2$Me | CH$_2$COPh |
| Me | OCH$_2$CH$_2$SMe | SO$_2$Me | CH$_2$COPh |
| Me | OCH$_2$CH$_2$SOMe | SO$_2$Me | CH$_2$COPh |
| Me | OCH$_2$CH$_2$SO$_2$Me | SO$_2$Me | CH$_2$COPh |
| Me | OCH$_2$CH$_2$SPr-i | SO$_2$Me | CH$_2$COPh |
| Me | OCH$_2$CH$_2$SO$_2$Pr-i | SO$_2$Me | CH$_2$COPh |
| Me | SCH$_2$CH$_2$OMe | SO$_2$Me | CH$_2$COPh |
| Me | SCH$_2$CH$_2$OPr-i | SO$_2$Me | CH$_2$COPh |
| Me | SO$_2$CH$_2$CH$_2$OMe | SO$_2$Me | CH$_2$COPh |
| Me | SO$_2$CH$_2$CH$_2$OPr-i | SO$_2$Me | CH$_2$COPh |
| Me | OCH$_2$CH$_2$OMe | Cl | H |
| Me | OCH$_2$CH$_2$OEt | Cl | H |
| Me | OCH$_2$CH$_2$OPr-i | Cl | H |
| Me | OCHMeCH$_2$OMe | Cl | H |
| Me | OCH$_2$COOMe | Cl | H |
| Me | OCH$_2$CH$_2$SMe | Cl | H |
| Me | OCH$_2$CH$_2$SO$_2$Me | Cl | H |
| Me | SCH$_2$CH$_2$OMe | Cl | H |
| Me | SO$_2$CH$_2$CH$_2$OMe | Cl | H |
| Me | OCH$_2$CH$_2$OMe | Cl | CH$_2$Ph |
| Me | OCH$_2$CH$_2$SMe | Cl | CH$_2$Ph |
| Me | OCH$_2$CH$_2$SOMe | Cl | CH$_2$Ph |
| Me | OCH$_2$CH$_2$SO$_2$Me | Cl | CH$_2$Ph |
| Me | SCH$_2$CH$_2$OMe | Cl | CH$_2$Ph |
| Me | SO$_2$CH$_2$CH$_2$OMe | Cl | CH$_2$Ph |
| Me | OCH$_2$CH$_2$OMe | Cl | CH$_2$COPh |
| Me | OCH$_2$CH$_2$SMe | Cl | CH$_2$COPh |
| Me | OCH$_2$CH$_2$SO$_2$Me | Cl | CH$_2$COPh |
| Me | SCH$_2$CH$_2$OMe | Cl | CH$_2$COPh |
| Me | SCH$_2$CH$_2$OEt | Cl | CH$_2$COPh |
| Me | SO$_2$CH$_2$CH$_2$OMe | Cl | CH$_2$COPh |
| Cl | Y1 | SO$_2$Me | H |
| Cl | Y2 | SO$_2$Me | H |
| Cl | Y3 | SO$_2$Me | H |
| Cl | Y4 | SO$_2$Me | H |
| Cl | Y5 | SO$_2$Me | H |
| Cl | Y6 | SO$_2$Me | H |
| Cl | Y7 | SO$_2$Me | H |
| Cl | OCH$_2$CH=CH$_2$ | SO$_2$Me | H |
| Cl | OCHMeCH=CH$_2$ | SO$_2$Me | H |
| Cl | OCMe$_2$CH=CH$_2$ | SO$_2$Me | H |
| Cl | OCH$_2$CMe=CH$_2$ | SO$_2$Me | H |
| Cl | OCH$_2$CH=CHMe | SO$_2$Me | H |
| Cl | OCH$_2$CH=CMe$_2$ | SO$_2$Me | H |
| Cl | OCH$_2$CH$_2$CH=CH$_2$ | SO$_2$Me | H |
| Cl | OCH$_2$C≡CH | SO$_2$Me | H |
| Cl | OCHMeC≡CH | SO$_2$Me | H |
| Cl | OCMe$_2$C≡CH | SO$_2$Me | H |
| Cl | OCH$_2$C≡CMe | SO$_2$Me | H |
| Cl | OCH$_2$CH$_2$F | SO$_2$Me | H |
| Cl | OCH$_2$CHF$_2$ | SO$_2$Me | H |
| Cl | OCH$_2$CF$_3$ | SO$_2$Me | H |
| Cl | OCH$_2$CH$_2$Cl | SO$_2$Me | H |
| Cl | OCH$_2$CCl$_3$ | SO$_2$Me | H |
| Cl | OCHMeCH$_2$Cl | SO$_2$Me | H |
| Cl | OCH$_2$CH$_2$CH$_2$Cl | SO$_2$Me | H |
| Cl | OCH$_2$CH$_2$Br | SO$_2$Me | H |
| Cl | Y8 | SO$_2$Me | H |
| Cl | OCH$_2$CCl=CH$_2$ | SO$_2$Me | H |
| Cl | OCH$_2$CCl=CHCl | SO$_2$Me | H |
| Cl | OCH$_2$CH$_2$NO$_2$ | SO$_2$Me | H |
| Cl | OPh | SO$_2$Me | H |
| Cl | OPh—Me-2 | SO$_2$Me | H |
| Cl | OPh—Cl-4 | SO$_2$Me | H |
| Cl | OPh—NO$_2$-4 | SO$_2$Me | H |
| Cl | OCH$_2$CH$_2$OMe | SO$_2$Me | H |
| Cl | OCH$_2$CH$_2$OEt | SO$_2$Me | H |
| Cl | OCH$_2$CH$_2$OPr-n | SO$_2$Me | H |
| Cl | OCH$_2$CH$_2$OPr-i | SO$_2$Me | H |
| Cl | OCH$_2$CH$_2$OBu-n | SO$_2$Me | H |
| Cl | OCH$_2$CH$_2$OBu-i | SO$_2$Me | H |
| Cl | OCH$_2$CH$_2$OBu-s | SO$_2$Me | H |
| Cl | OCH$_2$CH$_2$OBu-t | SO$_2$Me | H |
| Cl | OCH$_2$CH$_2$—Y4 | SO$_2$Me | H |
| Cl | OCHMeCH$_2$OMe | SO$_2$Me | H |
| Cl | OCH$_2$CHMeOMe | SO$_2$Me | H |
| Cl | OCH$_2$CH$_2$OPh | SO$_2$Me | H |
| Cl | OCH$_2$CH$_2$OCH$_2$CH$_2$OMe | SO$_2$Me | H |
| Cl | OCH$_2$CH$_2$OCH$_2$CH$_2$OPr-i | SO$_2$Me | H |
| Cl | OCH$_2$CH$_2$OCHMeCH$_2$OMe | SO$_2$Me | H |
| Cl | OCH$_2$CH$_2$OH | SO$_2$Me | H |
| Cl | OCH$_2$Ph | SO$_2$Me | H |
| Cl | OCHMePh | SO$_2$Me | H |
| Cl | OCH$_2$CH$_2$Ph | SO$_2$Me | H |
| Cl | OCH$_2$Ph-2-Cl | SO$_2$Me | H |
| Cl | OCH$_2$Ph-3-Me | SO$_2$Me | H |
| Cl | OCH$_2$Ph-4-OMe | SO$_2$Me | H |
| Cl | OCH$_2$Ph-4-NO$_2$ | SO$_2$Me | H |
| Cl | Y9 | SO$_2$Me | H |
| Cl | Y10 | SO$_2$Me | H |
| Cl | Y11 | SO$_2$Me | H |
| Cl | Y12 | SO$_2$Me | H |
| Cl | Y13 | SO$_2$Me | H |
| Cl | Y14 | SO$_2$Me | H |
| Cl | Y15 | SO$_2$Me | H |
| Cl | Y16 | SO$_2$Me | H |
| Cl | Y17 | SO$_2$Me | H |
| Cl | Y18 | SO$_2$Me | H |
| Cl | OCH$_2$CH$_2$NH$_2$ | SO$_2$Me | H |
| Cl | OCH$_2$CH$_2$NHMe | SO$_2$Me | H |
| Cl | OCH$_2$CH$_2$NHPr-i | SO$_2$Me | H |
| Cl | OCH$_2$CH$_2$NMe$_2$ | SO$_2$Me | H |
| Cl | OCH$_2$CH$_2$NEt$_2$ | SO$_2$Me | H |
| Cl | Y19 | SO$_2$Me | H |
| Cl | OCH$_2$COOMe | SO$_2$Me | H |
| Cl | OCH$_2$COOEt | SO$_2$Me | H |
| Cl | OCH$_2$COOPr-i | SO$_2$Me | H |
| Cl | OCH$_2$COOBu-i | SO$_2$Me | H |
| Cl | OCH$_2$COOBu-t | SO$_2$Me | H |
| Cl | OCH$_2$COO-Y4 | SO$_2$Me | H |
| Cl | OCHMeCOOMe | SO$_2$Me | H |
| Cl | OCHMeCOOEt | SO$_2$Me | H |
| Cl | OCHMeCOOPr-i | SO$_2$Me | H |
| Cl | OCH$_2$CH$_2$CN | SO$_2$Me | H |
| Cl | OCH$_2$SMe | SO$_2$Me | H |
| Cl | OCH$_2$CH$_2$SMe | SO$_2$Me | H |
| Cl | OCH$_2$CH$_2$S(O)Me | SO$_2$Me | H |
| Cl | OCH$_2$CH$_2$SO$_2$Me | SO$_2$Me | H |
| Cl | OCH$_2$CH$_2$SPr-i | SO$_2$Me | H |
| Cl | OCH$_2$CH$_2$S(O)Pr-i | SO$_2$Me | H |
| Cl | OCH$_2$CH$_2$SO$_2$Pr-i | SO$_2$Me | H |
| Cl | OCOOMe | SO$_2$Me | H |
| Cl | OCOOPr-i | SO$_2$Me | H |

TABLE 8-continued

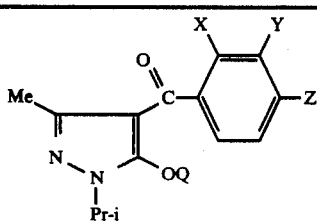

| X | Y | Z | Q |
|---|---|---|---|
| Cl | OCONH$_2$ | SO$_2$Me | H |
| Cl | OCONHMe | SO$_2$Me | H |
| Cl | OCONMe$_2$ | SO$_2$Me | H |
| Cl | OP(O)(OMe)$_2$ | SO$_2$Me | H |
| Cl | Y20 | SO$_2$Me | H |
| Cl | SCH$_2$CH=CH$_2$ | SO$_2$Me | H |
| Cl | SCH$_2$CH=CMe$_2$ | SO$_2$Me | H |
| Cl | SCH$_2$C≡CH | SO$_2$Me | H |
| Cl | SCH$_2$CF$_3$ | SO$_2$Me | H |
| Cl | SCH$_2$CCl$_3$ | SO$_2$Me | H |
| Cl | Y21 | SO$_2$Me | H |
| Cl | SPh | SO$_2$Me | H |
| Cl | SCH$_2$CH$_2$OMe | SO$_2$Me | H |
| Cl | SCH$_2$CH$_2$OEt | SO$_2$Me | H |
| Cl | SCH$_2$CH$_2$OPr-i | SO$_2$Me | H |
| Cl | Y22 | SO$_2$Me | H |
| Cl | S(O)CH$_2$CH=CH$_2$ | SO$_2$Me | H |
| Cl | S(O)CH$_2$CH=CMe$_2$ | SO$_2$Me | H |
| Cl | S(O)CH$_2$CH$_2$Cl | SO$_2$Me | H |
| Cl | Y23 | SO$_2$Me | H |
| Cl | SO$_2$CH$_2$CH=CH$_2$ | SO$_2$Me | H |
| Cl | SO$_2$CH$_2$CH=CMe$_2$ | SO$_2$Me | H |
| Cl | SO$_2$CH$_2$C≡CH | SO$_2$Me | H |
| Cl | SO$_2$CH$_2$CF$_3$ | SO$_2$Me | H |
| Cl | SO$_2$CH$_2$CH$_2$Cl | SO$_2$Me | H |
| Cl | Y24 | SO$_2$Me | H |
| Cl | Y25 | SO$_2$Me | H |
| Cl | SO$_2$Ph | SO$_2$Me | H |
| Cl | SO$_2$CH$_2$CH$_2$OMe | SO$_2$Me | H |
| Cl | SO$_2$CH$_2$CH$_2$OEt | SO$_2$Me | H |
| Cl | SO$_2$CH$_2$CH$_2$OPr-i | SO$_2$Me | H |
| Cl | OCH$_2$CH$_2$OMe | SO$_2$Me | CH$_2$Ph |
| Cl | OCH$_2$CH$_2$OEt | SO$_2$Me | CH$_2$Ph |
| Cl | OCH$_2$CH$_2$OPr-i | SO$_2$Me | CH$_2$Ph |
| Cl | OCHMeCH$_2$OMe | SO$_2$Me | CH$_2$Ph |
| Cl | OCH$_2$CH$_2$SMe | SO$_2$Me | CH$_2$Ph |
| Cl | OCH$_2$CH$_2$S(O)Me | SO$_2$Me | CH$_2$Ph |
| Cl | OCH$_2$CH$_2$SO$_2$Me | SO$_2$Me | CH$_2$Ph |
| Cl | OCH$_2$CH$_2$SPr-i | SO$_2$Me | CH$_2$Ph |
| Cl | OCH$_2$CH$_2$S(O)Pr-i | SO$_2$Me | CH$_2$Ph |
| Cl | OCH$_2$CH$_2$SO$_2$Pr-i | SO$_2$Me | CH$_2$Ph |
| Cl | SCH$_2$CH$_2$OMe | SO$_2$Me | CH$_2$Ph |
| Cl | SCH$_2$CH$_2$OPr-i | SO$_2$Me | CH$_2$Ph |
| Cl | SO$_2$CH$_2$CH$_2$OMe | SO$_2$Me | CH$_2$Ph |
| Cl | SO$_2$CH$_2$CH$_2$OPr-i | SO$_2$Me | CH$_2$Ph |
| Cl | OCH$_2$CH$_2$OMe | SO$_2$Me | CH$_2$COPh |
| Cl | OCH$_2$CH$_2$OPr-i | SO$_2$Me | CH$_2$COPh |
| Cl | OCH$_2$CH$_2$SMe | SO$_2$Me | CH$_2$COPh |
| Cl | OCH$_2$CH$_2$SOMe | SO$_2$Me | CH$_2$COPh |
| Cl | OCH$_2$CH$_2$SO$_2$Me | SO$_2$Me | CH$_2$COPh |
| Cl | OCH$_2$CH$_2$SPr-i | SO$_2$Me | CH$_2$COPh |
| Cl | OCH$_2$CH$_2$SO$_2$Pr-i | SO$_2$Me | CH$_2$COPh |
| Cl | SCH$_2$CH$_2$OMe | SO$_2$Me | CH$_2$COPh |
| Cl | SCH$_2$CH$_2$OPr-i | SO$_2$Me | CH$_2$COPh |
| Cl | SO$_2$CH$_2$CH$_2$OMe | SO$_2$Me | CH$_2$COPh |
| Cl | SO$_2$CH$_2$CH$_2$OPr-i | SO$_2$Me | CH$_2$COPh |
| Cl | OCH$_2$CH$_2$OMe | Cl | H |
| Cl | OCH$_2$CH$_2$OEt | Cl | H |
| Cl | OCH$_2$CH$_2$OPr-i | Cl | H |
| Cl | OCHMeCH$_2$OMe | Cl | H |
| Cl | OCH$_2$COOMe | Cl | H |
| Cl | OCH$_2$CH$_2$SMe | Cl | H |
| Cl | OCH$_2$CH$_2$SO$_2$Me | Cl | H |
| Cl | SCH$_2$CH$_2$OMe | Cl | H |
| Cl | SO$_2$CH$_2$CH$_2$OMe | Cl | H |
| Cl | OCH$_2$CH$_2$OMe | Cl | CH$_2$Ph |
| Cl | OCH$_2$CH$_2$SMe | Cl | CH$_2$Ph |
| Cl | OCH$_2$CH$_2$SOMe | Cl | CH$_2$Ph |
| Cl | OCH$_2$CH$_2$SO$_2$Me | Cl | CH$_2$Ph |
| Cl | SCH$_2$CH$_2$OMe | Cl | CH$_2$Ph |

TABLE 8-continued

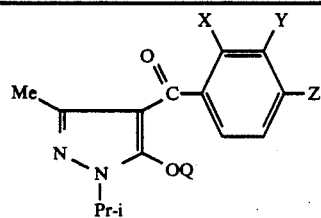

| X | Y | Z | Q |
|---|---|---|---|
| Cl | SO$_2$CH$_2$CH$_2$OMe | Cl | CH$_2$Ph |
| Cl | OCH$_2$CH$_2$OMe | Cl | CH$_2$COPh |
| Cl | OCH$_2$CH$_2$SMe | Cl | CH$_2$COPh |
| Cl | OCH$_2$CH$_2$SO$_2$Me | Cl | CH$_2$COPh |
| Cl | SCH$_2$CH$_2$OMe | Cl | CH$_2$COPh |
| Cl | SCH$_2$CH$_2$OEt | Cl | CH$_2$COPh |
| Cl | SO$_2$CH$_2$CH$_2$OMe | Cl | CH$_2$COPh |
| OMe | Y1 | SO$_2$Me | H |
| OMe | Y2 | SO$_2$Me | H |
| OMe | Y3 | SO$_2$Me | H |
| OMe | Y4 | SO$_2$Me | H |
| OMe | Y5 | SO$_2$Me | H |
| OMe | Y6 | SO$_2$Me | H |
| OMe | Y7 | SO$_2$Me | H |
| OMe | OCH$_2$CH=CH$_2$ | SO$_2$Me | H |
| OMe | OCHMeCH=CH$_2$ | SO$_2$Me | H |
| OMe | OCMe$_2$CH=CH$_2$ | SO$_2$Me | H |
| OMe | OCH$_2$CMe=CH$_2$ | SO$_2$Me | H |
| OMe | OCH$_2$CH=CHMe | SO$_2$Me | H |
| OMe | OCH$_2$CH=CMe$_2$ | SO$_2$Me | H |
| OMe | OCH$_2$CH$_2$CH=CH$_2$ | SO$_2$Me | H |
| OMe | OCH$_2$C≡CH | SO$_2$Me | H |
| OMe | OCHMeC≡CH | SO$_2$Me | H |
| OMe | OCMe$_2$C≡CH | SO$_2$Me | H |
| OMe | OCH$_2$C≡CMe | SO$_2$Me | H |
| OMe | OCH$_2$CH$_2$F | SO$_2$Me | H |
| OMe | OCH$_2$CHF$_2$ | SO$_2$Me | H |
| OMe | OCH$_2$CF$_3$ | SO$_2$Me | H |
| OMe | OCH$_2$CH$_2$Cl | SO$_2$Me | H |
| OMe | OCH$_2$CCl$_3$ | SO$_2$Me | H |
| OMe | OCHMeCH$_2$Cl | SO$_2$Me | H |
| OMe | OCH$_2$CH$_2$CH$_2$Cl | SO$_2$Me | H |
| OMe | OCH$_2$CH$_2$Br | SO$_2$Me | H |
| OMe | Y8 | SO$_2$Me | H |
| OMe | OCH$_2$CCl=CH$_2$ | SO$_2$Me | H |
| OMe | OCH$_2$CCl=CHCl | SO$_2$Me | H |
| OMe | OCH$_2$CH$_2$NO$_2$ | SO$_2$Me | H |
| OMe | OPh | SO$_2$Me | H |
| OMe | OPh—Me-2 | SO$_2$Me | H |
| OMe | OPh—Cl-4 | SO$_2$Me | H |
| OMe | OPh—NO$_2$-4 | SO$_2$Me | H |
| OMe | OCH$_2$CH$_2$OMe | SO$_2$Me | H |
| OMe | OCH$_2$CH$_2$OEt | SO$_2$Me | H |
| OMe | OCH$_2$CH$_2$OPr-n | SO$_2$Me | H |
| OMe | OCH$_2$CH$_2$OPr-i | SO$_2$Me | H |
| OMe | OCH$_2$CH$_2$OBu-n | SO$_2$Me | H |
| OMe | OCH$_2$CH$_2$OBu-i | SO$_2$Me | H |
| OMe | OCH$_2$CH$_2$OBu-s | SO$_2$Me | H |
| OMe | OCH$_2$CH$_2$OBu-t | SO$_2$Me | H |
| OMe | OCH$_2$CH$_2$—Y4 | SO$_2$Me | H |
| OMe | OCHMeCH$_2$OMe | SO$_2$Me | H |
| OMe | OCH$_2$CHMeOMe | SO$_2$Me | H |
| OMe | OCH$_2$CH$_2$OPh | SO$_2$Me | H |
| OMe | OCH$_2$CH$_2$OCH$_2$CH$_2$OMe | SO$_2$Me | H |
| OMe | OCH$_2$CH$_2$OCH$_2$CH$_2$OPr-i | SO$_2$Me | H |
| OMe | OCH$_2$CH$_2$OCHMeCH$_2$OMe | SO$_2$Me | H |
| OMe | OCH$_2$CH$_2$OH | SO$_2$Me | H |
| OMe | OCH$_2$Ph | SO$_2$Me | H |
| OMe | OCHMePh | SO$_2$Me | H |
| OMe | OCH$_2$CH$_2$Ph | SO$_2$Me | H |
| OMe | OCH$_2$Ph-2-Cl | SO$_2$Me | H |
| OMe | OCH$_2$Ph-3-Me | SO$_2$Me | H |
| OMe | OCH$_2$Ph-4-OMe | SO$_2$Me | H |
| OMe | OCH$_2$Ph-4-NO$_2$ | SO$_2$Me | H |
| OMe | Y9 | SO$_2$Me | H |
| OMe | Y10 | SO$_2$Me | H |
| OMe | Y11 | SO$_2$Me | H |
| OMe | Y12 | SO$_2$Me | H |
| OMe | Y13 | SO$_2$Me | H |
| OMe | Y14 | SO$_2$Me | H |

TABLE 8-continued

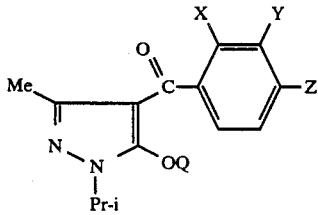

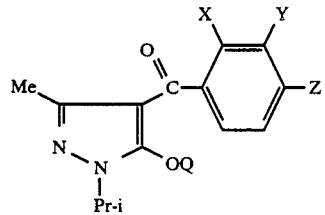

| X | Y | Z | Q |
|---|---|---|---|
| OMe | Y15 | $SO_2Me$ | H |
| OMe | Y16 | $SO_2Me$ | H |
| OMe | Y17 | $SO_2Me$ | H |
| OMe | Y18 | $SO_2Me$ | H |
| OMe | $OCH_2CH_2NH_2$ | $SO_2Me$ | H |
| OMe | $OCH_2CH_2NHMe$ | $SO_2Me$ | H |
| OMe | $OCH_2CH_2NHPr\text{-}i$ | $SO_2Me$ | H |
| OMe | $OCH_2CH_2NMe_2$ | $SO_2Me$ | H |
| OMe | $OCH_2CH_2NEt_2$ | $SO_2Me$ | H |
| OMe | Y19 | $SO_2Me$ | H |
| OMe | $OCH_2COOMe$ | $SO_2Me$ | H |
| OMe | $OCH_2COOEt$ | $SO_2Me$ | H |
| OMe | $OCH_2COOPr\text{-}i$ | $SO_2Me$ | H |
| OMe | $OCH_2COOBu\text{-}i$ | $SO_2Me$ | H |
| OMe | $OCH_2COOBu\text{-}t$ | $SO_2Me$ | H |
| OMe | $OCH_2COO-Y4$ | $SO_2Me$ | H |
| OMe | $OCHMeCOOMe$ | $SO_2Me$ | H |
| OMe | $OCHMeCOOEt$ | $SO_2Me$ | H |
| OMe | $OCHMeCOOPr\text{-}i$ | $SO_2Me$ | H |
| OMe | $OCH_2CH_2CN$ | $SO_2Me$ | H |
| OMe | $OCH_2SMe$ | $SO_2Me$ | H |
| OMe | $OCH_2CH_2SMe$ | $SO_2Me$ | H |
| OMe | $OCH_2CH_2S(O)Me$ | $SO_2Me$ | H |
| OMe | $OCH_2CH_2SO_2Me$ | $SO_2Me$ | H |
| OMe | $OCH_2CH_2SPr\text{-}i$ | $SO_2Me$ | H |
| OMe | $OCH_2CH_2S(O)Pr\text{-}i$ | $SO_2Me$ | H |
| OMe | $OCH_2CH_2SO_2Pr\text{-}i$ | $SO_2Me$ | H |
| OMe | $OCOOMe$ | $SO_2Me$ | H |
| OMe | $OCOOPr\text{-}i$ | $SO_2Me$ | H |
| OMe | $OCONH_2$ | $SO_2Me$ | H |
| OMe | $OCONHMe$ | $SO_2Me$ | H |
| OMe | $OCONME_2$ | $SO_2Me$ | H |
| OMe | $OP(O)(OMe)_2$ | $SO_2Me$ | H |
| OMe | Y20 | $SO_2Me$ | H |
| OMe | $SCH_2CH=CH_2$ | $SO_2Me$ | H |
| OMe | $SCH_2CH=CMe_2$ | $SO_2Me$ | H |
| OMe | $SCH_2C\equiv CH$ | $SO_2Me$ | H |
| OMe | $SCH_2CF_3$ | $SO_2Me$ | H |
| OMe | $SCH_2CCl_3$ | $SO_2Me$ | H |
| OMe | Y21 | $SO_2Me$ | H |
| OMe | SPh | $SO_2Me$ | H |
| OMe | $SCH_2CH_2OMe$ | $SO_2Me$ | H |
| OMe | $SCH_2CH_2OEt$ | $SO_2Me$ | H |
| OMe | $SCH_2CH_2OPr\text{-}i$ | $SO_2Me$ | H |
| OMe | Y22 | $SO_2Me$ | H |
| OMe | $S(O)CH_2CH=CH_2$ | $SO_2Me$ | H |
| OMe | $S(O)CH_2CH=CMe_2$ | $SO_2Me$ | H |
| OMe | $S(O)CH_2C\equiv CH$ | $SO_2Me$ | H |
| OMe | $S(O)CH_2CH_2Cl$ | $SO_2Me$ | H |
| OMe | Y23 | $SO_2Me$ | H |
| OMe | $SO_2CH_2CH=CH_2$ | $SO_2Me$ | H |
| OMe | $SO_2CH_2CH=CMe_2$ | $SO_2Me$ | H |
| OMe | $SO_2CH_2C\equiv CH$ | $SO_2Me$ | H |
| OMe | $SO_2CH_2CF_3$ | $SO_2Me$ | H |
| OMe | $SO_2CH_2CH_2Cl$ | $SO_2Me$ | H |
| OMe | Y24 | $SO_2Me$ | H |
| OMe | Y25 | $SO_2Me$ | H |
| OMe | $SO_2Ph$ | $SO_2Me$ | H |
| OMe | $SO_2CH_2CH_2OMe$ | $SO_2Me$ | H |
| OMe | $SO_2CH_2CH_2OEt$ | $SO_2Me$ | H |
| OMe | $SO_2CH_2CH_2OPr\text{-}i$ | $SO_2Me$ | H |
| OMe | $OCH_2CH_2OMe$ | $SO_2Me$ | $CH_2Ph$ |
| OMe | $OCH_2CH_2OEt$ | $SO_2Me$ | $CH_2Ph$ |
| OMe | $OCH_2CH_2OPr\text{-}i$ | $SO_2Me$ | $CH_2Ph$ |
| OMe | $OCHMeCH_2OMe$ | $SO_2Me$ | $CH_2Ph$ |
| OMe | $OCH_2CH_2SMe$ | $SO_2Me$ | $CH_2Ph$ |
| OMe | $OCH_2CH_2S(O)Me$ | $SO_2Me$ | $CH_2Ph$ |
| OMe | $OCH_2CH_2SO_2Me$ | $SO_2Me$ | $CH_2Ph$ |
| OMe | $OCH_2CH_2SPr\text{-}i$ | $SO_2Me$ | $CH_2Ph$ |
| OMe | $OCH_2CH_2S(O)Pr\text{-}i$ | $SO_2Me$ | $CH_2Ph$ |
| OMe | $OCH_2CH_2SO_2Pr\text{-}i$ | $SO_2Me$ | $CH_2Ph$ |
| OMe | $SCH_2CH_2OMe$ | $SO_2Me$ | $CH_2Ph$ |
| OMe | $SCH_2CH_2OPr\text{-}i$ | $SO_2Me$ | $CH_2Ph$ |
| OMe | $SO_2CH_2CH_2OMe$ | $SO_2Me$ | $CH_2Ph$ |
| OMe | $SO_2CH_2CH_2OPr\text{-}i$ | $SO_2Me$ | $CH_2Ph$ |
| OMe | $OCH_2CH_2OMe$ | $SO_2Me$ | $CH_2COPh$ |
| OMe | $OCH_2CH_2OPr\text{-}i$ | $SO_2Me$ | $CH_2COPh$ |
| OMe | $OCH_2CH_2SMe$ | $SO_2Me$ | $CH_2COPh$ |
| OMe | $OCH_2CH_2SOMe$ | $SO_2Me$ | $CH_2COPh$ |
| OMe | $OCH_2CH_2SO_2Me$ | $SO_2Me$ | $CH_2COPh$ |
| OMe | $OCH_2CH_2SPr\text{-}i$ | $SO_2Me$ | $CH_2COPh$ |
| OMe | $OCH_2CH_2SO_2Pr\text{-}i$ | $SO_2Me$ | $CH_2COPh$ |
| OMe | $SCH_2CH_2OMe$ | $SO_2Me$ | $CH_2COPh$ |
| OMe | $SCH_2CH_2OPr\text{-}i$ | $SO_2Me$ | $CH_2COPh$ |
| OMe | $SO_2CH_2CH_2OMe$ | $SO_2Me$ | $CH_2COPh$ |
| OMe | $SO_2CH_2CH_2OPr\text{-}i$ | $SO_2Me$ | $CH_2COPh$ |
| OMe | $OCH_2CH_2OMe$ | Cl | H |
| OMe | $OCH_2CH_2OEt$ | Cl | H |
| OMe | $OCH_2CH_2OPr\text{-}i$ | Cl | H |
| OMe | $OCHMeCH_2OMe$ | Cl | H |
| OMe | $OCH_2COOMe$ | Cl | H |
| OMe | $OCH_2CH_2SMe$ | Cl | H |
| OMe | $OCH_2CH_2SO_2Me$ | Cl | H |
| OMe | $SCH_2CH_2OMe$ | Cl | H |
| OMe | $SO_2CH_2CH_2OMe$ | Cl | H |
| OMe | $OCH_2CH_2OMe$ | Cl | $CH_2Ph$ |
| OMe | $OCH_2CH_2SMe$ | Cl | $CH_2Ph$ |
| OMe | $OCH_2CH_2SOMe$ | Cl | $CH_2Ph$ |
| OMe | $OCH_2CH_2SO_2Me$ | Cl | $CH_2Ph$ |
| OMe | $SCH_2CH_2OMe$ | Cl | $CH_2Ph$ |
| OMe | $SO_2CH_2CH_2OMe$ | Cl | $CH_2Ph$ |
| OMe | $OCH_2CH_2OMe$ | Cl | $CH_2COPh$ |
| OMe | $OCH_2CH_2SMe$ | Cl | $CH_2COPh$ |
| OMe | $OCH_2CH_2SO_2Me$ | Cl | $CH_2COPh$ |
| OMe | $SCH_2CH_2OMe$ | Cl | $CH_2COPh$ |
| OMe | $SCH_2CH_2OEt$ | Cl | $CH_2COPh$ |
| OMe | $SO_2CH_2CH_2OMe$ | Cl | $CH_2COPh$ |
| $CH_2OMe$ | Y1 | $SO_2Me$ | H |
| $CH_2OMe$ | Y2 | $SO_2Me$ | H |
| $CH_2OMe$ | Y3 | $SO_2Me$ | H |
| $CH_2OMe$ | Y4 | $SO_2Me$ | H |
| $CH_2OMe$ | Y5 | $SO_2Me$ | H |
| $CH_2OMe$ | Y6 | $SO_2Me$ | H |
| $CH_2OMe$ | Y7 | $SO_2Me$ | H |
| $CH_2OMe$ | $OCH_2CH=CH_2$ | $SO_2Me$ | H |
| $CH_2OMe$ | $OCHMeCH=CH_2$ | $SO_2Me$ | H |
| $CH_2OMe$ | $OCHMe_2CH=CH_2$ | $SO_2Me$ | H |
| $CH_2OMe$ | $OCH_2CMe=CH_2$ | $SO_2Me$ | H |
| $CH_2OMe$ | $OCH_2CH=CHMe$ | $SO_2Me$ | H |
| $CH_2OMe$ | $OCH_2CH=CMe_2$ | $SO_2Me$ | H |
| $CH_2OMe$ | $OCH_2CH_2CH=CH_2$ | $SO_2Me$ | H |
| $CH_2OMe$ | $OCH_2C\equiv CH$ | $SO_2Me$ | H |
| $CH_2OMe$ | $OCHMeC\equiv CH$ | $SO_2Me$ | H |
| $CH_2OMe$ | $OCMe_2C\equiv CH$ | $SO_2Me$ | H |
| $CH_2OMe$ | $OCH_2C\equiv CMe$ | $SO_2Me$ | H |
| $CH_2OMe$ | $OCH_2CH_2F$ | $SO_2Me$ | H |
| $CH_2OMe$ | $OCH_2CHF_2$ | $SO_2Me$ | H |
| $CH_2OMe$ | $OCH_2CF_3$ | $SO_2Me$ | H |
| $CH_2OMe$ | $OCH_2CH_2Cl$ | $SO_2Me$ | H |
| $CH_2OMe$ | $OCH_2CCl_3$ | $SO_2Me$ | H |
| $CH_2OMe$ | $OCHMeCH_2Cl$ | $SO_2Me$ | H |
| $CH_2OMe$ | $OCH_2CH_2CH_2Cl$ | $SO_2Me$ | H |
| $CH_2OMe$ | $OCH_2CH_2Br$ | $SO_2Me$ | H |
| $CH_2OMe$ | Y8 | $SO_2Me$ | H |
| $CH_2OMe$ | $OCH_2CCl=CH_2$ | $SO_2Me$ | H |
| $CH_2OMe$ | $OCH_2CCl=CHCl$ | $SO_2Me$ | H |
| $CH_2OMe$ | $OCH_2CH_2NO_2$ | $SO_2Me$ | H |
| $CH_2OMe$ | OPh | $SO_2Me$ | H |
| $CH_2OMe$ | $OPh-Me-2$ | $SO_2Me$ | H |
| $CH_2OMe$ | $OPh-Cl-4$ | $SO_2Me$ | H |

TABLE 8-continued

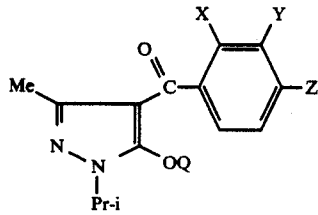

| X | Y | Z | Q |
|---|---|---|---|
| CH$_2$OMe | OPh—NO$_2$-4 | SO$_2$Me | H |
| CH$_2$OMe | OCH$_2$CH$_2$OMe | SO$_2$Me | H |
| CH$_2$OMe | OCH$_2$CH$_2$OEt | SO$_2$Me | H |
| CH$_2$OMe | OCH$_2$CH$_2$OPr-n | SO$_2$Me | H |
| CH$_2$OMe | OCH$_2$CH$_2$OPr-i | SO$_2$Me | H |
| CH$_2$OMe | OCH$_2$CH$_2$OBu-n | SO$_2$Me | H |
| CH$_2$OMe | OCH$_2$CH$_2$OBu-i | SO$_2$Me | H |
| CH$_2$OMe | OCH$_2$CH$_2$OBu-s | SO$_2$Me | H |
| CH$_2$OMe | OCH$_2$CH$_2$OBu-t | SO$_2$Me | H |
| CH$_2$OMe | OCH$_2$CH$_2$—Y4 | SO$_2$Me | H |
| CH$_2$OMe | OCHMeCH$_2$OMe | SO$_2$Me | H |
| CH$_2$OMe | OCH$_2$CHMeOMe | SO$_2$Me | H |
| CH$_2$OMe | OCH$_2$CH$_2$OPh | SO$_2$Me | H |
| CH$_2$OMe | OCH$_2$CH$_2$OCH$_2$CH$_2$OMe | SO$_2$Me | H |
| CH$_2$OMe | OCH$_2$CH$_2$OCH$_2$CH$_2$OPr-i | SO$_2$Me | H |
| CH$_2$OMe | OCH$_2$CH$_2$OCHMeCH$_2$OMe | SO$_2$Me | H |
| CH$_2$OMe | OCH$_2$CH$_2$OH | SO$_2$Me | H |
| CH$_2$OMe | OCH$_2$Ph | SO$_2$Me | H |
| CH$_2$OMe | OCHMePh | SO$_2$Me | H |
| CH$_2$OMe | OCH$_2$CH$_2$Ph | SO$_2$Me | H |
| CH$_2$OMe | OCH$_2$Ph-2-Cl | SO$_2$Me | H |
| CH$_2$OMe | OCH$_2$Ph-3-Me | SO$_2$Me | H |
| CH$_2$OMe | OCH$_2$Ph-4-OMe | SO$_2$Me | H |
| CH$_2$OMe | OCH$_2$Ph-4-NO$_2$ | SO$_2$Me | H |
| CH$_2$OMe | Y9 | SO$_2$Me | H |
| CH$_2$OMe | Y10 | SO$_2$Me | H |
| CH$_2$OMe | Y11 | SO$_2$Me | H |
| CH$_2$OMe | Y12 | SO$_2$Me | H |
| CH$_2$OMe | Y13 | SO$_2$Me | H |
| CH$_2$OMe | Y14 | SO$_2$Me | H |
| CH$_2$OMe | Y15 | SO$_2$Me | H |
| CH$_2$OMe | Y16 | SO$_2$Me | H |
| CH$_2$OMe | Y17 | SO$_2$Me | H |
| CH$_2$OMe | Y18 | SO$_2$Me | H |
| CH$_2$OMe | OCH$_2$CH$_2$NH$_2$ | SO$_2$Me | H |
| CH$_2$OMe | OCH$_2$CH$_2$NHMe | SO$_2$Me | H |
| CH$_2$OMe | OCH$_2$CH$_2$NHPr-i | SO$_2$Me | H |
| CH$_2$OMe | OCH$_2$CH$_2$NMe$_2$ | SO$_2$Me | H |
| CH$_2$OMe | OCH$_2$CH$_2$NEt$_2$ | SO$_2$Me | H |
| CH$_2$OMe | Y19 | SO$_2$Me | H |
| CH$_2$OMe | OCH$_2$COOMe | SO$_2$Me | H |
| CH$_2$OMe | OCH$_2$COOEt | SO$_2$Me | H |
| CH$_2$OMe | OCH$_2$COOPr-i | SO$_2$Me | H |
| CH$_2$OMe | OCH$_2$COOBu-i | SO$_2$Me | H |
| CH$_2$OMe | OCH$_2$COOBu-t | SO$_2$Me | H |
| CH$_2$OMe | OCH$_2$COO—Y4 | SO$_2$Me | H |
| CH$_2$OMe | OCHMeCOOMe | SO$_2$Me | H |
| CH$_2$OMe | OCHMeCOOEt | SO$_2$Me | H |
| CH$_2$OMe | OCHMeCOOPr-i | SO$_2$Me | H |
| CH$_2$OMe | OCH$_2$CH$_2$CN | SO$_2$Me | H |
| CH$_2$OMe | OCH$_2$SMe | SO$_2$Me | H |
| CH$_2$OMe | OCH$_2$CH$_2$SMe | SO$_2$Me | H |
| CH$_2$OMe | OCH$_2$CH$_2$S(O)Me | SO$_2$Me | H |
| CH$_2$OMe | OCH$_2$CH$_2$SO$_2$Me | SO$_2$Me | H |
| CH$_2$OMe | OCH$_2$CH$_2$SPr-i | SO$_2$Me | H |
| CH$_2$OMe | OCH$_2$CH$_2$S(O)Pr-i | SO$_2$Me | H |
| CH$_2$OMe | OCH$_2$CH$_2$SO$_2$Pr-i | SO$_2$Me | H |
| CH$_2$OMe | OCOOMe | SO$_2$Me | H |
| CH$_2$OMe | OCOOPr-i | SO$_2$Me | H |
| CH$_2$OMe | OCONH$_2$ | SO$_2$Me | H |
| CH$_2$OMe | OCONHME | SO$_2$Me | H |
| CH$_2$OMe | OCONMe$_2$ | SO$_2$Me | H |
| CH$_2$OMe | OP(O)(OMe)$_2$ | SO$_2$Me | H |
| CH$_2$OMe | Y20 | SO$_2$Me | H |
| CH$_2$OMe | SCH$_2$CH=CH$_2$ | SO$_2$Me | H |
| CH$_2$OMe | SCH$_2$CH=CMe$_2$ | SO$_2$Me | H |
| CH$_2$OMe | SCH$_2$C≡CH | SO$_2$Me | H |
| CH$_2$OMe | SCH$_2$CF$_3$ | SO$_2$Me | H |
| CH$_2$OMe | SCH$_2$CCl$_3$ | SO$_2$Me | H |
| CH$_2$OMe | Y21 | SO$_2$Me | H |

TABLE 8-continued

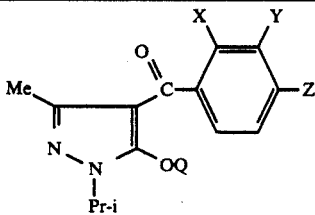

| X | Y | Z | Q |
|---|---|---|---|
| CH$_2$OMe | SPh | SO$_2$Me | H |
| CH$_2$OMe | SCH$_2$CH$_2$OMe | SO$_2$Me | H |
| CH$_2$OMe | SCH$_2$CH$_2$OEt | SO$_2$Me | H |
| CH$_2$OMe | SCH$_2$CH$_2$OPr-i | SO$_2$Me | H |
| CH$_2$OMe | Y22 | SO$_2$Me | H |
| CH$_2$OMe | S(O)CH$_2$CH=CH$_2$ | SO$_2$Me | H |
| CH$_2$OMe | S(O)CH$_2$CH=CMe$_2$ | SO$_2$Me | H |
| CH$_2$OMe | S(O)CH$_2$C≡CH | SO$_2$Me | H |
| CH$_2$OMe | S(O)CH$_2$CH$_2$Cl | SO$_2$Me | H |
| CH$_2$OMe | Y23 | SO$_2$Me | H |
| CH$_2$OMe | SO$_2$CH$_2$CH=CH$_2$ | SO$_2$Me | H |
| CH$_2$OMe | SO$_2$CH$_2$CH=CMe$_2$ | SO$_2$Me | H |
| CH$_2$OMe | SO$_2$CH$_2$C≡CH | SO$_2$Me | H |
| CH$_2$OMe | SO$_2$CH$_2$CF$_3$ | SO$_2$Me | H |
| CH$_2$OMe | SO$_2$CH$_2$CH$_2$Cl | SO$_2$Me | H |
| CH$_2$OMe | Y24 | SO$_2$Me | H |
| CH$_2$OMe | SO$_2$Ph | SO$_2$Me | H |
| CH$_2$OMe | SO$_2$CH$_2$CH$_2$OMe | SO$_2$Me | H |
| CH$_2$OMe | SO$_2$CH$_2$CH$_2$OEt | SO$_2$Me | H |
| CH$_2$OMe | SO$_2$CH$_2$CH$_2$OPr-i | SO$_2$Me | H |
| CH$_2$OMe | OCH$_2$CH$_2$OMe | SO$_2$Me | CH$_2$Ph |
| CH$_2$OMe | OCH$_2$CH$_2$OEt | SO$_2$Me | CH$_2$Ph |
| CH$_2$OMe | OCH$_2$CH$_2$OPr-i | SO$_2$Me | CH$_2$Ph |
| CH$_2$OMe | OCHMeCH$_2$OMe | SO$_2$Me | CH$_2$Ph |
| CH$_2$OMe | OCH$_2$CH$_2$SMe | SO$_2$Me | CH$_2$Ph |
| CH$_2$OMe | OCH$_2$CH$_2$S(O)Me | SO$_2$Me | CH$_2$Ph |
| CH$_2$OMe | OCH$_2$CH$_2$SO$_2$Me | SO$_2$Me | CH$_2$Ph |
| CH$_2$OMe | OCH$_2$CH$_2$SPr-i | SO$_2$Me | CH$_2$Ph |
| CH$_2$OMe | OCH$_2$CH$_2$S(O)Pr-i | SO$_2$Me | CH$_2$Ph |
| CH$_2$OMe | OCH$_2$CH$_2$SO$_2$Pr-i | SO$_2$Me | CH$_2$Ph |
| CH$_2$OMe | SCH$_2$CH$_2$OMe | SO$_2$Me | CH$_2$Ph |
| CH$_2$OMe | SCH$_2$CH$_2$OPr-i | SO$_2$Me | CH$_2$Ph |
| CH$_2$OMe | SO$_2$CH$_2$CH$_2$OMe | SO$_2$Me | CH$_2$Ph |
| CH$_2$OMe | SO$_2$CH$_2$CH$_2$OPr-i | SO$_2$Me | CH$_2$Ph |
| CH$_2$OMe | OCH$_2$CH$_2$OMe | SO$_2$Me | CH$_2$COPh |
| CH$_2$OMe | OCH$_2$CH$_2$OPr-i | SO$_2$Me | CH$_2$COPh |
| CH$_2$OMe | OCH$_2$CH$_2$SMe | SO$_2$Me | CH$_2$COPh |
| CH$_2$OMe | OCH$_2$CH$_2$SOMe | SO$_2$Me | CH$_2$COPh |
| CH$_2$OMe | OCH$_2$CH$_2$SO$_2$Me | SO$_2$Me | CH$_2$COPh |
| CH$_2$OMe | OCH$_2$CH$_2$SPr-i | SO$_2$Me | CH$_2$COPh |
| CH$_2$OMe | OCH$_2$CH$_2$SO$_2$Pr-i | SO$_2$Me | CH$_2$COPh |
| CH$_2$OMe | SCH$_2$CH$_2$OMe | SO$_2$Me | CH$_2$COPh |
| CH$_2$OMe | SCH$_2$CH$_2$OPr-i | SO$_2$Me | CH$_2$COPh |
| CH$_2$OMe | SO$_2$CH$_2$CH$_2$OMe | SO$_2$Me | CH$_2$COPh |
| CH$_2$OMe | SO$_2$CH$_2$CH$_2$OPr-i | SO$_2$Me | CH$_2$COPh |
| CH$_2$OMe | OCH$_2$CH$_2$OMe | Cl | H |
| CH$_2$OMe | OCH$_2$CH$_2$OEt | Cl | H |
| CH$_2$OMe | OCH$_2$CH$_2$OPr-i | Cl | H |
| CH$_2$OMe | OCHMeCH$_2$OMe | Cl | H |
| CH$_2$OMe | OCH$_2$COOMe | Cl | H |
| CH$_2$OMe | OCH$_2$CH$_2$SMe | Cl | H |
| CH$_2$OMe | OCH$_2$CH$_2$SO$_2$Me | Cl | H |
| CH$_2$OMe | SCH$_2$CH$_2$OMe | Cl | H |
| CH$_2$OMe | SO$_2$CH$_2$CH$_2$OMe | Cl | H |
| CH$_2$OMe | OCH$_2$CH$_2$OMe | Cl | CH$_2$Ph |
| CH$_2$OMe | OCH$_2$CH$_2$SMe | Cl | CH$_2$Ph |
| CH$_2$OMe | OCH$_2$CH$_2$SOMe | Cl | CH$_2$Ph |
| CH$_2$OMe | OCH$_2$CH$_2$SO$_2$Me | Cl | CH$_2$Ph |
| CH$_2$OMe | SCH$_2$CH$_2$OMe | Cl | CH$_2$Ph |
| CH$_2$OMe | SO$_2$CH$_2$CH$_2$OMe | Cl | CH$_2$Ph |
| CH$_2$OMe | OCH$_2$CH$_2$OMe | Cl | CH$_2$COPh |
| CH$_2$OMe | OCH$_2$CH$_2$SMe | Cl | CH$_2$COPh |
| CH$_2$OMe | OCH$_2$CH$_2$SO$_2$Me | Cl | CH$_2$COPh |
| CH$_2$OMe | SCH$_2$CH$_2$OMe | Cl | CH$_2$COPh |
| CH$_2$OMe | SCH$_2$CH$_2$OEt | Cl | CH$_2$COPh |
| CH$_2$OMe | SO$_2$CH$_2$CH$_2$OMe | Cl | CH$_2$COPh |

When the compound of the present invention is to be used as an agricultural or horticultural herbicide, it is usually mixed with a suitable carrier, for instance, a solid carrier such as clay, talc, bentonite or diatomaceous earth, or a liquid carrier such as water, an alcohol (such as benzene, toluene or xylene), a chlorinated hydrocarbon, an ether, a ketone, an ester (such as ethyl acetate) or an acid amide (such as dimethylformamide). If desired, an emulsifier, a dispersing agent, a suspending agent, a penetrating agent, a spreader or a stabilizer may be added to prepare an optional formulation such as a liquid formulation, an emulsifiable concentrate, a wettable powder, a dust, a granule or a flowable.

Further, if desired, other herbicides, various insecticides, bacteriocides, plant regulating agents or synergism agents may be combined at the time of the preparation of the formulations or at the time of the application of the herbicides.

As other herbicides to be combined with the herbicide of the present invention, there may be mentioned, for instance, compounds disclosed in Farm Chemicals Handbook, the 73rd Edition (1987). Among them, there may be mentioned, for example, atrazine, cyanazine, alachlor, metolachlor, EPTC, 2,4-D, butylate, dicamba, bromoxynil, tridiphane, isoproturon, chlortoluron, triallate, difluphenican, diclofop methyl, diphenzoquat, imazamethabenz methyl, ioxynil, methabenzthazuron, fluroxypil, chlorsulfuron and N-[(4,6-di(difluoromethoxy)pyrimidin-2-yl)aminocarbonyl]-2-methoxycarbonylbenzenesulfonamide. N-[(4,6-dimethoxypyrimidin-2-yl)-aminocarbonyl]-3-chloro-4-methoxycarbonyl-1-methylpyrazole-5-sulfonamide or N-[(4,6-dimethoxypyrimidin-2-yl)aminocarbonyl]-3-bromo-4-methoxycarbonyl-1-methylpyrazole-5sulfonamide as disclosed in U.S. Pat. No. 4,668,277, or N-[(4,6-dimethoxypyrimidin-2-yl)aminocarbonyl]-3-dimethylaminocarbonylpyridine-2-sulfonamide as disclosed in Japanese Unexamined Patent Publication No. 223180/1987 may also be combined with the herbicide of the present invention.

The dose varies depending upon the application site, the season for application, the method for application, the type of the crop plant, etc. In general, however, the dose is usually within a range of from 0.001 to 10 kg per hectare as the amount of the active ingredient.

Now, Formulation Examples of the herbicides containing the compounds of the present inveniton as active ingredients, will be given. However, it should be understood that the present invention is by no means restricted to such specific Examples. In the following Formulation Examples, "parts" means "parts by weight".

FORMULATION EXAMPLE 1

Wettable powder

| | |
|---|---|
| Compound No. 1 of the present invention | 60 parts |
| Zeeklite PFP (tradename for a kaolin-type clay, manufactured by Zeeklite Industries, Co., Ltd.) | 33 parts |
| Sorpol 5039 (tradename for a mixture of a nonionic surfactant and an anionic surfactant, manufactured by Toho Chemical Co., Ltd.) | 5 parts |
| Carplex (tradename for a coagulation-preventing agent composed of a mixture of a surfactant and fine silica powder, manufactured by Shionogi Pharmaceutical Co., Ltd.) | 2 parts |

The above ingredients are homogeneously pulverized and mixed to form a wettable powder.

FORMULATION EXAMPLE 2

Emulsifiable concentrate

| | |
|---|---|
| Compound No. 1 of the present invention | 1.5 parts |
| Xylene | 78.5 parts |
| N,N-dimethylformamide | 15 parts |
| Sorpol 2680 (tradename for a mixture of a nonionic surfactant and an anionic surfactant, manufactured by Toho Chemical Co., Ltd.) | 5 parts |

The above ingredients are homogeneously mixed to form an emulsifiable concentrate.

FORMULATION EXAMPLE 3

Flowable

| | |
|---|---|
| Compound No. 1 of the present invention | 40 parts |
| Agrizole B-710 (tradename for a nonionic surfactant, manufactured by Kao Corporation) | 10 parts |
| Runox 1000C (tradename for an anionic surfactant, manufactured by Toho Chemical Co., Ltd.) | 0.5 part |
| 1% Rodopol water (tradename for a thickner, manufactured by Rhone-Poulenc) | 20 parts |
| Water | 29.5 parts |

The above ingredients are homogeneously mixed to form a flowable.

FORMULATION EXAMPLE 4

Liquid formulation

| | |
|---|---|
| Sodium salt of Compound No 1 of the present invention | 30 parts |
| Nippol (tradename for a nonionic surfactant, manufactured by Nissan Chemical Industries Ltd.) | 10 parts |
| Water | 60 parts |

The above ingredients are homogeneously mixed to obtain a liquid formulation.

FORMULATION EXAMPLE 5

Liquid formulation

| | |
|---|---|
| Potassium salt of Compound No. 1 of the present invention | 30 parts |
| Nippol (tradename for a nonionic surfactant, manufactured by Nissan Chemical Industries Ltd.) | 10 parts |
| Water | 60 parts |

The above ingredients are homogeneously mixed to obtain a liquid formulation.

FORMULATION EXAMPLE 6

Liquid formulation

| | |
|---|---|
| Calcium salt of Compound No. 1 of the | 30 parts |

| | |
|---|---|
| present invention | |
| Nippol (tradename for a nonionic surfactant, manufactured by Nissan Chemical Industries Ltd.) | 10 parts |
| Water | 60 parts |

The above ingredients are homogeneously mixed to obtain a liquid formulation.

FORMULATION EXAMPLE 7

Liquid formulation

| | |
|---|---|
| Isopropylamine salt of Compound No. 1 of the present invention | 10 parts |
| Sorpol W-150 (tradename for a nonionic surfactant, manufactured by Toho Chemical Co., Ltd.) | 10 parts |
| Water | 80 parts |

The above ingredients are homogeneously mixed to form a liquid formulation.

In their use, the above wettable powder, emulsifiable concentrates, flowables or liquid formulations are diluted with water from 50 to 1,000 times and applied so that the respective active ingredients will be from 0.001 to 5 kg per hectare.

The compounds of the present invention are applicable not only to agricultural and horticultural fields such as upland fields, paddy fields and orchards, but also to non-agricultural fields such as athletic fields, vacant fields and railway sides for the control of various weeds. The dose in their application varies depending upon the application site, the season for application, the type of crop plants, etc. However, it is usually within a range of from 0.001 to 5 kg per hectare.

Now, the herbicidal activities of the compounds of the present invention will be described with respect to specific Test Examples.

TEST EXAMPLE 1:

Test on the herbicidal effects in soil treatment

A plastic box having a length of 15 cm, a width of 22 cm and a depth of 6 cm was filled with a sterilized diluvium soil, and seeds of *Echinochloa crus-galli, Setaria viridis, Eleusine indica, Digitaria adscendens, Panicum dichotomiflorum, Abutilon theophrasti, Amaranthus lividus, Polygonum longisetum* and *Zea mays* were sown, and tubers of *Cyperus esculentus* were further planted. The soil was covered thereon in the thickness of about 1.5 cm, and then a herbicide solution was applied onto the surface of the soil uniformly so that the active ingredient was distributed at a predetermined concentration. The herbicide solution was prepared by diluting the wettable powder, the emulsifiable concentrate, the liquid formulation or the flowable as described in the foregoing Formulation Examples with water and applied onto the entire soil surface by means of a small spray. Three weeks after the application of the herbicidal solution, the herbicidal effects against each weed were determined on the basis of the following standard ratings. The results thereby obtained are shown in Table 9. The Compound Nos. correspond to the Compound Nos. in Table 2.

Standard ratings

5: Growth control rate of more than 90% (almost completely withered)
4: Growth control rate of from 70 to 90%
3: Growth control rate of from 40 to 70%
2: Growth control rate of from 20 to 40%
1: Growth control rate of from 5 to 20%
0: Growth control rate of less than 5% (almost non-effective)

The above growth control rates were calculated by the following equation:

$$\text{Growth control rate (\%)} = \left(1 - \frac{T}{N}\right) \times 100$$

where
T: Weight of the weed growth above the soil surface of the treated area
N: Weight of the weed growth above the soil surface of the non-treated area

TEST EXAMPLE 2:

Test 1 on the herbicidal effects in foliage treatment

A plastic box having a length of 15 cm, a width of 22 cm and a depth of 6 cm was filled with a sterilized diluvium soil, and seeds of *Echinochloa crus-galli, Setaria viridis, Eleusine indica, Digitaria adscendens, Panicum dichotomiflorum, Xanthium strumatirum, Abutilon theophrasti, Amaranthus lividus, Polygonum longisetum* and *Zea mays* were spot-wisely sown, and tubers of *Cyperus esculentus* were further planted. Then, the soil was covered thereon in a thickness of about 1.5 cm. When the various weeds and crop plant grew to the 2 or 3 leaf stage, a herbicidal solution was uniformly sprayed on the foliages so that the active ingredient was applied in a predetermined concentration. The herbicidal solution was prepared by diluting the wettable powder, the emulsifiable concentrate, the liquid formulation or the flowable as described in the above Formulation Examples with water and applied onto the entire surface of the foliages of the weeds and the crop plants by a small spray. Two weeks after the application of the herbicide solution, the herbicidal effects against each weed and *Zea mays* were determined on the basis of the standard ratings described in Test Example 1. The results are shown in Table 10. The Compound Nos. in Table 10 correspond to the Compound Nos. in Table 2.

TEST EXAMPLE 3

Test 2 on the herbicidal effects in foliage treatment

A plastic box having a length of 15 cm, a width of 22 cm and a depth of 6 cm was filled with a sterilized diluvium soil, and seeds of *Veronica persica, Stellaria media, Galium spurium, Matricaria matricarioides, Polygonum persicaria, Lamium purpureum, Solanum nigrum* and *Triticum aestivum* were spot-wisely sown. Then, the soil was covered thereon in a thickness of about 1.5 cm. When the various weeds and crop plant grew to the 2 or 3 leaf atage, a herbicidal solution was uniformly sprayed on the foliages so that the active ingredient was applied in a predetermined concentration.

The herbicidal solution was prepared by diluting the wettable powder, the emulsifiable concentrate, the liquid formulation or the flowable as described in the above Formulation Examples with water and applied onto the entire surface of the foliages of the weeds and *Triticum aestivum* by a small spray. Two weeks after the application of the herbicide solution, the herbicidal effects against each weed and *Triticum aestivum* were determined on the basis of the standard ratings described in Test Example 1 The results are shown in Table 11. The Compound Nos in Table 11 correspond to Compound Nos. in Table 2.

In Tables 9, 10 and 11, the following abbreviations are used.

Dose: Dose of active ingredient (g/are)
EC: *Echinochloa crus-galli* (barnyardgrass)
SE: *Setaria viridis* (green foxtail)
EL: *Eleusine indica* (goosegrass)
DI: *Digitaria adscendens* (large crabgrass)
PA: *Panicum dichotomiflorum* (fall panicum)
AB: *Abutilon theophrasti* (velvet leaf)
AM: *Amaranthus lividus* (livid amaranth)
PO: *Polygonum longisetum* (persicaria blumei gross)
XA: *Xanthium strumarium* (cocklebur)
CY: *Cyperus esculentus* (yellow nutsedge)
ZE: *Zea mays* (corn)
VE: *Veronica persia* (birdseye speedweell)
ST: *Stellaria media* (chickweed)
GA: *Galium spurium* (catchweed)
MA: *Matricaria matricarioides* (pineappleweed)
PP: *Polygonum persicaria* (ladysthumb)
LA: *Lamium purpureum* (red deadnettle)
SO: *Solanum nigrum* (black nigthshade)
TR: *Triticum aestivum* (wheat)

TABLE 9

| Compound No. | Dose g/are | EC | SE | EL | DI | PA | AB | AM | PO | CY | ZE |
|---|---|---|---|---|---|---|---|---|---|---|---|
| 1 | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
|  | 4 | 5 | 5 | 5 | 5 | 5 | 5 | 5 | 5 | 5 | 0 |
| 4 | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
|  | 4 | 5 | 5 | 5 | 5 | 5 | 5 | 5 | 5 | 5 | 0 |
| 6 | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
|  | 4 | 5 | 5 | 5 | 5 | 5 | 5 | 5 | 5 | 5 | 0 |
| 7 | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
|  | 4 | 5 | 5 | 5 | 5 | 5 | 5 | 5 | 5 | 5 | 0 |
| 11 | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
|  | 4 | 5 | 5 | 5 | 5 | 5 | 5 | 5 | 5 | 5 | 0 |
| 18 | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
|  | 4 | 5 | 5 | 5 | 5 | 5 | 5 | 5 | 5 | 5 | 0 |
| 19 | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
|  | 4 | 5 | 5 | 5 | 5 | 5 | 5 | 5 | 5 | 5 | 0 |
| 20 | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
|  | 4 | 5 | 5 | 5 | 5 | 5 | 5 | 5 | 5 | 5 | 0 |
| Comparative Compound A | 4 | 3 | 1 | 3 | 3 | 1 | 4 | 5 | 5 | 0 | 0 |
|  | 8 | 4 | 2 | 4 | 4 | 2 | 5 | 5 | 5 | 0 | 0 |
|  | 16 | 5 | 3 | 5 | 5 | 3 | 5 | 5 | 5 | 1 | 1 |
| Comparative Compound B | 4 | 5 | 5 | 5 | 5 | 5 | 1 | 1 | 1 | 2 | 0 |
|  | 8 | 5 | 5 | 5 | 5 | 5 | 2 | 2 | 2 | 3 | 0 |
|  | 16 | 5 | 5 | 5 | 5 | 5 | 3 | 3 | 3 | 4 | 1 |

TABLE 10

| Compound No. | Dose g/are | EC | SE | EL | DI | PA | AB | AM | PO | XA | CY | ZE |
|---|---|---|---|---|---|---|---|---|---|---|---|---|
| 1 | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
|  | 4 | 5 | 5 | 5 | 5 | 5 | 5 | 5 | 5 | 5 | 5 | 0 |
| 4 | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
|  | 4 | 5 | 5 | 5 | 5 | 5 | 5 | 5 | 5 | 5 | 5 | 0 |
| 6 | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
|  | 4 | 5 | 5 | 5 | 5 | 5 | 5 | 5 | 5 | 5 | 5 | 0 |
| 7 | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
|  | 4 | 5 | 5 | 5 | 5 | 5 | 5 | 5 | 5 | 5 | 5 | 0 |
| 11 | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
|  | 4 | 5 | 5 | 5 | 5 | 5 | 5 | 5 | 5 | 5 | 5 | 0 |
| 18 | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
|  | 4 | 5 | 5 | 5 | 5 | 5 | 5 | 5 | 5 | 5 | 5 | 0 |
| 19 | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |

TABLE 10-continued

| Compound No. | Dose g/are | EC | SE | EL | DI | PA | AB | AM | PO | XA | CY | ZE |
|---|---|---|---|---|---|---|---|---|---|---|---|---|
|  | 4 | 5 | 5 | 5 | 5 | 5 | 5 | 5 | 5 | 5 | 5 | 0 |
| 20 | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
|  | 4 | 5 | 5 | 5 | 5 | 5 | 5 | 5 | 5 | 5 | 5 | 0 |
| Comparative Compound A | 4 | 3 | 1 | 2 | 3 | 0 | 3 | 5 | 5 | 4 | 0 | 0 |
|  | 8 | 4 | 2 | 3 | 4 | 1 | 5 | 5 | 5 | 5 | 0 | 1 |
|  | 16 | 4 | 2 | 3 | 4 | 1 | 5 | 5 | 5 | 5 | 0 | 1 |
| Comparative Compound B | 4 | 4 | 3 | 3 | 4 | 3 | 0 | 2 | 2 | 0 | 1 | 0 |
|  | 8 | 4 | 4 | 4 | 4 | 4 | 1 | 3 | 3 | 1 | 2 | 1 |
|  | 16 | 5 | 5 | 5 | 5 | 5 | 2 | 4 | 4 | 2 | 3 | 2 |

TABLE 11

| Compound No. | Dose g/are | VE | ST | GA | MA | PP | LA | SO | TR |
|---|---|---|---|---|---|---|---|---|---|
| 1 | 0.5 | 5 | 5 | 5 | 5 | 5 | 5 | 5 | 0 |
|  | 1 | 5 | 5 | 5 | 5 | 5 | 5 | 5 | 0 |
|  | 2 | 5 | 5 | 5 | 5 | 5 | 5 | 5 | 0 |
| 7 | 0.5 | 5 | 5 | 5 | 5 | 5 | 5 | 5 | 0 |
|  | 1 | 5 | 5 | 5 | 5 | 5 | 5 | 5 | 0 |
|  | 2 | 5 | 5 | 5 | 5 | 5 | 5 | 5 | 0 |
| 11 | 0.5 | 5 | 5 | 5 | 5 | 5 | 5 | 5 | 0 |
|  | 1 | 5 | 5 | 5 | 5 | 5 | 5 | 5 | 0 |
|  | 2 | 5 | 5 | 5 | 5 | 5 | 5 | 5 | 0 |
| 18 | 0.5 | 5 | 5 | 5 | 5 | 5 | 5 | 5 | 0 |
|  | 1 | 5 | 5 | 5 | 5 | 5 | 5 | 5 | 0 |
|  | 2 | 5 | 5 | 5 | 5 | 5 | 5 | 5 | 0 |
| Comparative Compound C | 1 | 4 | 4 | 3 | 2 | 4 | 2 | 4 | 0 |
|  | 2 | 5 | 5 | 4 | 4 | 5 | 4 | 5 | 1 |

In Tables 9 and 10, the Comparative Compounds are as follows:

Comparative Compound A: Atrazine

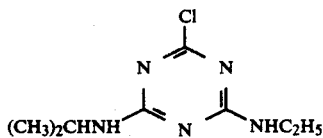

Comparative Compound B: Alachlor

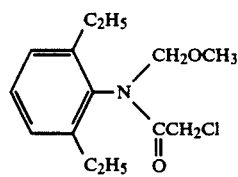

In Table 11, the Comparative Compound is as follows:

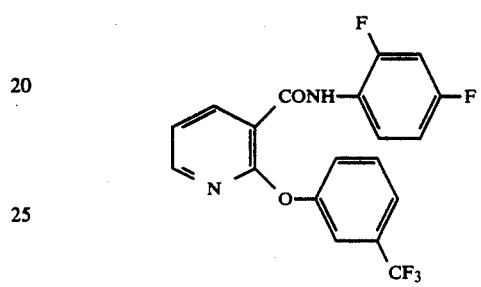

We claim:
1. A pyrazole derivative of the formula I

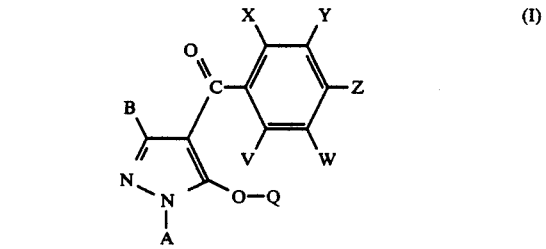

(I)

wherein
A is a $C_1$–$C_4$ alkyl group, a $C_2$–$C_4$ alkenyl group or a $C_2$–$C_4$ alkynyl group;
B is a hydrogen atom, a $C_1$–$C_3$ alkyl group, a halogen atom, a $C_1$–$C_3$ haloalkyl group, a $C_1$–$C_3$ alkoxy group, a $C_1$–$C_3$ alkylthio group, a $C_2$–$C_4$ alkoxyalkyl group, a $C_2$–$C_4$ alkylthioalkyl group or a $C_2$–$C_4$ alkoxycarbonyl group;
X is a $C_1$–$C_6$ alkyl group, a $C_1$–$C_6$ alkoxy group, a halogen atom, a nitro group, a cyano group, a $C_1$–$C_6$ haloalkyl group, a $C_2$–$C_6$ alkoxyalkyl group, a $C_2$–$C_6$ alkylcarbonyl group, a $C_2$–$C_6$ alkoxycarbonyl group, an aminocarbonyl group substituted independently by hydrogen or by a $C_1$–$C_6$ alkyl group, a $C_1$–$C_6$ haloalkoxy group, a $C_1$–$C_6$ alkylthio group or a $C_2$–$C_6$ alkylthioalkyl group;
Y is —$OR^1$ (wherein $R^1$ is a $C_3$–$C_8$ cycloalkyl group, a $C_4$–$C_8$ cycloalkylalkyl group, a $C_3$–$C_6$ alkenyl group, a $C_2$–$C_6$ alkynyl group, a $C_1$–$C_6$ haloalkyl group, a $C_3$–$C_8$ halocycloalkylalkyl group, a $C_3$–$C_6$ haloalkenyl group, a $C_2$–$C_6$ haloalkynyl group, a $C_2$–$C_6$ nitroalkyl group or a phenyl group which may be substituted by a $C_1$–$C_3$ alkyl group, a halogen atom, a nitro group or a $C_1$–$C_3$ alkoxy group), —O—L—O—$R^1$ (wherein L is a $C_1$–$C_6$ alkylene group which may be substituted by a C$_1$–C$_3$ alkyl group, and R$^1$ is as defined above), —O—L—OH (wherein L is as defined above), —O—L—O—L—O—R$^2$ (wherein L is as defined above, and R$^2$ is a hydrogen atom, a C$_1$–C$_6$ alkyl group or a phenyl group which may be substituted by a C$_1$–C$_3$ alkyl group, a halogen atom, a nitro group or a C$_1$–C$_3$ alkoxy group), —O—L—R$^3$ (wherein L is as defined above, and R$^3$ is a phenyl group which may be substituted by a C$_1$–C$_3$ alkyl group, a halogen atom, a nitro group Or a C$_1$–C$_3$ alkoxy group), —O—M (wherein M is a 3- to 6-membered alicyclic group containing not more than two sulfur or oxygen atoms and formed by a linkage of from 1 to 4 carbon atoms), —O—L—M (wherein L and M are as defined above), —O—L—NR$^4$R$^5$ (wherein L is as defined above and each of R$^4$ and R$^5$ which may be the same or different is a hydrogen atom or a C$_1$–C$_6$ alkyl group, or R$^4$ and R$^5$ form a 6-membered ring together with the adjacent nitrogen atom), —O—L—COOR$^4$ (wherein L and R$^4$ are as defined above), —O—CH=CH—COOR$^4$ (wherein R$^4$ is as defined above), —O—L—CN (wherein L is as defined above), —O—L—C(O)—R$^2$ (wherein L and R$^2$ are as defined above), —O—L—S(O)$_n$—R$^4$ (wherein L and R$^4$ are as defined above, and n is an integer of from 0 to 2), —O—COOR$^4$ (wherein R$^4$ is as defined above), —O—CONR$^4$R$^5$ (wherein R$^4$ and R$^5$ are as defined above), —OP(O)(OR$^4$)$_2$ (wherein R$^4$ is as defined above), —S(O)$_n$R$^1$ (wherein R$^1$ and n are as defined above), or —S(O)$_n$—L—O—R$^1$ (wherein L, R$^1$ and n are as defined above);

Z is a halogen atom, a nitro group, a C$_1$–C$_3$ alkoxy group, a trifluoromethyl group, a trifluoromethoxy group, a cyano group or —S(O)$_n$R$^6$ (wherein n is as defined above, and R$^6$ is a C$_1$–C$_3$ alkyl group or a C$_1$–C$_3$ haloalkyl group);

V is a hydrogen atom, a halogen atom, a C$_1$–C$_4$ alkyl group or a C$_1$–C$_4$ alkoxy group;

W is a hydrogen atom, a halogen atom, a C$_1$–C$_4$ alkyl group, a C$_1$–C$_4$ haloalkyl group, a C$_1$–C$_4$ alkoxy group, a C$_2$–C$_6$ alkoxyalkyl group, a C$_2$–C$_5$ alkoxycarbonyl group, a C$_1$–C$_3$ haloalkoxy group, a nitro group, a cyano group or —S(O)$_n$—R$^6$ (wherein n and R$^6$ are as defined above) and Q is a hydrogen atom, a C$_1$–C$_6$ alkyl group which may be substituted by a halogen atom, a C$_1$–C$_6$ alkenyl group which may be substituted by a halogen atom, a C$_1$–C$_6$ alkynyl group which may be substituted by a halogen atom, a cyanomethyl group, —C(O)—R$^7$ (wherein R$^7$ is a phenyl group which may be substituted by the same or different substituents selected from the group consisting of a C$_1$–C$_6$ alkyl group, a C$_1$–C$_6$ alkenyl group, a C$_1$–C$_6$ alkynyl group, a C$_1$–C$_6$ haloalkyl group, a C$_1$–C$_6$ haloalkenyl group, a C$_1$–C$_6$ haloalkynyl group, a halogen atom, a nitro group and a trifluoromethyl group, a C$_1$–C$_6$ alkyl group, a C$_1$–C$_6$ alkoxy group, or a hydroxyl group), —S(O)$_2$R$^7$ (wherein R$^7$ is as defined above), —P(O)(OR$^7$)$_2$ (wherein R$^7$ is as defined above), —L—C(O)—R$^7$ (wherein L and R$^7$ are as defined above), —L—C(O)—N(R$^8$)(R$^9$) (wherein L is as defined above, and each of R$^8$ and R$^9$ which may be the same or different is a hydrogen atom or a C$_1$–C$_6$ alkyl group), —L—R$^{10}$ (wherein L is as defined above, and R$^{10}$ is a phenyl group which may be substituted by the same or different substituents selected from the group consisting of a halogen atom, a nitro group and a trifluoromethyl group, a C$_1$–C$_6$ alkyl group, a C$_1$–C$_6$ alkoxy group, or a hydroxyl group), —L—N(R$^8$)(R$^9$) (wherein L, R$^8$ and R$^9$ are as defined above), —L—OR$^{11}$ (wherein L is as defined above, and R$^{11}$ is a hydrogen atom, a C$_1$–C$_6$ alkyl group, or a C$_1$–C$_6$ alkenyl group), —L—OC(O)R$^{12}$ (wherein L is as defined above, and R$^{12}$ is a C$_1$–C$_6$ alkyl group or a C$_1$–C$_6$ alkoxy group), —L—S(O)$_n$R$^{11}$ (wherein L, n and R$^{11}$ are as defined above), —L—SC(O)R$^8$ (wherein L and R$^8$ are as defined above),

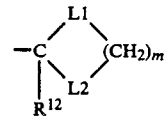

(wherein each of L1 and L2 which may be the same or different is a methylene group, an oxygen atom or a sulfur atom, R$^{12}$ is a hydrogen atom or a C$_1$–C$_3$ alkyl group, and m is 2 or 3); and a salt thereof.

2. The pyrazole derivative of the formula I according to claim 1, wherein A, B, X, Y, Z and Q are as follows:

A: Me, Et, n-Pr, i-Pr, CH$_2$CH=CH$_2$, CH$_2$C≡CH, t-Bu

B: H, Me, Et, n-Pr, i-Pr, Cl, Br, CH$_2$Cl, CF$_3$, OMe, OEt, OPr-i, SMe, CH$_2$OMe, CH$_2$SMe, CO$_2$Me, CO$_2$Et

X: Me, Et, n-Pr, i-Pr, n-Bu, i-Bu, S-Bu, t-Bu, OMe, OEt, OPr-n, OPr-i, OBu-n, OBu-i, OBu-s, OBu-t, F, Cl, Br, I, NO$_2$, CN, CH$_2$F, CHF$_2$, CF$_3$, CH$_2$CF$_3$, CHCl, CCl$_3$, CHClMe, CH$_2$CH$_2$Cl, CHClCH$_2$Cl, CH$_2$Br, CHBrMe, CH$_2$CH$_2$Br, CH$_2$CH$_2$Br, CH$_2$OMe, CH$_2$OEt, CH$_2$OPr-n, CH$_2$OPr-i, CH$_2$OBu-n, CH$_2$OBu-i, CH$_2$OBu-s, CH$_2$OBu-t, CHMeOMe, CHMeOEt, CHMeOPr-n, CHMeOPr-i, CHMeOBu-n, CHMeOBu-i, CHMeOBu-s, CHMeOBu-t, CH$_2$CH$_2$OMe, CH$_2$CH$_2$OEt, CH$_2$CH$_2$OPr-i, Ac, COEt, COPr-n, COPr-i, COOMe, COOEt, COOPr-i, CONHMe, CONHEt, CONMe$_2$, CONEt$_2$, CONEtMe, OCHF$_2$, OCF$_3$, OCH$_2$CF$_3$, SMe, SEt, CH$_2$SMe, CH$_2$SEt, CHMeSMe, CHMeSEt

Y:

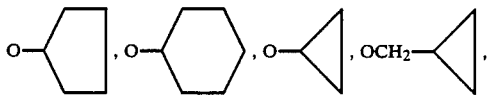

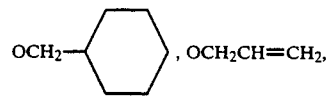

OCHMeCH=CH$_2$, OCMe$_2$CH=CH$_2$, OCH$_2$CMe=CH$_2$, OCH$_2$CH=CHMe, OCH$_2$CH=CMe$_2$, OCH$_2$C≡CH, OCHMeC≡CH, OCMe$_2$C≡CH, OCH$_2$C≡CMe, OCH$_2$CH$_2$F, OCH$_2$CHF$_2$, OCH$_2$CF$_3$, OCH$_2$CH$_2$Cl, OCH-

MeCH₂Cl, OCH₂CCl₃, OCH₂CH₂CH₂Cl, OCH₂CH₂Br,

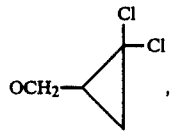

OCH₂CCl=CH₂, OCH₂CH₂CH=CH₂, OCH₂CCl=CHCl, OCH₂CH₂NO₂, OPh, OPh-Me-2 OPh-Cl-4, OPh-NO₂-4, OCH₂CH₂OMe, OCH₂CH₂OEt, OCH₂CH₂OPr-n, OCH₂CH₂OPr-i, OCH₂CH₂OBu-N, OCH₂CH₂OBu-i, OCH₂CH₂Bu-s, OCH₂CH₂OBu-t, OCHMeCH₂OMe, OCH₂CH₂OPh, OCH₂CH₂OCH₂CH₂OMe, OCH₂CH₂OH, OCH₂CH₂OCHMeCH₂OMe, OCH₂Ph, OCHMePh, OCH₂Ph-4-Me, OCH₂Ph-4-Cl, OCH₂CH₂Ph,

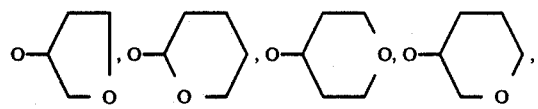

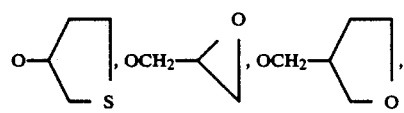

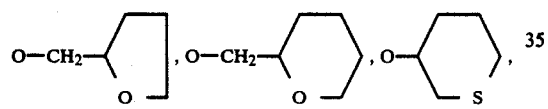

OCH₂CH₂NH₂, OCH₂CH₂NHMe, OCH₂CH₂NMe₂, OCH₂CH₂NEt₂,

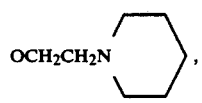

OCH₂COOMe, OCH₂COOEt, OCH₂COOPr-n, OCH₂COOPr-i, OCH₂COOBu-t, OCHMeCOOMe, OCHMeCOOEt OCHMeCOOPr-n, OCHMeCOOPr-i, OCHMeCOOBu-t, OCH₂CH₂CN, OCH₂CN, OCHMeCN, OCH₂SMe, OCH₂C(O)Ph, OCH₂C(O)Me, OCH₂CH₂SMe, OCH₂CH₂SOMe, OCH₂CH₂SO₂Me, OCH₂CH₂SEt, OCH₂CH₂SO₂Et, OCOOMe, OCOOEt, OCOOPr-i, OCONH₂, OCONHMe, OCONMe₂, OP(O)(OMe)₂, OP(O)(OEt)₂,

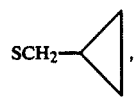

SCH₂CH=CH₂, SCH₂C≡CH, SCH₂CF₃, SCH₂CH₂Cl, SCH₂CCl₃,

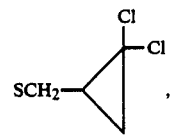

SPh, SCH₂CH₂OMe, SCH₂CH₂OEt, SCH₂CH₂OPr-i, SCH₂CH₂OPh,

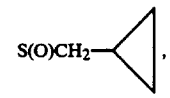

S(O)CH₂CH=CH₂, S(O)CH₂CH≡CH, S(O)CH₂CF₃, S(O)CH₂CH₂Cl, S(O)CH₂

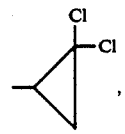

S(O)Ph, S(O)CH₂CH₂OMe, S(O)CH₂CH₂OEt, S(O)CH₂CH₂OPr-i, S(O)CH₂CH₂OPh,

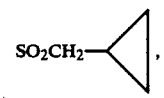

SO₂CH₂CH=CH₂, SO₂CH₂C≡CH, SO₂CH₂CF₃, SO₂CH₂CH₂Cl, SO₂CH₂

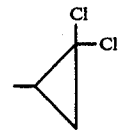

SO₂Ph, SO₂CH₂CH₂OMe, SO₂CH₂CH₂OEt, SO₂CH₂CH₂OPr-i,

Z: F, Cl, Br, I, NO₂, OMe, OEt, OPr-n, OPr-I, CF₃, CN, SMe, SOMe, SO₂Me, SCF₃, SOCF₃, SO₂CF₃

Q H, Me, Et, n-Pr, i-Pr, n-Bu, i-Bu, s-Bu, t-Bu, CH₂CH₂Cl, CH₂CF₃, CHClMe, CH₂CH₂Br, CHClCH₂Cl, CH₂CH=CH₂, CH₂CMe=CH₂, CH₂CH=CHMe, CH₂C≡CH, CH₂CCl=CH₂, CH₂CN, CH₂Ph, CH₂Ph-Cl-2, CH₂Ph-Cl-3, CH₂Ph-Me-2,

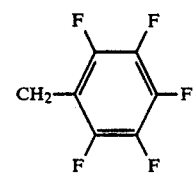

CH₂Ph-Me₂-2,4, CH₂Ph-Me-4, CHMePh, CHEtPh, CH₂Ph-NO₂-2, CH₂Ph-CF₃-3, CH₂OMe, CH₂OEt, CH₂OH, CHMeOH, CH₂NHMe, CH₂NMe₂, CHMeNMe₂, CH₂COPh, CH₂COPh-NO₂-4, CH₂COPh-Me-4, CH₂COPh-Cl-4, CH₂COPh-Me-2,4, CH₂COPh-CF₃-4,

CH2Ac, CH2COEt, CHMeAc, CH2CO2Me, CH2CO2Et, CH2CO2Pr-n, CH2CO2Pr-i, CH2CO2-Bu-t, CH2CO2H, CHMeCO2H, CH2CONHMe, CH2CONMe2, CH2CONHEt, CH2CONEt2, CH2CONPr-n2, CH2OCH2CH=CH2, CH2OAc, CH2COEt, CH2COPr-i, CH2COBu-t, CH2O-CO2Me, CH2OCO2Et, CH2OCO2Pr-i, CH2OCO2-Bu-t, CH2SMe, CH2SEt, CH2SCH2CH=CH2, CH2SAc, CH2SCOBu-t, CH2SO2Me, CH2SO2Et, CH2SO2CH2CH=CH2, COPh, COPh-Me-4, COPh-NO2-2, COPh-Cl2-2,4, Ac, COEt, COPr-n, COPr-i, COBu-n, COBu-t, CO2Me, CO2Et, CO2-Bu-t, CO2Pr-i, CO2Ph, SO2Me, SO2Et, SO2Ph, SO2Ph-Me-4, SO2Ph-Cl-4, SO2Ph-(NO2)2-2,4, P(=O)(OMe)2, P(=O)(OEt)2, P(=O)(OPr-n)2, P(=O)(OPr-i)2, P(=O)OMeOPh;

and a salt thereof.

3. A selective herbicidal composition comprising a herbicidally effective amount of a pyrazole derivative of the formula I as defined in claim 1 or its salt and an agricultural carrier or diluent.

4. A method for controlling weeds, which comprise applying a herbicidally effective amount of a pyrazole derivative of the formula I as defined in claim 1 or its salt to a locus to be protected.

5. A pyrazole derivative of the formula I

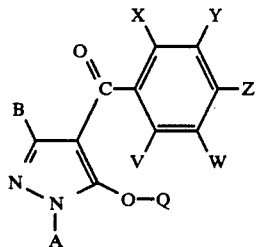

(I)

wherein

A is a $C_1$-$C_4$ alkyl group, a $C_2$-$C_4$ alkenyl group or a $C_2$-$C_4$ alkynyl group;

B is a hydrogen atom, a $C_1$-$C_3$ alkyl group, a halogen atom, a $C_1$-$C_3$ haloalkyl group, a $C_1$-$C_3$ alkoxy group, a $C_1$-$C_3$ alkylthio group, a $C_2$-$C_4$ alkoxyalkyl group, a $C_2$-$C_4$ alkylthioalkyl group or a $C_2$-$C_4$ alkoxycarbonyl group;

X is a $C_1$-$C_6$ alkyl group, a $C_1$-$C_6$ alkoxy group, a halogen atom, a nitro group, a cyano group, a $C_1$-$C_6$ haloalkyl group, a $C_2$-$C_6$ alkoxyalkyl group, a $C_2$-$C_6$ alkylcarbonyl group, a $C_2$-$C_6$ alkoxycarbonyl group, an aminocarbonyl group substituted independently by hydrogen or by a $C_1$-$C_6$ alkyl group, a $C_1$-$C_6$ haloalkoxy group, a $C_1$-$C_6$ alkylthio group or a $C_2$-$C_6$ alkylthioalkyl group;

Y is —$OR^1$ (wherein $R^1$ is a $C_3$-$C_8$ cycloalkyl group, a $C_4$-$C_8$ cycloalkylalkyl group, a $C_3$-$C_6$ alkenyl group, a $C_2$-$C_6$ alkynyl group, a $C_1$-$C_6$ haloalkyl group, a $C_3$-$C_8$ halocycloalkylalkyl group, a $C_3$-$C_6$ haloalkenyl group, a $C_2$-$C_6$ haloalkynyl group, a $C_2$-$C_6$ nitroalkyl group or a phenyl group which may be substituted by a $C_1$-$C_3$ alkyl group, a halogen atom, a nitro group or a $C_1$-$C_3$ alkoxy group), —O—L—O—$R^1$ (wherein L is a $C_1$-$C_6$ alkylene group which may be substituted by a $C_1$-$C_3$ alkyl group, and $R^1$ is as defined above), —O—L—OH (wherein L is as defined above), —O—L—O—L—O—$R^2$ (wherein L is as defined above, and $R^2$ is a hydrogen atom, a $C_1$-$C_6$ alkyl group or a phenyl group which may be substituted by a $C_1$-$C_3$ alkyl group, a halogen atom, a nitro group or a $C_1$-$C_3$ alkoxy group), —O—L—$R^3$ (wherein L is as defined above, and $R^3$ is a phenyl group which may be substituted by a $C_1$-$C_3$ alkyl group, a halogen atom, a nitro group or a $C_1$-$C_3$ alkoxy group), —O—M (wherein M is a 3- to 6-membered alicyclic group containing not more than two sulfur or oxygen atoms and formed by a linkage of from 1 to 4 carbon atoms), —O—L—M (wherein L and M are as defined above), —O—L—$NR^4R^5$ (wherein L is as defined above and each of $R^4$ and $R^5$ which may be the same or different is a hydrogen atom or a $C_1$-$C_6$ alkyl group, or $R^4$ and $R^5$ form a 6-membered ring together with the adjacent nitrogen atom), —O—L—$COOR^4$ (wherein L and $R^4$ are as defined above), —O—CH=CH—$COOR^4$ (wherein $R^4$ is as defined above), —O—L—CN (wherein L is as defined above), —O—L—C(O)—$R^2$ (wherein L and $R^2$ are as defined above), —O—L—$S(O)_n$—$R^4$ (wherein L and $R^4$ are as defined above, and n is an integer of from 0 to 2), —O—$COOR^4$ (wherein $R^4$ is as defined above), —O—$CONR^4R^5$ (wherein $R^4$ and $R^5$ are as defined above), —$OP(O)(OR^4)_2$ (wherein $R^4$ is as defined above), —$S(O)_nR^1$ (wherein $R^1$ and n are as defined above), or —$S(O)_n$—L—O—$R^1$ (wherein L, $R^1$ and n are as defined above);

Z is a halogen atom, a nitro group, a $C_1$-$C_3$ alkoxy group, a trifluoromethyl group, a trifluoromethoxy group, a cyano group or —$S(O)_nR^6$ (wherein n is as defined above, and $R^6$ is a $C_1$-$C_3$ alkyl group or a $C_1$-$C_3$ haloalkyl group);

V is a hydrogen atom, a halogen atom, a $C_1$-$C_4$ alkyl group or a $C_1$-$C_4$ alkoxy group;

W is a hydrogen atom, a halogen atom, a $C_1$-$C_4$ alkyl group, a $C_1$-$C_4$ haloalkyl group, a $C_1$-$C_4$ alkoxy group, a $C_2$-$C_6$ alkoxyalkyl group, a $C_2$-$C_5$ alkoxycarbonyl group, a $C_1$-$C_3$ haloalkoxy group, a nitro group, a cyano group or —$S(O)_n$—$R^6$ (wherein n and $R^6$ are as defined above); and Q is selected from the group consisting of CH2NHCH2CH=CH2, CH2NMeCH2CH=CH2, CH2NHAc, CH2NHCOEt, CH2NHCO2Me, CH2NHCO2Et, CH2NMeCO2Me, COCH2Cl, COCHCl2, COCCl3, COCF3, COCH2OMe, COCH2OPh, COCH2CH=CHCH3, CONHMe, CONMe2, CONHEt, CONEt2, CONPr-n2, CON(CH2CH=CH2)2, CONMePh,

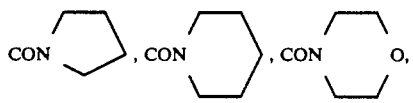

CO2CH2Ph, SO2CH2CH=CH2, SO2CF3, P(=S)(OMe)2, P(=S)(OEt)2, P(=O)-(OCH2CH=CH2)2, P(=O)OPhOCH2CH=CH2; and salts thereof.

* * * * *